US010849337B2

(12) United States Patent
Geremia et al.

(10) Patent No.: US 10,849,337 B2
(45) Date of Patent: Dec. 1, 2020

(54) OLIGOSACCHARIDE COMPOSITIONS FOR USE AS ANIMAL FEED AND METHODS OF PRODUCING THEREOF

(71) Applicant: Cadena Bio, Inc., Bedford, MA (US)

(72) Inventors: John M. Geremia, Watertown, MA (US); Raffi Mardirosian, Cambridge, MA (US); Michael J. Gidding, Cambridge, MA (US); Anastasia V. Murphy, Attleborough, MA (US)

(73) Assignee: Cadena Bio, Inc., Lexington, MA (US)

( * ) Notice: Subject to any disclaimer, the term of this patent is extended or adjusted under 35 U.S.C. 154(b) by 0 days.

(21) Appl. No.: 14/995,129

(22) Filed: Jan. 13, 2016

(65) Prior Publication Data

US 2016/0366909 A1     Dec. 22, 2016

Related U.S. Application Data

(60) Provisional application No. 62/255,343, filed on Nov. 13, 2015, provisional application No. 62/255,341, filed on Nov. 13, 2015, provisional application No. 62/216,945, filed on Sep. 10, 2015, provisional application No. 62/216,952, filed on Sep. 10, 2015, provisional application No. 62/108,037, filed on Jan. 26, 2015.

(51) Int. Cl.
| | |
|---|---|
| *A23K 20/163* | (2016.01) |
| *A23K 20/195* | (2016.01) |
| *A23K 50/75* | (2016.01) |
| *A61K 31/702* | (2006.01) |
| *A61K 45/06* | (2006.01) |
| *A23K 20/142* | (2016.01) |
| *A23K 20/24* | (2016.01) |
| *A23K 50/30* | (2016.01) |
| *A23K 20/26* | (2016.01) |
| *A23K 20/147* | (2016.01) |
| *A23K 20/22* | (2016.01) |

(52) U.S. Cl.
CPC .......... *A23K 20/163* (2016.05); *A23K 20/142* (2016.05); *A23K 20/147* (2016.05); *A23K 20/195* (2016.05); *A23K 20/22* (2016.05); *A23K 20/24* (2016.05); *A23K 20/26* (2016.05); *A23K 50/30* (2016.05); *A23K 50/75* (2016.05); *A61K 31/702* (2013.01); *A61K 45/06* (2013.01); *Y02P 20/582* (2015.11)

(58) Field of Classification Search
CPC .... A23K 20/163; A23K 50/75; A23K 20/195; A61K 31/702; A61K 45/06
USPC ........................................................ 514/54
See application file for complete search history.

(56) References Cited

U.S. PATENT DOCUMENTS

| | | | |
|---|---|---|---|
| 2,027,904 | A | 1/1936 | Farber |
| 2,436,967 | A | 3/1948 | Leuck |
| 2,719,179 | A | 9/1955 | Mora et al. |
| 3,766,165 | A | 10/1973 | Rennhard et al. |
| 3,876,794 | A | 4/1975 | Rennhard |
| 3,973,049 | A | 8/1976 | Furda et al. |
| 4,761,401 | A | 8/1988 | Couchman et al. |
| 4,927,811 | A | 5/1990 | Quarles |
| 4,965,354 | A | 10/1990 | Yanaki et al. |
| 5,051,500 | A | 9/1991 | Elmore |
| 5,424,418 | A | 6/1995 | Duflot |
| 5,556,899 | A | 9/1996 | Afzali-Ardakani et al. |
| 5,558,899 | A | 9/1996 | Kuzee et al. |
| 5,580,762 | A | 12/1996 | Karube et al. |
| 5,645,647 | A | 7/1997 | Guzek et al. |
| 5,780,620 | A | 7/1998 | Mandai et al. |
| 5,843,922 | A | 12/1998 | Whistler et al. |
| 6,423,833 | B1 | 7/2002 | Catani et al. |
| 6,475,552 | B1 | 11/2002 | Shah et al. |
| 6,559,302 | B1 | 5/2003 | Shah et al. |
| 6,638,916 | B1 | 10/2003 | Cowden et al. |
| 6,677,142 | B1 | 1/2004 | Weissmuller et al. |
| 7,608,291 | B2 | 10/2009 | Baillon et al. |
| 7,608,436 | B2 | 10/2009 | Harrison et al. |
| 7,615,365 | B2 | 11/2009 | Caimi et al. |
| 8,057,480 | B2 | 11/2011 | Dorawa et al. |
| 8,057,840 | B2 | 11/2011 | Harrison et al. |
| 8,148,505 | B2 | 4/2012 | Ando et al. |
| 8,227,448 | B2 | 7/2012 | Van Laere et al. |
| 8,466,242 | B2 | 6/2013 | Geremia et al. |
| 8,476,388 | B2 | 7/2013 | Geremia et al. |
| 8,741,376 | B2 | 6/2014 | Broekaert et al. |
| 8,835,403 | B2 | 9/2014 | Geng et al. |
| 8,993,039 | B2 | 3/2015 | Harrison et al. |

(Continued)

FOREIGN PATENT DOCUMENTS

| | | |
|---|---|---|
| CN | 1600146 A | 3/2005 |
| CN | 102892303 A | 1/2013 |

(Continued)

OTHER PUBLICATIONS

Winfree et al. Effects of Dietary Protein and Energy on Growth, Feed Conversion Efficiency and Body Composition of Tilapia aurea. J. Nutr. 111:1001-1012, 1981.*

(Continued)

*Primary Examiner* — Yih-Horng Shiao

(74) *Attorney, Agent, or Firm* — Clark & Elbing LLP

(57) ABSTRACT

Described herein are methods of producing animal feed made up of oligosaccharide compositions, as well as methods of producing such oligosaccharide compositions and animal feed compositions, and methods of using such animal feed compositions to enhance animal growth.

26 Claims, 19 Drawing Sheets

(56) References Cited

U.S. PATENT DOCUMENTS

| | | |
|---|---|---|
| 9,079,171 B2 | 7/2015 | Geremia et al. |
| 9,205,418 B2 | 12/2015 | Geremia et al. |
| 9,238,845 B2 | 1/2016 | Baynes et al. |
| 9,492,473 B2 | 11/2016 | von Maltzahn et al. |
| 9,757,403 B2 | 9/2017 | von Maltzahn et al. |
| 9,783,619 B2 | 10/2017 | Bureau et al. |
| 10,131,721 B2 | 11/2018 | Geremia et al. |
| 2004/0220389 A1 | 11/2004 | Buchwald et al. |
| 2004/0235789 A1 | 11/2004 | Day et al. |
| 2005/0004070 A1 | 1/2005 | Stahl et al. |
| 2005/0075311 A1 | 4/2005 | Lane |
| 2006/0008574 A1 | 1/2006 | Begli et al. |
| 2006/0014717 A1 | 1/2006 | Angstrom et al. |
| 2006/0051812 A1 | 3/2006 | Helin et al. |
| 2006/0127448 A1 | 6/2006 | Carlson et al. |
| 2007/0036840 A1 | 2/2007 | Tuduri et al. |
| 2007/0048432 A1 | 3/2007 | Holzgraefe et al. |
| 2007/0148728 A1 | 6/2007 | Johnson et al. |
| 2007/0254848 A1 | 11/2007 | Geng et al. |
| 2008/0051573 A1 | 2/2008 | Hirth et al. |
| 2012/0034366 A1 | 2/2012 | Hoffman et al. |
| 2012/0220740 A1 | 8/2012 | Geremia et al. |
| 2013/0005684 A1 | 1/2013 | Fichert et al. |
| 2013/0028869 A1 | 1/2013 | Bruggeman et al. |
| 2013/0216693 A1 | 8/2013 | Harrison et al. |
| 2014/0060522 A1 | 3/2014 | Baynes et al. |
| 2014/0187474 A1 | 7/2014 | Sonnenburg |
| 2015/0202607 A1 | 7/2015 | Geremia et al. |
| 2015/0238948 A1 | 8/2015 | Geremia |
| 2015/0352133 A1 | 12/2015 | Jennewein |
| 2016/0007642 A1 | 1/2016 | Geremia et al. |
| 2016/0015065 A1 | 1/2016 | Sumner et al. |
| 2016/0032038 A1 | 2/2016 | Baynes et al. |
| 2016/0122447 A1 | 5/2016 | Geremia et al. |
| 2017/0151268 A1 | 6/2017 | von Maltzahn et al. |
| 2017/0151269 A1 | 6/2017 | von Maltzahn et al. |
| 2018/0000145 A1 | 1/2018 | Geremia et al. |
| 2018/0000146 A1 | 1/2018 | Geremia |

FOREIGN PATENT DOCUMENTS

| | | |
|---|---|---|
| CN | 104171365 A | 12/2014 |
| EA | 11417 B1 | 9/2005 |
| EP | 0549478 A1 | 6/1993 |
| EP | 1634599 A1 | 3/2006 |
| EP | 1887017 A1 | 2/2008 |
| EP | 2138048 A1 | 12/2009 |
| EP | 2248907 A1 | 11/2010 |
| EP | 2401925 A1 | 1/2012 |
| EP | 2666788 A1 | 11/2013 |
| ES | 2304223 B2 | 5/2009 |
| JP | H06-121693 A | 5/1994 |
| JP | H10-316740 A | 12/1998 |
| JP | 2011-501670 A | 1/2011 |
| JP | 2012-158526 A | 8/2012 |
| JP | 2014-513985 A | 6/2014 |
| RU | 2153503 C2 | 7/2000 |
| RU | 2509477 C1 | 3/2014 |
| WO | WO-2004/052121 A1 | 6/2004 |
| WO | WO-2005/003329 A1 | 1/2005 |
| WO | WO-2007/010084 A2 | 1/2007 |
| WO | WO-2008/156354 A1 | 12/2008 |
| WO | WO-2009/051977 A1 | 4/2009 |
| WO | WO-2009/082214 A1 | 7/2009 |
| WO | WO-2010/143961 A1 | 12/2010 |
| WO | WO-2011/008086 A1 | 1/2011 |
| WO | WO-2011/016866 A1 | 2/2011 |
| WO | WO-2012/076321 A1 | 6/2012 |
| WO | WO-2012/156897 A1 | 11/2012 |
| WO | WO-2014/031956 A1 | 2/2014 |
| WO | WO-2014/145276 A1 | 9/2014 |
| WO | WO-2016/007778 A1 | 1/2016 |
| WO | WO-2016/122884 A1 | 8/2016 |
| WO | WO-2016/122885 A1 | 8/2016 |
| WO | WO-2016/122889 A1 | 8/2016 |
| WO | WO-2016/172657 A2 | 10/2016 |
| WO | WO-2016/172658 A2 | 10/2016 |
| WO | WO-2017/083520 A1 | 5/2017 |

OTHER PUBLICATIONS

Fasina et al. Comparative efficacy of a yeast product and bacitracin methylene disalicylate in enhancing early growth and intestinal maturation in broiler chicks from breeder hens of different ages. Poultry Science 90:1067-1073, 2011. (Year: 2011).*

Adeniji AA. Effects of Dietary Grit Inclusion on the Utilization of Rice Husk by Pullet Chicks. Tropical and Subtropical Agroecosystems, 12:175-180, 2010. (Year: 2010).*

Bergstrom et al., "Defective intestinal mucin-type O-glycosylation causes spontaneous colitis-associated cancer in mice," Gastroenterology. 151(1):152-64 (2016) (24 pages).

International Search Report and Written Opinion for International Application No. PCT/US2016/013280, dated Mar. 21, 2016 (12 pages).

Röytiö et al., "The fermentation of polydextrose in the large intestine and its beneficial effects," Benef Microbes. 5(3):305-13 (2014).

Sharon, "Carbohydrates as future anti-adhesion drugs for infectious diseases," Biochim Biophys Acta. 1760(4):527-37 (2006).

"Generally Recognized as Safe (GRAS) Determination for the Addition of Polydextrose to Infant Formula as a Prebiotic Ingredient in Combination with Galactooligosaccharides," Aug. 2007 (115 pages).

Aida et al., "Mushroom as a potential source of prebiotics: a review," Trends in Food Science & Technology. 20(11-12):567-75 (2009).

Coudray et al., "Effects of inulin-type fructans of different chain length and type of branching on intestinal absorption and balance of calcium and magnesium in rats," Eur J Nutr. 42(2):91-8 (2003).

Courtin et al., "Dietary inclusion of wheat bran arabinoxylooligosaccharides induces beneficial nutritional effects in chickens," Cereal Chem. 85(5):607-13 (2008).

Courtin et al., "Effects of dietary inclusion of xylooligosaccharides, arabinoxylooligosaccharides and soluble arabinoxylan on the microbial composition of caecal contents of chickens," J Sci Food Agric. 88(14):2517-22 (2008).

Dutton et al., "The constitution of a synthetic xylan," Can J Chem. 40(8):1479-82 (1962).

Extended European Search Report for European Application No. 16743841.5, dated Jul. 13, 2018 (10 pages).

Extended European Search Report for European Application No. 16743842.3, dated Jul. 9, 2018 (13 pages).

Extended European Search Report for European Application No. 16743843.1, dated Jun. 6, 2018 (8 pages).

Extended European Search Report for European Application No. 17206409.9, dated Jun. 21, 2018 (8 pages).

Extended European Search Report for European Patent Application No. 15819734.3, dated Feb. 7, 2018 (12 pages).

Final Office Action for U.S. Appl. No. 14/795,720, dated Dec. 28, 2017 (16 pages).

First Action Interview Pilot Program Pre-Interview Communication for U.S. Appl. No. 15/385,331, dated Apr. 17, 2017 (4 pages).

Fischer et al., "The gel-forming polysaccharide of psyllium husk (*Plantago ovata* Forsk)," Carbohydr Res. 339(11):2009-17 (2004).

Gietl et al., "Factors involved in the in vitro fermentability of short carbohydrates in static faecal batch cultures," International Journal of Carbohydrate Chemistry. 2012:197809 (2012) (10 pages).

Gómez et al., "Purification, characterization, and prebiotic properties of pectic oligosaccharides from orange peel wastes," J Agric Food Chem. 62(40):9769-82 (2014).

International Search Report and Written Opinion for International Application No. PCT/US2015/039795, dated Oct. 7, 2015 (9 pages).

International Search Report and Written Opinion for International Application No. PCT/US2016/013265, dated Mar. 11, 2016 (9 pages).

(56) References Cited

OTHER PUBLICATIONS

International Search Report and Written Opinion for International Application No. PCT/US2016/013271, dated Mar. 11, 2016 (8 pages).
International Search Report and Written Opinion for International Application No. PCT/US2016/029082, dated Oct. 14, 2016 (17 pages).
International Search Report and Written Opinion for International Application No. PCT/US2016/029083, dated Oct. 14, 2016 (16 pages).
Koropatkin et al., "How glycan metabolism shapes the human gut microbiota," Nat Rev Microbiol. 10(5):323-35 (2012).
Louis et al., "How to manipulate the microbiota: prebiotics," Adv Exp Med Biol. 902:119-42 (2016).
Mora et al., "Synthetic Polysaccharides. V. Polymerization of Various Aldoses," J Am Chem Soc. 82(13):3418-21 (1960).
Non-Final Office Action for U.S. Appl. No. 14/795,720, dated Jun. 9, 2017 (12 pages).
Non-Final Office Action for U.S. Appl. No. 15/017,396, dated May 20, 2016 (7 pages).
Notice of Allowance for U.S. Appl. No. 15/286,382, dated Oct. 11, 2017 (7 pages).
Office Action for Chinese Patent Application No. 201580048065.6, dated Oct. 31, 2018 (12 pages).
Sanz et al., "Influence of glycosidic linkages and molecular weight on the fermentation of maltose-based oligosaccharides by human gut bacteria," J Agric Food Chem. 54(26):9779-84 (2006).
Synytsya et al., "Glucans from fruit bodies of cultivated mushrooms Pleurotus ostreatus and Pleurotus eryngii: Structure and potential prebiotic activity," Carbohydrate Polymers. 76(4):548-56 (2009).
Wang et al., "Preparation and structural characterization of polymannose synthesized by phosphoric acid catalyzation under microwave irradiation," Carbohydr Polym. 121:355-61 (2015).
Wang et al., "Rapid microwave-assisted synthesis of polydextrose and identification of structure and function," Carbohydrate Polymers. 113:225-30 (2014).
Zeuner et al., "Methods for improving enzymatic transglycosylation for synthesis of human milk oligosaccharide biomimetics," J Agric Food Chem. 62(40):9615-31 (2014).
ADM Ingredients Catalog, Archer Daniels Midland Company, Decatur, IL (2016).
Ahmad and Kaleem, "β-Glucan as a Food Ingredient" in Biopolymers for Food Design, Handbook for Food Design, vol. 20, Eds.: Grumezescu and Holban; Academic Press, 2018, p. 386.
Search Report for Russian Patent Application No. 2017130166/10(052504), dated May 13, 2019 (4 pages).
Si, et al., "Quantification of cell proliferation and alpha-toxin gene expression of Clostridium perfringens in the development of necrotic enteritis in broiler chickens," Appl Environ Microbiol. 73(21):7110-3 (2007).
Timbermont, et al., "Necrotic enteritis in broilers: an updated review on the pathogenesis," Avian Pathol. 40(4):341-7 (2011).
Olano-Martin et al., "In vitro fermentability of dextran, oligodextran and maltodextrin by human gut bacteria," Br J Nutr. 83(3):247-55 (2000).
Roberfroid, "Prebiotics: the concept revisited," J Nutr. 137(3 Suppl 2):830S-7S (2007).
Coulier et al., "In-depth characterization of prebiotic galacto-oligosaccharides by a combination of analytical techniques," J Agric Food Chem. 57(18):8488-95 (2009).
Rodriguez-Colinas et al., "Galacto-oligosaccharide synthesis from lactose solution or skim milk using the beta-galactosidase from Bacillus circulans," J Agric Food Chem. 60(25):6391-8 (2012).
Aggrawal et al., "Technical Application Note 1151. Profiling galactosyloligosaccharide-containing samples by high-performance anion-exchange chromatography with pulsed amperometric detection (HPAE-PAD)," ThermoFisher Scientific, retrieved from <https://assets.thermofisher.com/TFS-Assets/CMD/Application-Notes/AN-1151-IC-Galactosyloligosaccharides-Prebiotics-AN71993-EN.pdf> on Aug. 27, 2019 (2018) (8 pages).
Mountzouris et al., "Modeling of oligodextran production in an ultrafiltration stirred-cell membrane reactor," Enzyme Microb Technol. 24(1): 75-85 (1999).
Caligur et al., "Glycobiology: glycosaminoglycans and polysaccharides," BioFiles. 3(10):1-26 (2008) (28 pages).
Office Action for Brazilian Patent Application No. BR112017015944-9, dated Nov. 10, 2019 (6 pages).
Pfenninger et al., "Structural analysis of underivatized neutral human milk oligosaccharides in the negative ion mode by nano-electrospray MS(n) (part 2: application to isomeric mixtures)," J Am Soc Mass Spectrom. 13(11):1341-8 (2002) (8 pages).
Kobata, "Structures and application of oligosaccharides in human milk," Proc Jpn Acad Ser B Phys Biol Sci. 86(7):731-47 (2010) (17 pages).
Examination Report for Indonesian Patent Application No. P00201700913, dated Feb. 5, 2020 (4 pages).
Extended European Search Report for European Application No. 19191223.7, dated Feb. 17, 2020 (7 pages).
Office Action for Chinese Patent Application No. 201680016822.6, dated Apr. 24, 2020 (21 pages).
Office Action for Japanese Patent Application No. 2017-557271, dated Feb. 18, 2020 (15 pages).
Communication pursuant to Article 94(3) EPC for European Patent Application No. 16743842.3, dated Aug. 4, 2020 (5 pages).
Examination Report for Indian Patent Application No. 201717026993, dated Aug. 24, 2020 (7 pages).
Velayudhan et al., "Characterization of Dietary Energy in Swine Feed and Feed Ingredients: A Review of Recent Research Results," Asian-Australas J Anim Sci. 28(1):1-13 (2015).
Houdijk et al., "Effects of dietary oligosaccharides on the growth performance and faecal characteristics of young growing pigs," Anim Feed Sci Tech. 71:35-48 (1998).

* cited by examiner

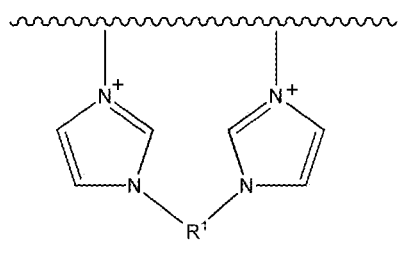
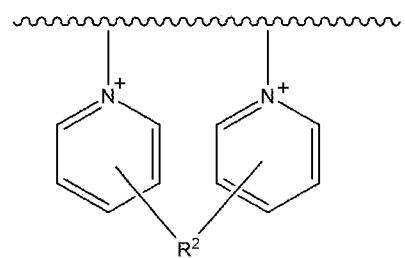
*FIG. 5A*   *FIG. 5B*
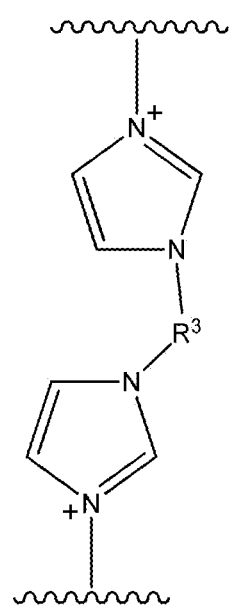
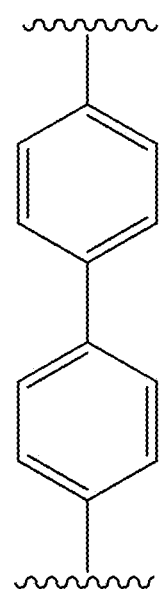
*FIG. 6A*   *FIG. 6B*

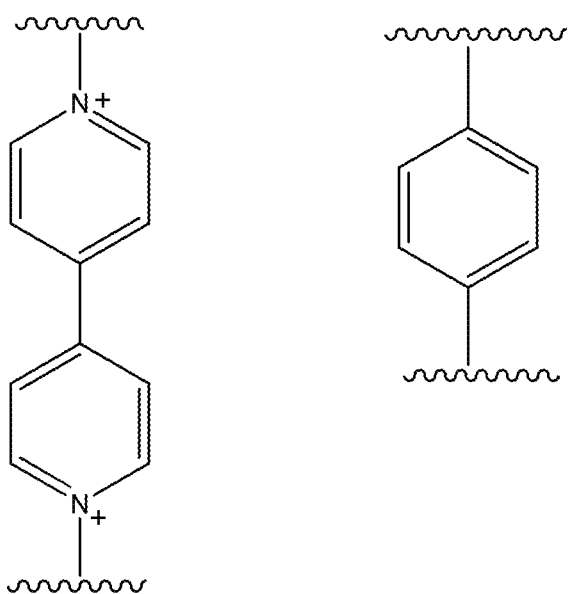
*FIG. 6C*  *FIG. 6D*
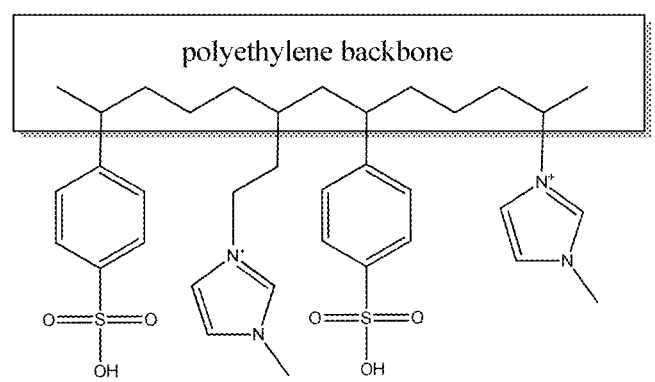
*FIG. 7*

OLIGOSACCHARIDE COMPOSITIONS FOR USE AS ANIMAL FEED AND METHODS OF PRODUCING THEREOF

CROSS-REFERENCE TO RELATED APPLICATIONS

This application claims priority to U.S. Provisional Patent Applications Nos. 62/108,037 filed Jan. 26, 2015, 62/216,945 filed Sep. 10, 2015, 62/216,952 filed Sep. 10, 2015, 62/255,341 filed Nov. 13, 2015, and 62/255,343 filed Nov. 13, 2015, the disclosures of which are hereby incorporated by reference in their entireties.

FIELD

The present disclosure relates generally to feed materials suitable for animal consumption, and more specifically to animal feed that include oligosaccharide compositions, methods of increasing animal growth by feeding an animal such oligosaccharide compositions, and methods of producing such oligosaccharide compositions.

BACKGROUND

As the global human population rises, the demand for animal products also grows. Meeting this demand requires raising increasingly more animals while maximizing utilization of limited resources. Furthermore, animals raised under commercial conditions often face challenges, such as living in close proximity to many other animals. These conditions can have a negative impact on animal health by, for example, facilitating the spread of disease, lowering overall growth performance, and increasing stress-induced mortality.

Additives have been developed for use in animal feed to counteract these challenges. For example, antibiotics are often used to promote health and increase weight gain in poultry, swine, fish, and other production animals. However, concerns about the effect of antibiotic additives on human health and development of drug-resistant bacteria have led to an increased demand in the consumer market for animals raised without antibiotic additives.

Oligosaccharide additives can also be used to improve animal health, growth rate, and the efficient conversion of feed by the animal. The impact of oligosaccharides on animal growth and well-being depends on their physiochemical properties, which can have physiological and morphological effects on the digestive tract. For example, factors including viscosity, monomer composition, and molecular mass can alter intestinal transit time, intestinal mucosa, nutrient absorption, and hormonal regulation.

Methods of producing such additives known in the art include the enzymatic hydrolysis or acid hydrolysis of longer chain oligosaccharides and polysaccharides to produce oligosaccharide additives. Enzymatic methods can generate degradation side products that cause metabolic problems when consumed by poultry, swine and livestock. Additionally, it can sometimes be difficult to control the physiochemical properties of oligosaccharides produced using acid hydrolysis.

Thus, there is a need in the art for animal feed additives, that can be provided at a lower inclusion rate, while maintaining or increasing animal weight. There is also a need in the art for methods of producing such animal feed additives.

BRIEF SUMMARY

The present application addresses this need in the art by providing oligosaccharide compositions suitable for use in animal feed compositions, and methods for producing oligosaccharide compositions suitable for use in animal feed compositions. In one aspect, provided is a method of producing an animal feed composition, by: combining feed sugar with a catalyst to form a reaction mixture; producing an oligosaccharide composition from at least a portion of the reaction mixture; and combining the oligosaccharide composition with a base feed to produce an animal feed composition.

In embodiments of the foregoing, the catalyst is a polymeric catalyst that includes acidic monomers and ionic monomers connected to form a polymeric backbone; or the catalyst is a solid-supported catalyst that includes a solid support, acidic moieties attached to the solid support, and ionic moieties attached to the solid support.

In some variations, the animal feed composition is poultry feed. In other variations, the animal feed composition is swine feed. In certain variations, the animal feed composition is in liquid or solid form.

In another aspect, provided is a method of increasing weight gain in an animal, by: feeding to the animal an animal feed composition produced according to any of the methods described herein, wherein the animal feed composition is fed to the animal at an inclusion rate of less than 1,000 mg/kg, or less than 500 mg/kg. In yet another aspect, provided is a method of improving weight gain and reducing feed conversion ratio of an animal, by: feeding to the animal an animal feed composition produced according to any of the methods described herein. In some variations of the foregoing aspects, the animal is a monogastric species. In certain variations of the foregoing aspects, the animal is a chicken. In other variations of the foregoing aspects, the animal is a pig. In yet other variations of the foregoing aspects, the animal is a fish. In other variations of the foregoing aspects, the animal is a ruminant species, for example a cow.

Provided is also an animal feed composition produced according to any of the methods described herein.

In one aspect, provided herein is an animal feed composition which includes (i) a base feed, and (ii) an oligosaccharide composition; wherein the oligosaccharide composition has a glycosidic bond type distribution of at least 10 mol % α-(1,3) glycosidic linkages, and at least 10 mol % β-(1,3) glycosidic linkages; and wherein at least 10 dry wt % of the oligosaccharide composition has a degree of polymerization of at least 3.

In another aspect, provided herein is an animal feed composition which includes (i) a base feed, and (ii) an oligosaccharide composition, wherein the oligosaccharide composition has a glycosidic bond type distribution of less than 9 mol % α-(1,4) glycosidic linkages and less than 19 mol % α-(1,6) glycosidic linkages; and wherein at least 10 dry wt % of the oligosaccharide composition has a degree of polymerization of at least 3.

In certain embodiments, the oligosaccharidee composition has a glycosidic bond type distribution of at least 15 mol % β-(1,2) glycosidic linkages. In some embodiments, at least 50 dry wt % of the oligosaccharide composition has a degree of polymerization of at least 3. In some embodiments, the base feed is poultry feed.

In other aspects, provided herein is an animal feed premix, which includes (i) a carrier material, and (ii) an oligosaccharide composition, wherein the oligosaccharide composition has a glycosidic bond type distribution of at least 1 mol % α-(1,3) glycosidic linkages and at least 1 mol % β-(1,3) glycosidic linkages; and wherein at least 10 dry wt % of the oligosaccharide composition has a degree of polymerization of at least 3.

In another aspect, provided herein is an animal feed pre-mix, which includes (i) a carrier material, and (ii) an oligosaccharide composition, wherein the oligosaccharide composition has a glycosidic bond type distribution of less than 20 mol % α-(1,4) glycosidic linkages and less than 30 mol % α-(1,6) glycosidic linkages; and wherein at least 10 dry wt % of the oligosaccharide composition has a degree of polymerization of at least 3.

In certain embodiments, the oligosaccharide composition has a glycosidic bond type distribution of at least 15 mol % β-(1,6) glycosidic linkages. In some embodiments, the animal feed pre-mix reduces feed conversion ratio (FCR) by between 1 to 10% when fed to an animal as compared to an animal fed a feed composition without the oligosaccharide composition.

In yet another aspect, provided herein is a method of enhancing growth of poultry by providing feed to poultry, wherein the feed includes (i) a base feed, and (ii) an oligosaccharide composition, wherein the oligosaccharide composition has a glycosidic bond type distribution of at least 1 mol % α-(1,3) glycosidic linkages and at least 1 mol % β-(1,3) glycosidic linkages; and wherein at least 10 dry wt % of the oligosaccharide composition has a degree of polymerization of at least 3; and enhancing growth in the poultry.

In still another aspect, provided herein is a method of decreasing feed conversion ratio of feed provided to poultry by providing feed to poultry, wherein the feed includes (i) a base feed, and (ii) an oligosaccharide composition, wherein the oligosaccharide composition has a glycosidic bond type distribution of at least 1 mol % α-(1,3) glycosidic linkages and at least 1 mol % β-(1,3) glycosidic linkages; wherein at least 10 dry wt % of the oligosaccharide composition has a degree of polymerization of at least 3; and decreasing the feed conversion ratio (FCR) of feed provided to the poultry.

In some embodiments, the oligosaccharide composition has a bond distribution of at least 15 mol % β-(1,6) glycosidic linkages. In certain embodiments, the feed conversion ratio (FCR) is between 0 to 4% higher than the performance target minimum. In other embodiments, the animal is poultry, and the poultry has an average daily weight gain, and wherein the average daily weight gain is at least 2% greater than the average daily weight gain of poultry provided feed without the oligosaccharide composition. In other embodiments, the animal is swine, and the swine has an average daily weight gain, and wherein the average daily weight gain is at least 2% greater than the average daily weight gain of swine provided feed without the oligosaccharide composition.

In yet another aspect, provided herein is a method of enhancing growth of an animal population, by feeding to the animal population an animal feed, wherein the animal feed comprises an oligosaccharide composition at an inclusion rate of less than 5,000 ppm wt % dry oligosaccharide composition per weight of animal feed; wherein the oligosaccharide composition has a glycosidic bond type distribution of at least 1 mol % α-(1,3) glycosidic linkages and at least 1 mol % β-(1,3) glycosidic linkages; and wherein at least 10 dry wt % of the oligosaccharide composition has a degree of polymerization of at least 3; and enhancing growth of the animal population.

In some embodiments, the animal population is a poultry population. In some embodiments, the animal population is a swine population.

DESCRIPTION OF THE FIGURES

The present application can be understood by reference to the following description taken in conjunction with the accompanying figures.

FIG. 5A illustrates a portion of a polymeric catalyst with cross-linking within a given polymeric chain.

FIG. 5B illustrates a portion of a polymeric catalyst with cross-linking within a given polymeric chain.

FIG. 6A illustrates a portion of a polymeric catalyst with cross-linking between two polymeric chains.

FIG. 6B illustrates a portion of a polymeric catalyst with cross-linking between two polymeric chains.

FIG. 6C illustrates a portion of a polymeric catalyst with cross-linking between two polymeric chains.

FIG. 6D illustrates a portion of a polymeric catalyst with cross-linking between two polymeric chains.

FIG. 7 illustrates a portion of a polymeric catalyst with a polyethylene backbone.

DETAILED DESCRIPTION

Figure 1:
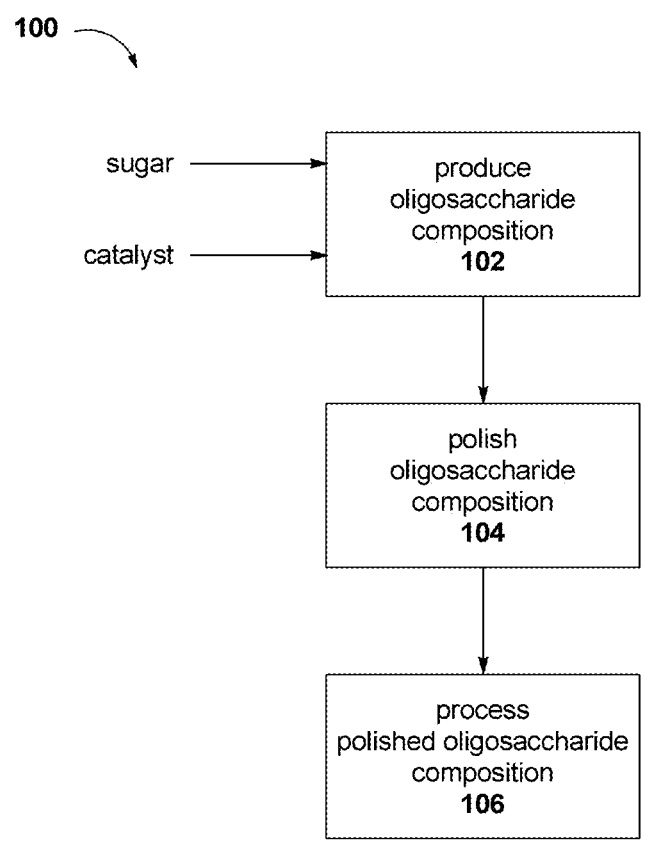
FIG. 1 depicts an exemplary process to produce an oligosaccharide composition from sugars in the presence of a catalyst.

The following description sets forth exemplary methods, parameters and the like. It should be recognized, however, that such description is not intended as a limitation on the scope of the present disclosure but is instead provided as a description of exemplary embodiments.

Provided herein are oligosaccharide compositions suitable for use in animal feed compositions. In some aspects, the oligosaccharide compositions described herein may be fed directly to animals, or may be incorporated into animal feed to form an animal feed composition. The oligosaccharide compositions provided herein may be fed to an animal at an inclusion rate lower than what is typically used in the art, and either maintain or increase the weight of the animal. The oligosaccharide compositions provided herein fed to animals may enhance animal growth, including, for example, increasing weight gain, decreasing the food conversion ratio (FCR), increasing digestibility of provided feed, increasing released nutrients from provided feed, reducing mortality rate, and/or increasing animal uniformity.

Moreover, the oligosaccharide compositions provided herein fed to animals can help the animals get closer to their genetic potential and optimum growth, by helping the animal grow under conditions that do not otherwise allow it to reach optimal growth.

The oligosaccharide compositions, the animal feed compositions, the use of such animal feed compositions, and the methods of producing such oligosaccharide compositions and animal feeds are described herein further detail below. For example, the animals may suffer from a disease or disorder, or may be raised in a stressed environment (due to, for example, pathogenic stress, heat stress, humidity stress, crowding, or other social interaction effects, such as difficulty accessing feed or drinking water.

The oligosaccharide compositions, and their uses and methods of making thereof, are described in further detail below.

Oligosaccharide Compositions

In some aspects, provided herein are oligosaccharide compositions suitable for use as, or incorporation into, animal feed. As used herein, "animal feed" generally refers to feed suitable for non-human consumption. For example, poultry feed refers to feed suitable for poultry consumption; swine feed refers to feed suitable for swine consumption. The oligosaccharide compositions produced according to the methods described herein and the properties of such compositions may vary, depending on the type of sugars as well as the reaction conditions used. The oligosaccharide compositions may be characterized based on the type of oligosaccharides present, degree of polymerization, glass transition temperature, hygroscopicity, and glycosidic bond type distribution.

Types of Oligosaccharides

In some embodiments, the oligosaccharide compositions include an oligosaccharide comprising one type of sugar monomer. For example, in some embodiments, the oligosaccharide compositions may include a gluco-oligosaccharide, a galacto-oligosaccharide, a fructo-oligosaccharide, a manno-oligosaccharide, an arabino-oligosaccharide, or a xylo-oligosaccharide, or any combinations thereof. In some embodiments, the oligosaccharide compositions include an oligosaccharide comprising two different types of sugar monomers. For example, in some embodiments, the oligosaccharide compositions may include a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, or an arabino-xylo-oligosaccharide, or any combinations thereof. In some embodiments, the oligosaccharide compositions include an oligosaccharide comprising more than two different types of sugar monomers. In some variations, the oligosaccharide compositions include an oligosaccharide comprising 3, 4, 5, 6, 7, 8, 9, or 10 different types of sugar monomers. For example, in certain variations the oligosaccharide compositions include an oligosaccharide comprising a galacto-arabino-xylo-oligosaccharide, a fructo-galacto-xylo-oligosaccharide, a arabino-fructo-manno-xylo-oligosaccharide, a gluco-fructo-galacto-arabino-oligosaccharide, a fructo-gluco-arabino-manno-xylo oligosaccharide, or a gluco-galacto-fructo-manno-arabino-xylo-oligosaccharide.

In some embodiments, the oligosaccharide compositions include a gluco-oligosaccharide, a manno-oligosaccharide, a gluco-galacto-oligosaccharide, a xylo-oligosaccharide, an arabino-galacto-oligosaccharide, a gluco-galacto-xylo-oligosaccharide, an arabino-xylo-oligosaccharide, a gluco-xylo-oligosaccharide, or a xylo-gluco-galacto-oligosaccharide, or any combinations thereof. In one variation, the oligosaccharide compositions include a gluco-galacto-oligosaccharide. In another variation, the oligosaccharide compositions include a xylo-gluco-galacto-oligosaccharide.

As used herein, "oligosaccharide" refers to a compound containing two or more monosaccharide units linked by glycosidic bonds.

In some embodiments, at least one of the two or more monosaccharide units is a sugar in L-form. In other embodiments, at least one of the two or more monosaccharides is a sugar in D-form. In yet other embodiments, the two or more monosaccharide units are sugars in L- or D-form according to their naturally-abundant form (e.g., D-glucose, D-xylose, L-arabinose).

In some embodiments, the oligosaccharide composition comprises a mixture of L- and D-forms of monosaccharide units, e.g. of a ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 L- to D-forms or D- to L-forms. In some embodiments, the oligosaccharide comprises monosaccharide units with substantially all L- or D-forms of glycan units, optionally comprising 1%, 2%, 3%, 4% 5%, 6%, 7%, 8%, 9%, 10%, 11%, 12%, 13%, 14%, 15%, 16%, 17%, 18%, 19%, or 20% of the respective other form.

As used herein, "gluco-oligosaccharide" refers to a compound containing two or more glucose monosaccharide units linked by glycosidic bonds. Similarly, "galacto-oligosaccharide" refers to a compound containing two or more galactose monosaccharide units linked by glycosidic bonds.

As used herein, "gluco-galacto-oligosaccharide" refers to a compound containing one or more glucose monosaccharide units linked by glycosidic bonds, and one or more galactose monosaccharide units linked by glycosidic bonds. In some embodiments, the ratio of glucose to galactose on a dry mass basis is between 10:1 glucose to galactose to 0.1:1 glucose to galactose, 5:1 glucose to galactose to 0.2:1 glucose to galactose, 2:1 glucose to galactose to 0.5:1 glucose to galactose. In one embodiment, the ratio of glucose to galactose is 1:1.

In one variation, the oligosaccharide composition is a long oligosaccharide composition, while in another variation the oligosaccharide composition is a short oligosaccharide composition. As used herein, the term "long oligosaccharide composition" refers to an oligosaccharide composition with an average degree of polymerization (DP) of about 8, about 9, about 10, about 11, about 12, about 13, about 14, about 15, about 16, about 17, about 18, about 19, or about 20. As used herein, the term "short oligosaccharide composition" refers to oligosaccharide composition with an average DP of about 2, about 3, about 4, about 5, about 6, or about 7.

Functionalized Oligosaccharide Compositions

In some variations, the oligosaccharide compositions described herein are functionalized oligosaccharide compositions. Functionalized oligosaccharide compositions may be produced by, for example, combining one or more sugars (e.g., feed sugars) with one or more functionalizing compounds in the presence of a catalyst, including, for example, polymeric catalysts and solid-supported catalysts as described in WO 2012/118767 and WO 2014/031956. In certain variations, a functionalized oligosaccharide is a compound comprising two or more monosaccharide units linked by glycosidic bonds in which one or more hydroxyl groups in the monosaccharide units are independently replaced by a functionalizing compound, or comprise a linkage to a functionalizing compound. The functionalizing compound may be a compound that can attach to the oligosaccharide through an ether, ester, oxygen-sulfur, amine, or oxygen-phosphorous bond, and which does not contain a monosaccharide unit.

Functionalizing Compounds

In certain variations, the functionalizing compound comprises one or more functional groups independently selected from amine, hydroxyl, carboxylic acid, sulfur trioxide, sulfate, and phosphate. In some variations, one or more functionalizing compounds are independently selected from the group consisting of amines, alcohols, carboxylic acids, sulfates, phosphates, or sulfur oxides.

In some variations, the functionalizing compound has one or more hydroxyl groups. In some variations, the functionalizing compound with one or more hydroxyl groups is an alcohol. Such alcohols may include, for example, alkanols and sugar alcohols.

In certain variations, the functionalizing compound is an alkanol with one hydroxyl group. For example, in some variations, the functionalizing compound is selected from ethanol, propanol, butanol, pentanol, and hexanol. In other variations, the functionalizing compound has two or more hydroxyl groups. For example, in some variations, the functionalizing compound is selected from propanediol, butanediol, and pentanediol.

For example, in one variation, one or more sugars (e.g., feed sugars) may be combined with a sugar alcohol in the presence of a polymeric catalyst to produce a functionalized oligosaccharide composition. Suitable sugar alcohols may include, for example, sorbitol (also known as glucitol), xylitol, lacitol, arabinatol (also known as arabitol), glycerol, erythritol, mannitol, galacitol, fucitol, iditol, inositol, or volemitol, or any combinations thereof.

In another variation, wherein the functionalizing compound comprises a hydroxyl group, the functionalizing compound may become attached to the monosaccharide unit through an ether bond. The oxygen of the ether bond may be derived from the monosaccharide unit, or from the functionalizing compound.

In yet other variations, the functionalizing compound comprises one or more carboxylic acid functional groups. For example, in some variations, the functionalizing compound is selected from lactic acid, acetic acid, citric acid, pyruvic acid, succinic acid, glutamic acid, itaconic acid, malic acid, maleic acid, propionic acid, butanoic acid, pentanoic acid, hexanoic acid, adipic acid, isobutyric acid, formic acid, levulinic acid, valeric acid, and isovaleric acid. In other variations, the functionalizing compound is a sugar acid. For example, in one embodiment, the functionalizing compound is gluconic acid. In certain variations, wherein the functionalizing compound comprises a carboxylic acid group, the functionalizing compound may become attached to the monosaccharide unit through an ester bond. The non-carbonyl oxygen of the ester bond may be derived from the monosaccharide unit, or from the functionalizing compound.

In still other variations, the functionalizing compound comprises one or more amine groups. For example, in some variations, the functionalizing compound is an amino acid, while in other variations the functionalizing compound is an amino sugar. In one variation, the functionalizing compound is selected from glutamic acid, aspartic acid, glucosamine and galactosamine. In certain variations, wherein the functionalizing compound comprises an amine group, the functionalizing compound may become attached to the monosaccharide unit through an amine bond.

In yet other variations, the functionalizing compound comprises a sulfur trioxide group or a sulfate group. For example, in one variation, the functionalizing compound is dimethylformamide sulfur trioxide complex. In another variation, the functionalizing compound is sulfate. In one embodiment, the sulfate is produced in situ, from, for example, sulfur trioxide. In certain variations wherein the functionalizing compound comprises a sulfur trioxide or sulfate group, the functionalizing compound may become attached to the monosaccharide unit through an oxygen-sulfur bond.

In still other variations, the functionalizing compound comprises a phosphate group. In certain variations wherein the functionalizing compound comprises a phosphate group, the functionalizing compound may become attached to the monosaccharide unit through an oxygen-phosphorous bond.

It should be understood that the functionalizing compounds described herein may contain a combination of functional groups. For example, the functionalizing compound may comprise one or more hydroxyl groups and one or more amine groups (for example, amino sugars). In other embodiments, the functionalizing compound may comprise one or more hydroxyl groups and one or more carboxylic acid groups (for example, sugar acids). In yet other embodiments, the functionalizing compound may comprise one or more amine groups and one or more carboxylic acid groups (for example, amino acids). In still other embodiments, the functionalizing compound comprises one or more additional functional groups, such as esters, amides, and/or ethers. For example, in certain embodiments, the functionalizing compound is a sialic acid (for example, N-acetylneuraminic acid, 2-keto-3-deoxynonic acid, and other N- or O-substituted derivatives of neuraminic acid).

It should further be understood that a functionalizing compound may belong to one or more of the groups described above. For example, a glutamic acid is both an amine and a carboxylic acid, and a gluconic acid is both a carboxylic acid and an alcohol.

In some variations, the functionalizing compound forms a pendant group on the oligosaccharide. In other variations, the functionalizing compound forms a bridging group between an oligomer backbone and a second oligomer backbone; wherein each oligomer backbone independently comprises two or more monosaccharide units linked by glycosidic bonds; and the functionalizing compound is attached to both backbones. In other variations, the functionalizing compound forms a bridging group between an oligomer backbone and a monosaccharide; wherein the oligomer backbone comprises two or more monosaccharide units linked by glycosidic bonds; and the functionalizing compound is attached to the backbone and the monosaccharide.

Pendant Functional Groups

In certain variations, combining one or more sugars (e.g., feed sugars) and one or more functionalizing compounds in the presence of a catalyst, including polymeric catalysts and solid-supported catalysts as described in WO 2012/118767 and WO 2014/031956, produces a functionalized oligosaccharide composition. In certain embodiments, a functionalizing compound is attached to a monosaccharide subunit as a pendant functional group.

A pendant functional group may include a functionalization compound attached to one monosaccharide unit, and not attached to any other monosaccharide units. In some variations, the pendant functional group is a single functionalization compound attached to one monosaccharide unit. For example, in one variation, the functionalizing compound is acetic acid, and the pendant functional group is acetate bonded to a monosaccharide through an ester linkage. In another variation, the functionalizing compound in propionic acid, and the pendant functional group is propionate bonded to a monosaccharide through an ester linkage. In yet another variation, the functionalizing compound is butanoic acid, and the pendant functional group is butanoate bonded to a monosaccharide through an ester linkage. In other variations, a pendant functional group is formed from linking multiple functionalization compounds together. For example, in some embodiments, the functionalization compound is glutamic acid, and the pendant functional group is a peptide chain of two, three, four, five, six, seven, or eight glutamic acid residues, wherein the chain is attached to a monosaccharide through an ester linkage. In other embodiments, the peptide chain is attached to the monosaccharide through an amine linkage.

The pendant functional group may comprise a single linkage to the monosaccharide, or multiple linkages to the monosaccharide. For example, in one embodiment, the functionalization compound is ethanediol, and the pendant functional group is ethyl connected to a monosaccharide through two ether linkages.

Figure 19:
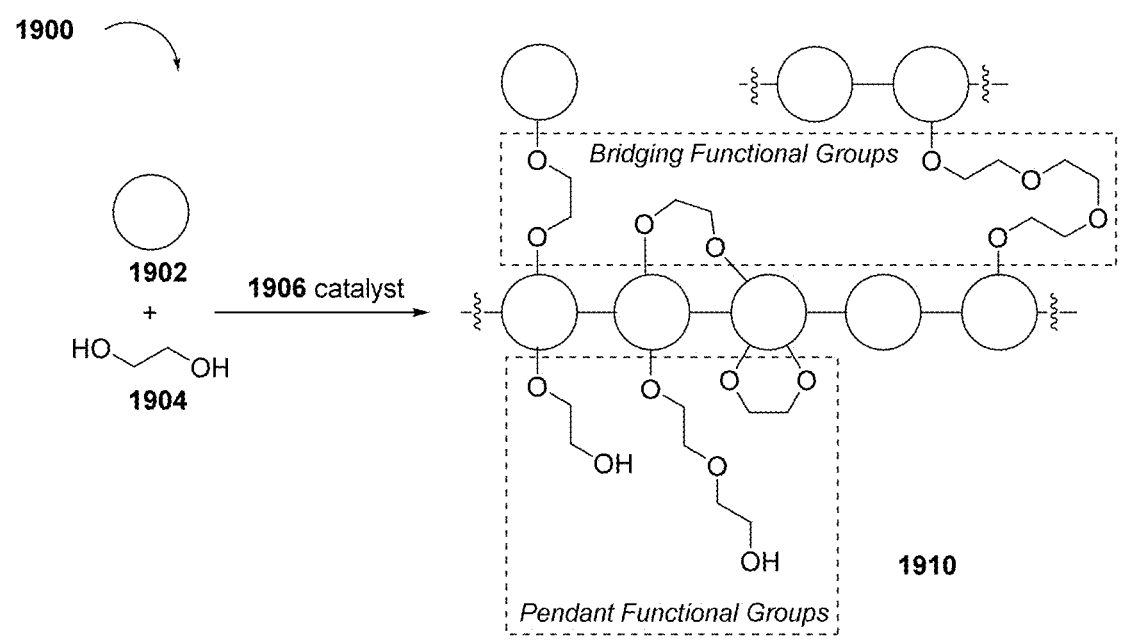
FIG. 19 depicts an exemplary process to produce a functionalized oligosaccharide composition, wherein a portion of an oligosaccharide comprising pendant functional groups and bridging functional groups is shown.
Figure 20:
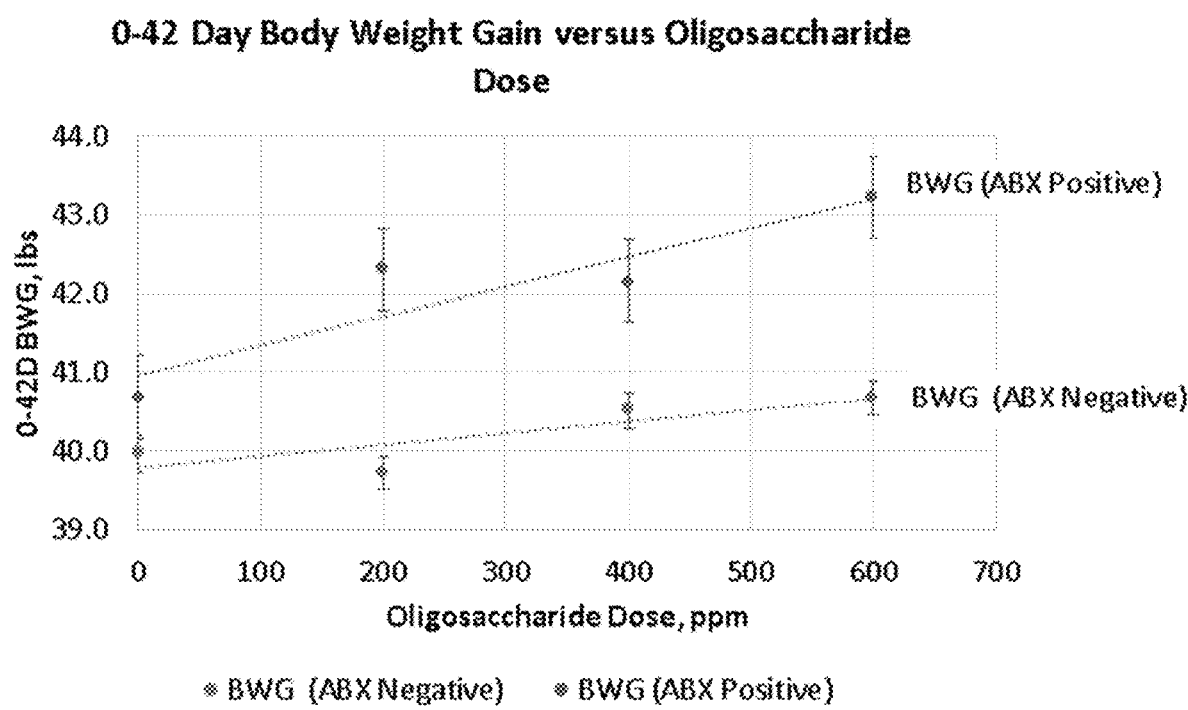
FIG. 20 is a graph that depicts 0-42 day Body Weight Gain (BWG) versus oligosaccharide dose, and a linear regression analysis in the absence (ABX Negatitve) and presence (ABX Positive) of antibiotic growth promoters.
Figure 21:
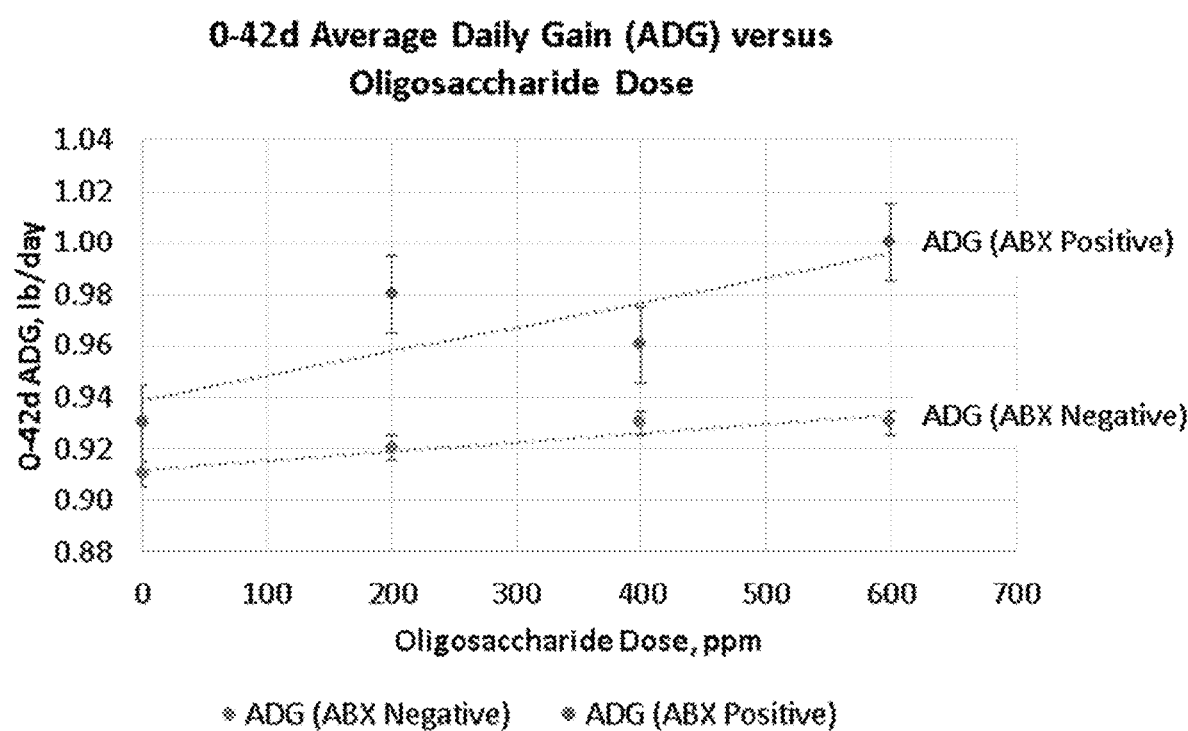
FIG. 21 is a graph that depicts 0-42 day Average Daily Gain (ADG) versus oligosaccharide dose and linear regression analysis in the absence (ABX Negatitve) and presence (ABX Positive) of antibiotic growth promoters.
Figure 22:
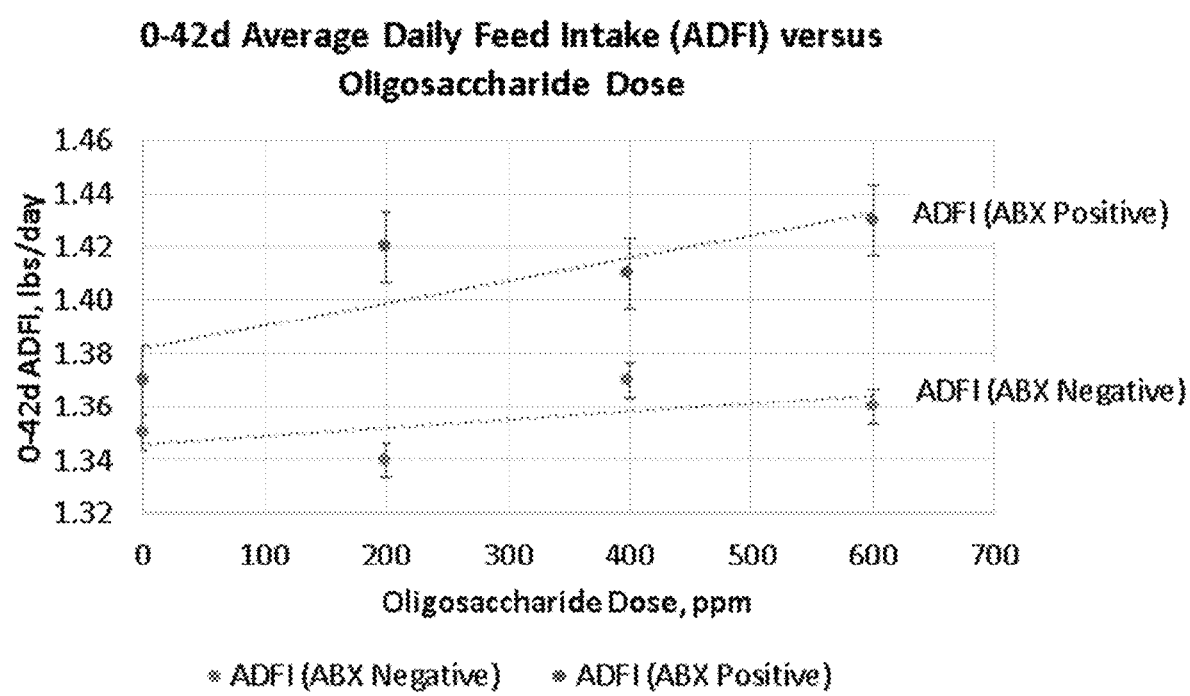
FIG. 22 is a graph that depicts 0-42 day Average Daily Feed Intake (ADFI) versus oligosaccharide dose and linear regression analysis in the absence (ABX Negatitve) and presence (ABX Positive) of antibiotic growth promoters.
Figure 23:
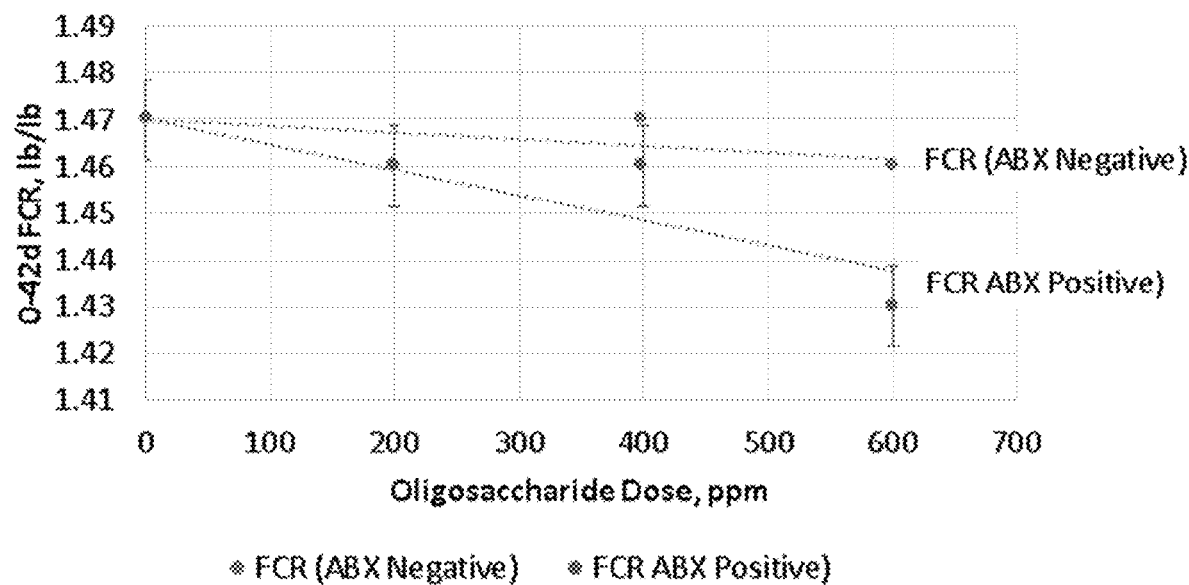
FIG. 23 is a graph that depicts 0-42 day Feed Conversion Ratio (FCR) versus oligosaccharide dose and linear regression analysis in the absence (ABX Negatitve) and presence (ABX Positive) of antibiotic growth promoters.

Referring to FIG. 19, process 1900 depicts an exemplary scheme to produce an oligosaccharide containing different pendant functional groups. In process 1900, monosaccharides 1902 (represented symbolically) are combined with the functionalizing compound ethane diol 1904 in the presence of catalyst 1906 to produce an oligosaccharide. Portion 1910 of the oligosaccharide is shown in FIG. 19, wherein the monosaccharides linked through glycosidic bonds are represented symbolically by circles and lines. The oligosaccharide comprises three different pendant functional groups, as indicated by the labeled section. These pendant functional groups include a single functionalization compound attached to a single monosaccharide unit through one linkage; two functionalization compounds linked together to form a pendant functional group, wherein the pendant functional group is linked to a single monosaccharide unit through one linkage; and a single functionalization compound attached to a single monosaccharide unit through two linkages. It should be understood that while the functionalization compound used in process 1900 is ethanediol, any of the functionalization compounds or combinations thereof described herein may be used. It should be further understood that while a plurality of pendant functional groups is present in portion 1910 of the oligosaccharide, the number and type of pendant functional groups may vary in other variations of process 1900.

It should be understood that any functionalization compounds may form a pendant functional group. In some variations, the functionalized oligosaccharide composition contains one or more pendant groups selected from the group consisting of glucosamine, galactosamine, citric acid, succinic acid, glutamic acid, aspartic acid, glucuronic acid, butyric acid, itaconic acid, malic acid, maleic acid, propionic acid, butanoic acid, pentanoic acid, hexanoic acid, adipic acid, isobutyric acid, formic acid, levulinic acid, valeric acid, isovaleric acid, sorbitol, xylitol, arabitol, glycerol, erythritol, mannitol, galacitol, fucitol, iditol, inositol, volemitol, lacitol, ethanol, propanol, butanol, pentanol, hexanol, propanediol, butanediol, pentanediol, sulfate and phosphate.

Bridging Functional Groups

In certain variations, combining one or more sugars (e.g., feed sugars) and one or more functionalizing compounds in the presence of a catalyst, including polymeric catalysts and solid-supported catalysts as described in WO 2012/118767 and WO 2014/031956, produces a functionalized oligosaccharide comprising a bridging functional group.

Bridging functional groups may include a functionalization compound attached to one monosaccharide unit and attached to at least one additional monosaccharide unit. The monosaccharide units may independently be monosaccharide units of the same oligosaccharide backbone, monosaccharide units of separate oligosaccharide backbones, or monosaccharide sugars that are not bonded to any additional monosaccharides. In some variations, the bridging functional compound is attached to one additional monosaccharide unit. In other variations, the bridging functional compound is attached to two or more additional monosaccharide units. For example, in some embodiments, the bridging functional compound is attached to two, three, four, five, six, seven, or eight additional monosaccharide units. In some variations, the bridging functional group is formed by linking a single functionalization compound to two monosaccharide units. For example, in one embodiment, the functionalization compound is glutamic acid, and the bridging functional group is a glutamate residue attached to one monosaccharide unit through an ester bond, and an additional monosaccharide unit through an amine bond. In other embodiments, the bridging functionalization group is formed by linking multiple functionalization compound molecules to each other. For example, in one embodiment, the functionalization compound is ethanediol, and the bridging functional group is a linear oligomer of four ethanediol molecules attached to each other through ether bonds, the first ethanediol molecule in the oligomer is attached to one monosaccharide unit through an ether bond, and the fourth ethanediol molecule in the oligomer is attached to an additional monosaccharide unit through an ether bond.

Referring again to FIG. 19, portion 1910 of the oligosaccharide produced according to process 1900 comprises three different bridging functional groups, as indicated by the labeled section. These bridging functional groups include a single functionalization compound attached to a monosaccharide unit of an oligosaccharide through one linkage, and attached to a monosaccharide sugar through an additional linkage; a single functionalization compound attached to two different monosaccharide units of the same oligosaccharide backbone; and two functionalization compounds linked together to form a bridging functional group, wherein the bridging functional group is linked to one monosaccharide unit through one linkage and to an additional monosaccharide unit through a second linkage. It should be understood that while the functionalization compound used in process 1900 is ethanediol, any of the functionalization compounds or combinations thereof described herein may be used. It should be further understood that while a plurality of bridging functional groups is present in portion 1910 of the oligosaccharide, the number and type of bridging functional groups may vary in other variations of process 1900.

It should be understood that any functionalization compounds with two or more functional groups able to form bonds with a monosaccharide may form a bridging functional group. For example, bridging functional groups may be selected from polycarboxylic acids (such as succinic acid, itaconic acid, malic acid, maleic acid, and adipic acid), polyols (such as sorbitol, xylitol, arabitol, glycerol, erythritol, mannitol, galacitol, fucitol, iditol, inositol, volemitol, and lacitol), and amino acids (such as glutamic acid). In some variations, the functionalized oligosaccharide composition comprises one or more bridging groups selected from the group consisting of glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate and phosphate.

Functionalized oligosaccharide compositions comprising a mixture of pendant functional groups and bridging functional groups may also be produced using the methods described herein. For example, in certain embodiments, one or more sugars are combined with a polyol in the presence of a catalyst, and a functionalized oligosaccharide composition is produced wherein at least a portion of the composition comprises pendant polyol functional groups attached to oligosaccharides through ether linkages, and at least a portion comprises bridging polyol functional groups wherein each group is attached to a first oligosaccharide through a first ether linkage and a second oligosaccharide through a second ether linkage.

It should further be understood that the one or more functionalization compounds combined with the sugars, oligosaccharide composition, or combination thereof may form bonds with other functionalization compounds, such that the functionalized oligosaccharide composition comprises monosaccharide units bonded to a first functionalization compound, wherein the first functionalization compound is bonded to a second functionalization compound.

Degree of Polymerization

The oligosaccharide content of reaction products can be determined, e.g., by a combination of high performance liquid chromatography (HPLC) and spectrophotometric methods. For example, the average degree of polymerization (DP) for the oligosaccharides can be determined as the number average of species containing one, two, three, four, five, six, seven, eight, nine, ten to fifteen, and greater than fifteen, anhydrosugar monomer units.

In some embodiments, the oligosaccharide degree of polymerization (DP) distribution for the one or more oligosaccharides after combining the one or more sugars with the catalyst (e.g., at 2, 3, 4, 8, 12, 24, or 48 hours after combining the one or more sugars with the catalyst) is: DP2=0%-40%, such as less than 40%, less than 30%, less than 20%, less than 10%, less than 5%, or less than 2%; or 10%-30% or 15%-25%; DP3=0%-20%, such as less than 15%, less than 10%, less than 5%; or 5%-15%; and DP4+ =greater than 15%, greater than 20%, greater than 30%, greater than 40%, greater than 50%; or 15%-75%, 20%-40% or 25%-35%.

In some embodiments, the oligosaccharide degree of polymerization (DP) distribution for the one or more oligosaccharides after combining the one or more sugars with the catalyst (e.g., at 2, 3, 4, 8, 12, 24, or 48 hours after combining the one or more sugars with the catalyst) is any one of entries (1)-(192) of Table 1A.

TABLE 1A

| Entry | DP4+ (%) | DP3 (%) | DP2 (%) |
| --- | --- | --- | --- |
| 1 | 20-25 | 0-5 | 0-5 |
| 2 | 20-25 | 0-5 | 5-10 |
| 3 | 20-25 | 0-5 | 10-15 |
| 4 | 20-25 | 0-5 | 15-20 |
| 5 | 20-25 | 0-5 | 20-25 |
| 6 | 20-25 | 0-5 | 25-30 |
| 7 | 20-25 | 5-10 | 0-5 |
| 8 | 20-25 | 5-10 | 5-10 |
| 9 | 20-25 | 5-10 | 10-15 |
| 10 | 20-25 | 5-10 | 15-20 |
| 11 | 20-25 | 5-10 | 20-25 |
| 12 | 20-25 | 5-10 | 25-30 |
| 13 | 20-25 | 10-15 | 0-5 |
| 14 | 20-25 | 10-15 | 5-10 |
| 15 | 20-25 | 10-15 | 10-15 |
| 16 | 20-25 | 10-15 | 15-20 |
| 17 | 20-25 | 10-15 | 20-25 |
| 18 | 20-25 | 10-15 | 25-30 |
| 19 | 20-25 | 15-20 | 0-5 |
| 20 | 20-25 | 15-20 | 5-10 |
| 21 | 20-25 | 15-20 | 10-15 |
| 22 | 20-25 | 15-20 | 15-20 |
| 23 | 20-25 | 15-20 | 20-25 |

TABLE 1A-continued

| Entry | DP4+ (%) | DP3 (%) | DP2 (%) |
|---|---|---|---|
| 24 | 20-25 | 15-20 | 25-30 |
| 25 | 20-25 | 20-25 | 0-5 |
| 26 | 20-25 | 20-25 | 5-10 |
| 27 | 20-25 | 20-25 | 10-15 |
| 28 | 20-25 | 20-25 | 15-20 |
| 29 | 20-25 | 20-25 | 20-25 |
| 30 | 20-25 | 20-25 | 25-30 |
| 31 | 25-30 | 0-5 | 0-5 |
| 32 | 25-30 | 0-5 | 5-10 |
| 33 | 25-30 | 0-5 | 10-15 |
| 34 | 25-30 | 0-5 | 15-20 |
| 35 | 25-30 | 0-5 | 20-25 |
| 36 | 25-30 | 0-5 | 25-30 |
| 37 | 25-30 | 5-10 | 0-5 |
| 38 | 25-30 | 5-10 | 5-10 |
| 39 | 25-30 | 5-10 | 10-15 |
| 40 | 25-30 | 5-10 | 15-20 |
| 41 | 25-30 | 5-10 | 20-25 |
| 42 | 25-30 | 5-10 | 25-30 |
| 43 | 25-30 | 10-15 | 0-5 |
| 44 | 25-30 | 10-15 | 5-10 |
| 45 | 25-30 | 10-15 | 10-15 |
| 46 | 25-30 | 10-15 | 15-20 |
| 47 | 25-30 | 10-15 | 20-25 |
| 48 | 25-30 | 10-15 | 25-30 |
| 49 | 25-30 | 15-20 | 0-5 |
| 50 | 25-30 | 15-20 | 5-10 |
| 51 | 25-30 | 15-20 | 10-15 |
| 52 | 25-30 | 15-20 | 15-20 |
| 53 | 25-30 | 15-20 | 20-25 |
| 54 | 25-30 | 15-20 | 25-30 |
| 55 | 25-30 | 20-25 | 0-5 |
| 56 | 25-30 | 20-25 | 5-10 |
| 57 | 25-30 | 20-25 | 10-15 |
| 58 | 25-30 | 20-25 | 15-20 |
| 59 | 25-30 | 20-25 | 20-25 |
| 60 | 25-30 | 20-25 | 25-30 |
| 61 | 30-35 | 0-5 | 0-5 |
| 62 | 30-35 | 0-5 | 5-10 |
| 63 | 30-35 | 0-5 | 10-15 |
| 64 | 30-35 | 0-5 | 15-20 |
| 65 | 30-35 | 0-5 | 20-25 |
| 66 | 30-35 | 0-5 | 25-30 |
| 67 | 30-35 | 5-10 | 0-5 |
| 68 | 30-35 | 5-10 | 5-10 |
| 69 | 30-35 | 5-10 | 10-15 |
| 70 | 30-35 | 5-10 | 15-20 |
| 71 | 30-35 | 5-10 | 20-25 |
| 72 | 30-35 | 5-10 | 25-30 |
| 73 | 30-35 | 10-15 | 0-5 |
| 74 | 30-35 | 10-15 | 5-10 |
| 75 | 30-35 | 10-15 | 10-15 |
| 76 | 30-35 | 10-15 | 15-20 |
| 77 | 30-35 | 10-15 | 20-25 |
| 78 | 30-35 | 10-15 | 25-30 |
| 79 | 30-35 | 15-20 | 0-5 |
| 80 | 30-35 | 15-20 | 5-10 |
| 81 | 30-35 | 15-20 | 10-15 |
| 82 | 30-35 | 15-20 | 15-20 |
| 83 | 30-35 | 15-20 | 20-25 |
| 84 | 30-35 | 15-20 | 25-30 |
| 85 | 30-35 | 20-25 | 0-5 |
| 86 | 30-35 | 20-25 | 5-10 |
| 87 | 30-35 | 20-25 | 10-15 |
| 88 | 30-35 | 20-25 | 15-20 |
| 89 | 30-35 | 20-25 | 20-25 |
| 90 | 30-35 | 20-25 | 25-30 |
| 91 | 35-40 | 0-5 | 0-5 |
| 92 | 35-40 | 0-5 | 5-10 |
| 93 | 35-40 | 0-5 | 10-15 |
| 94 | 35-40 | 0-5 | 15-20 |
| 95 | 35-40 | 0-5 | 20-25 |
| 96 | 35-40 | 0-5 | 25-30 |
| 97 | 35-40 | 5-10 | 0-5 |
| 98 | 35-40 | 5-10 | 5-10 |
| 99 | 35-40 | 5-10 | 10-15 |
| 100 | 35-40 | 5-10 | 15-20 |
| 101 | 35-40 | 5-10 | 20-25 |
| 102 | 35-40 | 5-10 | 25-30 |
| 103 | 35-40 | 10-15 | 0-5 |
| 104 | 35-40 | 10-15 | 5-10 |
| 105 | 35-40 | 10-15 | 10-15 |
| 106 | 35-40 | 10-15 | 15-20 |
| 107 | 35-40 | 10-15 | 20-25 |
| 108 | 35-40 | 10-15 | 25-30 |
| 109 | 35-40 | 15-20 | 0-5 |
| 110 | 35-40 | 15-20 | 5-10 |
| 111 | 35-40 | 15-20 | 10-15 |
| 112 | 35-40 | 15-20 | 15-20 |
| 113 | 35-40 | 15-20 | 20-25 |
| 114 | 35-40 | 15-20 | 25-30 |
| 115 | 35-40 | 20-25 | 0-5 |
| 116 | 35-40 | 20-25 | 5-10 |
| 117 | 35-40 | 20-25 | 10-15 |
| 118 | 35-40 | 20-25 | 15-20 |
| 119 | 35-40 | 20-25 | 20-25 |
| 120 | 35-40 | 20-25 | 25-30 |
| 121 | 40-45 | 0-5 | 0-5 |
| 122 | 40-45 | 0-5 | 5-10 |
| 123 | 40-45 | 0-5 | 10-15 |
| 124 | 40-45 | 0-5 | 15-20 |
| 125 | 40-45 | 0-5 | 20-25 |
| 126 | 40-45 | 0-5 | 25-30 |
| 127 | 40-45 | 5-10 | 0-5 |
| 128 | 40-45 | 5-10 | 5-10 |
| 129 | 40-45 | 5-10 | 10-15 |
| 130 | 40-45 | 5-10 | 15-20 |
| 131 | 40-45 | 5-10 | 20-25 |
| 132 | 40-45 | 5-10 | 25-30 |
| 133 | 40-45 | 10-15 | 0-5 |
| 134 | 40-45 | 10-15 | 5-10 |
| 135 | 40-45 | 10-15 | 10-15 |
| 136 | 40-45 | 10-15 | 15-20 |
| 137 | 40-45 | 10-15 | 20-25 |
| 138 | 40-45 | 10-15 | 25-30 |
| 139 | 40-45 | 15-20 | 0-5 |
| 140 | 40-45 | 15-20 | 5-10 |
| 141 | 40-45 | 15-20 | 10-15 |
| 142 | 40-45 | 15-20 | 15-20 |
| 143 | 40-45 | 15-20 | 20-25 |
| 144 | 40-45 | 15-20 | 25-30 |
| 145 | 40-45 | 20-25 | 0-5 |
| 146 | 40-45 | 20-25 | 5-10 |
| 147 | 40-45 | 20-25 | 10-15 |
| 148 | 40-45 | 20-25 | 15-20 |
| 149 | 40-45 | 20-25 | 20-25 |
| 150 | 40-45 | 20-25 | 25-30 |
| 151 | >50 | 0-5 | 0-5 |
| 152 | >50 | 0-5 | 5-10 |
| 153 | >50 | 0-5 | 10-15 |
| 154 | >50 | 0-5 | 15-20 |
| 155 | >50 | 0-5 | 20-25 |
| 156 | >50 | 0-5 | 25-30 |
| 157 | >50 | 5-10 | 0-5 |
| 158 | >50 | 5-10 | 5-10 |
| 159 | >50 | 5-10 | 10-15 |
| 160 | >50 | 5-10 | 15-20 |
| 161 | >50 | 5-10 | 20-25 |
| 162 | >50 | 5-10 | 25-30 |
| 163 | >50 | 10-15 | 0-5 |
| 164 | >50 | 10-15 | 5-10 |
| 165 | >50 | 10-15 | 10-15 |
| 166 | >50 | 10-15 | 15-20 |
| 167 | >50 | 10-15 | 20-25 |
| 168 | >50 | 10-15 | 25-30 |
| 169 | >50 | 15-20 | 0-5 |
| 170 | >50 | 15-20 | 5-10 |
| 171 | >50 | 15-20 | 10-15 |
| 172 | >50 | 15-20 | 15-20 |
| 173 | >50 | 15-20 | 20-25 |
| 174 | >50 | 15-20 | 25-30 |
| 175 | >50 | 20-25 | 0-5 |
| 176 | >50 | 20-25 | 5-10 |
| 177 | >50 | 20-25 | 10-15 |
| 178 | >50 | 20-25 | 15-20 |
| 179 | >50 | 20-25 | 20-25 |

TABLE 1A-continued

| Entry | DP4+ (%) | DP3 (%) | DP2 (%) |
| --- | --- | --- | --- |
| 180 | >60 | 10-20 | 10-20 |
| 181 | >60 | 5-10 | 10-20 |
| 182 | >60 | 0-10 | 0-10 |
| 183 | >70 | 10-20 | 10-20 |
| 184 | >70 | 5-10 | 10-20 |
| 185 | >70 | 0-10 | 0-10 |
| 186 | >80 | 10-20 | 10-20 |
| 187 | >80 | 5-10 | 10-20 |
| 188 | >80 | 0-10 | 0-10 |
| 189 | >85 | 10-20 | 10-20 |
| 190 | >85 | 0-10 | 0-10 |
| 191 | >85 | 0-10 | 0-5 |
| 192 | >90 | 0-10 | 0-10 |

The yield of conversion for the one or more sugars to the one or more oligosaccharides in the methods described herein can be determined by any suitable method known in the art, including, for example, high performance liquid chromatography (HPLC). In some embodiments, the yield of conversion to one or more oligosaccharides to with DP>1 after combining the one or more sugars with the catalyst (e.g., at 2, 3, 4, 8, 12, 24, or 48 hours after combining the one or more sugars with the catalyst) is greater than about 50% (or greater than about 55%, 60%, 65%, 70%, 75%, 80%, 85%, 90%, 95%, or 98%). In some embodiments, the yield of conversion to one or more oligosaccharides of >DP2 after combining the one or more sugars with the catalyst (e.g., at 2, 3, 4, 8, 12, 24, or 48 hours after combining the one or more sugars with the catalyst) is greater than 30% (or greater than 35%, 40%, 45%, 50%, 55%. 60%, 65%, 70%, 75%, 80%, 85%, 90%, 95%, or 98%).

In some embodiments, the methods described herein produce an oligosaccharide composition having lower levels of degradation products, resulting in relatively higher selectivity. The molar yield to sugar degradation products and selectivity may be determined by any suitable method known in the art, including, for example, HPLC. In some embodiments, the amount of sugar degradation products after combining the one or more sugars with the catalyst (e.g., at 2, 3, 4, 8, 12, 24, or 48 hours after combining the one or more sugars with the catalyst) is less than about 10% (or less than about 9%, 8%, 7%, 6%, 5%, 4%, 3%, 2%, 1%, 0.75%, 0.5%, 0.25%, or 0.1%), such as less than about 10% of any one or combination of 1,6-anhydroglucose (levoglucosan), 5-hydroxymethylfurfural, 2-furaldehyde, acetic acid, formic acid, levulinic acid and/or humins. In some embodiments, the molar selectivity to oligosaccharide product after combining the one or more sugars with the catalyst (e.g., at 2, 3, 4, 8, 12, 24, or 48 hours after combining the one or more sugars with the catalyst) is greater than about 90% (or greater than about 95%, 97%, 98%, 99%, 99.5%, or 99.9%).

In some variations, at least 10 dry wt % of the oligosaccharide composition produced according to the methods described herein has a degree of polymerization of at least 3. In some embodiments, at least 10 dry wt %, at least 20 dry wt %, at least 30 dry wt %, at least 40 dry wt %, at least 50 dry wt %, at least 60 dry wt %, at least 70 dry wt %, between 10 to 90 dry wt %, between 20 to 80 dry wt %, between 30 to 80 dry wt %, between 50 to 80 dry wt %, or between 70 to 80 dry wt % of the oligosaccharide composition has a degree of polymerization of at least 3.

In some variations, the oligosaccharide composition produced according to methods described herein has a DP3+ of at least 10% on a dry-weight basis. In certain variations, the oligosaccharide composition produced according to methods described herein has a DP3+ of at least 10% on a dry-weight basis, at least 20% on a dry-weight basis, at least 30% on a dry-weight basis, at least 40% on a dry-weight basis, at least 50% on a dry-weight basis, at least 60% on a dry-weight basis, at least 70% on a dry-weight basis, between 10 to 90% on a dry-weight basis, between 20 to 80% on a dry-weight basis, between 30 to 80% on a dry-weight basis, between 50 to 80% on a dry-weight basis, or between 70 to 80% on a dry-weight basis.

In some variations, the oligosaccharide composition has an average molecular weight of between 100 g/mol and 2000 g/mol, or between 300 g/mol and 1800 g/mol, or between 300 g/mol and 1700 g/mol, or between 500 g/mol and 1500 g/mol; or about 300 g/mol, 350 g/mol, 400 g/mol, 450 g/mol, 500 g/mol, 550 g/mol, 600 g/mol, 650 g/mol, 700 g/mol, 750 g/mol, 800 g/mol, 850 g/mol, 900 g/mol, 950 g/mol, 1000 g/mol, 1100 g/mol, 1200 g/mol, 1300 g/mol, 1400 g/mol, 1500 g/mol, 1600 g/mol, 1700 g/mol, or about 1800 g/mol. In certain variations of the foregoing, the average molecular weight of the oligosaccharide composition is determined as the number average molecular weight. In other variations, the average molecular weight of the oligosaccharide composition is determined as the weight average molecular weight. In yet another variation, the oligosaccharide composition contains only monosaccharide units that have the same molecular weight, in which case the number average molecular weight is identical to the product of the average degree of polymerization and the molecular weight of the monosaccharide unit.

Glass Transition Temperature

In some variations, "glass transition" refers to the reversible transition of some compounds from a hard and relatively brittle state to a softer, flexible state. In some variations, "glass transition temperature" refers to the temperature determined by differential scanning calorimetry.

The glass transition temperature of a material can impart desirable characteristics to that material, and/or can impart desirable characteristics to a composition comprising that material. For example, varying the glass transition temperature of the oligosaccharide composition can affect its blendability in the animal feed composition. In some embodiments, the methods described herein are used to produce one or more oligosaccharides with a specific glass transition temperature, or within a glass transition temperature range. In some variations, the glass transition temperature of one or more oligosaccharides produced according to the methods described herein imparts desirable characteristics to the one or more oligosaccharides (e.g., texture, storage, or processing characteristics). In certain variations, the glass transition temperature of the one or more oligosaccharides imparts desirable characteristics to a composition including the one or more oligosaccharides (e.g., texture, storage, or processing characteristics).

For example, in some variations, animal feed compositions or animal feed pre-mix that include the one or more oligosaccharides with a lower glass transition temperature have a softer texture than animal feed compositions or animal feed pre-mix that includes the one or more oligosaccharides with a higher glass transition temperature, or animal feed compositions or animal feed pre-mix that do not include the one or more oligosaccharides. In other variations, animal feed compositions including the one or more oligosaccharides with a higher glass transition temperature have reduced caking and can be dried at higher temperatures than animal feed compositions or animal feed pre-mix including the one or more oligosaccharides with a lower glass transition temperature, or animal feed compositions or animal feed pre-mix that do not include the one or more oligosaccharides.

In some embodiments, the glass transition temperature of the one or more oligosaccharides when prepared in a dry powder form with a moisture content below 6% is at least −20 degrees Celsius (° C.), at least −10 degrees Celsius, at least 0 degrees Celsius, at least 10 degrees Celsius, at least 20 degrees Celsius, at least 30 degrees Celsius, at least 40 degrees Celsius, at least 50 degrees Celsius, at least 60 degrees Celsius, at least 70 degrees Celsius, at least 80 degrees Celsius, at least 90 degrees Celsius, or at least 100 degrees Celsius. In certain embodiments, the glass transition temperature of the one or more oligosaccharides is between 40 degrees Celsius and 80 degrees Celsius.

In some variations, the oligosaccharide composition has a glass transition temperature of at least −20 degrees Celsius (° C.), at least −10 degrees Celsius, at least 0 degrees Celsius, at least 10 degrees Celsius, at least 20 degrees Celsius, at least 30 degrees Celsius, at least 40 degrees Celsius, at least 50 degrees Celsius, at least 60 degrees Celsius, at least 70 degrees Celsius, at least 80 degrees Celsius, at least 90 degrees Celsius, or at least 100 degrees Celsius, when measured at less than 10 wt % water. In certain embodiments, the oligosaccharide composition has a glass transition temperature of between 40 degrees Celsius and 80 degrees Celsius, when measured at less than 10 wt % water. In one variation, the oligosaccharide composition has a glass transition temperature between −20 and 115 degrees Celsius, when measured at less than 10 wt % water.

Hygroscopicity

In some variations, "hygroscopicity" refers to the ability of a compound to attract and hold water molecules from the surrounding environment. The hygroscopicity of a material can impart desirable characteristics to that material, and/or can impart desirable characteristics to a composition comprising that material. In some embodiments, the methods described herein are used to produce one or more oligosaccharides with a specific hygroscopicity value or a range of hygroscopicity values. In some variations, the hygroscopicity of one or more oligosaccharides produced according to the methods described herein imparts desirable characteristics to the one or more oligosaccharides (e.g., texture, storage, or processing characteristics). In certain variations, the hygroscopicity of the one or more oligosaccharides imparts desirable characteristics to a composition including the one or more oligosaccharides (e.g., texture, storage, or processing characteristics).

For example, in some variations, animal feed compositions or animal feed pre-mix that include the one or more oligosaccharides with a higher hygroscopicity have a softer texture than animal feed compositions or animal feed pre-mix that include the one or more oligosaccharides with a lower hygroscopicity, or animal feed compositions or animal feed pre-mix without the one or more oligosaccharides. In certain variations, the one or more oligosaccharides with a higher hygroscopicity are included in animal feed compositions or animal feed pre-mix to reduce water activity, increase shelf life, produce a softer composition, produce a moister composition, and/or enhance the surface sheen of the composition.

In other variations, animal feed compositions including the one or more oligosaccharides with a lower hygroscopicity have reduced caking and can be dried at a higher temperature than animal feed compositions including the one or more oligosaccharides with a higher hygroscopicity, or animal feed compositions without the one or more oligosaccharides. In certain variations, the one or more oligosaccharides with a lower hygroscopicity are included in animal feed compositions to increase crispness, increase shelf life, reduce clumping, reduce caking, improve, and/or enhance the appearance of the composition.

The hygroscopicity of a composition, including the one or more oligosaccharides, can be determined by measuring the mass gain of the composition after equilibration in a fixed water activity atmosphere (e.g., a desiccator held at a fixed relative humidity).

In some embodiments, the hygroscopicity of the one or more oligosaccharides is at least 5% moisture content at a water activity of at least 0.6, at least 10% moisture content at a water activity of at least 0.6, at least 15% moisture content at a water activity of at least 0.6, at least 20% moisture content at a water activity of at least 0.6, or at least 30% moisture content at a water activity of at least 0.6. In certain embodiments, the hygroscopicity of the one or more oligosaccharides is between 5% moisture content and 15% moisture content at a water activity of at least 0.6.

In certain variations, the oligosaccharide composition has a hygroscopicity of at least 5%, at least 10%, at least 15%, at least 20%, or at least 30% moisture content, when measured at a water activity of at least 0.6. In certain embodiments, the oligosaccharide composition has a hygroscopicity of between 5% moisture content and 15% moisture content, when measured at a water activity of at least 0.6.

In one variation, the oligosaccharide composition has a hygroscopicity of at least 0.05 g/g, when measured at a water activity of 0.6.

In some embodiments, the mean degree of polymerization (DP), glass transition temperature (Tg), and hygroscopicity of the oligosaccharide composition produced by combining the one or more sugars with the catalyst (e.g., at 2, 3, 4, 8, 12, 24, or 48 hours after combining the one or more sugars with the catalyst) is any one of entries (1)-(180) of Table 1B.

TABLE 1B

| Number | Mean DP | Tg at <10 wt % H2O (° C.) | Hygroscopicity (wt % H2O @ 0.6 Aw) |
| --- | --- | --- | --- |
| 1 | 5-10 | >50 | >5% |
| 2 | 5-10 | >50 | >5% |
| 3 | 5-10 | >50 | >5% |
| 4 | 5-10 | >50 | >5% |
| 5 | 5-10 | >50 | >5% |
| 6 | 5-10 | >50 | >10% |
| 7 | 5-10 | >50 | >10% |
| 8 | 5-10 | >50 | >10% |
| 9 | 5-10 | >50 | >10% |
| 10 | 5-10 | >50 | >10% |
| 11 | 5-10 | >50 | >15% |
| 12 | 5-10 | >50 | >15% |
| 13 | 5-10 | >50 | >15% |
| 14 | 5-10 | >50 | >15% |
| 15 | 5-10 | >50 | >15% |
| 16 | 5-10 | >50 | >5% |
| 17 | 5-10 | >50 | >5% |
| 18 | 5-10 | >50 | >5% |
| 19 | 5-10 | >50 | >5% |
| 20 | 5-10 | >50 | >5% |
| 21 | 5-10 | >50 | >10% |
| 22 | 5-10 | >50 | >10% |
| 23 | 5-10 | >50 | >10% |
| 24 | 5-10 | >50 | >10% |
| 25 | 5-10 | >50 | >10% |
| 26 | 5-10 | >50 | >15% |
| 27 | 5-10 | >50 | >15% |
| 28 | 5-10 | >50 | >15% |
| 29 | 5-10 | >50 | >15% |
| 30 | 5-10 | >50 | >15% |

TABLE 1B-continued

| Number | Mean DP | Tg at <10 wt % H2O (° C.) | Hygroscopicity (wt % H2O @ 0.6 Aw) |
| --- | --- | --- | --- |
| 31 | 5-10 | >75 | >5% |
| 32 | 5-10 | >75 | >5% |
| 33 | 5-10 | >75 | >5% |
| 34 | 5-10 | >75 | >5% |
| 35 | 5-10 | >75 | >5% |
| 36 | 5-10 | >75 | >10% |
| 37 | 5-10 | >75 | >10% |
| 38 | 5-10 | >75 | >10% |
| 39 | 5-10 | >75 | >10% |
| 40 | 5-10 | >75 | >10% |
| 41 | 5-10 | >75 | >15% |
| 42 | 5-10 | >75 | >15% |
| 43 | 5-10 | >75 | >15% |
| 44 | 5-10 | >75 | >15% |
| 45 | 5-10 | >75 | >15% |
| 46 | 5-10 | >75 | >5% |
| 47 | 5-10 | >75 | >5% |
| 48 | 5-10 | >75 | >5% |
| 49 | 5-10 | >75 | >5% |
| 50 | 5-10 | >75 | >5% |
| 51 | 5-10 | >75 | >10% |
| 52 | 5-10 | >75 | >10% |
| 53 | 5-10 | >75 | >10% |
| 54 | 5-10 | >75 | >10% |
| 55 | 5-10 | >75 | >10% |
| 56 | 5-10 | >75 | >15% |
| 57 | 5-10 | >75 | >15% |
| 58 | 5-10 | >75 | >15% |
| 59 | 5-10 | >75 | >15% |
| 60 | 5-10 | >75 | >15% |
| 61 | 5-10 | >100 | >5% |
| 62 | 5-10 | >100 | >5% |
| 63 | 5-10 | >100 | >5% |
| 64 | 5-10 | >100 | >5% |
| 65 | 5-10 | >100 | >5% |
| 66 | 5-10 | >100 | >10% |
| 67 | 5-10 | >100 | >10% |
| 68 | 5-10 | >100 | >10% |
| 69 | 5-10 | >100 | >10% |
| 70 | 5-10 | >100 | >10% |
| 71 | 5-10 | >100 | >15% |
| 72 | 5-10 | >100 | >15% |
| 73 | 5-10 | >100 | >15% |
| 74 | 5-10 | >100 | >15% |
| 75 | 5-10 | >100 | >15% |
| 76 | 5-10 | >100 | >5% |
| 77 | 5-10 | >100 | >5% |
| 78 | 5-10 | >100 | >5% |
| 79 | 5-10 | >100 | >5% |
| 80 | 5-10 | >100 | >5% |
| 81 | 5-10 | >100 | >10% |
| 82 | 5-10 | >100 | >10% |
| 83 | 5-10 | >100 | >10% |
| 84 | 5-10 | >100 | >10% |
| 85 | 5-10 | >100 | >10% |
| 86 | 5-10 | >100 | >15% |
| 87 | 5-10 | >100 | >15% |
| 88 | 5-10 | >100 | >15% |
| 89 | 5-10 | >100 | >15% |
| 90 | 5-10 | >100 | >15% |
| 91 | 10-15 | >50 | >5% |
| 92 | 10-15 | >50 | >5% |
| 93 | 10-15 | >50 | >5% |
| 94 | 10-15 | >50 | >5% |
| 95 | 10-15 | >50 | >5% |
| 96 | 10-15 | >50 | >10% |
| 97 | 10-15 | >50 | >10% |
| 98 | 10-15 | >50 | >10% |
| 99 | 10-15 | >50 | >10% |
| 100 | 10-15 | >50 | >10% |
| 101 | 10-15 | >50 | >15% |
| 102 | 10-15 | >50 | >15% |
| 103 | 10-15 | >50 | >15% |
| 104 | 10-15 | >50 | >15% |
| 105 | 10-15 | >50 | >15% |
| 106 | 10-15 | >50 | >5% |
| 107 | 10-15 | >50 | >5% |
| 108 | 10-15 | >50 | >5% |
| 109 | 10-15 | >50 | >5% |
| 110 | 10-15 | >50 | >5% |
| 111 | 10-15 | >50 | >10% |
| 112 | 10-15 | >50 | >10% |
| 113 | 10-15 | >50 | >10% |
| 114 | 10-15 | >50 | >10% |
| 115 | 10-15 | >50 | >10% |
| 116 | 10-15 | >50 | >15% |
| 117 | 10-15 | >50 | >15% |
| 118 | 10-15 | >50 | >15% |
| 119 | 10-15 | >50 | >15% |
| 120 | 10-15 | >50 | >15% |
| 121 | 10-15 | >75 | >5% |
| 122 | 10-15 | >75 | >5% |
| 123 | 10-15 | >75 | >5% |
| 124 | 10-15 | >75 | >5% |
| 125 | 10-15 | >75 | >5% |
| 126 | 10-15 | >75 | >10% |
| 127 | 10-15 | >75 | >10% |
| 128 | 10-15 | >75 | >10% |
| 129 | 10-15 | >75 | >10% |
| 130 | 10-15 | >75 | >10% |
| 131 | 10-15 | >75 | >15% |
| 132 | 10-15 | >75 | >15% |
| 133 | 10-15 | >75 | >15% |
| 134 | 10-15 | >75 | >15% |
| 135 | 10-15 | >75 | >15% |
| 136 | 10-15 | >75 | >5% |
| 137 | 10-15 | >75 | >5% |
| 138 | 10-15 | >75 | >5% |
| 139 | 10-15 | >75 | >5% |
| 140 | 10-15 | >75 | >5% |
| 141 | 10-15 | >75 | >10% |
| 142 | 10-15 | >75 | >10% |
| 143 | 10-15 | >75 | >10% |
| 144 | 10-15 | >75 | >10% |
| 145 | 10-15 | >75 | >10% |
| 146 | 10-15 | >75 | >15% |
| 147 | 10-15 | >75 | >15% |
| 148 | 10-15 | >75 | >15% |
| 149 | 10-15 | >75 | >15% |
| 150 | 10-15 | >75 | >15% |
| 151 | 10-15 | >100 | >5% |
| 152 | 10-15 | >100 | >5% |
| 153 | 10-15 | >100 | >5% |
| 154 | 10-15 | >100 | >5% |
| 155 | 10-15 | >100 | >5% |
| 156 | 10-15 | >100 | >10% |
| 157 | 10-15 | >100 | >10% |
| 158 | 10-15 | >100 | >10% |
| 159 | 10-15 | >100 | >10% |
| 160 | 10-15 | >100 | >10% |
| 161 | 10-15 | >100 | >15% |
| 162 | 10-15 | >100 | >15% |
| 163 | 10-15 | >100 | >15% |
| 164 | 10-15 | >100 | >15% |
| 165 | 10-15 | >100 | >15% |
| 166 | 10-15 | >100 | >5% |
| 167 | 10-15 | >100 | >5% |
| 168 | 10-15 | >100 | >5% |
| 169 | 10-15 | >100 | >5% |
| 170 | 10-15 | >100 | >5% |
| 171 | 10-15 | >100 | >10% |
| 172 | 10-15 | >100 | >10% |
| 173 | 10-15 | >100 | >10% |
| 174 | 10-15 | >100 | >10% |
| 175 | 10-15 | >100 | >10% |
| 176 | 10-15 | >100 | >15% |
| 177 | 10-15 | >100 | >15% |
| 178 | 10-15 | >100 | >15% |
| 179 | 10-15 | >100 | >15% |
| 180 | 10-15 | >100 | >15% |

Glycosidic Bond Type Distribution

In certain variations, the oligosaccharide composition produced according to the methods described herein has a distribution of glycosidic bond linkages. The distribution of glycosidic bond types may be determined by any suitable methods known in the art, including, for example, proton NMR or two dimentional J-resolved nuclear magnetic resonance spectroscopy (2D-JRES NMR). In some variations, the distribution of glycosidic bond types described herein is determined by 2D-JRES NMR.

As described above, the oligosaccharide composition may comprise hexose sugar monomers (such as glucose) or pentose sugar monomers (such as xylose), or combinations thereof. It should be understood by one of skill in the art that certain types of glycosidic linkages may not be applicable to oligosaccharides comprising pentose sugar monomers.

In some variations, the oligosaccharide composition has a bond distribution with:

(i) α-(1,2) glycosidic linkages;
(ii) α-(1,3) glycosidic linkages;
(iii) α-(1,4) glycosidic linkages;
(iv) α-(1,6) glycosidic linkages;
(v) β-(1,2) glycosidic linkages;
(vi) β-(1,3) glycosidic linkages;
(vii) β-(1,4) glycosidic linkages; or
(viii) β-(1,6) glycosidic linkages, or any combination of (i) to (viii) above.

For example, in some variations, the oligosaccharide composition has a bond distribution with a combination of (ii) and (vi) glycosidic linkages. In other variations, the oligosaccharide composition has a bond distribution with a combination of (i), (viii), and (iv) glycosidic linkages. In another variation, the oligosaccharide composition has a bond distribution with a combination of (i), (ii), (v), (vi), (vii), and (viii) glycosidic linkages.

In certain variations, the oligosaccharide composition has a bond distribution with any combination of (i), (ii), (iii), (v), (vi), and (vii) glycosidic linkages, and comprises oligosaccharides with pentose sugar monomers. In other variations, the oligosaccharide composition has a bond distribution with any combination of (i), (ii), (iii), (iv), (v), (vi), (vii) and (viii) glycosidic linkages, and comprises oligosaccharides with hexose sugar monomers. In still other variations, the oligosaccharide composition has a bond distribution with any combination of (i), (ii), (iii), (iv), (v), (vi), (vii) and (viii) glycosidic linkages, and comprises oligosaccharides with hexose sugar monomers, and oligosaccharides with pentose sugar monomers. In still other variations, the oligosaccharide composition has a bond distribution with any combination of (i), (ii), (iii), (iv), (v), (vi), (vii) and (viii) glycosidic linkages, and comprises oligosaccharides with hexose sugar monomers and pentose sugar monomers. In yet another variation, the oligosaccharide composition has a bond distribution with any combination of (i), (ii), (iii), (iv), (v), (vi), (vii) and (viii) glycosidic linkages, and comprises oligosaccharides with hexose sugar monomers, oligosaccharides with pentose sugar monomers, and oligosaccharides with hexose and pentose sugar monomers.

In some variations, the oligosaccharide composition has a glycosidic bond type distribution of less than 20 mol % α-(1,2) glycosidic linkages, less than 10 mol % α-(1,2) glycosidic linkages, less than 5 mol % α-(1,2) glycosidic linkages, between 0 to 25 mol % α-(1,2) glycosidic linkages, between 1 to 25 mol % α-(1,2) glycosidic linkages, between 0 to 20 mol % α-(1,2) glycosidic linkages, between 1 to 15 mol % α-(1,2) glycosidic linkages, between 0 to 10 mol % α-(1,2) glycosidic linkages, or between 1 to 10 mol % α-(1,2) glycosidic linkages.

In some variations, the oligosaccharide composition has a glycosidic bond type distribution of less than 50 mol % β-(1,2) glycosidic linkages, less than 40 mol % β-(1,2) glycosidic linkages, less than 35 mol % β-(1,2) glycosidic linkages, less than 30 mol % β-(1,2) glycosidic linkages, less than 25 mol % β-(1,2) glycosidic linkages, less than 10 mol % β-(1,2) glycosidic linkages, at least 1 mol % β-(1,2) glycosidic linkages, at least 5 mol % β-(1,2) glycosidic linkages, at least 10 mol % β-(1,2) glycosidic linkages, at least 15 mol % β-(1,2) glycosidic linkages, at least 20 mol % β-(1,2) glycosidic linkages, between 0 to 30 mol % β-(1,2) glycosidic linkages, between 1 to 30 mol % β-(1,2) glycosidic linkages, between 0 to 25 mol % β-(1,2) glycosidic linkages, between 1 to 25 mol % β-(1,2) glycosidic linkages, between 10 to 30 mol % β-(1,2) glycosidic linkages, between 15 to 25 mol % β-(1,2) glycosidic linkages, between 0 to 10 mol % β-(1,2) glycosidic linkages, between 1 to 10 mol % β-(1,2) glycosidic linkages, between 10 to 50 mol % β-(1,2) glycosidic linkages, between 10 to 40 mol % β-(1,2) glycosidic linkages, between 20 to 35 mol % β-(1,2) glycosidic linkages, between 20 to 35 mol % β-(1,2) glycosidic linkages, between 20 to 50 mol % β-(1,2) glycosidic linkages, between 30 to 40 mol % β-(1,2) glycosidic linkages, between 10 to 30 mol % β-(1,2) glycosidic linkages, or between 10 to 20 mol % β-(1,2) glycosidic linkages.

In some variations, the oligosaccharide composition has a glycosidic bond type distribution of less than 40 mol % α-(1,3) glycosidic linkages, less than 30 mol % α-(1,3) glycosidic linkages, less than 25 mol % α-(1,3) glycosidic linkages, less than 20 mol % α-(1,3) glycosidic linkages, less than 15 mol % α-(1,3) glycosidic linkages, at least 1 mol % α-(1,3) glycosidic linkages, at least 5 mol % α-(1,3) glycosidic linkages, at least 10 mol % α-(1,3) glycosidic linkages, at least 15 mol % α-(1,3) glycosidic linkages, at least 20 mol % α-(1,3) glycosidic linkages, at least 25 mol % α-(1,3) glycosidic linkages, between 0 to 30 mol % α-(1,3) glycosidic linkages, between 1 to 30 mol % α-(1,3) glycosidic linkages, between 5 to 30 mol % (1,3) glycosidic linkages, between 10 to 25 mol % α-(1,3) glycosidic linkages, between 1 to 20 mol % α-(1,3) glycosidic linkages, or between 5 to 15 mol % α-(1,3) glycosidic linkages.

In some variations, the oligosaccharide composition has a glycosidic bond type distribution of less than 25 mol % β-(1,3) glycosidic linkages, less than 20 mol % β-(1,3) glycosidic linkages, less than 15 mol % β-(1,3) glycosidic linkages, less than 10 mol % β-(1,3) glycosidic linkages, at least 1 mol % β-(1,3) glycosidic linkages, at least 2 mol % β-(1,3) glycosidic linkages, at least 5 mol % β-(1,3) glycosidic linkages, at least 10 mol % β-(1,3) glycosidic linkages, at least 15 mol % β-(1,3) glycosidic linkages, between 1 to 20 mol % β-(1,3) glycosidic linkages, between 5 to 15 mol % β-(1,3) glycosidic linkages, between 1 to 15 mol % β-(1,3) glycosidic linkages, or between 2 to 10 mol % β-(1,3) glycosidic linkages.

In some variations, the oligosaccharide composition has a glycosidic bond type distribution of less than 20 mol % α-(1,4) glycosidic linkages, less than 15 mol % α-(1,4) glycosidic linkages, less than 10 mol % α-(1,4) glycosidic linkages, less than 9 mol % α-(1,4) glycosidic linkages, between 1 to 20 mol % α-(1,4) glycosidic linkages, between 1 to 15 mol % (1,4) glycosidic linkages, between 2 to 15 mol % α-(1,4) glycosidic linkages, between 5 to 15 mol % α-(1,4) glycosidic linkages, between 1 to 15 mol % α-(1,4) glycosidic linkages, or between 1 to 10 mol % α-(1,4) glycosidic linkages.

In some variations, the oligosaccharide composition has a glycosidic bond type distribution of less than 55 mol %

β-(1,4) glycosidic linkages, less than 50 mol % β-(1,4) glycosidic linkages, less than 45 mol % β-(1,4) glycosidic linkages, less than 40 mol % β-(1,4) glycosidic linkages, less than 35 mol % β-(1,4) glycosidic linkages, less than 25 mol % β-(1,4) glycosidic linkages, less than 15 mol % β-(1,4) glycosidic linkages, less than 10 mol % β-(1,4) glycosidic linkages, at least 1 mol % β-(1,4) glycosidic linkages, at least 5 mol % β-(1,4) glycosidic linkages, at least 10 mol % β-(1,4) glycosidic linkages, at least 20 mol % β-(1,4) glycosidic linkages, at least 30 mol % β-(1,4) glycosidic linkages, between 0 to 55 mol % β-(1,4) glycosidic linkages, between 5 to 55 mol % β-(1,4) glycosidic linkages, between 10 to 50 mol % β-(1,4) glycosidic linkages, between 0 to 40 mol % β-(1,4) glycosidic linkages, between 1 to 40 mol % β-(1,4) glycosidic linkages, between 0 to 35 mol % β-(1,4) glycosidic linkages, between 1 to 35 mol % β-(1,4) glycosidic linkages, between 1 to 30 mol % β-(1,4) glycosidic linkages, between 5 to 25 mol % β-(1,4) glycosidic linkages, between 10 to 25 mol % β-(1,4) glycosidic linkages, between 15 to 25 mol % β-(1,4) glycosidic linkages, between 0 to 15 mol % β-(1,4) glycosidic linkages, between 1 to 15 mol % β-(1,4) glycosidic linkages, between 0 to 10 mol % β-(1,4) glycosidic linkages, or between 1 to 10 mol % β-(1,4) glycosidic linkages.

In some variations, the oligosaccharide composition has a glycosidic bond type distribution of less than 30 mol % α-(1,6) glycosidic linkages, less than 25 mol % α-(1,6) glycosidic linkages, less than 20 mol % α-(1,6) glycosidic linkages, less than 19 mol % α-(1,6) glycosidic linkages, less than 15 mol % α-(1,6) glycosidic linkages, less than 10 mol % α-(1,6) glycosidic linkages, between 0 to 30 mol % α-(1,6) glycosidic linkages, between 1 to 30 mol % α-(1,6) glycosidic linkages, between 5 to 25 mol % α-(1,6) glycosidic linkages, between 0 to 25 mol % α-(1,6) glycosidic linkages, between 1 to 25 mol % α-(1,6) glycosidic linkages, between 0 to 20 mol % α-(1,6) glycosidic linkages, between 0 to 15 mol % α-(1,6) glycosidic linkages, between 1 to 15 mol % α-(1,6) glycosidic linkages, between 0 to 10 mol % α-(1,6) glycosidic linkages, or between 1 to 10 mol % α-(1,6) glycosidic linkages. In some embodiments, the oligosaccharide composition comprises oligosaccharides with hexose sugar monomers.

In some variations, the oligosaccharide composition has a glycosidic bond type distribution of less than 55 mol % β-(1,6) glycosidic linkages, less than 50 mol % β-(1,6) glycosidic linkages, less than 35 mol % β-(1,6) glycosidic linkages, less than 30 mol % β-(1,6) glycosidic linkages, at least 1 mol % β-(1,6) glycosidic linkages, at least 5 mol % β-(1,6) glycosidic linkages, at least 10 mol % β-(1,6) glycosidic linkages, at least 15 mol % β-(1,6) glycosidic linkages, at least 20 mol % β-(1,6) glycosidic linkages, at least 25 mol % β-(1,6) glycosidic linkages, at least 20 mol % β-(1,6) glycosidic linkages, at least 25 mol % β-(1,6) glycosidic linkages, at least 30 mol % β-(1,6) glycosidic linkages, between 10 to 55 mol % β-(1,6) glycosidic linkages, between 5 to 55 mol % β-(1,6) glycosidic linkages, between 15 to 55 mol % β-(1,6) glycosidic linkages, between 20 to 55 mol % β-(1,6) glycosidic linkages, between 20 to 50 mol % β-(1,6) glycosidic linkages, between 25 to 55 mol % β-(1,6) glycosidic linkages, between 25 to 50 mol % β-(1,6) glycosidic linkages, between 5 to 40 mol % β-(1,6) glycosidic linkages, between 5 to 30 mol % β-(1,6) glycosidic linkages, between 10 to 35 mol % β-(1,6) glycosidic linkages, between 5 to 20 mol % β-(1,6) glycosidic linkages, between 5 to 15 mol % β-(1,6) glycosidic linkages, between 8 to 15 mol % β-(1,6) glycosidic linkages, or between 15 to 30 mol % β-(1,6) glycosidic linkages. In some embodiments, the oligosaccharide composition comprises oligosaccharides with hexose sugar monomers.

In some variations, the oligosaccharide composition has a glycosidic bond type distribution of at least 1 mol % α-(1,3) glycosidic linkages. In some variations, the oligosaccharide composition has a glycosidic bond type distribution of at least 10 mol % α-(1,3) glycosidic linkages.

In some variations, the oligosaccharide composition has a glycosidic bond type distribution of at least 1 mol % β-(1,3) glycosidic linkages. In some variations, the oligosaccharide composition has a glycosidic bond type distribution of at least 10 mol % β-(1,3) glycosidic linkages.

In some variations, the oligosaccharide composition has a glycosidic bond type distribution of at least 15 mol % β-(1,6) glycosidic linkages. In some variations, the oligosaccharide composition has a glycosidic bond type distribution of at least 10 mol % β-(1,6) glycosidic linkages.

In some variations, the oligosaccharide composition has a glycosidic bond type distribution of at least 15 mol % β-(1,2) glycosidic linkages. In some variations, the oligosaccharide composition has a glycosidic bond type distribution of at least 10 mol % β-(1,2) glycosidic linkages.

It should be understood that the glycosidic linkage distributions described herein for the various types of linkages (e.g., α-(1,2), α-(1,3), α-(1,4), α-(1,6), β-(1,2), β-(1,3), β-(1,4), or β-(1,6) glycosidic linkages) may be combined as if each and every combination were individually listed, as applicable.

In some variations, the distribution of glycosidic bond types described above for any of the oligosaccharide compositions herein is determined by two dimensional J-resolved nuclear magnetic resonance (2D-JRES NMR) spectroscopy.

In certain variations, the oligosaccharide composition comprises only hexose sugar monomers, and has any glycosidic bond type distribution as described herein. In some variations, the oligosaccharide composition comprises only pentose sugar monomers, and has any glycosidic bond type distribution as described herein, as applicable. In yet other variations, the oligosaccharide composition comprises both pentose and hexose sugar monomers, and has any glycosidic bond type distribution as described herein, as applicable.

It should be further understood that variations for the type of oligosaccharides present in the composition, as well as the degree of polymerization, glass transition temperature, and hygroscopicity of the oligosaccharide composition, may be combined as if each and every combination were listed separately. For example, in some variations, the oligosaccharide composition is made up of a plurality of oligosaccharides, wherein the composition has a glycosidic bond distribution of:
at least 1 mol % α-(1,3) glycosidic linkages;
at least 1 mol % β-(1,3) glycosidic linkages;
at least 15 mol % β-(1,6) glycosidic linkages;
less than 20 mol % α-(1,4) glycosidic linkages; and
less than 30 mol % α-(1,6) glycosidic linkages, and
wherein at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

For example, in some variations, the oligosaccharide composition has a glycosidic bond type distribution of less than 20 mol % α-(1,4) glycosidic linkages, and less than 30 mol % α-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In another variation, the oligosaccharide composition comprises a glycosidic bond type distribution of between 0 to 15 mol % α-(1,2) glycosidic linkages; between 0 to 30 mol % β-(1,2) glycosidic linkages; between 1 to 30 mol % α-(1,3) glycosidic linkages; between 1 to 20 mol % β-(1,3) glycosidic linkages; between 0 to 55 mol % β-(1,4) glycosidic linkages; and between 15 to 55 mol % β-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In yet another variation, the oligosaccharide composition has a glycosidic bond type distribution of between 0 to 15 mol % α-(1,2) glycosidic linkages; between 10 to 30 mol % β-(1,2) glycosidic linkages; between 5 to 30 mol % α-(1,3) glycosidic linkages; between 1 to 20 mol % β-(1,3) glycosidic linkages; between 0 to 15 mol % β-(1,4) glycosidic linkages; between 20 to 55 mol % β-(1,6) glycosidic linkages; less than 20 mol % α-(1,4) glycosidic linkages; and less than 15 mol % α-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In still other variations, the oligosaccharide composition has a glycosidic bond type distribution of between 0 to 10 mol % α-(1,2) glycosidic linkages, between 15 to 25 mol % β-(1,2) glycosidic linkages, between 10 to 25 mol % α-(1,3) glycosidic linkages, between 5 to 15 mol % β-(1,3) glycosidic linkages, between 5 to 15 mol % α-(1,4) glycosidic linkages, between 0 to 10 mol % β-(1,4) glycosidic linkages, between 0 to 10 mol % α-(1,6) glycosidic linkages, and between 25 to 50 mol % β-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In certain variations, the oligosaccharide composition has a glycosidic bond type distribution of between 0 to 15 mol % α-(1,2) glycosidic linkages; between 0 to 15 mol % β-(1,2) glycosidic linkages; between 1 to 20 mol % α-(1,3) glycosidic linkages; between 1 to 15 mol % β-(1,3) glycosidic linkages; between 5 to 55 mol % β-(1,4) glycosidic linkages; between 15 to 55 mol % β-(1,6) glycosidic linkages; less than 20 mol % α-(1,4) glycosidic linkages; and less than 30 mol % α-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In yet other variations, the oligosaccharide composition has a glycosidic bond type distribution of between 0 to 10 mol % α-(1,2) glycosidic linkages, between 0 to 10 mol % β-(1,2) glycosidic linkages, between 5 to 15 mol % α-(1,3) glycosidic linkages, between 2 to 10 mol % β-(1,3) glycosidic linkages, between 2 to 15 mol % α-(1,4) glycosidic linkages, between 10 to 50 mol % β-(1,4) glycosidic linkages, between 5 to 25 mol % α-(1,6) glycosidic linkages, and between 20 to 50 mol % β-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In other variations, the oligosaccharide composition has a glycosidic bond type distribution of between 0 to 15 mol % α-(1,2) glycosidic linkages, between 0 to 30 mol % β-(1,2) glycosidic linkages, between 5 to 30 mol % α-(1,3) glycosidic linkages, between 1 to 20 mol % β-(1,3) glycosidic linkages, between 1 to 20 mol % α-(1,4) glycosidic linkages, between 0 to 40 mol % β-(1,4) glycosidic linkages, between 0 to 25 mol % α-(1,6) glycosidic linkages, and between 10 to 35 mol % β-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In still other variations, the oligosaccharide composition has a glycosidic bond type distribution of between 0 to 10 mol % α-(1,2) glycosidic linkages, between 0 to 25 mol % β-(1,2) glycosidic linkages, between 10 to 25 mol % α-(1,3) glycosidic linkages, between 5 to 15 mol % β-(1,3) glycosidic linkages, between 5 to 15 mol % α-(1,4) glycosidic linkages, between 0 to 35 mol % β-(1,4) glycosidic linkages, between 0 to 20 mol % α-(1,6) glycosidic linkages, and between 15 to 30 mol % β-(1,6) glycosidic linkages. In some variations, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

In still other variations, the oligosaccharide composition has a glycosidic bond type distribution of at least 1 mol % α-(1,3) glycosidic linkages, and at least 1 mol % β-(1,3) glycosidic linkages, wherein at least 10 dry wt % of the oligosaccharide composition has a degree of polymerization of at least 3. In some variations, the oligosaccharide composition further has a glycosidic bond type distribution of at least 15 mol % β-(1,6) glycosidic linkages. In yet other variations, at least 50 dry wt %, or between 65 and 80 dry wt % of the oligosaccharide composition has a degree of polymerization of at least 3.

In some variations, the oligosaccharide composition has a glycosidic bond type distribution of at least 10 mol % α-(1,3) glycosidic linkages; and at least 10 mol % β-(1,3) glycosidic linkages. In some variations, the oligosaccharide composition has a glycosidic bond type distribution of less than 9 mol % α-(1,4) glycosidic linkages; and less than 19 mol % α-(1,6) glycosidic linkages. In some variations, the oligosaccharide composition further has a glycosidic bond type distribution of at least 15 mol % β-(1,2) glycosidic linkages.

In other variations, the oligosaccharide composition has a glycosidic bond type distribution of less than 9 mol % α-(1,4) glycosidic linkages, and less than 19 mol % α-(1,6) glycosidic linkages.

In still other variations, the oligosaccharide composition has a glycosidic bond type distribution of between 0 to 20 mol % α-(1,2) glycosidic linkages; between 10 to 45 mol % β-(1,2) glycosidic linkages; between 1 to 30 mol % α-(1,3) glycosidic linkages; between 1 to 20 mol % β-(1,3) glycosidic linkages; between 0 to 55 mol % β-(1,4) glycosidic linkages; and between 10 to 55 mol % β-(1,6) glycosidic linkages.

In some variations, the oligosaccharide composition has a glycosidic bond type distribution of between 10 to 20 mol % α-(1,2) glycosidic linkages, between 23 to 31 mol % β-(1,2) glycosidic linkages, between 7 to 9 mol % α-(1,3) glycosidic linkages, between 4 to 6 mol % β-(1,3) glycosidic linkages, between 0 to 2 mol % α-(1,4) glycosidic linkages, between 18 to 22 mol % β-(1,4) glycosidic linkages, between 9 to 13 mol % α-(1,6) glycosidic linkages, and between 14 to 16 mol % β-(1,6) glycosidic linkages In yet other variations, the oligosaccharide composition has a glycosidic bond type distribution of between 10 to 12 mol % α-(1,2) glycosidic linkages, between 31 to 39 mol % β-(1,2) glycosidic linkages, between 5 to 7 mol % α-(1,3) glycosidic linkages, between 2 to 4 mol % β-(1,3) glycosidic linkages, between 0 to 2 mol % α-(1,4) glycosidic linkages, between 19 to 23 mol % β-(1,4) glycosidic linkages, between 13 to 17 mol % α-(1,6) glycosidic linkages, and between 7 to 9 mol % β-(1,6) glycosidic linkages.

In some embodiments, which may be combined with any of the foregoing embodiments, at least 10 dry wt % of the oligosaccharide composition has a degree of polymerization of at least 3. In some variations, at least 50 dry wt %, or between 65 and 80 dry wt % of the oligosaccharide composition has a degree of polymerization of at least 3.

Animal Feed Composition and Animal Feed Pre-Mix

In some embodiments, the oligosaccharide composition, the animal feed pre-mix, or the animal feed composition is provided to an animal to increase the rate of weight gain for an animal, to decrease mortality, and/or to decrease the feed conversion ratio for an animal. In some embodiments, the oligosaccharide composition, the animal feed pre-mix, or the animal feed composition is provided to an animal population to decrease mortality and/or decrease variability of the final body weight across the population.

In certain embodiments, feeding an animal the oligosaccharide composition, the animal feed pre-mix, or the animal feed composition may have beneficial health effects, including, for example, reducing mortality, improving gut microflora, improving nutrient absorption, maintaining gastrointestinal health, and/or reducing the need for antibiotics.

a) Inclusion Rate

A person of skill in the art would recognize that the inclusion rate may be different for different types of animal, and may be different for different breeds of one type of animal (for example, different breeds of broiler chickens or swine). The inclusion rate may also be different depending on age of the animal (for example, chickens in a grower phase compared to a finisher phase; or swine in nursery phase compared to grower phase).

In some embodiments, the oligosaccharide composition may be provided to an animal at an inclusion rate of less than 0.01 mg/kg, 0.05 mg/kg, 0.1 mg/kg, 1 mg/kg, 10 mg/kg, 50 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 1500 mg/kg, 2000 mg/kg, 2500 mg/kg, 3000 mg/kg, 3500 mg/kg, 4000 mg/kg, 4500 mg/kg, or 5000 mg/kg. In some variations, the oligosaccharide composition may be provided to an animal at an inclusion rate of less than 5,000 ppm, less than 4,000 ppm, less than 3,000 ppm, less than 2,000 ppm, less than 2,500 ppm, less than 1,000 ppm, less than 750 ppm, less than 500 ppm, less than 250 ppm, between 10 ppm to 5,000, between 10 ppm and 4,000 ppm, between 10 ppm and 3,000 ppm, between 10 ppm and 2,500 ppm, between 10 ppm and 2,000 ppm, between 10 ppm and 1,000 ppm, between 10 ppm and 500 ppm, between 50 pp and 500 ppm, between 1,000 ppm to 5,000 ppm, between 2,000 ppm to 5,000 ppm, between 3,000 ppm to 5,000 ppm, or between 1,000 ppm to 3,000 ppm.

In some variations, inclusion rate refers to the amount of oligosaccharide composition included in the total animal feed composition, on a dry weight basis. For example, adding 1 g of dry oligosaccharide composition to 999 g of dry base feed results in an animal feed composition with an oligosaccharide composition inclusion rate of 1 g/kg, or 0.1%, or 1000 ppm.

In other variations, the inclusion rate refers to the amount of dry oligosaccharide composition included in the total animal feed composition, including moisture. For example, adding 1 g of dry oligosaccharide composition to 999 g of base feed including moisture results in an animal feed composition with an oligosaccharide composition inclusion rate of 1 g/kg, or 0.1%, or 1000 ppm.

In yet other variations, the inclusion rate refers to the amount of dry oligosaccharide composition included in the total animal diet. For example, feeding an animal 1 g of dry oligosaccharide directly, wherein the animal also otherwise consumes 999 g of feed in its diet, results in an animal diet with an oligosaccharide composition inclusion rate of 1 g/kg, or 0.1%, or 1000 ppm. It should be understood that while inclusion rate may refer to the amount of dry oligosaccharide included in the total animal diet, the oligosaccharide composition may be provided to the animal in any suitable form. For example, in some variations, the oligosaccharide composition may be provided to the animal as a dry powder, dry solid, mash, or syrup. In other variations, the oligosaccharide composition may be provided to the animal via drinking water. For example, dry oligosaccharide may be dissolved in drinking water to form a solution with a particular concentration, and the solution provided to the animal.

In certain variations, the inclusion rate refers the amount of dry oligosaccharide composition included in a solution provided to the animal (for example, as drinking water). In some variations, the concentration of oligosaccharide composition in an aqueous solution (such as drinking water) is between 0.01 to 0.5 grams dry oligosaccharide composition per gram aqueous solution, between 0.1 to 0.5 grams dry oligosaccharide composition per gram aqueous solution, or between 0.2 to 0.4 grams dry oligosaccharide composition per gram aqueous solution.

In some variations, the animal feed pre-mix is combined with a base feed to produce an animal feed composition. For example, in one embodiment, 2 g of an animal feed pre-mix is combined with 998 g of base feed, wherein the animal feed pre-mix comprises 50 wt % kg dry oligosaccharide composition per kg total premix, including moisture, resulting in an animal feed composition with an oligosaccharide composition inclusion rate of 1 g/kg, or 0.1%, or 1000 ppm.

It should be understood that the inclusion rate of oligosaccharide composition may be selected based on the type of animal being fed, the growth stage of the animal, or the animal product produced, or any combinations thereof. For example, the inclusion rate of oligosaccharide composition for a ruminant animal may be different than that selected for a monogastric animal. In a second example, the inclusion rate of oligosaccharide composition selected for an animal in the grower phase may be different than that selected for an animal in the finisher phase. In yet a third example, the inclusion rate of oligosaccharide composition selected for an animal producing meat may be different than that for an animal producing milk. In another example, the inclusion rate of oligosaccharide composition selected for an animal, such as swine, in the nursery phase may be different than that selected for swine in the grower phase.

In some embodiments, the swine feed composition further comprises copper and/or zinc. In certain variations, the swine feed composition comprises both copper and zinc. In certain variations, the swine feed composition comprises growth promoting levels of copper and/or zinc. For example, in one variation, the swine feed composition comprises (i) between 10 ppm and 500 ppm copper; and/or (ii) between 10 ppm and 5000 ppm zinc.

In some embodiments, the animal feed composition further comprises an ionophore or other coccidiostat. In other embodiments, the animal feed composition does not comprise an ionophore. In certain variations, the animal feed composition comprises less than 1,000 ppm, less than 500 ppm, less than 100 ppm, or less than 50 ppm of an ionophore or other coccidiostat. In some embodiments, the ionophore is monensin, salinomycin, narasin, or lasolocid, or any combinations thereof.

In some embodiments, the animal feed composition does not include an antiobiotic. In certain variations, the animal feed composition comprises less than 1,000 ppm, less than 500 ppm, less than 100 ppm, less than 50 ppm, less than 40 ppm, less than 30 ppm, less than 20 ppm, less than 25 ppm, less than 24 ppm, less than 23 ppm, less than 22 ppm, less than 21 ppm, less than 20 ppm, less than 19 ppm, less than 18 ppm, less than 17 ppm, less than 16 ppm, less than 15 ppm, less than 14 ppm, less than 13 ppm, less than 12 ppm, less than 11 ppm, less than 10 ppm, less than 5 ppm, or less than 1 ppm of antibiotic. In some variations, the animal feed composition comprises has than 1,000 ppm; or between 10 ppm and 200 ppm, or between 50 ppm and 200 ppm, or between 500 ppm and 100 ppm of antibiotic.

In some embodiments, the antibiotic is bacitracin, bacitracin methylene disalicylate, bacitracin-zinc, virginiamycin, bambermycin, avilamycin, or efrotomycin, or any combinations thereof. In one variation, no antibiotic is fed with the oligosaccharide composition.

b) Base Feed

It should be understood by one skilled in the art that the base feed selected for an animal (such as poultry or swine), may be a nutritionally sufficient diet to sustain growth. Such diets may be well-known in the industry, and the nutritional content of such diets (including, for example, the content of apparent metabolizable energy, protein, fats, vitamins, and minerals) may fall within industry-recognized ranges or values.

One of skill in the art would recognize that the type of base feed combined with the oligosaccharide composition may also vary depending on the animal. For example, the base feed for monogastrics, such as poultry or swine, may include wheat, corn and/or soybean; and the base feed for a ruminant is typically hay or live grass.

One of skill in the art would also recognize that the type of base feed combined with the oligosaccharide composition may also vary depending on the growth stage of the animal, or the target animal product, or a combination thereof. For example, the base feed selected for an animal in the starter phase may be different from that in the grower phase, and the base feed selected for an animal in the grower phase may be different than that selected for an animal in the finisher phase. In another example, the base feed selected for an animal with a target animal product of meat may be different than that for an animal with a target animal product of milk.

Suitable base feed may include, for example, additional ingredients and/or nutrients in any suitable form (including, for example, solid form or liquid form) comprising protein, carbohydrates, and fat, used in the body of an animal to sustain growth, repair processes, vital processes, and/or furnish energy. In some variations, base feed may include biomass, such as grass, grain, or legumes. In other variations, base feed may include hay, stover, straw, silage, wheat, barley, maize, sorghum, rye, oats, triticale, rice, soybeans, peas, seaweed, yeast, molasses, or any combinations thereof. In yet other variations, base feed may include animal products, for example lactose, milk, milk solids, chicken meal, fish meal, bone meal, or blood, or any combinations thereof. In yet other variations, base feed may include oil, for example, plant oil or animal oil. In another variation, base feed may include hay, straw, silage, oils, grains, legumes, bone meal, blood meal, and meat, or any combinations thereof. In still other variations, base feed may include, for example, fodder, corn-soy based diets, or wheat-soy based diets.

Any other suitable compounds may be included in the animal feed composition, including, for example, essential amino acids, salts, minerals, protein, carbohydrates, and/or vitamins Some examples of animal feed compositions are provided in the Examples below.

In some variations, the base feed is a poultry feed. In some embodiments, the base feed is commercial poultry feed. In certain variations, the base feed is a corn-soy poultry feed, while in other variations the base feed is a wheat-soy poultry feed.

In certain variations, the poultry feed comprises an apparent metabolizable energy of at least 1000 cal/lb, 1200 cal/lb, at least 1300 cal/lb, at least 1400 cal/lb, between 1000 to 1600 cal/lb, or between 1300 to 1500 cal/lb.

In some embodiments, apparent metabolizable energy is the gross energy of the feed consumed by the animal minus the gross energy contained in the animal excreta. In other embodiments, apparent metabolizable energy is the is the gross energy of the feed consumed by the animal minus the gross energy contained in the animal excreta and gaseous products of digestion.

In certain variations, the poultry feed comprises a crude protein content of at least 5 wt %, at least 10 wt %, at least 15 wt %, at least 20 wt %, at least 25 wt %, between 5 to 30 wt %, between 10 to 25 wt %, or between 15 to 25 wt %.

In some variations, the poultry feed comprises a total lysine content of at least 0.8 wt %, at least 0.9 wt %, at least 1.0 wt %, at least 1.2 wt %, at least 1.3 wt %, between 0.8 wt % to 1.5 wt %, or between 0.9 to 1.4 wt %.

In certain variations, the poultry feed comprises a total methionine content of at least 0.4 wt %, at least 0.5 wt %, at least 0.6 wt %, at least 0.7 wt %, between 0.4 to 0.9 wt %, or between 0.5 to 0.8 wt %.

In certain variations, the poultry feed comprises a total sulfur amino acid content of at least 0.6 wt %, at least 0.7 wt %, at least 0.8 wt %, at least 0.9 wt %, at least 1.0 wt %, between 0.6 to 1.2 wt %, or between 0.8 to 1.1 wt %.

In certain variations, the poultry feed comprises a total threonine content of at least 0.5 wt %, at least 0.6 wt %, at least 0.7 wt %, at least 0.8 wt %, at least 0.9 wt %, at least 1.0 wt %, at least 1.1 wt %, between 0.6 to 1.1 wt %, or between 0.7 to 1.0 wt %.

In certain variations, the poultry feed comprises a total calcium content of at least 0.6 wt %, at least 0.7 wt %, at least 0.8 wt %, at least 0.9 wt %, at least 1.0 wt %, at least 1.1 wt %, between 0.6 to 1.1 wt %, between 0.7 to 1.0 wt %, or between 0.8 to 0.95 wt %.

In certain variations, the poultry feed comprises a total available phosphorous content of at least 0.2 wt %, at least 0.3 wt %, at least 0.4 wt %, at least 0.5 wt %, between 0.2 to 0.6 wt %, between 0.3 to 0.5 wt %, or between 0.4 to 0.5 wt %. It should be understood that total available phosphorous includes bio-available phosphorous, including, for example, phosphorous liberated from phytic acid by phytase enzymes. Total available phosphorous may be determined, for example, from digestibility analysis.

In certain variations, the poultry feed comprises a total sodium content of at least 0.05 wt %, at least 0.1 wt %, at least 0.2 wt %, at least 0.25 wt %, at least 0.3 wt %, at least 0.35 wt %, between 0.05 to 0.35 wt %, between 0.1 to 0.3 wt %, or between 0.2 to 0.25 wt %.

The nutritional content of the animal feed, including poultry feed and swine feed, may be determined by any suitable methods known in the art, including, for example, elemental analysis or digestibility analysis.

In certain variations, the base feed comprises copper and/or zinc. In certain variations, the base feed comprises both copper and zinc. In certain variations, the base feed comprises growth promoting levels of copper and/or zinc. For example, in one variation, the base feed comprises (i) between 10 ppm and 500 ppm copper; and/or (ii) between 10 ppm and 5000 ppm zinc.

In certain variations, the base feed includes an ionophore or other coccidiostat. In other variations, the base feed does not include an ionophore or other coccidiostat. In some variations, the base feed comprises less than 1,000 ppm, less than 500 ppm, less than 100 ppm, or less than 50 ppm of an ionophore or other coccidiostat. In some embodiments, the ionophore is monensin, salinomycin, narasin, or lasolocid, or any combinations thereof.

In some embodiments, the base feed does not include an antibiotic. In certain variations, the base feed comprises less than 1,000 ppm, less than 500 ppm, less than 100 ppm, less than 50 ppm, less than 22 ppm, or less than 11 ppm of antibiotic. In some embodiments, the antibiotic is bacitracin, bacitracin methylene disalicylate, bacitracin-zinc, virginiamycin, bambermycin, avilamycin, or efrotomycin, or any combinations thereof.

Starter Feed, Nursery Feed

In some variations, the base feed is a starter feed, wherein the starter feed is provided during the first week of growth, first two weeks of growth, first three weeks of growth, or first four weeks of growth. In certain variations, the nutritional content of the starter feed is optimized for the nutritional needs of the animal during the starter phase of growth. In some variations, the starter feed may comprise medications and/or vaccines. The term starter feed may apply to animals, such as poultry.

In other variations, the base feed is a nursery feed, wherein the nursery feed is provided during the nursery phase. One of skill in the art would recognize that the duration of the nursery phase is determined based on a certain cut-off weight of the swine. In some variations, the nursury phase is the period of time until the animal reaches about 40 to 60 pounds. In certain variations, the nutritional content of the nursery feed is optimized for the nutritional needs of the animal during the nursery phase of growth. In some variations, the nursery feed may comprise medications and/or vaccines. The term nursery feed may apply to animals, such as swine.

Grower Feed

In other variations, the base feed is a grower feed, wherein the grower feed is provided during the second week of growth through the final productive lifetime of the animal. In some variations, the grower feed is provided from the second week of growth through the final productive lifetime of the animal, while in other variations the grower feed is provided for a a portion of time between the second week of growth through the final productive lifetime of the animal, or for multiple separate periods of time between the second week of growth through the final productive lifetime of the animal. In some variations, the grower feed is provided to the animal for a portion of time between the second week of growth until the final week of the lifetime of the animal. For example, such animal may be poultry.

In other variations, the base feed is a grower feed, wherein the grower feed is provided during the grower phase. One of skill in the art would recognize that the duration of the grower phase is determined based on a certain cut-off weight of the animal. In some variations, the grower phase is the period of time when the animal leaves the nursery (e.g., at about 40 to 60 pounds as described above) until the swine reach about 280 pounds. For example, such animal may be swine.

In certain variations, the nutritional content of the grower feed is optimized to minimize cost while supporting the nutritional needs of the animal. In some variations, the grower feed may comprise medications.

Finisher Feed

In yet other variations, the base feed is a finisher feed, wherein the finisher feed is provided during the final period of the productive lifetime of the animal. In some variations, the final period of the productive lifetime of the animal is the final week of the lifetime of the animal. In some variations, the finisher feed is provided during the final week, the final two weeks, the final 14 days, the final 10 days, the final 9 days, the final 8 days, the final 7 days, the final 6 days, the final 5 days, or the final 4 days of the productive lifetime of the animal, or any portion thereof. In certain variations, the finisher feed contains a reduced content of medication, chemicals, therapeutics, or other ingredients as compared to an earlier diet (for example, the starter feed or finisher feed) to allow the animal to clear those materials from their bodies prior to consumption by humans, consumption by other animals, or processing. For example, such animals may be poultry.

In yet other variations, the base feed is a finisher feed, wherein the finisher feed is provided during the finisher phase. One of skill in the art would recognize that, in some variations, the finisher phase refers to the final period of the productive lifetime of the animal during which the diet of the animal is modified to purge any antibiotics that may not be suitable for human consumption. In some variations, during the finisher phase, the animal (e.g., swine) may have a weight of about 270 pounds to 290 pounds. In some variations, the finisher phase may be two or three days up to a week or two weeks. In certain variations, the finisher feed contains a reduced content of medication, chemicals, therapeutics, or other ingredients as compared to an earlier diet (for example, the nursery feed or grower feed) to allow the swine to clear those materials from their bodies prior to consumption by humans, consumption by other animals, or processing. For example, such animals may be swine.

It should be understood that the length of time the animal is provided starter feed, grower feed, or finisher feed may depend on the intended use of the animal. For example, in some embodiments the animal is poultry, and the length of time the poultry is provided starter feed, grower feed, and finisher feed may be different if the intended use of the poultry is as a broiler chicken, compared to processing for tray-pack chicken meat.

It should be understood that any of the characteristics of the base feed described herein, including the type of base feed, compounds included in the base feed, or nutritional content of base feed described herein (such as apparent metabolizable energy, crude protein content, total lysine content, total methionine content, total sulfur amino acid content, total threonine content, total calcium content, total available phosphorous, or total sodium content), may be combined as if each and every combination were individually listed.

For example, in some embodiments, the base feed comprises:
(i) between 1200 to 1600 cal/lb apparent metabolizable energy;
(ii) between 16 to 24 wt % crude protein;
(iii) between 1.0 and 1.4 wt % lysine;
(iv) between 0.5 and 0.75 wt % methionine;
(v) between 0.75 and 1.1 wt % total sulfur amino acids;
(vi) between 0.7 and 1.0 wt % calcium;
(vii) between 0.35 and 0.5 wt % total available phosphorous; and
(viii) between 0.15 and 0.3 wt % sodium, or any combinations of (i)-(viii) above. In some variations, the base fee comprises at least two, at least three, at least four, at least five, at least six, at least seven or all eight of (i)-(viii) described above.

In certain variations, a base feed is combined with an oligosaccharide composition to produce an animal feed composition, wherein the oligosaccharide composition has a distribution of glycosidic bond linkages, as described above. Thus, the animal feed composition may comprise an oligosaccharide composition, wherein the oligosaccharide composition has any distribution of glycosidic bond linkages described herein. It should be understood that the base feed may also have a distribution of glycosidic bond linkages, and that in some embodiments the distribution may differ from the distribution of glycosidic bond linkages of the oligosaccharide composition.

It should be understood that the animal feed composition may comprise a base feed as described herein and an oligosaccharide composition described herein as if each and every combination were individually listed. For example, in some variations, provided herein is an animal feed composition comprising (i) a base feed, and (ii) an oligosaccharide composition, wherein the oligosaccharide composition has a glycosidic bond type distribution of less than 20 mol % α-(1,4) glycosidic linkages, and less than 30 mol % α-(1,6) glycosidic linkages, wherein at least 10 dry wt % of the oligosaccharide composition has a degree of polymerization of at least 3.

In some variations, the oligosaccharide composition has a glycosidic bond type distribution of at least 15 mol % β-(1,6) glycosidic linkages.

In other variations, provided herein is an animal feed composition comprising (i) a base feed, and (ii) an oligosaccharide composition, wherein the oligosaccharide composition has a glycosidic bond type distribution of: between 0 to 15 mol % α-(1,2) glycosidic linkages; between 0 to 30 mol % β-(1,2) glycosidic linkages; between 1 to 30 mol % α-(1,3) glycosidic linkages; between 1 to 20 mol % β-(1,3) glycosidic linkages; between 0 to 55 mol % β-(1,4) glycosidic linkages; and between 15 to 55 mol % β-(1,6) glycosidic linkages.

In certain variations, the oligosaccharide composition is present in the animal feed composition at below 5,000 ppm, below 3,000 ppm, between 10 to 1,000 ppm, or between 10 to 500 ppm weight dry oligosaccharide composition per weight of the animal feed composition. In still other variations, at least 50 dry wt % of the oligosaccharide composition comprises one or more gluco-oligosaccharides, or at least 50 dry wt % of the oligosaccharide composition comprises one or more gluco-galacto-oligosaccharides. In one variation of the foregoing, the animal feed composition is a poultry feed composition.

In some variations, the oligosaccharide composition is present in the animal feed composition at below 5,000 ppm, below 3,000 ppm, between 10 to 1,000 ppm, between 10 ppm and 750 ppm, between 10 ppm and 600 ppm, between 10 to 500 ppm, between 100 ppm and 750 ppm, between 100 ppm and 600 ppm, or between 200 ppm and 600 ppm weight dry oligosaccharide composition per weight of the animal feed composition. In one variation of the foregoing, the animal feed composition is a swine feed composition.

c) Animal Feed Pre-Mix

Any suitable carrier material may be combined with the oligosaccharide compositon to produce the animal feed pre-mix. Suitable carrier materials may include, for example, ground rice hulls, ground oat hulls, feed grade silica gel, feed grade fumed silica, corn gluten feed, corn gluten meal, dried distiller's grains, clay, vermiculite, diatamacious earth, or milled corn, or any combinations thereof. In one variation, the carrier material is milled corn. In another variation, the carrier material is ground rice hulls. In yet another variation, the carrier material is ground oat hulls.

In certain variations, a syrup comprising the oligosaccharide composition is combined with a carrier material to produce the animal feed pre-mix. In some variations, the syrup comprises the oligosaccharide composition and water, wherein the syurup has a final solids content of at least 40%, at least 45%, at least 50%, at least 55%, at least 60%, at least 65%, at least 70%, at least 75%, between 40% and 75%, between 50% and 75%, or between 60 and 70% kg dry solids per kg of syrup. In one embodiment, the syrup comprises the oligosaccharide composition and water, wherein the syrup has a final solids content of about 65% kg dry solids per kg of syrup.

In some embodiments, the oligosaccharide composition is combined with the carrier material to produce an animal feed pre-mix, wherein the animal feed pre-mix is a dry powder. In some variations, the animal feed pre-mix is a dry, flowable powder. In certain variations, the animal feed pre-mix has a final moisture content of less than 20 wt %, less than 15 wt %, less than 12 wt %, less than 10 wt %, or less than 5 wt %. In one variation, the animal feed pre-mix has a final moisture content of less than 12 wt %, or less than 10 wt %.

In some variations, the oligosaccharide composition is combined with the carrier material to produce a mixture, and the mixture is dried to produce an animal feed pre-mix with the desired moisture content. Any suitable method of drying may be used. For example, in certain embodiments the oligosaccharide composition is combined with the carrier material to produce a mixture, and the mixture is dried using a rotating drum drier to produce an animal feed pre-mix with the desired moisture content.

The animal feed pre-mix may comprise the oligosaccharide composition at any suitable concentration. In some embodiments, the animal feed pre-mix comprises at least 1 wt %, at least 5 wt %, at least 10 wt %, at least 15 wt %, at least 20 wt %, at least 25 wt %, at least 30 wt %, at least 35 wt %, at least 40 wt %, at least 45 wt %, between 1 to 80 wt %, between 5 to 70 wt %, between 10 to 60 wt %, between 15 to 50 wt %, or between 20 to 50 wt % kg dry oligosaccharide composition per kg total premix, including moisture.

In some embodiments, the carrier material comprises copper and/or zinc. In certain variations, the carrier material comprises both copper and zinc. In certain variations, the carrier material comprises growth promoting levels of copper and/or zinc. For example, in one variation, the carrier material comprises (i) between 10 ppm and 500 ppm copper; and/or (ii) between 10 ppm and 5000 ppm zinc.

In certain variations, the carrier material comprises an ionophore or other coccidiostat. In other variations, the carrier material does not comprise an ionophore. In some variations, the carrier material comprises less than 1,000 ppm, less than 500 ppm, less than 100 ppm, or less than 50 ppm of an ionophore or other coccidiostat. In some embodiments, the ionophore is monensin, salinomycin, narasin, or lasolocid, or any combinations thereof.

In some embodiments, the carrier material does not comprise an antiobiotic. In certain variations, the carrier material comprises less than 1,000 ppm, less than 500 ppm, less than 100 ppm, less than 50 ppm, less than 22 ppm, or less than 11 ppm of antibiotic. In some embodiments, the antibiotic is bacitracin, bacitracin methylene disalicylate, bacitracin-zinc, virginiamycin, bambermycin, avilamycin, or efrotomycin, or any combinations thereof.

In certain variations, a carrier material is combined with an oligosaccharide composition to produce an animal feed pre-mix, wherein the oligosaccharide composition has a distribution of glycosidic bond linkages, as described above. Thus, the animal feed pre-mix may comprise an oligosaccharide composition, wherein the oligosaccharide composition has any distribution of glycosidic bond linkages described herein. It should be understood that the carrier material may also have a distribution of glycosidic bond linkages, and that in some embodiments the distribution may differ from the distribution of glycosidic bond linkages of the oligosaccharide composition.

It should be understood that the animal feed pre-mix may comprise a carrier material as described herein and an oligosaccharide composition as described herein, as if each and every combination were individually listed. For example, in some variations, provided herein is an animal feed pre-mix comprising (i) a carrier material, and (ii) an oligosaccharide composition, wherein the oligosaccharide composition has a glycosidic bond type distribution of at least 1 mol % α-(1,3) glycosidic linkages, and at least 1 mol % β-(1,3) glycosidic linkages, wherein at least 10 dry wt % of the oligosaccharide composition has a degree of polymerization of at least 3. In some variations, the oligosaccharide composition further has a glycosidic bond distribution of at least 15 mol % β-(1,6) glycosidic linkages.

In other variations, provided herein is an animal feed pre-mix comprising (i) a carrier material, and (ii) an oligosaccharide composition, wherein the oligosaccharide composition has a glycyosidic bond type distribution of less than 20 mol % α-(1,4) glycosidic linkages, and less than 30 mol % α-(1,6) glycosidic linkages, wherein at least 10 dry wt % of the oligosaccharide composition has a degree of polymerization of at least 3.

In other variations, provided herein is an animal feed pre-mix comprising (i) a carrier material, and (ii) an oligosaccharide composition, wherein the oligosaccharide composition has a glycyosidic bond type distribution of between 0 to 15 mol % α-(1,2) glycosidic linkages; between 0 to 30 mol % β-(1,2) glycosidic linkages; between 1 to 30 mol % α-(1,3) glycosidic linkages; between 1 to 20 mol % β-(1,3) glycosidic linkages; and between 0 to 55 mol % β-(1,4) glycosidic linkages. In some variations, the oligosaccharide composition further has a bond distribution of between 15 to 55 mol % β-(1,6) glycosidic linkages.

In another embodiment that may be combined with any of the foregoing embodiments, the oligosaccharide composition has a glycosidic bond type distribution of less than 20 mol % α-(1,4) glycosidic linkages, and less than 30 mol % α-(1,6) glycosidic linkages. In still another embodiment, the animal feed pre-mix comprises at least 10 wt %, between 10 to 60 wt %, or between 20 to 50 wt % dry oligosaccharide composition per weight animal feed pre-mix. In certain embodiments, at least 50 dry wt %, or between 65 and 80 dry wt % of the oligosaccharide composition has a degree of polymerization of at least 3. In some embodiments, the moisture content of the animal feed pre-mix is less than 20 wt %. In still other variations, at least 50 dry wt % of the oligosaccharide composition comprises one or more gluco-oligosaccharides, or at least 50 dry wt % of the oligosaccharide composition comprises one or more gluco-galacto-oligosaccharides.

Methods of Producing Animal Feed Compositions

The oligosaccharide compositions produced according to the methods described herein may be fed directly to animals, or may be combined with a base feed to produce animal feed compositions. Thus, in some aspects, provided is a method of producing an animal feed composition, by: combining the oligosaccharide composition produced according to any of the methods described herein with a base feed to produce an animal feed composition. Suitable base feed may include, for example, fodder, corn-soy based diets, or wheat-soy based diets. In some variations, the oligosaccharide composition is combined with a carrier material to produce an animal feed pre-mix. The animal feed pre-mix may then be combined with a base feed to produce an animal feed composition. Thus, in some aspects, provided is a method of producing an animal feed pre-mix by: combining the oligosaccharide composition produced according to any of the methods described herein with a carrier material to produce an animal feed pre-mix. In some variations, the method further comprises: combining the animal feed pre-mix with a base feed to produce an animal feed composition.

In some embodiments, the oligosaccharide composition is combined with a carrier material to produce an animal feed pre-mix. This animal feed pre-mix may be fed directly to animals, or may be combined with a base feed to produce an animal feed composition. In some variations, the pre-mix is produced in one location, shipped to a second location, and combined with a base feed to produce an animal feed composition.

Use of Oligosaccharide Composition to Enhance Growth in Animals

In some aspects, provided is a method of enhancing growth of an animal, by:
  providing feed to the animal, wherein the feed is made up of a base feed, and an oligosaccharide composition; and
  enhancing growth in the animal.

In some variations, the animal is poultry. In other variations, the animal is swine. Any of the oligosaccharide compositions described herein may be used in the foregoing method. For example, in one embodiment, the oligosaccharide composition has a glycosidic bond type distribution of: at least 1 mol % α-(1,3) glycosidic linkages; and at least 1 mol % β-(1,3) glycosidic linkages. In another embodiment that may be combined with the foregoing embodiment, the oligosaccharide composition has a bond distribution of at least 15 mol % β-(1,6) glycosidic linkages. In still other embodiments, at least 10 dry wt % of the oligosaccharide composition has a degree of polymerization of at least 3.

In another embodiment, the oligosaccharide composition is present in teh feed at below 5,000 ppm, below 3,000 ppm, between 10 to 1,000 ppm, or between 10 to 500 ppm weight dry oligosaccharide composition per weight of the feed.

The oligosaccharide composition may be fed directly to the animal, be processed into an animal feed pre-mix, or incorporated into an animal feed composition fed to the animal. In some embodiments, an animal fed the oligosaccharide composition, animal feed pre-mix, or animal feed composition as described herein may experience enhanced growth as compared to an animal that is not fed the oligosaccharide composition, animal feed pre-mix, or animal feed composition over the same period of time. In some embodiments, an animal population fed the oligosaccharide composition, animal feed pre-mix, or animal feed composition as described herein may experience enhanced growth as compared to an animal population that is not fed the oligosaccharide composition, animal feed pre-mix, or animal feed composition over the same period of time Enhanced growth may include, for example, an increase in weight gain, a decrease in the food conversion ratio (FCR), an increase in digestibility of provided feed, an increase in released nutrients from provided feed, or a reduced mortality rate, or any combinations thereof.

In some embodiments, an animal population provided the oligosaccharide composition, animal feed pre-mix, or animal feed composition as described herein may experience enhanced growth as compared to an animal population that is not provided the oligosaccharide composition, animal feed pre-mix, or animal feed composition Enhanced growth of the animal population may include, for example, an increase in weight gain, an increase in average daily feed intake, a decrease in the food conversion ratio (FCR), an increase in digestibility of provided feed, an increase in released nutrients from provided feed, a reduced mortality rate, or an increase in animal uniformity, or any combinations thereof.

a) Weight Gain

In some embodiments, a subject animal that is fed the oligosaccharide composition, animal feed pre-mix, or the animal feed composition may experience an increase in weight gain, compared to a control animal that is not fed the oligosaccharide composition, animal feed pre-mix, or the animal feed composition. In certain embodiments, both the subject animal and the control animal comsume the same quantity of feed on a weight basis, but the subject animal provided the oligosaccharide composition, animal feed pre-mix, or animal feed composition experiences an increase in weight gain compared to the control animal that is fed a diet that does not include the oligosaccharide composition.

The weight gain of an animal may be determined by any suitable methods known in the art. For example, to determine weight gain of an animal that is subjected to a feeding regimen of the oligosaccharide composition, animal feed pre-mix, or animal feed composition, one of skill in the art can measure the mass of an animal prior to the feeding regimen, measure the mass of the animal after the animal is fed the oligosaccharide composition, animal feed pre-mix, or animal feed composition, and determine the difference between those two measurements.

In some variations, the weight gain may be an average daily weight gain (also referred to as average daily gain (ADG)), an average weekly weight gain (AWG), or a final body weight gain (BWG).

Average Daily Weight Gain (or Average Daily Gain)

In some variations, providing an animal with an oligosaccharide composition, animal feed pre-mix, or animal feed composition results in an increased average daily weight gain than an animal provided feed without the oligosaccharide composition. In some variations, providing an animal population with an oligosaccharide composition, animal feed pre-mix, or animal feed composition results in an increased average daily weight gain than an animal population provided feed without the oligosaccharide composition.

In one embodiment, the average daily weight gain for an animal is the weight gained each day by an individual animal, averaged over a given period of time. In some variations, the average daily weight gain for an animal population is the average daily weight gain for each individual animal, averaged over the population; wherein the average daily weight gain is the weight gained each day by the individual animal, averaged over a given period of time. In yet other variations, the average daily weight gain for an animal population is the total weight gained by the population each day, divided by the number of individual animals in the population, averaged over a given period of time. It should be understood that the daily weight gain or average daily weight gain may be further averaged, for example to provide an average daily weight gain across animal populations.

In certain embodiments, the animal is poultry, and the poultry provided an oligosaccharide composition, animal feed pre-mix, or animal feed composition has an average daily weight gain of at least 20 grams per day, at least 30 grams per day, at least 40 grams per day, at least 50 grams per day, at least 60 grams per day, at least 70 grams per day, at least 80 grams per day, at least 90 grams per day, between 20 to 100 grams per day, between 20 to 80 grams per day, between 30 to 50 grams per day, between 40 to 60 grams per day, between 50 to 70 grams per day, or between 70 to 90 grams per day. In one embodiment, the animal is poultry, and the poultry provided an oligosaccharide composition, animal feed pre-mix, or animal feed composition has an average daily weight gain of at least 50 grams per day. In certain embodiments, the poultry provided an oligosaccharide composition, animal feed pre-mix, or animal feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of poultry provided a diet that does not include the oligosaccharide composition.

In certain embodiments, the animal is poultry, and the poultry is between 0 to 14 days of age, and the average daily weight gain is at least 30 grams, at least 40 grams, or at least 50 grams per day.

In other embodiments, the animal is poultry, the poultry is between 14 to 28 days of age, and the average daily weight gain is at least 70 grams, at least 80 grams, or at least 90 grams per day.

In still other embodiments, the animal is poultry, the poultry is between 29 to 35 days of age, and the average daily weight gain is at least 50 grams, at least 60 grams, or at least 70 grams per day.

In some variations that may be combined with the foregoing, the animal is poultry, and the animal feed composition is poultry feed, wherein the oligosaccharide composition, poultry feed pre-mix, or poultry feed composition increases average daily gain in poultry by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the oligosaccharide composition.

In certain variations, the poultry suffers from a disease or a disorder, or is raised in a challenged environment, wherein the oligosaccharide composition, poultry feed pre-mix, or poultry feed composition increases average daily gain in poultry by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the oligosaccharide composition.

In some variations that may be combined with the foregoing, the animal is swine, and the animal feed composition is swine feed, wherein the oligosaccharide composition, swine feed pre-mix, or swine feed composition increases average daily gain in swine by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

In certain variations, the swine suffers from a disease or a disorder, or is raised in a challenged environment, wherein the oligosaccharide composition, swine feed pre-mix, or swine feed composition increases average daily gain in swine by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

In certain embodiments, the animal is swine, and the swine provided an oligosaccharide composition, swine feed pre-mix, or swine feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of swine provided a diet that does not include the oligosaccharide composition.

Average Weekly Weight Gain

In some variations, providing an animal with an oligosaccharide composition, animal feed pre-mix, or animal feed composition results in an increased average weekly weight gain than an animal provided feed without the oligosaccharide composition. In some variations, providing an animal population with an oligosaccharide composition, animal feed pre-mix, or animal feed composition results in an increased average weekly weight gain than an animal population provided feed without the oligosaccharide composition.

In one embodiment, the average weekly weight gain for an animal is the weight gained each week by an individual animal, averaged over a given period of time. In some variations, the average weekly weight gain for an animal population is the average weekly weight gain for each individual animal, averaged over the population; wherein the average weekly weight gain is the weight gained each week by the individual animal, averaged over a given period of time. In yet other variations, the average weekly weight gain for an animal population is the total weight gained by the population each week, divided by the number of individual animals in the population, averaged over a given period of time. It should be understood that the average weekly weight gain may be further averaged, for example to provide an average weekly weight gain across animal populations.

In certain embodiments, the animal is poultry, and poultry provided an oligosaccharide composition, animal feed pre-mix, or animal feed composition has an average weekly weight gain of at least 100 grams per week, at least 200 grams per week, at least 300 grams per week, at least 400 grams per week, at least 500 grams per week, at least 600 grams per week, at least 700 grams per week, at least 800 grams per week, between 100 to 800 grams per week, between 100 to 400 grams per week, between 300 to 600 grams per week, between 500 to 800 grams per week, or between 350 to 550 grams per week. In one embodiment, poultry provided an oligosaccharide composition, animal feed pre-mix, or animal feed composition has an average weekly weight gain of at least 400 grams per week. In certain embodiments, poultry provided an oligosaccharide composition, animal feed pre-mix, or animal feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of poultry provided a diet that does not include the oligosaccharide composition.

In certain embodiments, the animal is swine, and swine provided an oligosaccharide composition, swine feed pre-mix, or swine feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of swine provided a diet that does not include the oligosaccharide composition.

Final Body Weight Gain

In some variations, providing an animal with an oligosaccharide composition, animal feed pre-mix, or animal feed composition results in an increased final body weight gain than an animal provided feed without the oligosaccharide composition. In some variations, providing an animal population with an oligosaccharide composition, animal feed pre-mix, or animal feed composition results in an increased average final body weight gain than an animal population provided feed without the oligosaccharide composition.

In some variations, providing an animal or animal population with an oligosaccharide composition, animal feed pre-mix, or animal feed composition results in a final body weight gain or average final body weight gain that is closer to the performance target maximum than an animal or animal population that is provided feed without the oligosaccharide composition. The performance target maximum generally refers to the highest practical body weight gain observed for a given type of animal and breed under ideal growing conditions, ideal animal health, and ideal dietary nutrition.

In one embodiment, the final body weight gain is the quantity of weight an individual animal gains over a period of time. For example, in one embodiment, the total body weight gain is the quantity of weight an individual animal gains from 0 days of age until the final weight taken prior to processing of the animal, or the final weight taken on the day of processing of the animal. For example, in one embodiment, the day 0 to 28 total body weight gain for an animal is the quantity of weight an individual animal gains from 0 days of age until 28 days of age.

In another embodiment, the average total body weight gain is the quantity of weight an individual animal gains over a period of time, averaged across an animal population. For example, in one embodiment, the average total body weight gain is the quantity of weight an individual animal gains from 0 days of age until the final weight taken prior to processing of the animal, or the final weight taken on the day of processing of the animal, averaged across the animal population. In yet another embodiment, the average total body weight gain is the quantitity of weight an animal population gains over a period of time, divided by the number of individual animals in the population. For example, in one embodiment, the average total body weight gain is the quantity of weight an animal population gains from 0 days of age until the final weight taken prior to processing of the animal population, or the final weight taken on the day of processing of the animal, divided by the number of individual animals in the population.

It should be understood that the values for total body weight gain and average total body weight gain can be further averaged. For example, the average total body weight gain for different populations of the same type of animal may be averaged to obtain an average total body weight gain across populations.

In certain embodiments, the animal is poultry, and poultry provided an oligosaccharide composition, animal feed pre-mix, or animal feed composition has a final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided an oligosaccharide composition, animal feed pre-mix, or animal feed composition has a final body weight gain of at least 2 kg. In certain embodiments, poultry provided an oligosaccharide composition, animal feed pre-mix, or animal feed composition has a final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the final body weight gain of poultry provided a diet that does not include the oligosaccharide composition. In certain embodiments, poultry provided an oligosaccharide composition, animal feed pre-mix, or animal feed composition has a final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the final body weight gain of poultry provided a diet that does not include the oligosaccharide composition.

In certain embodiments, the animal is poultry, and poultry provided an oligosaccharide composition, animal feed pre-mix, or animal feed composition has an average final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided an oligosaccharide composition, animal feed pre-mix, or animal feed composition has an average final body weight gain of at least 2 kg. In certain embodiments, poultry provided an oligosaccharide composition, animal feed pre-mix, or animal feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of poultry provided a diet that does not include the oligosaccharide composition. In certain embodiments, poultry provided an oligosaccharide composition, animal feed pre-mix, or animal feed composition has an average final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the average final body weight gain of poultry provided a diet that does not include the oligosaccharide composition.

In some embodiments, the animal is poultry, and the poultry is between 0 to 14 days of age, between 15 to 28 days of age, between 29 to 35 days of age, between 0 to 42 days of age, between 0 to 6 weeks of age, or between 0 to 6.5 weeks of age. In some embodiments, the starter phase is 0 to 14 days of age, the grower phase is 15 to 28 days of age, and the finisher phase is 29 to 35 days of age. In other embodiments, the starter phase is 0 to 14 days of age, the grower phase is 15 to 35 days of age, and the finisher phase is 36 to 42 days of age. In yet other embodiments, the starter phase is 0 to 14 days of age, the grower phase is 15 to 39 days of age, and the finisher phase is 40 to 46 days of age. It should be understood that the length of the starter phase, growing phase, and finisher phase for poultry may change depending on the intended use of the poultry, or the poultry product. For example, in some embodiments the length of the starter phase, grower phase, and finisher phase may be different if the intended use of the poultry is as a broiler chicken, compared to processing for tray-pack chicken meat.

In some embodiments that may be combined with any of the foregoing embodiments, the poultry is an individual poultry, while in other embodiments the poultry is a poultry population.

In certain embodiments, swine provided an oligosaccharide composition, swine feed pre-mix, or swine feed composition has a final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the final body weight gain of swine provided a diet that does not include the oligosaccharide composition.

In certain embodiments, swine provided an oligosaccharide composition, swine feed pre-mix, or swine feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of swine provided a diet that does not include the oligosaccharide composition.

In some embodiments that may be combined with any of the foregoing embodiments, the swine is an individual swine, while in other embodiments the swine is a swine population.

b) Average Daily Feed Intake

In certain variations, providing an animal with an oligosaccharide compositions, animal feed pre-mix, or animal feed composition as described herein results in an increased average daily feed intake, as compared to an animal provided feed that does not include the oligosaccharide composition.

Average daily feed intake (ADFI) refers to the average mass of feed consumed by an animal over a specified period of time. In certain variations, the average daily feed intake is measured by dispensing a known mass of feed to a group of a fixed number of animals, allowing the animals in the group to consume the dispensed feed freely (ad libidum) for a specified number of days, weighing the mass of unconsumed feed at the end of the period, and calculating the average daily feed intake (ADFI) as the difference between the dispensed feed mass minus the residual feed mass, divided by the number of animals in the group, and divided by the number of days in the period. In other variations, the average daily feed intake may be corrected for any animals that die or are culled from the group, using methods that are known to one skilled in the art.

In some variations, the animal is poultry, and the animal feed composition is poultry feed, wherein the oligosaccharide composition, poultry feed pre-mix, or poultry feed composition feed increases average daily feed intake by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the oligosaccharide composition.

In certain variations, the poultry suffers from a disease or is raised in a challenged environment, wherein the oligosaccharide composition, poultry feed pre-mix, or poultry feed composition increases average daily feed intake by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the oligosaccharide composition In some variations that may be combined with the foregoing, the animal is swine, and the animal feed composition is swine feed, wherein the oligosaccharide composition, swine feed pre-mix, or swine feed composition increases average daily feed intake by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

In certain variations, the swine suffers from a disease or is raised in a challenged environment, wherein the oligosaccharide composition, swine feed pre-mix, or swine feed composition increases average daily feed intake by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

c) Yield of Animal Product

In certain variations, providing an animal with an oligosaccharide compositions, animal feed pre-mix, or animal feed composition as described herein results in an increased yield of animal product, as compared to an animal provided feed that does not include the oligosaccharide composition. In some embodiments, the animal provided an oligosaccharide composition, animal feed pre-mix, or animal feed composition yields at least 1%, at least 2%, at least 3%, at least 4%, at least 5%, at least 6%, at least 7%, at least 8%, at least 9%, at least 10%, between 1 to 10%, between 4 to 10%, between 6 to 10%, or between 2 to 8% more animal product compared to an animal provided feed that does nto include the oligosaccharide composition. For example, in some embodiments, the animal product is the meat of the animal, and an animal provided an oligosaccharide composition as described herein yields a greater quantity of meat compared to an animal that is not provided the oligosaccharide composition. In some embodiments, providing an animal population the oligosaccharide composition, animal feed pre-mix, or animal feed composition results in an increased average yield of animal product, as compared to an animal population provided feed that does not include the oligosaccharide composition. In some variations, the average animal product yield is the quantity of animal product yielded from each individual animal, averaged across the animal population.

In some embodiments, the animal product is the meat of an animal (e.g., that may be sold to consumers, processed to produce a food product, or consumed by a human) In certain embodiments, the animal is poultry, and the animal product is a poultry eviscerated carcass, leg meat from a poultry eviscerated carcass, breast meat from a poultry eviscerated carcass, drumstick meat from a poultry eviscerated carcass, fat from a poultry eviscerated carcass, breast meat from a poultry deboned carcass, or leg meat from a poultry deboned carcass. In other embodiments, the animal is poultry, and the animal product is white meat, breast meat filets, and breast meat tenders. In another embodiement, the animal is poultry and the product is tray-pack chicken meat. In yet another embodiment, the animal is poultry and the product is whole bird without giblets (WOG).

In some embodiments, the yield of animal product is the yield obtained from an individual animal. In some embodiments, the average yield of animal product is the yield obtained from each individual animal in an animal population, averaged across the population. In yet another embodiment, the average yield of animal product is the total yield of animal product yielded from an animal population, divided by the number of individual animals in the animal population.

In some variations, the animal is poultry, the yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided an oligosaccharide compositions, animal feed pre-mix, or animal feed composition. In certain variations, the yield of leg meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided an oligosaccharide compositions, animal feed pre-mix, or animal feed composition. In certain variations, the average yield of leg meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided an oligosaccharide compositions, animal feed pre-mix, or animal feed composition. In certain variations, the yield of breast meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided an oligosaccharide compositions, animal feed pre-mix, or animal feed composition. In certain variations, the average yield of breast meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided an oligosaccharide compositions, animal feed pre-mix, or animal feed composition. In certain variations, the yield of drumstick meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided an oligosaccharide compositions, animal feed pre-mix, or animal feed composition. In certain variations, the average yield of drumstick meat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided an oligosaccharide compositions, animal feed pre-mix, or animal feed composition. In certain variations, the yield of breast meat from a poultry deboned carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided an oligosaccharide compositions, animal feed pre-mix, or animal feed composition. In certain variations, the average yield of breast meat from a poultry deboned carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided an oligosaccharide compositions, animal feed pre-mix, or animal feed composition. In certain variations, the yield of leg meat from a poultry deboned carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided an oligosaccharide compositions, animal feed pre-mix, or animal feed composition. In certain variations, the average yield of leg meat from a poultry deboned carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided an oligosaccharide compositions, animal feed pre-mix, or animal feed composition. In certain variations, the yield of fat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided an oligosaccharide compositions, animal feed pre-mix, or animal feed composition. In certain variations, the average yield of fat from a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided an oligosaccharide compositions, animal feed pre-mix, or animal feed composition. In certain variations, the yield of a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

In some variations, the animal is poultry, and the average yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided an oligosaccharide compositions, animal feed pre-mix, or animal feed composition. In certain variations, the average yield of a poultry eviscerated carcass from poultry provided an oligosaccharide composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the oligosaccharide composition.

Methods for deboning a poultry carcass are well known to one skilled in the art of poultry processing. It should be understood that meat yielded from poultry may be measured, for example, as the ratio of the mass of recovered meat to the final weight of the bird prior to processing.

In some variations, the animal is poultry, and the poultry is at least 35 days old, at least 42 days old, at least 6 weeks old, at least 6.5 weeks old before the poultry is processed to produce a poultry eviscerated carcass, poultry deboned carcass, white meat, breast meat filets, and breast meat tenders, tray-pack chicken meat, whole bird without giblets (WOG), or meat as described above.

In other variations, the animal is poultry, and the animal product is eggs.

In some embodiments, the animal is swine, and the swine product is the meat of swine (e.g., that may be sold to consumers, processed to produce a food product, or consumed by a human). In some embodiments, the yield of swine product is the yield obtained from an individual swine. In some embodiments, the average yield of swine product is the yield obtained from each individual swine in a swine population, averaged across the population. In yet another embodiment, the average yield of swine product is the total yield of swine product yielded from swine population, divided by the number of individual swine in the swine population.

In certain variations, an animal or animal population provided an oligosaccharide composition, animal feed pre-mix, or animal feed composition has a higher average daily weight gain, higher average weekly weight gain, higher final body weight gain, higher average final body weight gain, or increased average yield of animal product, or any combinations thereof, than an animal or animal population provided a diet that does not include the oligosaccharide composition, but which does include one or more antibiotics, one or more ionophores, soluble corn fiber, modified wheat starch, or yeast mannan, or any combinations thereof.

A person of skill in the art would recognize that the maximum theoretical weight gain may be different for different types of animals and may be different for different breeds of the same type of animal (for example, different types of broiler chickens, or different types of swine).

In some embodiments, the animal is poultry. In some embodiments that may be combined with any of the foregoing embodiments, the poultry is an individual poultry, while in other embodiments the poultry is a poultry population. In other embodiments, the animal is swine. In some embodiments that may be combined with any of the foregoing embodiments, the swine is an individual swine, while in other embodiments the swine is a swine population.

d) Feed Conversion Ratio

In some variations, an animal provided an oligosaccharide composition, animal feed pre-mix, or animal feed composition as described herein has a lower feed conversion ratio compared to an animal provided a diet that does not include the oligosaccharide composition. In some variations, feed conversion ratio (FCR) refers to the ratio of feed mass input (for example, consumed by the animal) to the animal output, wherein the animal output is the target animal product. For example, the animal output for dairy animals is milk, whereas the animal output for animals raised for meat is body mass.

In some variations, the animal is raised for meat, and the target animal output is body mass. Thus, in some variations, the FCR refers to the ratio of the weight of feed consumed compared to the final body weight of the animal prior to processing. In some variations, the FCR refers to the ratio of the weight of feed consumed compared to the final body weight gain of the animal prior to processing. It should be understood that FCR may be measured for an animal or population of animals over different time periods. For example, in some variations, the FCR is an FCR over the entire lifetime of the animal. In other variations, the FCR is a daily FCR, or a weekly FCR, or a cumulative FCR measured up until a particular moment in time (for example, a particular day).

A person of skill in the art would recognize that the performance target minimum feed conversion ratio (optimal FCR) may be different for different types of animal, and may be different for different breeds of one type animal (for example, different breeds of broiler chickens, or different breeds of swine). The performance target minimum feed conversion ratio may also be different depending on age of the animal (for example, chickens or swine in a grower phase compared to a finisher phase), or the sex of the animal. It should be clear that the optimal FCR may be different depending on any combination of these factors.

Performance target minimum generally refers to the lowest feed efficiency observed for a given animal and breed under ideal growing conditions, ideal animal health, and ideal dietary nutrition. It is well known to one skilled in the art that under common growing conditions, an animal may not achieve the performance target minimum FCR. An animal may not achieve its performance target minimum FCR due to a variety of health, nutrition, environmental, and/or community influences. An animal may not achieve its performance target minimum FCR when raised in a challenged environment, which may include, for example, environmental pathogenic stress, excessive environmental temperature (heat stress), excessive environmental humidity, crowding, or other social interaction effects, such as difficulty accessing feed or drinking water. In some embodiments, an animal may not achieve its performance target minimum FCR due to disease or environmental pathogenic stress. In other embodiments, an animal may not achieve its performance target minimum FCR due to excessive environmental temperature (heat stress), or excessive environmental humidity. In yet other embodiments, an animal may not achieve its performance target minimum FCR due to crowding, or other social interaction effects, such as difficulty accessing feed or drinking water.

In some variations, an animal provided a diet which does not include the oligosaccharide composition as described herein has an FCR that is at least 1% higher than the performance target minimum, at least 2% higher than the performance target minimum, at least 3% higher than the performance target minimum, at least 4% higher than the performance target minimum, at least 5% higher than the performance target minimium, at least 6% higher than the performance target minimum, at least 7% higher than the performance target minimum, at least 8% higher than the performance target minimum, at least 9% higher than the performance target minimum, or at least 10% higher than the performance target minimum FCR. In certain embodiments, an animal provided a diet wich does not include an oligosaccharide composition as described herein has an FCR that is 1% to 10% higher than the performance target minimum, 2% to 10% higher than the performance target minimum, or 5% to 10% higher than the performance target minimum.

In some variations, an animal provided an oligosaccharide composition, animal feed pre-mix, or animal feed composition as described herein has an FCR that is closer to the performance target minimum compared to an animal provided a diet that does not include the oligosaccharide composition. In particular embodiments, the animal provided an oligosaccharide composition, animal feed pre-mix, or animal feed composition as described herein has an FCR that is between 0 to 10% higher than the performance target minimum, between 0 to 5% higher than the performance target minimum, or between 0 to 2% higher than the performance target minimum.

In some variations, an animal provided an oligosaccharide composition, animal feed pre-mix, or animal feed composition as described herein has a lower feed conversion ratio compared to an animal provided a diet that does not include the oligosaccharide composition. For example, in certain variations, the animal provided a diet comprising the oligosaccharide composition consumes less food but has the same animal output as compared to an animal provided a diet that does not include the oligosaccharide composition. In other variations, the animal provided a diet comprising the oligosaccharide composition consumes the same amount of food but has a higher animal output as compared to an animal provided a diet that does not include the oligosaccharide composition. In yet other variations, the animal provided a diet comprising the oligosaccharide composition consumes less food and has a higher animal output as compared to an animal provided a diet that does not include the oligosaccharide composition.

In some variations, the FCR of an animal provided an oligosaccharide composition, animal feed pre-mix, or animal feed composition as described herein is reduced at least 1%, at least 2%, at least 4%, at least 6%, at least 8%, at least 10%, at least 12%, between 1 to 10%, between 4 to 10%, between 1 to 8%, between 4 to 8%, between 1 to 6%, or between 4 to 6% as compared to an animal provided a diet that does not include the oligosaccharide composition. In some variations, the animal is poultry. In certain variations, the FCR of the poultry is reduced over 0 to 14 days of age, over 15 to 28 days of age, over 29 to 35 days of age, over 35 days, over 42 days, over 6 weeks, over 6.5 weeks, over 0 to 35 days of age, over 0 to 42 days of age, over 0 to 6 weeks of age, over 0 to 6.5 weeks of age, over 15 to 35 days of age, over 36 to 42 days of age, over 15 to 39 days of age, or over 40 to 46 days of age.

In one embodiment, the FCR over 35 days for poultry provided an oligosaccharide composition, animal feed pre-mix, or animal feed composition as described herein is reduced by between 4 to 6% as compared to poultry provided a diet that does not include the oligosaccharide composition. For example, in a certain embodiment, the FCR over 35 days for poultry provided an oligosaccharide composition, animal feed pre-mix, or animal feed composition as described herein is 1.53, the FCR over 35 days for poultry provided a diet without the oligosaccharide composition is 1.61, and the FCR of the poultry provided the oligosaccharide composition, animal feed pre-mix, or animal feed composition is reduced about 5% compared to the poultry provided a diet without the oligosaccharide composition. In some embodiments, the FCR over 42 days, over 6 weeks, or over 6.5 weeks days for poultry provided an oligosaccharide composition, animal feed pre-mix, or animal feed composition as described herein is reduced by between 4 to 6% as compared to poultry provided a diet that does not include the oligosaccharide composition.

In some variations, an animal population provided an oligosaccharide composition, animal feed pre-mix, or animal feed composition as described herein has a lower FCR compared to an animal population provided a diet that does not include the oligosaccharide composition, wherein the FCR is corrected for mortality in the animal population.

In certain variations, an animal provided an oligosaccharide composition, animal feed pre-mix, or animal feed composition has a lower FCR than an animal provided a diet that does not include the oligosaccharide composition, but which does include one or more antibiotics, one or more ionophores, soluble corn fiber, modified wheat starch, or yeast mannan, or any combinations thereof.

It is known to one skilled in the art, that when determining FCR, the FCR may be adjused for mortality to reduce noise due to small number statistics. Methods for adjusting FCR for mortality are well known to one skilled in the art.

In some embodiments that may be combined with any of the foregoing embodiments, the poultry is an individual poultry, while in other embodiments the poultry is a poultry population.

In some variations, the animal is poultry, and the animal feed composition is poultry feed, wherein the oligosaccharide composition, poultry feed pre-mix, or poultry feed composition feed reduces feed conversion ratio (FCR) by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the oligosaccharide composition.

In certain variations, the poultry suffers from a disease or a disorder, or is raised in a challenged environment, wherein the oligosaccharide composition, poultry feed pre-mix, or poultry feed composition feed reduces feed conversion ratio (FCR) by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the oligosaccharide composition.

In some variations, the animal is swine, and the animal feed composition is swine feed, wherein the oligosaccharide composition, swine feed pre-mix, or swine feed composition reduces feed conversion ratio (FCR) by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

In certain variations, the swine suffers from a disease or a disorder, or is raised in a challenged environment, wherein the oligosaccharide composition, swine feed pre-mix, or swine feed composition reduces feed conversion ratio (FCR) by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the oligosaccharide composition.

e) Mortality

In some variations, the mortality of an animal or animal population provided the oligosaccharide composition, animal feed pre-mix, or animal feed composition as described herein may be reduced relative to the mortality rate of an animal or animal population not provided the oligosaccharide composition, animal feed pre-mix, or animal feed composition. The reduction of mortality may include, for example, a decrease in the mortality rate on a per head basis. One of skill in the art would recognize that the mortality rate on a per head basis is determined as the ratio of the number of dead animals to the total number of animals at the start of the performance period. The reduction in mortality may include, for example, a reduction in the mortality rate on a per weight basis. One skilled in the art would recognize that the mortality rate on a per weight basis is determined as the ratio of the total weight of animals lost to mortality to the total weight of live animals plus the total weight of dead animals.

In some embodiments, the mortality rate on a per head basis for animals provided a base feed that does not include the oligosaccharide composition is at least 2%, at least 3%, at least 4%, at least 5%, at least 10%, or at least 20%.

In some embodiments, providing the oligosaccharide composition, animal feed pre-mix, or animal feed composition to an animal or animal population results in a reduction in mortality rate on a per head basis of between 0 to 90%, between 0 to 80%, between 20 to 70%, between 30 to 60%, between 40 to 60%, or between 45 to 55%, as compared to an animal or animal population that is not provided the oligosaccharide composition, animal feed pre-mix, or animal feed composition.

For example, in one embodiment, a poultry population is provided an animal feed composition as described herein and has a mortality rate of 0.8% on a per head basis, compared to the mortality rate of 1.7% on a per head basis for a poultry population provided feed without an oligosaccharide composition. Thus, in one example, the mortality rate on a per head basis of a poultry population provided an animal feed composition is reduced 51% compared to a poultry population provided feed without the oligosaccharide composition.

In certain variations, an animal provided an oligosaccharide composition, animal feed pre-mix, or animal feed composition has a lower mortality rate than an animal provided a diet that does not include the oligosaccharide composition, but which does include one or more antibiotics, one or more ionophores, soluble corn fiber, modified wheat starch, or yeast mannan, or any combinations thereof.

f) Uniformity

In other embodiments, an animal population provided the oligosaccharide composition, animal feed pre-mix, or animal feed composition has in improved uniformity compared to an animal population that is not provided the oligosaccharide composition, animal feed pre-mix, or animal feed composition Improving uniformity may include, for example, decreasing the relative variability of final body weight in a population of animals, wherein the relative variability is the standard deviation of final body weight divided by the mean final body weight. In some embodiments, the relative variability in final body weight is reduced by at least 10%, at least 15%, at least 20%, at least 25%, at least 30%, at least 35%, at least 40%, at least 45%, at least 50%, at least 55%, at least 60%, at least 65%, at least 70%, between 10 to 75%, between 20 to 60%, between 25 to 50%, between 25 to 40%, or between 30 to 40% for an animal population provided the oligosaccharide composition, animal feed pre-mix, or animal feed composition has in improved uniformity compared to an animal population that is not provided the oligosaccharide composition, animal feed pre-mix, or animal feed composition.

In some variations, improving the uniformity of an animal population may increase the efficiency of animal processing, including, for example, mechanical processing to obtain meat from the animals.

In certain variations, an animal population provided an oligosaccharide composition, animal feed pre-mix, or animal feed composition has greater uniformity than an animal population provided a diet that does not include the oligosaccharide composition, but which does include one or more antibiotics, one or more ionophores, soluble corn fiber, modified wheat starch, or yeast mannan, or any combinations thereof.

In some embodiments that may be combined with any of the foregoing embodiments, the poultry is an individual poultry, while in other embodiments the poultry is a poultry population.

g) Fatty Acid Concentration

In some embodiments, an animal that is fed the oligosaccharide composition, animal feed pre-mix, or animal feed composition will experience an increase in the volatile fatty acid (VFA) concentration in the digestive system, compared to an animal not fed the oligosaccharide composition, animal feed pre-mix, or animal feed composition. Volatile fatty acids may include, for example, acetic acid, butyric acid, or valeric acid, or combinations thereof. In some embodiments, an animal that is fed the oligosaccharide composition or the animal feed composition will experience an increase in the VFA concentration in the digestive system, compared to the same animal before being fed the oligosaccharide composition or the animal feed composition. The VFA concentration may be determined by any appropriate method known in the art (i.e. for example, gas chromatography). In certain embodiments, an animal that is fed the oligosaccharide composition or the animal feed composition will experience an increase in VFA concentration in the digestive system of about 1%, about 5%, about 8%, about 10%, about 15%, about 20%, about 25%, about 30%, about 40%, about 50%, about 60%, about 70%, about 80%, about 90%, or about 100%.

In some embodiments, an animal that is fed the oligosaccharide composition, animal feed pre-mix, or the animal feed composition will experience an increase in the short chain fatty acid (SCFA) concentration in the digestive system, compared to an animal not fed the oligosaccharide composition, animal feed pre-mix, or the animal feed composition. In some embodiments, an animal that is fed the oligosaccharide composition, animal feed pre-mix, or the animal feed composition will experience an increase in the SCFA concentration in the digestive system, compared to the same animal before being fed the oligosaccharide composition, animal feed pre-mix, or the animal feed composition.

Short chain fatty acids include acetic, propionic, butyric, iso-butyric, 2-methyl-butyric, valeric, iso-valeric, and lactic acid. The SCFA concentration may be determined by any appropriate method known in the art (i.e. for example, gas chromatography). One of skill in the art would appreciate that short chain fatty acids may exist and/or be determined as their respective conjugate bases (e.g., acetate, propionate, butyrate, iso-butyrate, 2-methyl-butyrate, valerate, iso-valerate, lactate).

In certain embodiments, an animal that is fed the oligosaccharide composition, animal feed pre-mix, or the animal feed composition will experience an increase in SCFA concentration in the digestive system of about 1%, about 5%, about 8%, about 10%, about 15%, about 20%, about 25%, about 30%, about 40%, about 50%, about 60%, about 70%, about 80%, about 90%, or about 100%.

In some embodiments, the animal will experience an increase in the ileal concentration of SCFA. In other embodiments, the animal will experience an increase in the cecal concentration of SCFA. In some variations, the animal provided the oligosaccharide composition, animal feed pre-mix, or animal feed composition as described herein will experience an increase in ileal concentration of SCFA or cecal concentration of SCFA, or combination thereof, of at least 1%, at least 10%, at least 20%, at least 30%, at least 40%, at least 50%, at least 60%, at least 70%, between 1 to 80%, between 10 to 80%, between 10 to 50%, between 30 to 80%, or between 30 to 50% compared to an animal not provided the oligosaccharide composition, animal feed pre-mix, or animal feed composition. In certain variations, the SCFA is butyric acid, propionic acid, acetic acid, valeric acid, isobutyric acid, isovaleric acid, 2-methyl-butyric acid, or lactic acid, or any combinations thereof. In one variation, the SCFA is butyric acid or propionic acid, or a combination thereof.

In some embodiments, an animal that is fed the oligosaccharide composition will experience a reduction in the presence of pathogenic or otherwise harmful microorganisms within its digestive system. In some embodiments, the oligosaccharide composition provides a preferential food source for gut microorganisms that are natural competitors to pathogenic or otherwise harmful microorganisms. In other embodiments, the oligosaccharide composition binds to the exterior surface (e.g., exterior wall carbohydrate receptors) of pathogenic or otherwise harmful microorganisms, suppressing their ability to colonize the gut, for example by decreasing gut-adherence. In some embodiments, the pathogenic or otherwise harmful microorganisms are enterotoxigenic species or strains. In certain embodiments, the pathogenic or otherwise harmful microorganisms are selected from set including members of *Campylobacter* spp, *Salmonella* spp, and *Eschericia* spp. In one embodiment, the pathogenic or otherwise harmful microorganism is *Campylobater jejuni* or *Campylobacter coli*.

In some embodiments, an animal that is fed the oligosaccharide composition may not need to be provided antibiotics, or may require a lower dose of antibiotics, in its diet. In some embodiment, an animal that is fed the oligosaccharide composition but not fed antibiotics may exhibit the same or better feed conversion ratio or feed efficiency than an animal that is fed antibiotics but not the oligosaccharide composition.

In certain variations, an animal provided an oligosaccharide composition, animal feed pre-mix, or animal feed composition has a higher digestive system SCFA concentration, cecal SCFA concentration, or ileal SCFA concentration than an animal provided a diet that does not include the oligosaccharide composition, but which does include one or more antibiotics, one or more ionophores, soluble corn fiber, modified wheat starch, or yeast mannan, or any combinations thereof.

In some embodiments, an animal that is provided an oligosaccharide composition, animal feed pre-mix, or animal feed composition as described herein may have greater access to nutrients in the diet than an animal provided a diet that does not include the oligosaccharide composition. Nutrients to which an animal provided an oligosaccharide composition, animal feed pre-mix, or animal feed composition as described herein may have greater access may include, for example, amino acids, metabolic energy, minerals, or vitamins, or any combinations thereof. For example, in certain embodiments, a diet comprising the oligosaccharhide composition is more digestible to an animal than a diet that does not comprise the oligosaccharide composition. Digestability may be measured by, for example, comparing the amount of undigested nutrient residual in the excreta of the animal relative to the amount of nutrient present in the feed.

In some embodiments that may be combined with any of the foregoing embodiments, the animal is poultry. In certain embodiments, the poultry is an individual poultry, while in other embodiments the poultry is a poultry population.

It should be understood that the methods described herein include providing to an animal or animal population any oligosaccharide composition, animal feed pre-mix, or animal feed composition as described herein, to enhance the growth of the animal or animal population in any way described herein. For example, provided herein is a method of enhancing growth of an animal population, comprising feeding to the animal population an animal feed, wherein the animal feed comprises an oligosaccharide composition at an inclusion rate of less than 5,000 ppm wt % dry oligosaccharide composition per weight of animal feed;

wherein the oligosaccharide composition has a glycosidic bond type distribution of:
at least 1 mol % α-(1,3) glycosidic linkages;
at least 1 mol % β-(1,3) glycosidic linkages; and
at least 15 mol % β-(1,6) glycosidic linkages, and
wherein at least 10 dry wt % of the oligosaccharide composition has a degree of polymerization of at least 3; and
enhancing growth of the animal population.

In some embodiments that may be combined with any of the foregoing embodiments, enhancing the growth of the animal population may include, for example, an increase in weight gain, a decrease in the food conversion ratio (FCR), an increase in digestibility of provided feed, an increase in released nutrients from provided feed, increase in average animal product yield, a reduced mortality rate, or an increase in animal uniformity, or any combinations thereof. The methods of enhancing growth described herein may include providing an animal or animal population with any oligosaccharide composition, animal feed pre-mix, or animal feed composition described herein.

In other embodiments that may be combined with any of the foregoing embodiments, the animal population may suffer from a disease or disorder. For example, in certain embodiments, the disease or disorder is necrotic enteritis, coccidiosis, nutrient malabsorption syndrome, intestinal barrier breakdown, colisepticemia, yolk sack infection, salmonella infection, or campylobacter infection. In one embodiment, the disease or disorder is necrotic enteritis. In some variations, the administration of the oligosaccharide compositions, animal feed pre-mixes, or animal feed compositions described herein enhance the growth of the animal population suffering from such disease or disorder.

Methods of Providing the Oligosaccharide Composition to an Animal

The methods of enhancing growth of an animal or animal population described herein include providing an oligosaccharide composition, animal feed pre-mix, or animal feed to the animal or animal population. The oligosaccharide composition, animal feed pre-mix, or animal feed may be provided in any suitable form, to any suitable type of animal, using any suitable feeding schedule to enhance the growth of the animal or animal population.

Type of Animal

The oligosaccharide composition, animal feed pre-mix, or the animal feed composition may be provided to any suitable animals. In some embodiments, the animal is monogastric. It is generally understood that a monogastric animal has a single-chambered stomach. In other embodiments, the animal is a ruminant. It is generally understood that a ruminant has a multi-chambered stomach. In some variations, the animal is a ruminant in the pre-ruminant phase. Examples of such ruminants in the pre-ruminant phase include nursery calves.

In some variations, the animal is poultry. Examples of poultry include chicken, duck, turkey, goose, quail, or Cornish game hen. In one variation, the animal is a chicken. In some embodiments, the poultry is a layer hen, a broiler chicken, or a turkey.

In other embodiments, the animal is a mammal, including, for example, a cow, a pig, a goat, a sheep, a deer, a bison, a rabbit, an alpaca, a llama, a mule, a horse, a reindeer, a water buffalo, a yak, a guinea pig, a rat, a mouse, an alpaca, a dog, or a cat. In one variation, the animal is a cow. In another variation, the animal is a pig.

The animal feed composition may also be used in aquaculture. In some embodiments, the animal is an aquatic animal. Examples of aquatic animals may include a trout, a salmon, a bass, a tilapia, a shrimp, an oyster, a mussel, a clam, a lobster, or a crayfish. In one variation, the animal is a fish.

The oligosaccharide compositions described herein may be fed to individual animals or an animal population. For example, in one variation where the animal is poultry, the oligosaccharide compositions may be fed to an individual poultry or a poultry population.

Form of Animal Feed Composition

The oligosaccharide composition, animal feed pre-mix, or the animal feed composition may be provided to an animal in any appropriate form, including, for example, in solid form, in liquid form, or a combination thereof. In certain embodiments, the oligosaccharide composition or the animal feed composition is a liquid, such as a syrup or a solution. In other embodiments, the oligosaccharide composition, animal feed pre-mix, or the animal feed composition is a solid, such as pellets or powder. In yet other embodiments, the oligosaccharide composition, animal feed pre-mix, or the animal feed composition may be fed to the animal in both liquid and solid components, such as in a mash.

Feeding Schedule

The oligosaccharide composition, animal feed pre-mix, or animal feed composition may be provided to the animal on any appropriate schedule. In some embodiments, the animal is provided the oligosaccharide composition, animal feed pre-mix, or animal feed composition on a daily basis, on a weekly basis, on a monthly basis, on an every other day basis, for at least three days out of every week, or for at least seven days out of every month. In some embodiments, the animal is provided the oligosaccharide composition, animal feed pre-mix, or animal feed composition during certain diet phases.

For example, some animals are provided a starter diet between 0 to 14 days of age. In other embodiments, an animal is provided a grower diet between 15 to 28 days of age, between 15 to 35 days of age, or between 15 to 39 days of age. In still other embodiments, an animal is provided a finisher diet between 29 to 35 days of age, between 36 to 42 days of age, or between 40 to 46 days of age.

In certain variations, the oligosaccharide composition, animal feed pre-mix, or animal feed composition is provided to the animal during the starter diet phase, the grower diet phase, or the finisher diet phase, or any combinations thereof.

In certain embodiments, the animal is poultry, and the poultry is provided a starter diet between 0 to 15 days of age, a grower diet between 16 to 28 days of age, and a finisher diet between 29 to 35 days of age. In other embodiments, the animal is poultry, and the poultry is provided a starter diet between 0 to 14 days of age, a grower diet between 15 to 35 days of age, and a finisher diet between 36 to 42 days of age. In still other embodiments, the animal is poultry, and the poultry is provided a starter diet between 0 to 14 days of age, a grower diet between 15 to 39 days of age, and a finisher diet between 20 to 46 days of age.

In some variations, the oligosaccharide composition, animal feed pre-mix, or animal feed composition is provided to the poultry during the starter diet phase, the grower diet phase, or the finisher diet phase, or any combinations thereof.

Methods of Producing Oligosaccharide Compositions

In one aspect, provided herein are methods of producing oligosaccharide compositions suitable for use in an animal feed composition, an animal feed pre-mix, or being fed directly to an animal. In some variations, the method includes combining feed sugar with a catalyst to form a reaction mixture, and producing an oligosaccharide composition from at least a portion of the reaction mixture. With reference to FIG. 1, process 100 depicts an exemplary process to produce an oligosaccharide composition from sugars, and such oligosaccharide composition produced can subsequently be polished and further processed to form an animal feed ingredient, such as an oligosaccharide syrup or powder. In step 102, one or more sugars are combined with a catalyst in a reactor. The sugars may include, for example, monosaccharides, disaccharides, and/or trisaccharides. The catalyst has both acidic and ionic groups. In some variations, the catalyst is a polymeric catalyst that includes acidic monomers and ionic monomers. In other variations, the catalyst is a solid-supported catalyst that includes acidic moieties and ionic moieties.

In step 104, the oligosaccharide composition in step 102 is polished to remove fine solids, reduce color, and reduce conductivity, and/or modify the molecular weight distribution. Any suitable methods known in the art to polish the oligosaccharide composition may be used, including, for example, the use of filtration units, carbon or other absorbents, chromatographic separators, or ion exchange columns. For example, in one variation, the oligosaccharide composition is treated with powdered activated carbon to reduce color, microfiltered to remove fine solids, and passed over a strong-acid cationic exchange resin and a weak-base anionic exchange resin to remove salts. In another variation, the oligosaccharide composition is microfiltered to remove fine solids and passed over a weak-base anionic exchange resin. In yet another variation, the oligosaccharide composition is passed through a simulated moving bed chromatographic separator to remove low molecular mass species.

In step 106, the polished oligosaccharide composition undergoes further processing to produce either an oligosaccharide syrup or powder. For example, in one variation, the polished oligosaccharide is concentrated to form a syrup. Any suitable methods known in the art to concentrate a solution may be used, such as the use of a vacuum evaporator. In another variation, the polished oligosaccharide composition is spray dried to form a powder. Any suitable methods known in the art to spray dry a solution to form a powder may be used.

In other variations, process 100 may be modified to have additional steps. For example, the oligosaccharide composition produced in step 102 may be diluted (e.g., in a dilution tank) and then undergo a carbon treatment to decolorize the oligosaccharide composition prior to polishing in step 104. In other variations, the oligosaccharide composition produced in step 102 may undergo further processing in a simulated moving bed (SMB) separation step to reduce digestible carbohydrate content.

In other variations, process 100 may be modified to have fewer steps. For example, in one variation, step 106 to produce the oligosaccharide syrup or powder may be omitted, and the polished oligosaccharide composition of step 104 may be used directly as an ingredient to produce an animal feed composition.

Each of the steps in exemplary process 100, the reactants and processing conditions in each step, as well as the compositions produced in each step are described in further detail below.

a) Feed Sugars

The feed sugar used in the methods of making oligosaccharide compositions described herein may include one or more sugars. In some embodiments, the one or more sugars are selected from monosaccharides, disaccharides, trisaccharides, and short-chain oligosaccharides, or any mixtures thereof. In some embodiments, the one or more sugars are monosaccharides, such as one or more C5 or C6 monosaccharides. Exemplary monosaccharides include glucose, galactose, mannose, fructose, xylose, xylulose, and arabinose. In some embodiments, the one or more sugars are C5 monosaccharides. In other embodiments, the one or more sugars are C6 monosaccharides. In some embodiments, the one or more sugars are selected from glucose, galactose, mannose, lactose, or their corresponding sugar alcohols. In other embodiments, the one or more sugars are selected from fructose, xylose, arabinose, or their corresponding sugar alcohols. In some embodiments, the one or more sugars are disaccharides. Exemplary disaccharides include lactose, sucrose and cellobiose. In some embodiments, the one or more sugars are trisaccharides, such as maltotriose or raffinose. In some embodiments, the one or more sugars comprise a mixture of short-chain oligosaccharides, such as malto-dextrins. In certain embodiments, the one or more sugars are corn syrup obtained from the partial hydrolysis of corn starch. In a particular embodiment, the one or more sugars is corn syrup with a dextrose equivalent (DE) below 50 (e.g., 10 DE corn syrup, 18 DE corn syrup, 25 DE corn syrup, or 30 DE corn syrup).

In some embodiments, the method includes combining two or more sugars with the catalyst to produce one or more oligosaccharides. In some embodiments, the two or more sugars are selected from glucose, galactose, mannose and lactose (e.g., glucose and galactose).

In other embodiments, the method includes combining a mixture of sugars (e.g., monosaccharides, disaccharides, trisaccharides, etc., and/or other short oligosaccharides) with the catalyst to produce one or more oligosaccharides. In one embodiment, the method includes combining corn glucose syrup with the catalyst to produce one or more oligosaccharides.

In other embodiments, the method includes combining a polysaccharide with the catalyst to produce one or more oligosaccharides. In some embodiments, the polysaccharide is selected from starch, guar gum, xanthan gum and acacia gum.

In other embodiments, the method includes combining a mixture of sugars and sugar alcohols with the catalyst to produce one or more oligosaccharides. In particular embodiments, the method includes combining one or more sugars and one or more alcohols selected from the group consisting of glucitol, sorbitol, xylitol and arabinatol, with the catalyst to produce one or more oligosaccharides.

In certain variations, the feed sugar includes glucose, mannose, galactose, xylose, malto-dextrin, arabinose, or galactose, or any combinations thereof. The choice of feed sugars will impact the resulting oligosaccharide composition produced. For example, in one variation where the feed sugar is all glucose, the resulting oligosaccharide composition is a gluco-oligosaccharide. In another variation where the feed sugar is all mannose, the resulting oligosaccharide composition is a manno-oligosaccharide. In another variation wherein the feed sugar includes glucose and galactose, the resulting oligosaccharide composition is a gluco-galacto-oligosaccharide. In yet another variation where the feed sugar is all xylose, the resulting oligosaccharide composition is a xylo-oligosaccharide. In another variation where the feed sugar includes malto-dextrin, the resulting oligosaccharide composition is a gluco-oligosaccharide. In yet another variation where the feed sugar includes xylose, glucose and galactose, the resulting oligosaccharide composition is a gluco-galacto-xylo-oligosaccharide. In one variation where the feed sugar includes arabinose and xylose, the resulting oligosaccharide composition is an arabino-xylo-oligosaccharide. In another variation where the feed sugar includes glucose and xylose, the resulting oligosaccharide composition is a gluco-xylo-oligosaccharide. In yet another variation where the feed sugar includes glucose, galactose and xylose, the resulting oligosaccharide composition is a xylo-gluco-galacto-oligosaccharide.

In some variations to produce the oligosaccharide compositions herein, the sugars may be provided as a feed solution, in which the sugars are combined with water and fed into the reactor. In other variations, the sugars may be fed into the reactor as a solid and combined with water in the reactor.

The sugars used in the methods described herein may be obtained from any commercially known sources, or produced according to any methods known in the art.

b) Catalysts

The catalysts used in the methods of making oligosaccharide compositions described herein include polymeric catalysts and solid-supported catalysts.

Figure 2A:
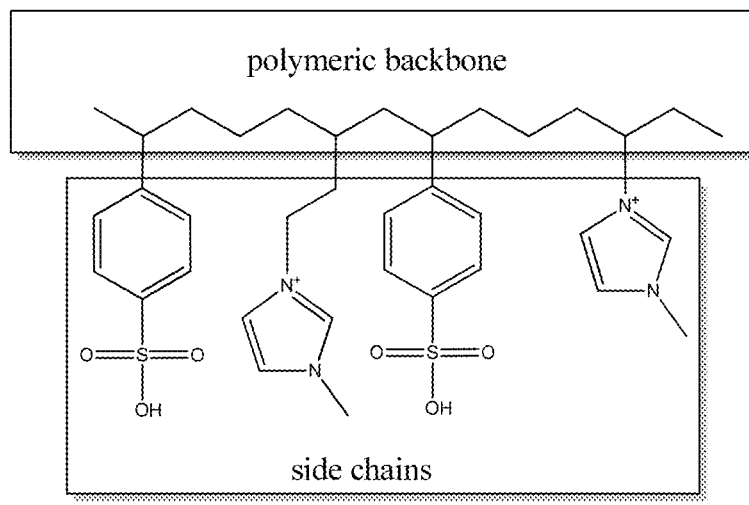
FIG. 2A illustrates a portion of a catalyst with a polymeric backbone and side chains.
Figure 2B:
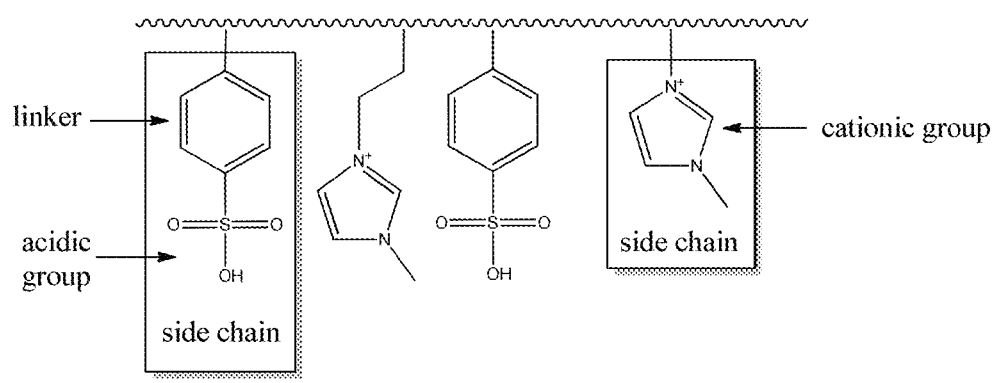
FIG. 2B illustrates a portion of an exemplary catalyst, in which a side chain with the acidic group is connected to the polymeric backbone by a linker and in which a side chain with the cationic group is connected directly to the polymeric backbone.

In some embodiments, the catalyst is a polymer made up of acidic monomers and ionic monomers (which are also referred to herein as "ionomers") connected to form a polymeric backbone. Each acidic monomer includes at least one Bronsted-Lowry acid, and each ionic monomer includes at least one nitrogen-containing cationic group, at least one phosphorous-containing cationic group, or any combination thereof. In certain embodiments of the polymeric catalyst, at least some of the acidic and ionic monomers may independently include a linker connecting the Bronsted-Lowry acid or the cationic group (as applicable) to a portion of the polymeric backbone. For the acidic monomers, the Bronsted-Lowry acid and the linker together form a side chain. Similarly, for the ionic monomers, the cationic group and the linker together form a side chain. With reference to the portion of the polymeric catalyst depicted in FIGS. 2A and 2B, the side chains are pendant from the polymeric backbone.

Figure 3:
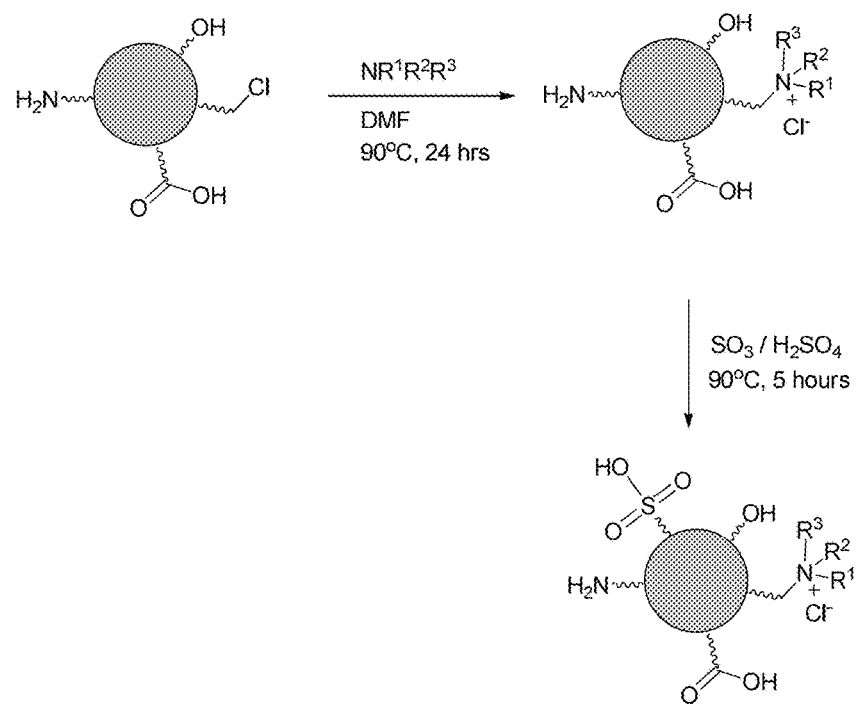
FIG. 3 depicts a reaction scheme to prepare a dual-functionalized catalyst from an activated carbon support, in which the catalyst has both acidic and ionic moieties.

In another aspect, the catalyst is solid-supported, having acidic moieties and ionic moieties each attached to a solid support. Each acidic moiety independently includes at least one Bronsted-Lowry acid, and each ionic moiety includes at least one nitrogen-containing cationic group, at least one phosphorous-containing cationic group, or any combination thereof. In certain embodiments of the solid-supported catalyst, at least some of the acidic and ionic moieties may independently include a linker connecting the Bronsted-Lowry acid or the cationic group (as applicable) to the solid support. With reference to FIG. 3, the produced catalyst is a solid-supported catalyst with acidic and ionic moieties.

Acidic Monomers and Moieties

The polymeric catalysts include a plurality of acidic monomers, where as the solid-supported catalysts include a plurality of acidic moieties attached to a solid support.

In some embodiments, a plurality of acidic monomers (e.g., of a polymeric catalyst) or a plurality of acidic moieties (e.g., of a solid-supported catalyst) has at least one Bronsted-Lowry acid. In certain embodiments, a plurality of acidic monomers (e.g., of a polymeric catalyst) or a plurality of acidic moieties (e.g., of a solid-supported catalyst) has one Bronsted-Lowry acid or two Bronsted-Lowry acids. In certain embodiments, a plurality of the acidic monomers (e.g., of a polymeric catalyst) or a plurality of the acidic moieties (e.g., of a solid-supported catalyst) has one Bronsted-Lowry acid, while others have two Bronsted-Lowry acids.

In some embodiments, each Bronsted-Lowry acid is independently selected from sulfonic acid, phosphonic acid, acetic acid, isophthalic acid, and boronic acid. In certain embodiments, each Bronsted-Lowry acid is independently sulfonic acid or phosphonic acid. In one embodiment, each Bronsted-Lowry acid is sulfonic acid. It should be understood that the Bronsted-Lowry acids in an acidic monomer (e.g., of a polymeric catalyst) or an acidic moiety (e.g., of a solid-supported catalyst) may be the same at each occurrence or different at one or more occurrences.

In some embodiments, one or more of the acidic monomers of a polymeric catalyst are directly connected to the polymeric backbone, or one or more of the acidic moieties of a solid-supported catalyst are directly connected to the solid support. In other embodiments, one or more of the acidic monomers (e.g., of a polymeric catalyst) or one or more acidic moieties (e.g., of a solid-supported catalyst) each independently further includes a linker connecting the Bronsted-Lowry acid to the polymeric backbone or the solid support (as the case may be). In certain embodiments, some of the Bronsted-Lowry acids are directly connected to the polymeric backbone or the solid support (as the case may be), while other the Bronsted-Lowry acids are connected to the polymeric backbone or the solid support (as the case may be) by a linker.

In those embodiments where the Bronsted-Lowry acid is connected to the polymeric backbone or the solid support (as the case may be) by a linker, each linker is independently selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker. In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

In other embodiments, each linker in an acidic monomer (e.g., of a polymeric catalyst) or an acidic moiety (e.g., of a solid-supported catalyst) is independently selected from:
 unsubstituted alkyl linker;
 alkyl linker substituted 1 to 5 substituents independently selected from oxo, hydroxy, halo, amino;
 unsubstituted cycloalkyl linker;
 cycloalkyl linker substituted 1 to 5 substituents independently selected from oxo, hydroxy, halo, amino;
 unsubstituted alkenyl linker;
 alkenyl linker substituted 1 to 5 substituents independently selected from oxo, hydroxy, halo, amino;
 unsubstituted aryl linker;
 aryl linker substituted 1 to 5 substituents independently selected from oxo, hydroxy, halo, amino;
 unsubstituted heteroaryl linker; or heteroaryl linker substituted 1 to 5 substituents independently selected from oxo, hydroxy, halo, amino.

Further, it should be understood that some or all of the acidic monomers (e.g., of a polymeric catalyst) or one or more acidic moieties (e.g., of a solid-supported catalyst) connected to the polymeric backbone by a linker may have the same linker, or independently have different linkers.

In some embodiments, each acidic monomer (e.g., of a polymeric catalyst) and each acidic moiety (e.g., of a solid-supported catalyst) may independently have the structure of Formulas IA-VIA:

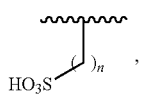

IA

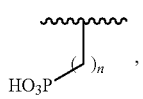

IB

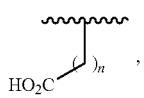

IC

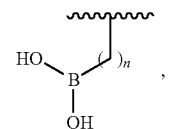

ID

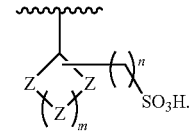

IIA

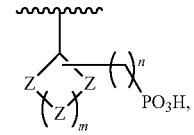

IIB

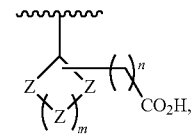

IIC

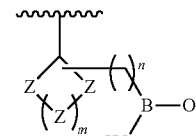

IID

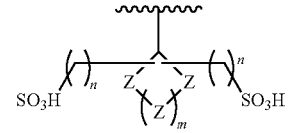

IIIA

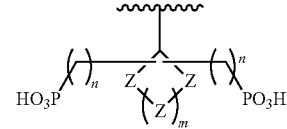

IIIB

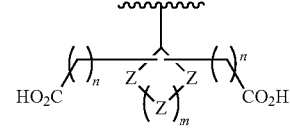

IIIC

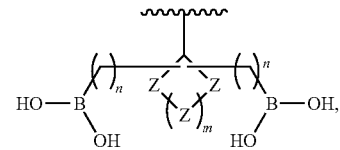

IIID

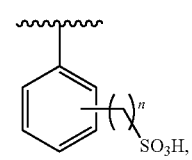

IVA

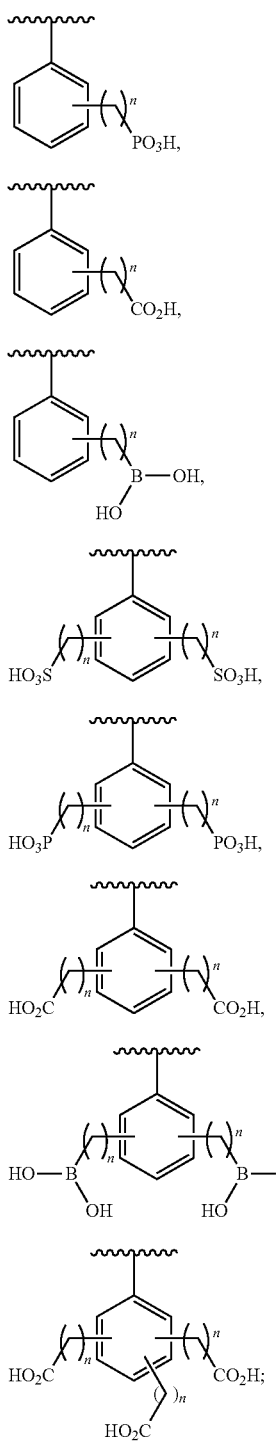

IVB

IVC

IVD

VA

VB

VC

VD

VIA wherein:
each Z is independently $C(R^2)(R^3)$, $N(R^4)$, S, $S(R^5)(R^6)$, $S(O)(R^5)(R^6)$, $SO_2$, or O, wherein any two adjacent Z can (to the extent chemically feasible) be joined by a double bond, or taken together to form cycloalkyl, heterocycloalkyl, aryl or heteroaryl;
each m is independently selected from 0, 1, 2, and 3;
each n is independently selected from 0, 1, 2, and 3;
each $R^2$, $R^3$, and $R^4$ is independently hydrogen, alkyl, heteroalkyl, cycloalkyl, heterocyclyl, aryl, or heteroaryl; and each $R^5$ and $R^6$ is independently alkyl, heteroalkyl, cycloalkyl, heterocyclyl, aryl, or heteroaryl.

In some embodiments, each acidic monomer (e.g., of a polymeric catalyst) and each acidic moiety (e.g., of a solid-supported catalyst) may independently have the structure of Formulas IA, IB, IVA, or IVB. In other embodiments, each acidic monomer (e.g., of a polymeric catalyst) and each acidic moiety (e.g., of a solid-supported catalyst) may independently have the structure of Formulas IIA, IIB, IIC, IVA, IVB, or IVC. In other embodiments, each acidic monomer (e.g., of a polymeric catalyst) and each acidic moiety (e.g., of a solid-supported catalyst) may independently have the structure of Formulas IIIA, IIIB, or IIIC. In some embodiments, each acidic monomer (e.g., of a polymeric catalyst) and each acidic moiety (e.g., of a solid-supported catalyst) may independently have the structure of Formulas VA, VB, or VC. In some embodiments, each acidic monomer (e.g., of a polymeric catalyst) and each acidic moiety (e.g., of a solid-supported catalyst) may independently have the structure of Formula IA. In other embodiments, each acidic monomer (e.g., of a polymeric catalyst) and each acidic moiety (e.g., of a solid-supported catalyst) may independently have the structure of Formula IB.

In some embodiments, Z can be chosen from $C(R_2)(R_3)$, $N(R_4)$, $SO_2$, and O. In some embodiments, any two adjacent Z can be taken together to form a group selected from a heterocycloalkyl, aryl, and heteroaryl. In other embodiments, any two adjacent Z can be joined by a double bond. Any combination of these embodiments is also contemplated (as chemically feasible).

In some embodiments, m is 2 or 3. In other embodiments, n is 1, 2, or 3. In some embodiments, $R^1$ can be hydrogen, alkyl or heteroalkyl. In some embodiments, $R^1$ can be hydrogen, methyl, or ethyl. In some embodiments, each $R^2$, $R^3$, and $R^4$ can independently be hydrogen, alkyl, heterocyclyl, aryl, or heteroaryl. In other embodiments, each $R^2$, $R^3$ and $R^4$ can independently be heteroalkyl, cycloalkyl, heterocyclyl, or heteroaryl. In some embodiments, each $R^5$ and $R^6$ can independently be alkyl, heterocyclyl, aryl, or heteroaryl. In another embodiment, any two adjacent Z can be taken together to form cycloalkyl, heterocycloalkyl, aryl or heteroaryl.

In some embodiments, the polymeric catalysts and solid-supported catalysts described herein contain monomers or moieties, respectively, that have at least one Bronsted-Lowry acid and at least one cationic group. The Bronsted-Lowry acid and the cationic group can be on different monomers/moieties or on the same monomer/moiety.

In certain embodiments, the acidic monomers of the polymeric catalyst may have a side chain with a Bronsted-Lowry acid that is connected to the polymeric backbone by a linker. In certain embodiments, the acidic moieties of the solid-supported catalyst may have a Bronsted-Lowry acid that is attached to the solid support by a linker. Side chains (e.g., of a polymeric catalyst) or acidic moieties (e.g., of a solid-supported catalyst) with one or more Bronsted-Lowry acids connected by a linker can include, for example,

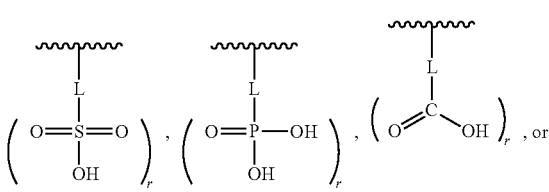

-continued

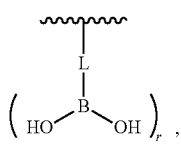

wherein:
L is an unsubstituted alkyl linker, alkyl linker substituted with oxo, unsubstituted cycloalkyl, unsubstituted aryl, unsubstituted heterocycloalkyl, and unsubstituted heteroaryl; and r is an integer.

In certain embodiments, L is an alkyl linker. In other embodiments L is methyl, ethyl, propyl, or butyl. In yet other embodiments, the linker is ethanoyl, propanoyl, or benzoyl. In certain embodiments, r is 1, 2, 3, 4, or 5 (as applicable or chemically feasible).

In some embodiments, at least some of the acidic side chains (e.g., of a polymeric catalyst) and at least some of the acidic moieties (e.g., of a solid-supported catalyst) may be:

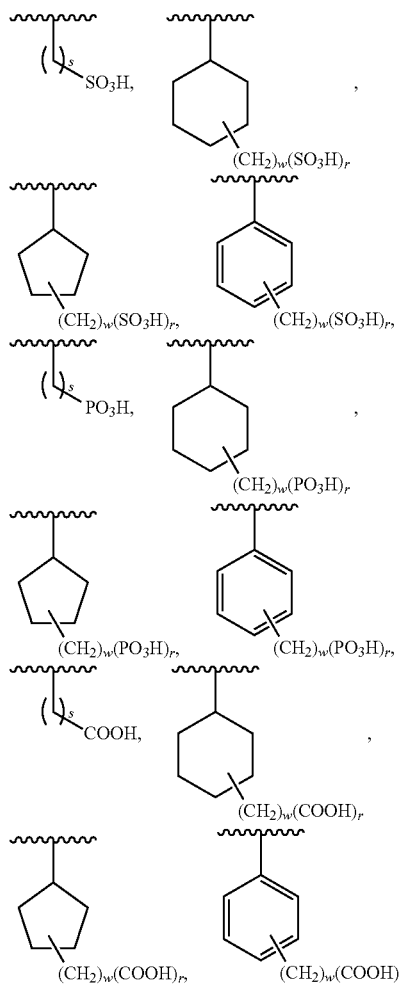

wherein:
s is 1 to 10;
each r is independently 1, 2, 3, 4, or 5 (as applicable or chemically feasible); and
w is 0 to 10.

In certain embodiments, s is 1 to 9, or 1 to 8, or 1 to 7, or 1 to 6, or 1 to 5, or 1 to 4, or 1 to 3, or 2, or 1. In certain embodiments, w is 0 to 9, or 0 to 8, or 0 to 7, or 0 to 6, or 0 to 5, or 0 to 4, or 0 to 3, or 0 to 2, 1 or 0).

In certain embodiments, at least some of the acidic side chains (e.g., of a polymeric catalyst) and at least some of the acidic moieties (e.g., of a solid-supported catalyst) may be:

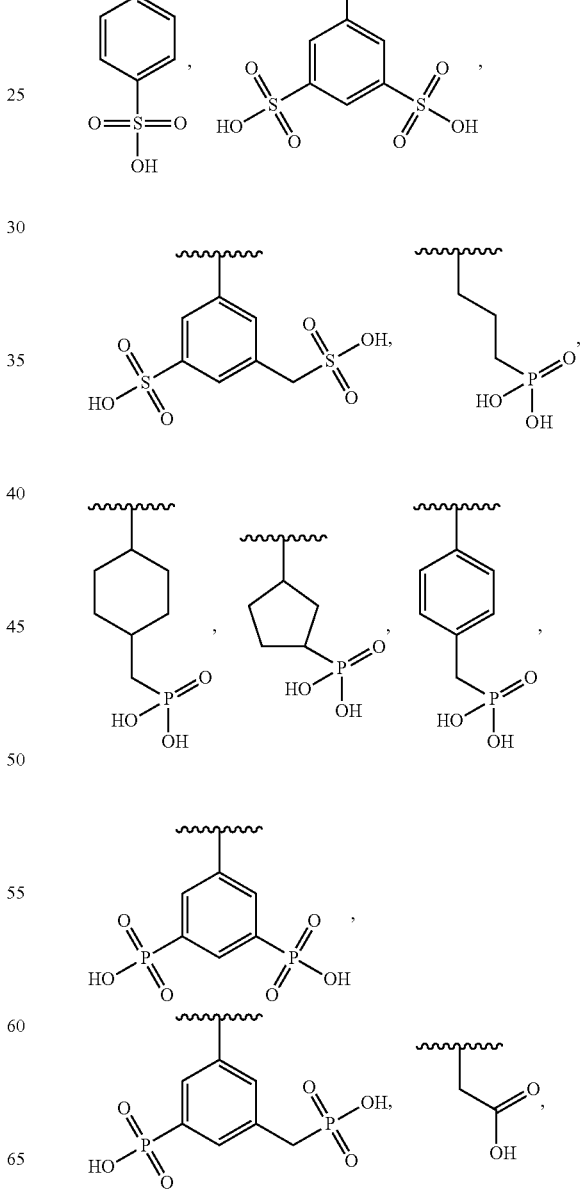

-continued

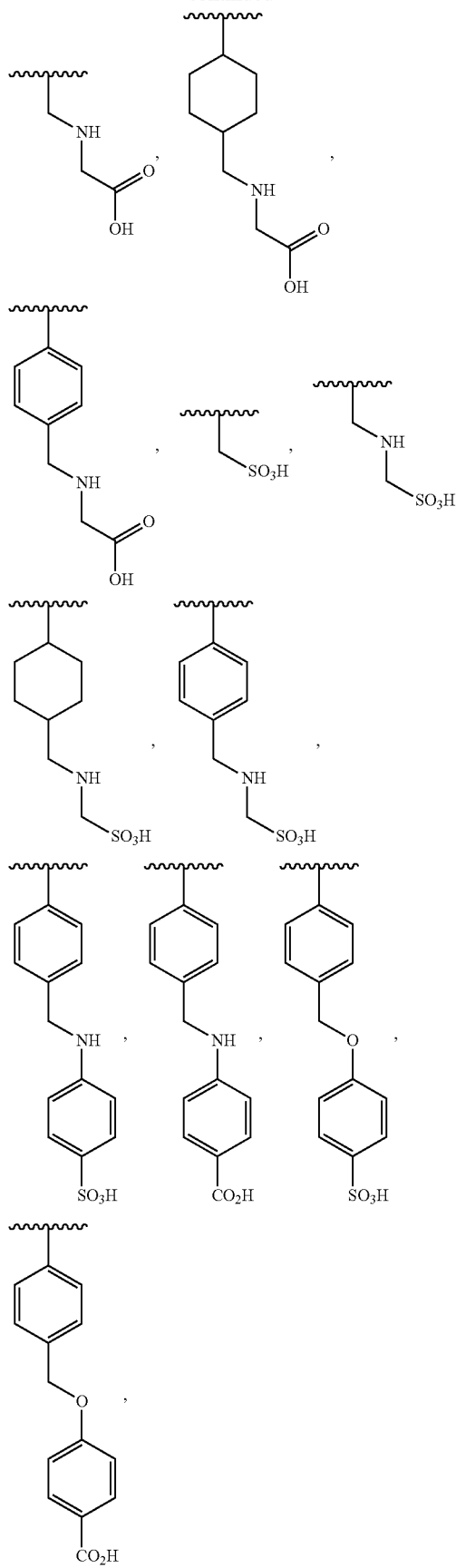

-continued

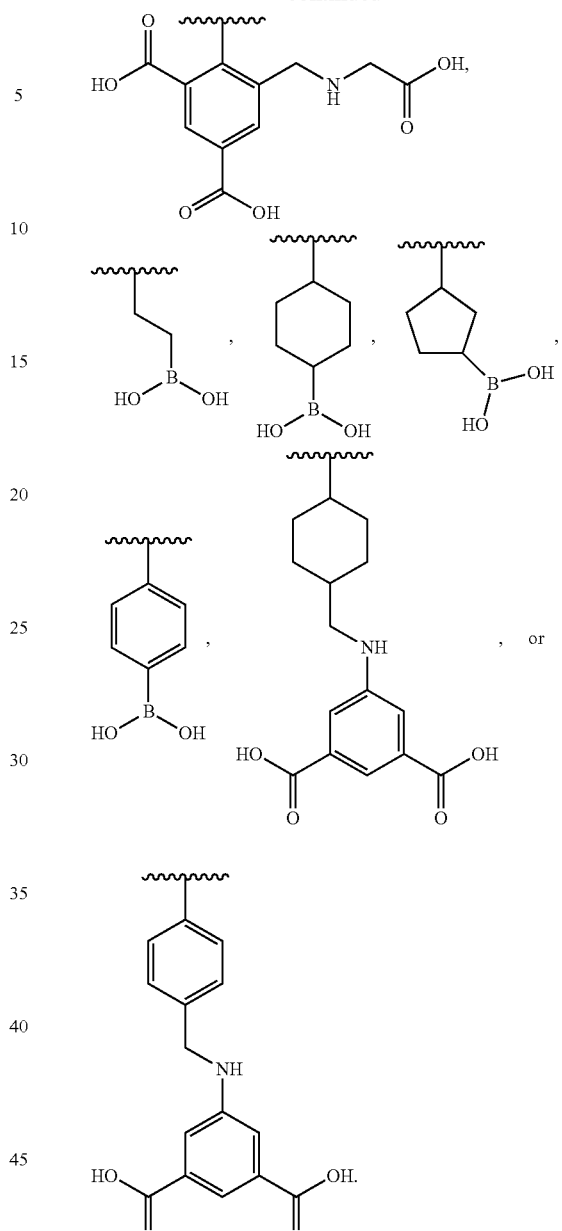

In other embodiments, the acidic monomers (e.g., of a polymeric catalyst) can have a side chain with a Bronsted-Lowry acid that is directly connected to the polymeric backbone. In other embodiments, the acidic moieties (e.g., of a solid-supported catalyst) may be directly attached to a solid support. Side chains directly connect to the polymeric backbone (e.g., of a polymeric catalyst) or acidic moieties (e.g., of a solid-supported catalyst) directly attached to the solid support may can include, for example,

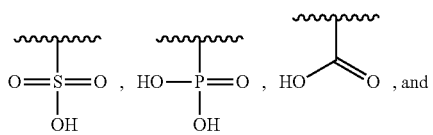, and

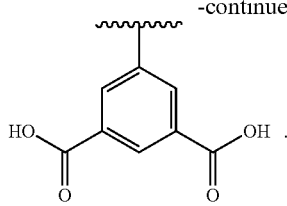

Ionic Monomers and Moieties

The polymeric catalysts include a plurality of ionic monomers, where as the solid-supported catalysts include a plurality of ionic moieties attached to a solid support.

In some embodiments, a plurality of ionic monomers (e.g., of a polymeric catalyst) or a plurality of ionic moieties (e.g., of a solid-supported catalyst) has at least one nitrogen-containing cationic group, at least one phosphorous-containing cationic group, or any combination thereof. In certain embodiments, a plurality of ionic monomers (e.g., of a polymeric catalyst) or a plurality of ionic moieties (e.g., of a solid-supported catalyst) has one nitrogen-containing cationic group or one phosphorous-containing cationic group. In some embodiments, a plurality of ionic monomers (e.g., of a polymeric catalyst) or a plurality of ionic moieties (e.g., of a solid-supported catalyst) has two nitrogen-containing cationic groups, two phosphorous-containing cationic group, or one nitrogen-containing cationic group and one phosphorous-containing cationic group. In other embodiments, a plurality of ionic monomers (e.g., of a polymeric catalyst) or a plurality of ionic moieties (e.g., of a solid-supported catalyst) has one nitrogen-containing cationic group or phosphorous-containing cationic group, while others have two nitrogen-containing cationic groups or phosphorous-containing cationic groups.

In some embodiments, a plurality of ionic monomers (e.g., of a polymeric catalyst) or a plurality of ionic moieties (e.g., of a solid-supported catalyst) can have one cationic group, or two or more cationic groups, as is chemically feasible. When the ionic monomers (e.g., of a polymeric catalyst) or ionic moieties (e.g., of a solid-supported catalyst) have two or more cationic groups, the cationic groups can be the same or different.

In some embodiments, each ionic monomer (e.g., of a polymeric catalyst) or each ionic moiety (e.g., of a solid-supported catalyst) is a nitrogen-containing cationic group. In other embodiments, each ionic monomer (e.g., of a polymeric catalyst) or each ionic moiety (e.g., of a solid-supported catalyst) is a phosphorous-containing cationic group. In yet other embodiments, at least some of ionic monomers (e.g., of a polymeric catalyst) or at least some of the ionic moieties (e.g., of a solid-supported catalyst) are a nitrogen-containing cationic group, whereas the cationic groups in other ionic monomers (e.g., of a polymeric catalyst) or ionic moieties (e.g., of a solid-supported catalyst) are a phosphorous-containing cationic group. In an exemplary embodiment, each cationic group in the polymeric catalyst or solid-supported catalyst is imidazolium. In another exemplary embodiment, the cationic group in some monomers (e.g., of a polymeric catalyst) or moieties (e.g., of a solid-supported catalyst) is imidazolium, while the cationic group in other monomers (e.g., of a polymeric catalyst) or moieties (e.g., of a solid-supported catalyst) is pyridinium. In yet another exemplary embodiment, each cationic group in the polymeric catalyst or solid-supported catalyst is a substituted phosphonium. In yet another exemplary embodiment, the cationic group in some monomers (e.g., of a polymeric catalyst) or moieties (e.g., of a solid-supported catalyst) is triphenyl phosphonium, while the cationic group in other monomers (e.g., of a polymeric catalyst) or moieties (e.g., of a solid-supported catalyst) is imidazolium.

In some embodiments, the nitrogen-containing cationic group at each occurrence can be independently selected from pyrrolium, imidazolium, pyrazolium, oxazolium, thiazolium, pyridinium, pyrimidinium, pyrazinium, pyridazinium, thiazinium, morpholinium, piperidinium, piperizinium, and pyrollizinium. In other embodiments, the nitrogen-containing cationic group at each occurrence can be independently selected from imidazolium, pyridinium, pyrimidinium, morpholinium, piperidinium, and piperizinium. In some embodiments, the nitrogen-containing cationic group can be imidazolium.

In some embodiments, the phosphorous-containing cationic group at each occurrence can be independently selected from triphenyl phosphonium, trimethyl phosphonium, triethyl phosphonium, tripropyl phosphonium, tributyl phosphonium, trichloro phosphonium, and trifluoro phosphonium. In other embodiments, the phosphorous-containing cationic group at each occurrence can be independently selected from triphenyl phosphonium, trimethyl phosphonium, and triethyl phosphonium. In other embodiments, the phosphorous-containing cationic group can be triphenyl phosphonium.

In some embodiments, one or more of the ionic monomers of a polymeric catalyst are directly connected to the polymeric backbone, or one or more of the ionic moieties of a solid-supported catalyst are directly connected to the solid support. In other embodiments, one or more of the ionic monomers (e.g., of a polymeric catalyst) or one or more ionic moieties (e.g., of a solid-supported catalyst) each independently further includes a linker connecting the cationic group to the polymeric backbone or the solid support (as the case may be). In certain embodiments, some of the cationic groups are directly connected to the polymeric backbone or the solid support (as the case may be), while other the cationic groups are connected to the polymeric backbone or the solid support (as the case may be) by a linker.

In those embodiments where the cationic group is connected to the polymeric backbone or the solid support (as the case may be) by a linker, each linker is independently selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker. In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

In other embodiments, each linker in an ionic monomer (e.g., of a polymeric catalyst) or an ionic moiety (e.g., of a solid-supported catalyst) is independently selected from:
  unsubstituted alkyl linker;
  alkyl linker substituted 1 to 5 substituents independently selected from oxo, hydroxy, halo, amino;
  unsubstituted cycloalkyl linker;
  cycloalkyl linker substituted 1 to 5 substituents independently selected from oxo, hydroxy, halo, amino;
  unsubstituted alkenyl linker;
  alkenyl linker substituted 1 to 5 substituents independently selected from oxo, hydroxy, halo, amino;
  unsubstituted aryl linker;

aryl linker substituted 1 to 5 substituents independently selected from oxo, hydroxy, halo, amino;

unsubstituted heteroaryl linker; or heteroaryl linker substituted 1 to 5 substituents independently selected from oxo, hydroxy, halo, amino.

Further, it should be understood that some or all of the ionic monomers (e.g., of a polymeric catalyst) or one or more ionic moieties (e.g., of a solid-supported catalyst) connected to the polymeric backbone by a linker may have the same linker, or independently have different linkers.

In some embodiments, each ionic monomer (e.g., of a polymeric catalyst) or each ionic moiety (e.g., of a solid-supported catalyst) is independently has the structure of Formulas VIIA-XIB:

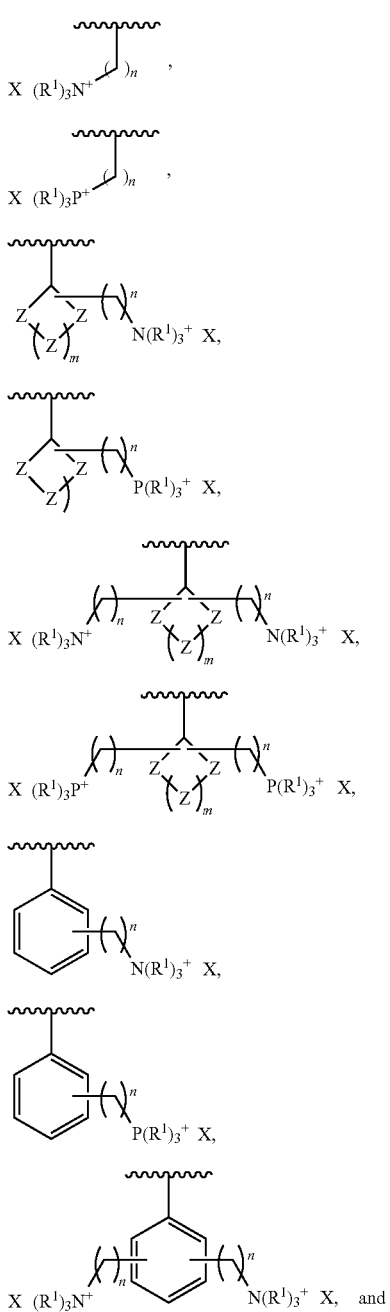

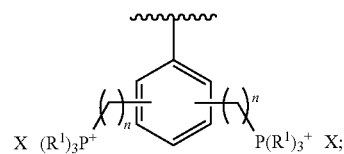

wherein:

each Z is independently $C(R^2)(R^3)$, $N(R^4)$, S, $S(R^5)(R^6)$, $S(O)(R^5)(R^6)$, $SO_2$, or O, wherein any two adjacent Z can (to the extent chemically feasible) be joined by a double bond, or taken together to form cycloalkyl, heterocycloalkyl, aryl or heteroaryl;

each X is independently $F^-$, $Cl^-$, $Br^-$, $I^-$, $NO_2$, $NO_3^-$, $SO_4^{2-}$, $R^7SO_4^-$, $R^7CO_2^-$, $PO_4^{2-}$, $R^7PO_3$, or $R^7PO_2^-$, where $SO_4^{2-}$ and $PO_4^{2-}$ are each independently associated with at least two cationic groups at any X position on any ionic monomer, and each m is independently 0, 1, 2, or 3;

each n is independently 0, 1, 2, or 3;

each $R^1$, $R^2$, $R^3$ and $R^4$ is independently hydrogen, alkyl, heteroalkyl, cycloalkyl, heterocyclyl, aryl, or heteroaryl;

each $R^5$ and $R^6$ is independently alkyl, heteroalkyl, cycloalkyl, heterocyclyl, aryl, or heteroaryl; and each $R^7$ is independently hydrogen, $C_{1-4}$alkyl, or $C_{1-4}$heteroalkyl.

In some embodiments, Z can be chosen from $C(R^2)(R^3)$, $N(R^4)$, $SO_2$, and O. In some embodiments, any two adjacent Z can be taken together to form a group selected from a heterocycloalkyl, aryl and heteroaryl. In other embodiments, any two adjacent Z can be joined by a double bond. In some embodiments, each X can be $Cl^-$, $NO_3^-$, $SO_4^{2-}$, $R^7SO_4^-$, or $R^7CO_2^-$, where $R^7$ can be hydrogen or $C_{1-4}$alkyl. In another embodiment, each X can be $Cl^-$, $Br^-$, $I^-$, $HSO_4^-$, $HCO_2^-$, $CH_3CO_2^-$, or $NO_3^-$. In other embodiments, X is acetate. In other embodiments, X is bisulfate. In other embodiments, X is chloride. In other embodiments, X is nitrate.

In some embodiments, m is 2 or 3. In other embodiments, n is 1, 2, or 3. In some embodiments, each $R^2$, $R^3$, and $R^4$ can be independently hydrogen, alkyl, heterocyclyl, aryl, or heteroaryl. In other embodiments, each $R^2$, $R^3$ and $R^4$ can be independently heteroalkyl, cycloalkyl, heterocyclyl, or heteroaryl. In some embodiments, each $R^5$ and $R^6$ can be independently alkyl, heterocyclyl, aryl, or heteroaryl. In another embodiment, any two adjacent Z can be taken together to form cycloalkyl, heterocycloalkyl, aryl or heteroaryl.

In certain embodiments, the ionic monomers of the polymeric catalyst may have a side chain with a cationic group that is connected to the polymeric backbone by a linker. In certain embodiments, the ionic moieties of the solid-supported catalyst may have a cationic group that is attached to the solid support by a linker. Side chains (e.g., of a polymeric catalyst) or ionic moieties (e.g., of a solid-supported catalyst) with one or more cationic groups connected by a linker can include, for example,

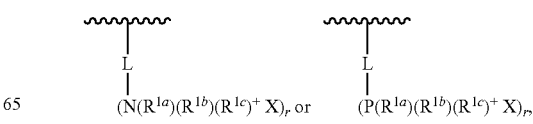

wherein:

L is an unsubstituted alkyl linker, alkyl linker substituted with oxo, unsubstituted cycloalkyl, unsubstituted aryl, unsubstituted heterocycloalkyl, and unsubstituted heteroaryl;

each $R^{1a}$, $R^{1b}$ and $R^{1c}$ are independently hydrogen or alkyl; or $R^{1a}$ and $R^{1b}$ are taken together with the nitrogen atom to which they are attached to form an unsubstituted heterocycloalkyl; or $R^{1a}$ and $R^{1b}$ are taken together with the nitrogen atom to which they are attached to form an unsubstituted heteroaryl or substituted heteroaryl, and $R^{1c}$ is absent;

r is an integer; and

X is as described above for Formulas VIIA-XIB.

In other embodiments L is methyl, ethyl, propyl, butyl. In yet other embodiments, the linker is ethanoyl, propanoyl, benzoyl. In certain embodiments, r is 1, 2, 3, 4, or 5 (as applicable or chemically feasible).

In other embodiments, each linker is independently selected from: unsubstituted alkyl linker;

alkyl linker substituted 1 to 5 substituents independently selected from oxo, hydroxy, halo, amino;

unsubstituted cycloalkyl linker;

cycloalkyl linker substituted 1 to 5 substituents independently selected from oxo, hydroxy, halo, amino;

unsubstituted alkenyl linker;

alkenyl linker substituted 1 to 5 substituents independently selected from oxo, hydroxy, halo, amino;

unsubstituted aryl linker;

aryl linker substituted 1 to 5 substituents independently selected from oxo, hydroxy, halo, amino;

unsubstituted heteroaryl linker; or heteroaryl linker substituted 1 to 5 substituents independently selected from oxo, hydroxy, halo, amino.

In certain embodiments, each linker is an unsubstituted alkyl linker or an alkyl linker with an oxo substituent. In one embodiment, each linker is —(CH$_2$)(CH$_2$)— or —(CH$_2$)(C=O). In certain embodiments, r is 1, 2, 3, 4, or 5 (as applicable or chemically feasible).

In some embodiments, at least some of the ionic side chains (e.g., of a polymeric catalyst) and at least some of the ionic moieties (e.g., of a solid-supported catalyst) may be:

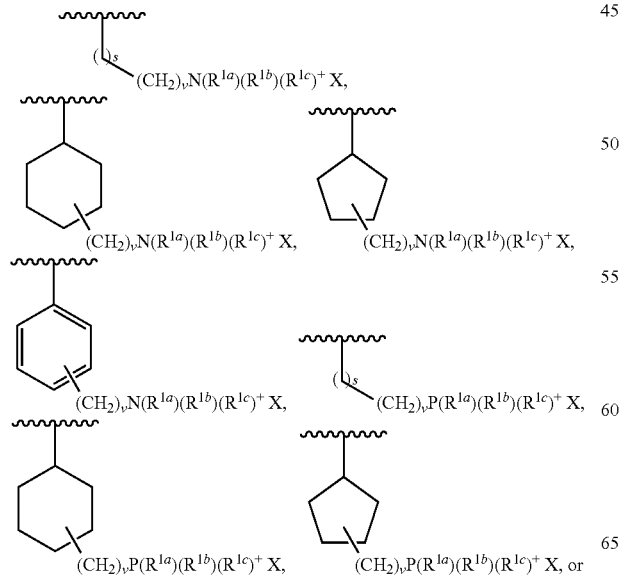

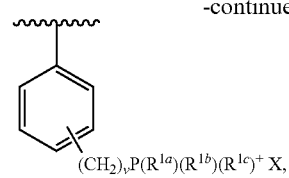

wherein:

each $R^{1a}$, $R^{1b}$ and $R^{1c}$ are independently hydrogen or alkyl; or $R^{1a}$ and $R^{1b}$ are taken together with the nitrogen atom to which they are attached to form an unsubstituted heterocycloalkyl; or $R^{1a}$ and $R^{1b}$ are taken together with the nitrogen atom to which they are attached to form an unsubstituted heteroaryl or substituted heteroaryl, and $R^{1c}$ is absent;

s is an integer;

v is 0 to 10; and

X is as described above for Formulas VIIA-XIB.

In certain embodiments, s is 1 to 9, or 1 to 8, or 1 to 7, or 1 to 6, or 1 to 5, or 1 to 4, or 1 to 3, or 2, or 1. In certain embodiments, v is 0 to 9, or 0 to 8, or 0 to 7, or 0 to 6, or 0 to 5, or 0 to 4, or 0 to 3, or 0 to 2, 1 or 0).

In certain embodiments, at least some of the ionic side chains (e.g., of a polymeric catalyst) and at least some of the ionic moieties (e.g., of a solid-supported catalyst) may be:

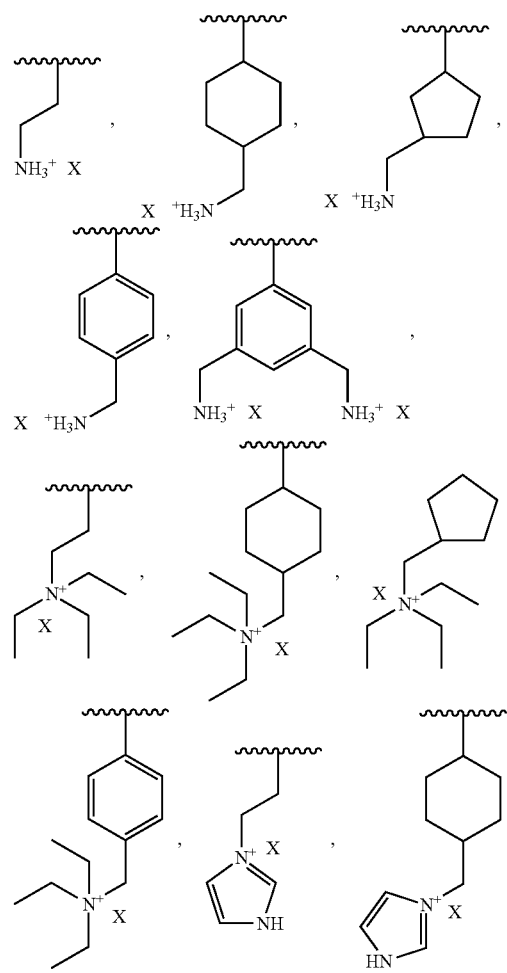

75
-continued
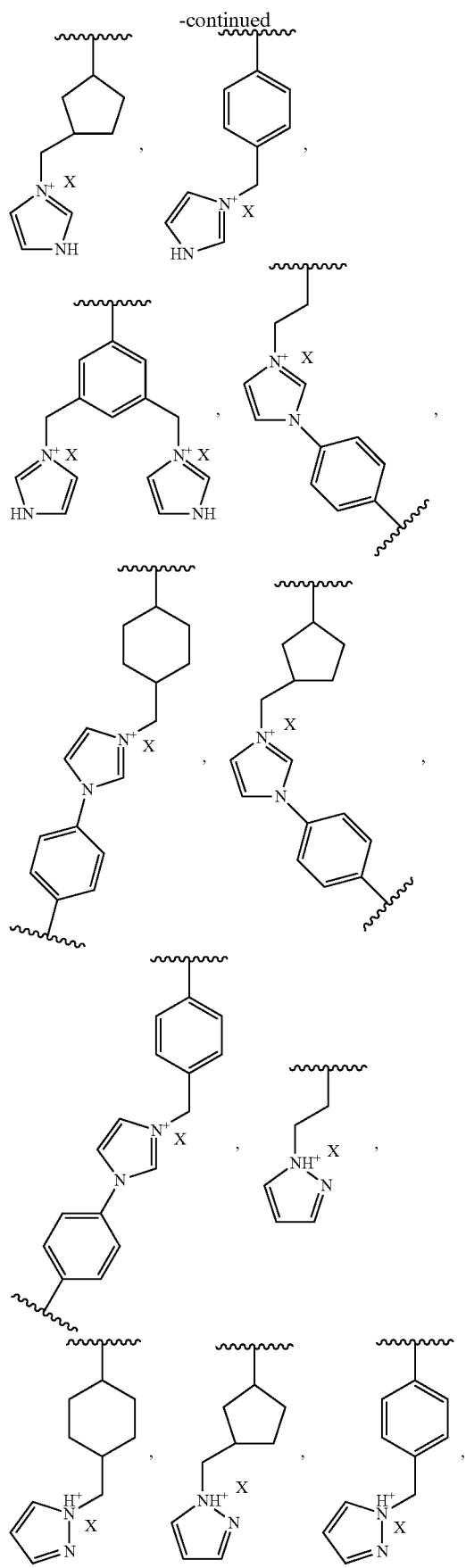
76
-continued
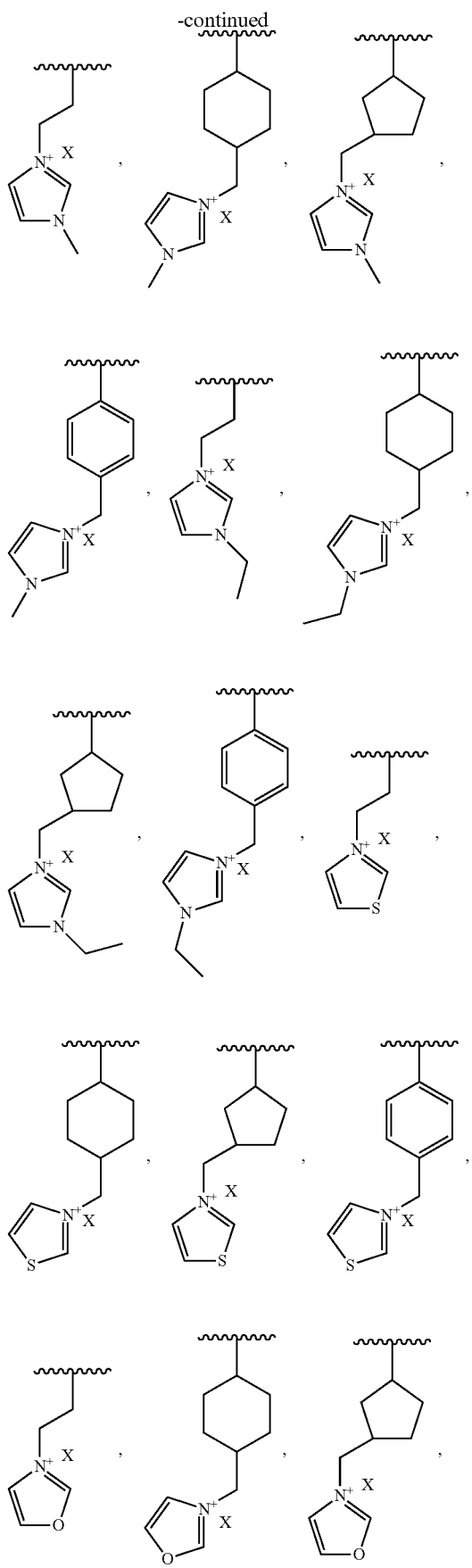

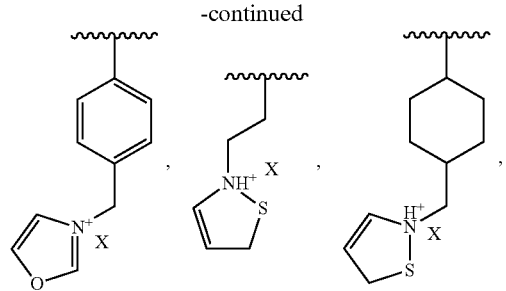
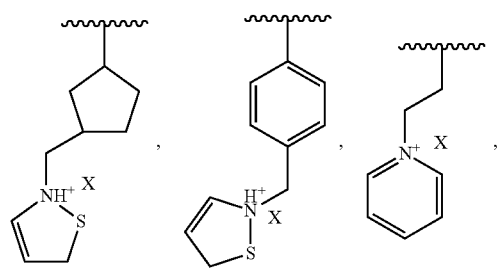
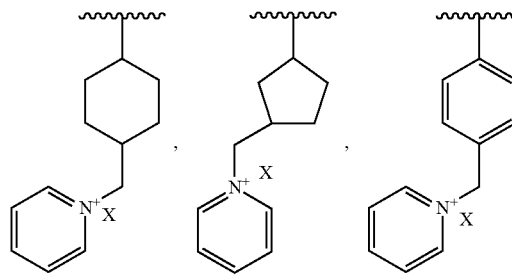
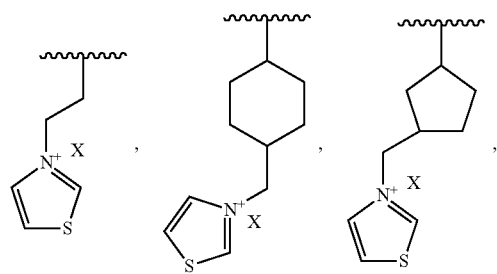
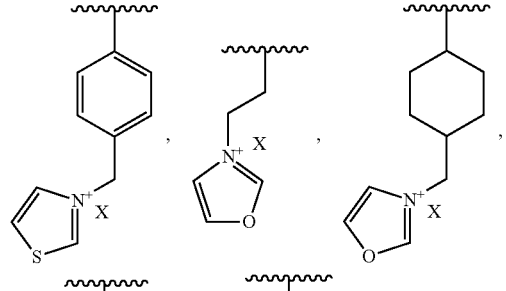
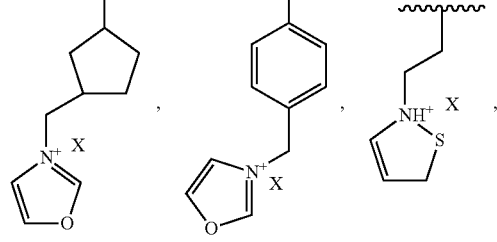
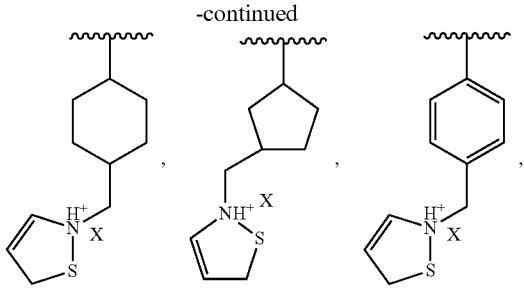
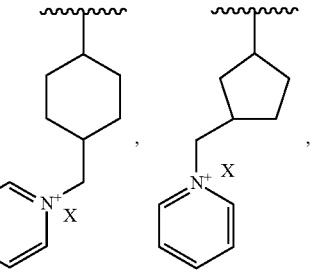
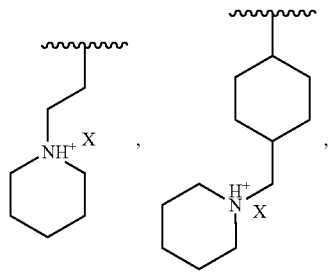
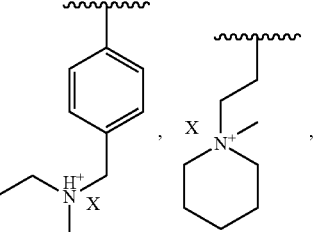
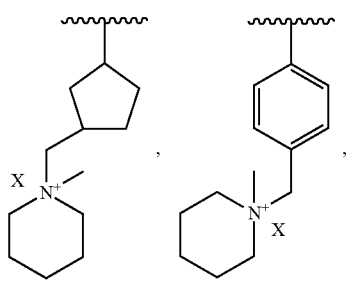
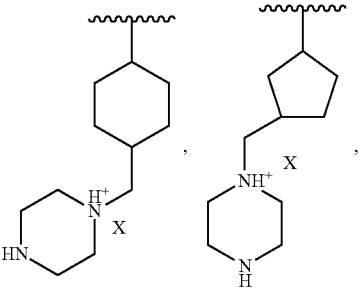

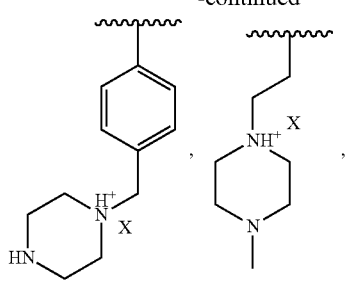
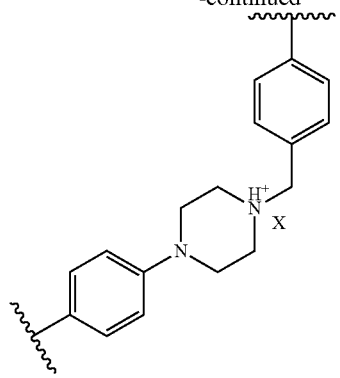
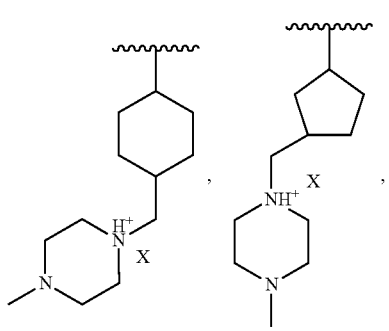
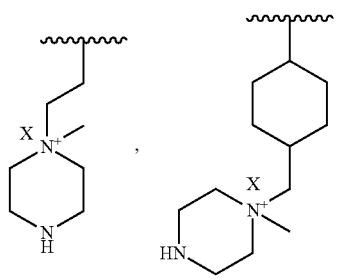
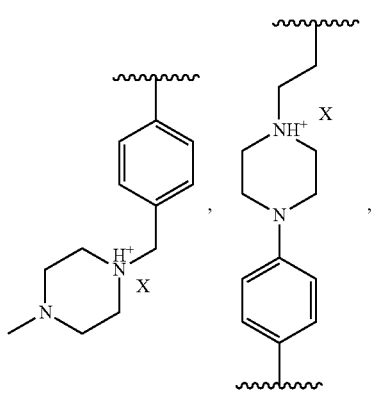
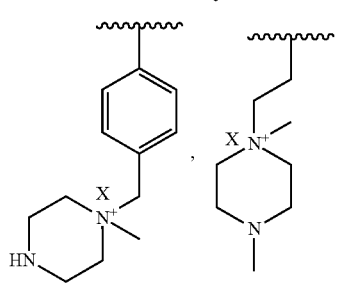
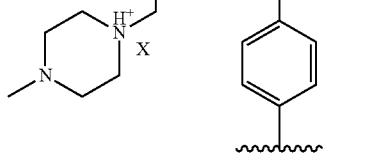
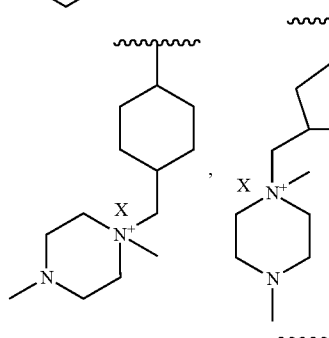
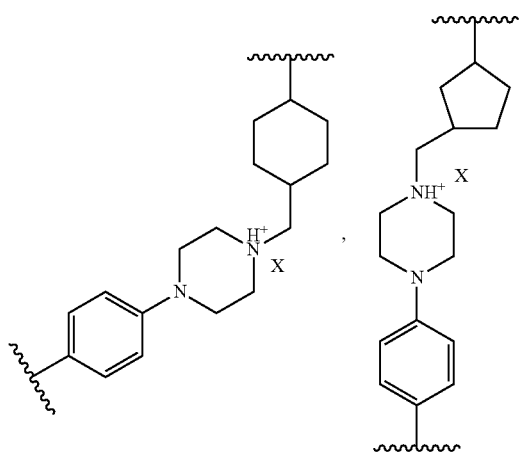
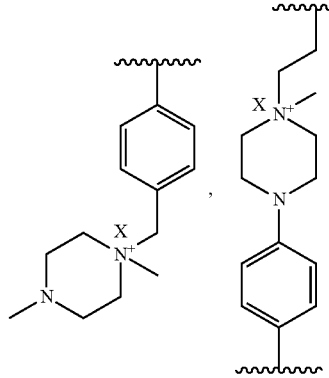

81
-continued
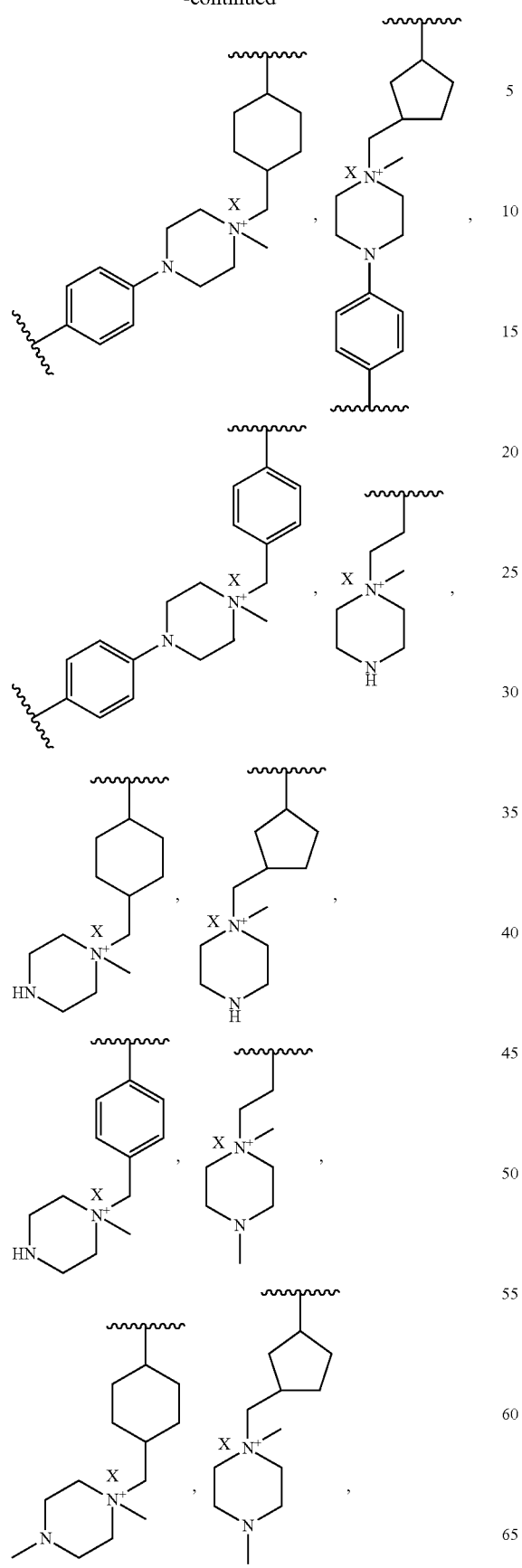
82
-continued
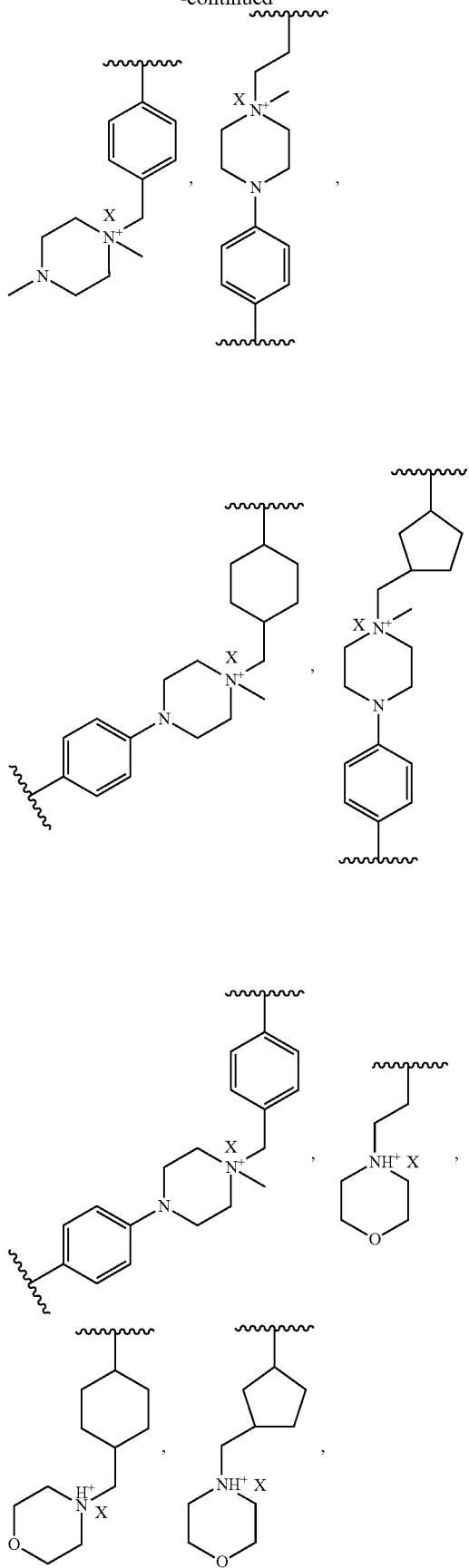

-continued
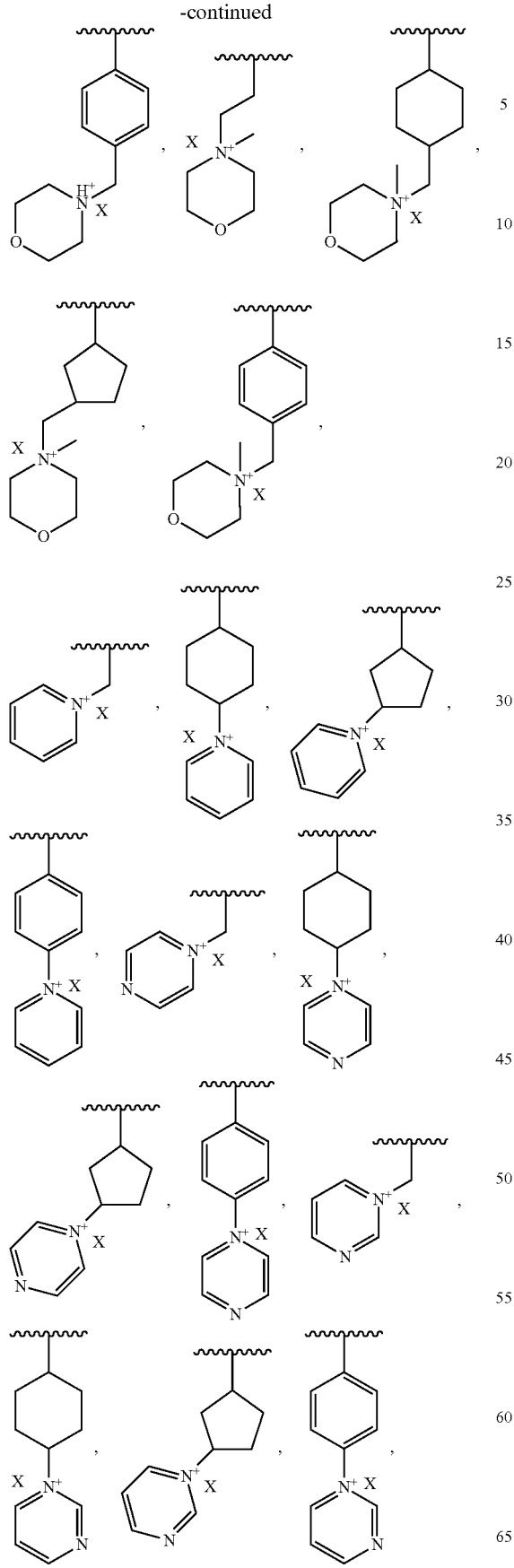
-continued
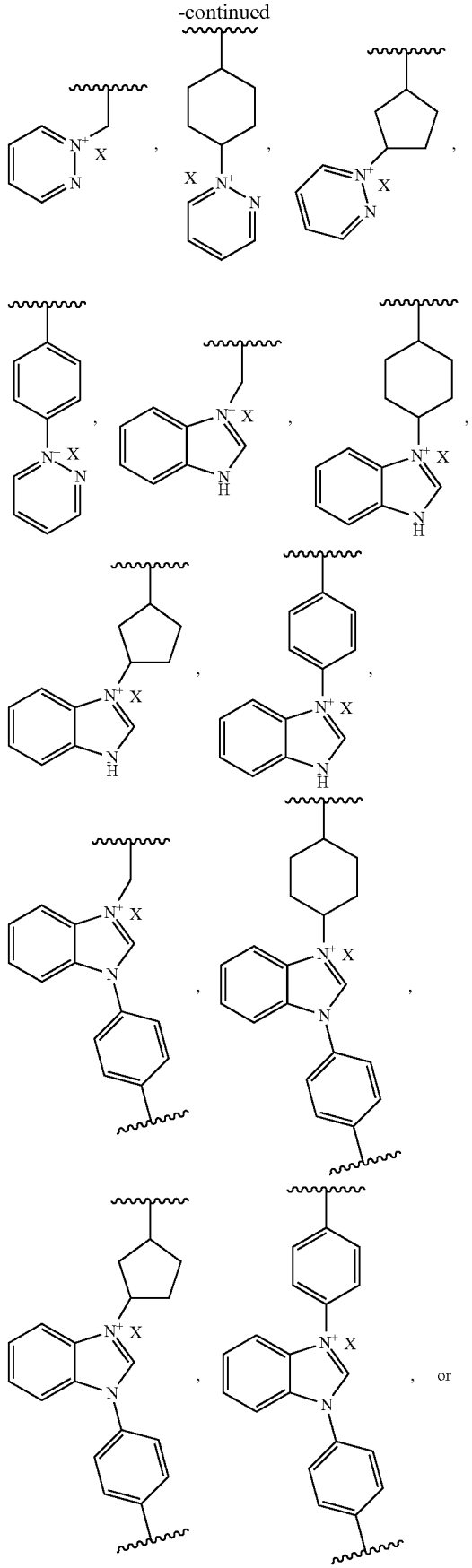

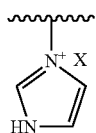

In other embodiments, the ionic monomers (e.g., of a polymeric catalyst) can have a side chain with a cationic group that is directly connected to the polymeric backbone. In other embodiments, the ionic moieties (e.g., of a solid-supported catalyst) can have a cationic group that is directly attached to the solid support. Side chains (e.g., of a polymeric catalyst) directly connect to the polymeric backbone or ionic moieties (e.g., of a solid-supported catalyst) directly attached to the solid support may can include, for example,

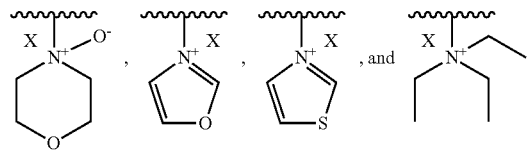

In some embodiments, the nitrogen-containing cationic group can be an N-oxide, where the negatively charged oxide (O—) is not readily dissociable from the nitrogen cation. Non-limiting examples of such groups include, for example,

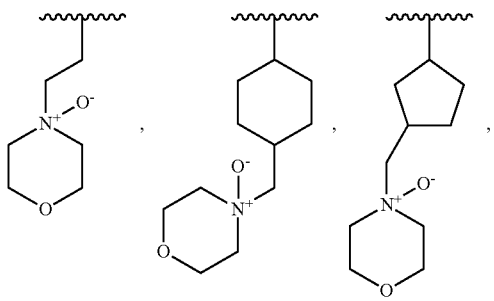

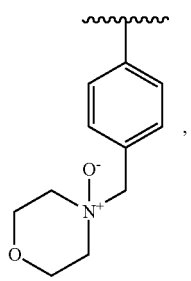

In some embodiments, the phosphorous-containing side chain (e.g., of a polymeric catalyst) or moiety (e.g., of a solid-supported catalyst) is independently:

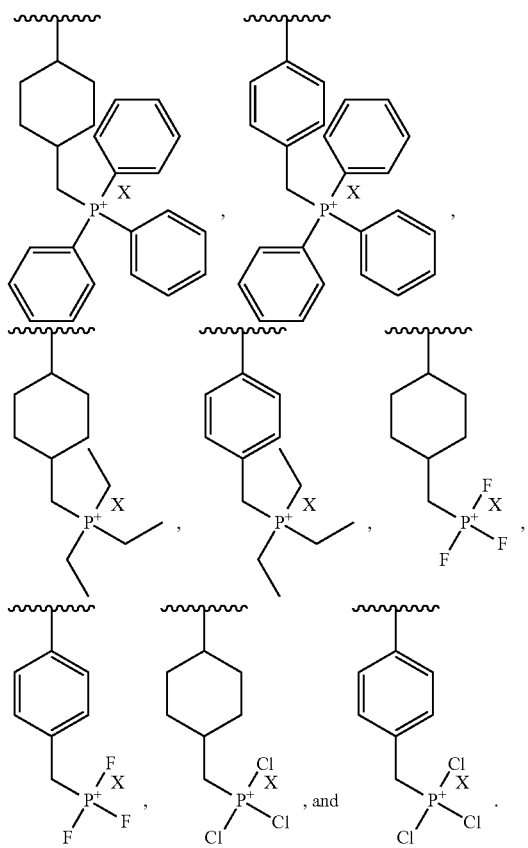

In other embodiments, the ionic monomers (e.g., of a polymeric catalyst) can have a side chain with a cationic group that is directly connected to the polymeric backbone. In other embodiments, the ionic moieties (e.g., of a solid-supported catalyst) can have a cationic group that is directly attached to the solid support. Side chains (e.g., of a polymeric catalyst) directly connect to the polymeric backbone or ionic moieties (e.g., of a solid-supported catalyst) directly attached to the solid support may can include, for example,

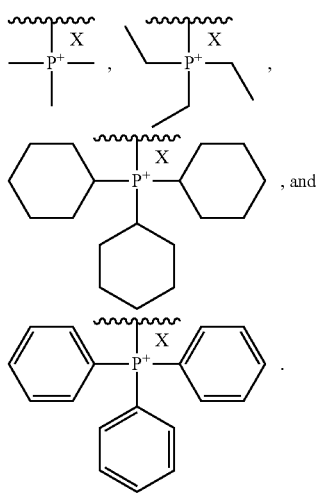

The ionic monomers (e.g., of a polymeric catalyst) or ionic moieties (e.g., of a solid-supported catalyst) can either all have the same cationic group, or can have different cationic groups. In some embodiments, each cationic group in the polymeric catalyst or solid-supported catalyst is a nitrogen-containing cationic group. In other embodiments, each cationic group in the polymeric catalyst or solid-supported catalyst is a phosphorous-containing cationic group. In yet other embodiments, the cationic group in some monomers or moieties of the polymeric catalyst or solid-supported catalyst, respectively, is a nitrogen-containing cationic group, whereas the cationic group in other monomers or moieties of the polymeric catalyst or solid-supported catalyst, respectively, is a phosphorous-containing cationic group. In an exemplary embodiment, each cationic group in the polymeric catalyst or solid-supported catalyst is imidazolium. In another exemplary embodiment, the cationic group in some monomers or moieties of the polymeric catalyst or solid-supported catalyst is imidazolium, while the cationic group in other monomers or moieties of the polymeric catalyst or solid-supported catalyst is pyridinium. In yet another exemplary embodiment, each cationic group in the polymeric catalyst or solid-supported catalyst is a substituted phosphonium. In yet another exemplary embodiment, the cationic group in some monomers or moieties of the polymeric catalyst or solid-supported catalyst is triphenyl phosphonium, while the cationic group in other monomers or moieties of the polymeric catalyst or solid-supported catalyst is imidazolium.

Acidic-Ionic Monomers and Moieties

Some of the monomers in the polymeric catalyst contain both the Bronsted-Lowry acid and the cationic group in the same monomer. Such monomers are referred to as "acidic-ionic monomers". Similarly, some of the moieties in the solid-supported catalyst contain both the Bronsted-Lowry acid and the cationic group in the same moieties. Such moieties are referred to as "acidic-ionic moieties". For example, in exemplary embodiments, the acidic-ionic monomer (e.g., of a polymeric catalyst) or an acidic-ionic moiety (e.g., of a solid-supported catalyst) can contain imidazolium and acetic acid, or pyridinium and boronic acid.

In some embodiments, the monomers (e.g., of a polymeric catalyst) or moieties (e.g., of a solid-supported catalyst) include both Bronsted-Lowry acid(s) and cationic group(s), where either the Bronsted-Lowry acid is connected to the polymeric backbone (e.g., of a polymeric catalyst) or solid support (e.g., of a solid-supported catalyst) by a linker, and/or the cationic group is connected to the polymeric backbone (e.g., of a polymeric catalyst) or is attached to the solid support (e.g., of a solid-supported catalyst) by a linker.

It should be understood that any of the Bronsted-Lowry acids, cationic groups and linkers (if present) suitable for the acidic monomers/moieties and/or ionic monomers/moieties may be used in the acidic-ionic monomers/moieties.

In certain embodiments, the Bronsted-Lowry acid at each occurrence in the acidic-ionic monomer (e.g., of a polymeric catalyst) or the acidic-ionic moiety (e.g., of a solid-supported catalyst) is independently selected from sulfonic acid, phosphonic acid, acetic acid, isophthalic acid, and boronic acid. In certain embodiments, the Bronsted-Lowry acid at each occurrence in the acidic-ionic monomer (e.g., of a polymeric catalyst) or the acidic-ionic moiety (e.g., of a solid-supported catalyst) is independently sulfonic acid or phosphonic acid. In one embodiment, the Bronsted-Lowry acid at each occurrence in the acidic-ionic monomer (e.g., of a polymeric catalyst) or the acidic-ionic moiety (e.g., of a solid-supported catalyst) is sulfonic acid.

In some embodiments, the nitrogen-containing cationic group at each occurrence in the acidic-ionic monomer (e.g., of a polymeric catalyst) or the acidic-ionic moiety (e.g., of a solid-supported catalyst) is independently selected from pyrrolium, imidazolium, pyrazolium, oxazolium, thiazolium, pyridinium, pyrimidinium, pyrazinium, pyridazinium, thiazinium, morpholinium, piperidinium, piperizinium, and pyrollizinium. In one embodiment, the nitrogen-containing cationic group is imidazolium.

In some embodiments, the phosphorous-containing cationic group at each occurrence in the acidic-ionic monomer (e.g., of a polymeric catalyst) or the acidic-ionic moiety (e.g., of a solid-supported catalyst) is independently selected from triphenyl phosphonium, trimethyl phosphonium, triethyl phosphonium, tripropyl phosphonium, tributyl phosphonium, trichloro phosphonium, and trifluoro phosphonium. In one embodiment, the phosphorous-containing cationic group is triphenyl phosphonium.

In some embodiments, the polymeric catalyst or solid-supported catalyst can include at least one acidic-ionic monomer or moiety, respectively, connected to the polymeric backbone or solid support, wherein at least one acidic-ionic monomer or moiety includes at least one Bronsted-Lowry acid and at least one cationic group, and wherein at least one of the acidic-ionic monomers or moieties includes a linker connecting the acidic-ionic monomer to the polymeric backbone or solid support. The cationic group can be a nitrogen-containing cationic group or a phosphorous-containing cationic group as described herein. The linker can also be as described herein for either the acidic or ionic moieties. For example, the linker can be selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker.

In other embodiments, the monomers (e.g., of a polymeric catalyst) or moieties (e.g., of a solid-supported catalyst) can have a side chain containing both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support.

In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

Monomers of a polymeric catalyst that have side chains containing both a Bronsted-Lowry acid and a cationic group can also be called "acidic ionomers". Acidic-ionic side chains (e.g., of a polymeric catalyst) or acidic-ionic moieties (e.g., of a solid-supported catalyst) that are connected by a linker can include, for example,

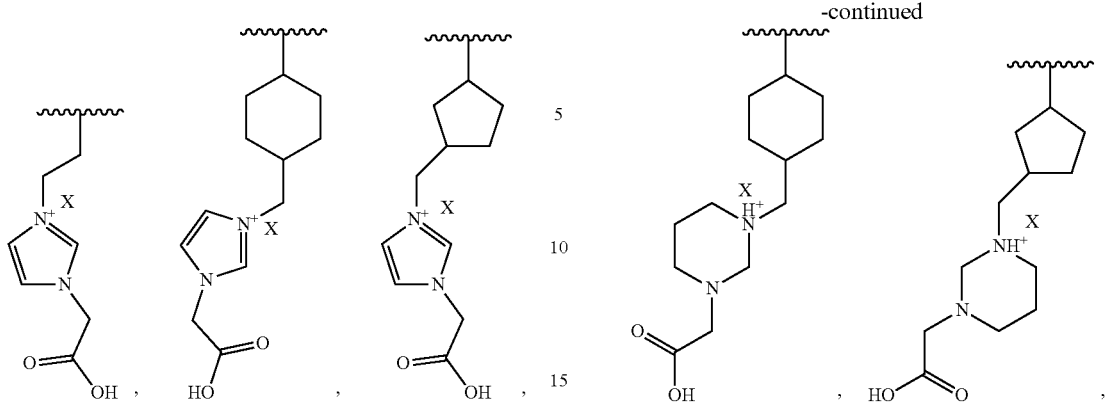
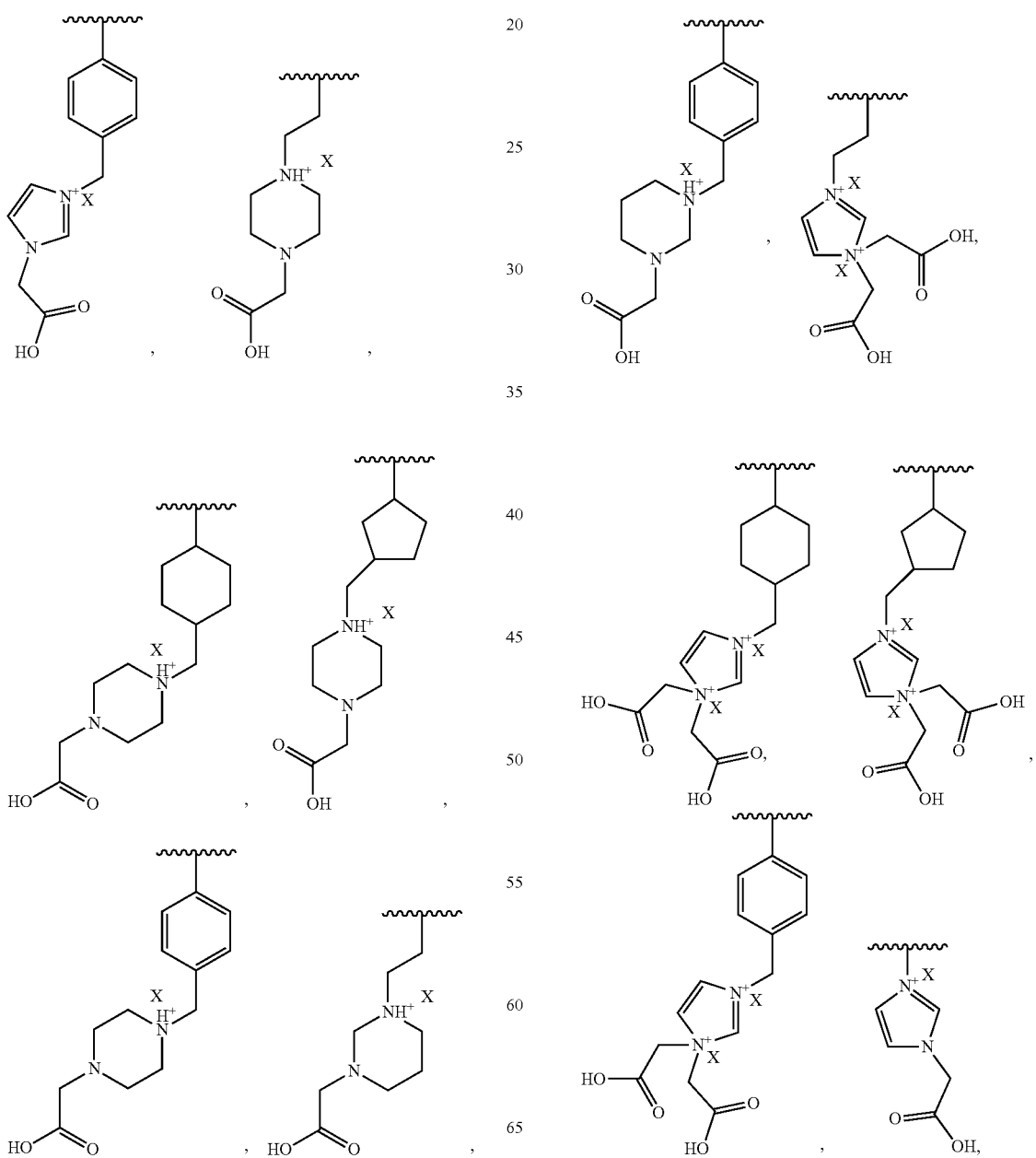

91
-continued
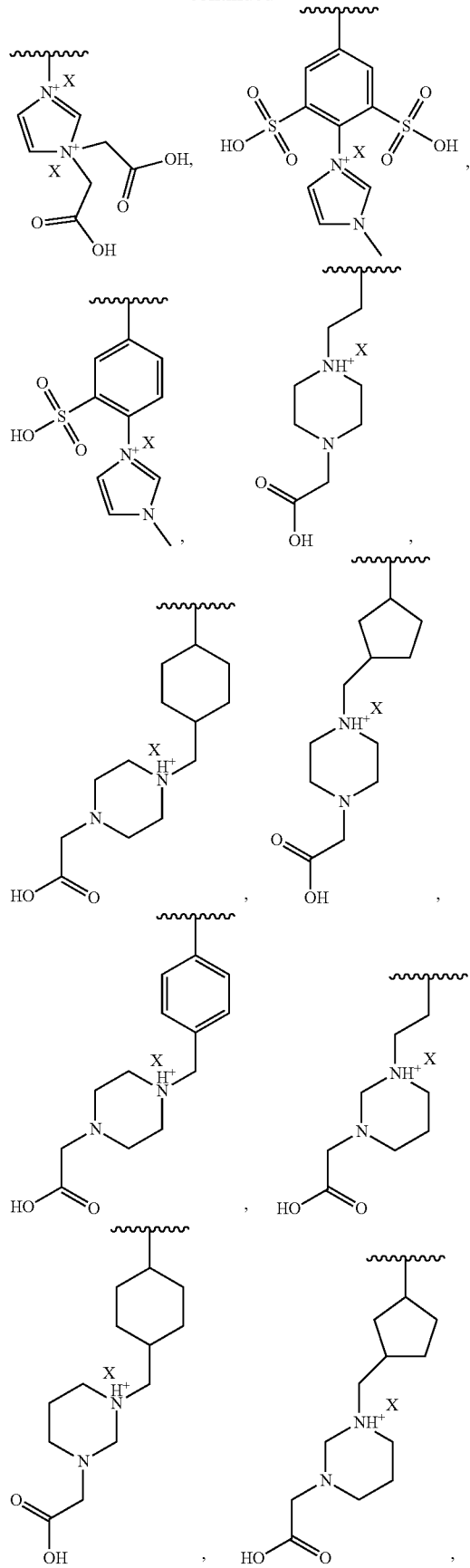
92
-continued
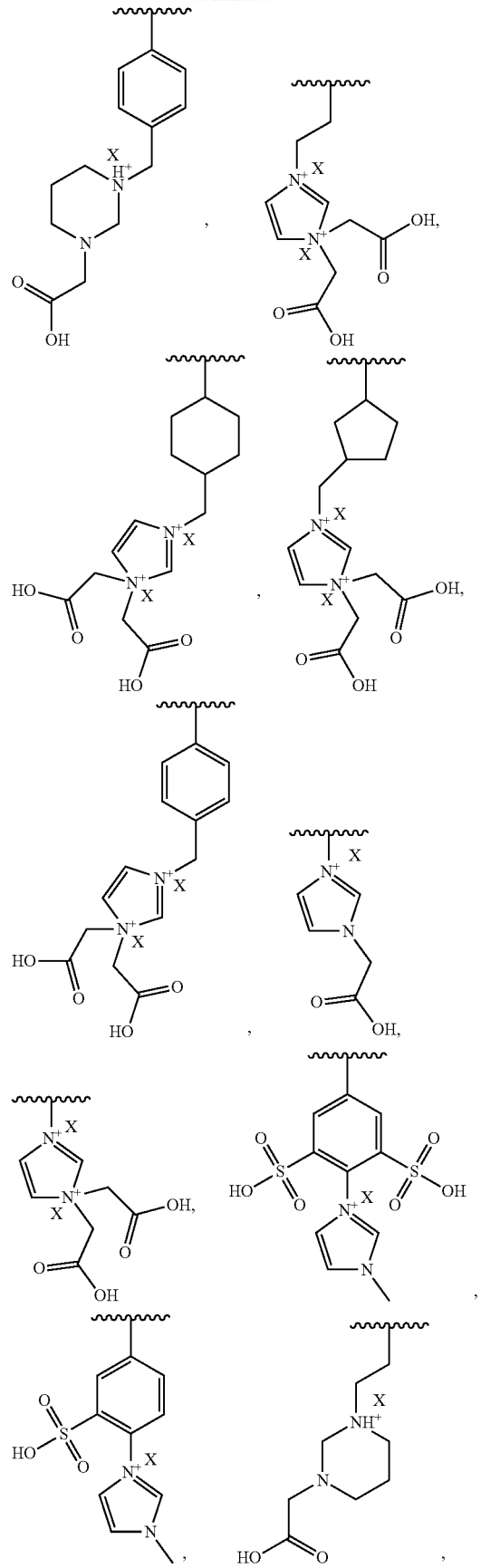

-continued

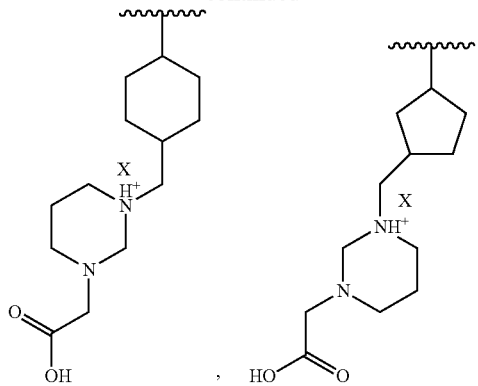

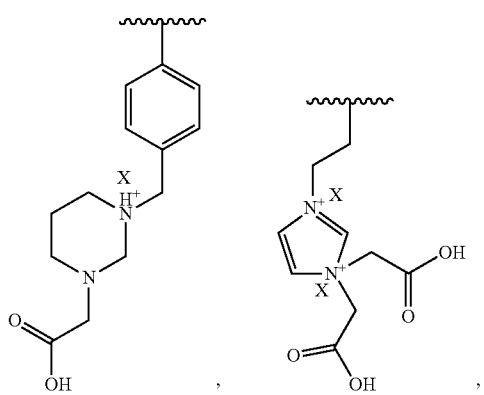

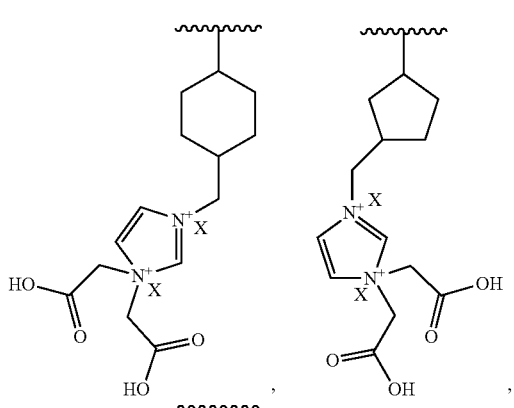

-continued

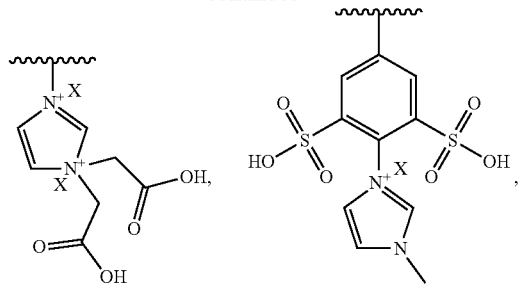

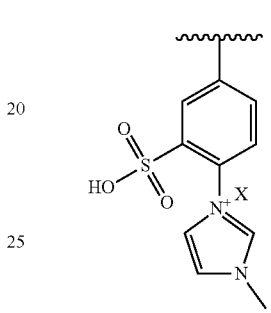

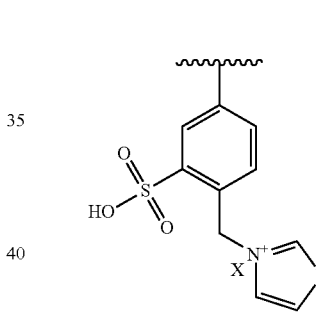

, and

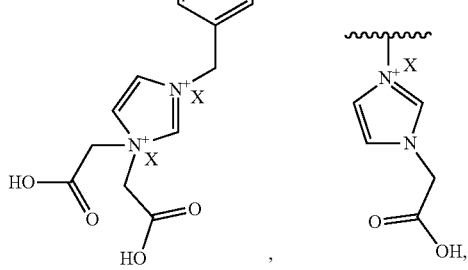

;

wherein:

each X is independently selected from $F^-$, $Cl^-$, $Br^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $SO_4^{2-}$ and $PO_4^{2-}$ are each independently associated with at least two Bronsted-Lowry acids at any X position on any side chain, and each $R^7$ is independently selected from hydrogen, $C_{1-4}$alkyl, and $C_{1-4}$heteroalkyl.

In some embodiments, $R^1$ can be selected from hydrogen, alkyl, and heteroalkyl. In some embodiments, $R^1$ can be selected from hydrogen, methyl, or ethyl. In some embodiments, each X can be selected from $Cl^-$, $NO_3^-$, $SO_4^{2-}$, $R^7SO_4^-$, and $R^7CO_2^-$, where $R^7$ can be selected from hydrogen and $C_{1-4}$alkyl. In another embodiment, each X can be selected from $Cl^-$, $Br^-$, $HSO_4^-$, $HCO_2^-$, $CH_3CO_2^-$, and $NO_3^-$. In other embodiments, X is acetate. In other embodiments, X is bisulfate. In other embodiments, X is chloride. In other embodiments, X is nitrate.

In some embodiments, the acidic-ionic side chain (e.g., of a polymeric catalyst) or the acidic-ionic moiety (e.g., of a solid-supported catalyst) is independently:

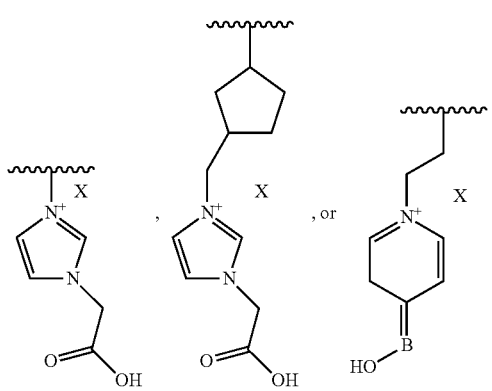

In some embodiments, the acidic-ionic side chain (e.g., of a polymeric catalyst) or the acidic-ionic moiety (e.g., of a solid-supported catalyst) is independently:

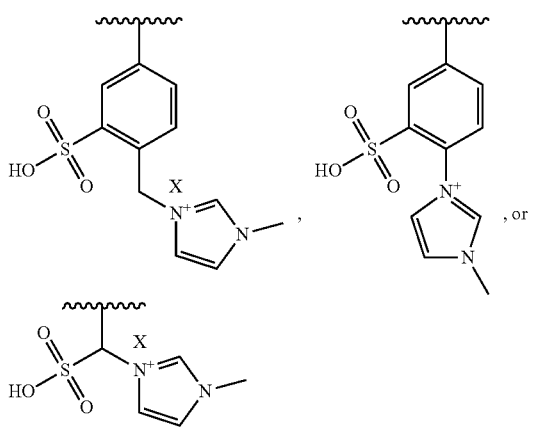

In other embodiments, the monomers (e.g., of a polymeric catalyst) or moieties (e.g., of a solid-supported catalyst) can have both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support. Such side chains in acidic-ionic monomers (e.g., of a polymeric catalyst) or moieties (e.g., of a solid-supported catalyst) can include, for example,

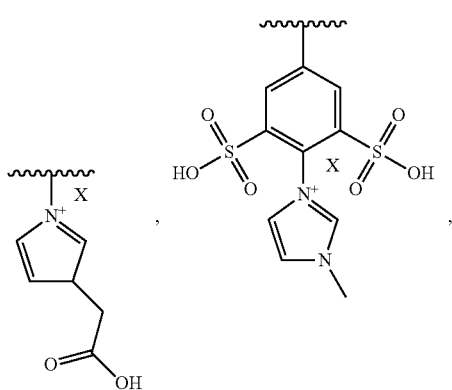

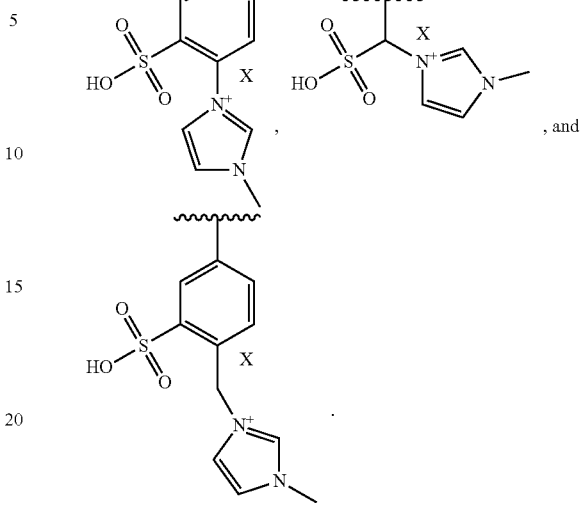

Hydrophobic Monomers and Moieties

In some embodiments, the polymeric catalyst further includes hydrophobic monomers connected to form the polymeric backbone. Similarly, in some embodiments, the solid-supported catalyst further includes hydrophobic moieties attached to the solid support. In either instance, each hydrophobic monomer or moiety has at least one hydrophobic group. In certain embodiments of the polymeric catalyst or solid-supported catalyst, each hydrophobic monomer or moiety, respectively, has one hydrophobic group. In certain embodiments of the polymeric catalyst or solid-supported catalyst, each hydrophobic monomer or moiety has two hydrophobic groups. In other embodiments of the polymeric catalyst or solid-supported catalyst, some of the hydrophobic monomers or moieties have one hydrophobic group, while others have two hydrophobic groups.

In some embodiments of the polymeric catalyst or solid-supported catalyst, each hydrophobic group is independently selected from an unsubstituted or substituted alkyl, an unsubstituted or substituted cycloalkyl, an unsubstituted or substituted aryl, and an unsubstituted or substituted heteroaryl. In certain embodiments of the polymeric catalyst or solid-supported catalyst, each hydrophobic group is an unsubstituted or substituted aryl, or an unsubstituted or substituted heteroaryl. In one embodiment, each hydrophobic group is phenyl. Further, it should be understood that the hydrophobic monomers may either all have the same hydrophobic group, or may have different hydrophobic groups.

In some embodiments of the polymeric catalyst, the hydrophobic group is directly connected to form the polymeric backbone. In some embodiments of the solid-supported catalyst, the hydrophobic group is directly attached to the solid support.

Other Characteristics of the Catalysts

In some embodiments, the acidic and ionic monomers make up a substantial portion of the polymeric catalyst. In some embodiments, the acidic and ionic moieties make up a substantial portion solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers or moieties of the catalyst, based on the ratio of the number of acidic and ionic monomers/moieties to the total number of monomers/moieties present in the catalyst.

In some embodiments, the polymeric catalyst or solid-supported catalyst has a total amount of Bronsted-Lowry acid of between about 0.1 and about 20 mmol, between about 0.1 and about 15 mmol, between about 0.01 and about 12 mmol, between about 0.05 and about 10 mmol, between about 1 and about 8 mmol, between about 2 and about 7 mmol, between about 3 and about 6 mmol, between about 1 and about 5, or between about 3 and about 5 mmol per gram of the polymeric catalyst or solid-supported catalyst.

In some embodiments of the polymeric catalyst or solid-supported catalyst, each ionic monomer further includes a counterion for each nitrogen-containing cationic group or phosphorous-containing cationic group. In certain embodiments of the polymeric catalyst or solid-supported catalyst, each counterion is independently selected from halide, nitrate, sulfate, formate, acetate, or organosulfonate. In some embodiments of the polymeric catalyst or solid-supported catalyst, the counterion is fluoride, chloride, bromide, or iodide. In one embodiment of the polymeric catalyst or solid-supported catalyst, the counterion is chloride. In another embodiment of the polymeric catalyst or solid-supported catalyst, the counterion is sulfate. In yet another embodiment of the polymeric catalyst or solid-supported catalyst, the counterion is acetate.

In some embodiments, the polymeric catalyst or solid-supported catalyst has a total amount of nitrogen-containing cationic groups and counterions or a total amount of phosphorous-containing cationic groups and counterions of between about 0.01 and about 10 mmol, between about 0.05 and about 10 mmol, between about 1 and about 8 mmol, between about 2 and about 6 mmol, or between about 3 and about 5 mmol per gram of the polymeric catalyst or solid-supported catalyst.

In some embodiments, the acidic and ionic monomers make up a substantial portion of the polymeric catalyst or solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers of the polymeric catalyst or solid-supported catalyst, based on the ratio of the number of acidic and ionic monomers or moieties to the total number of monomers or moieties present in the polymeric catalyst or solid-supported catalyst.

The ratio of the total number of acidic monomers or moieties to the total number of ionic monomers or moieties can be varied to tune the strength of the catalyst. In some embodiments, the total number of acidic monomers or moieties exceeds the total number of ionic monomers or moieties in the polymer or solid support. In other embodiments, the total number of acidic monomers or moieties is at least about 2, at least about 3, at least about 4, at least about 5, at least about 6, at least about 7, at least about 8, at least about 9 or at least about 10 times the total number of ionic monomers or moieties in the polymeric catalyst or solid-supported catalyst. In certain embodiments, the ratio of the total number of acidic monomers or moieties to the total number of ionic monomers or moieties is about 1:1, about 2:1, about 3:1, about 4:1, about 5:1, about 6:1, about 7:1, about 8:1, about 9:1 or about 10:1.

In some embodiments, the total number of ionic monomers or moieties exceeds the total number of acidic monomers or moieties in the catalyst. In other embodiments, the total number of ionic monomers or moieties is at least about 2, at least about 3, at least about 4, at least about 5, at least about 6, at least about 7, at least about 8, at least about 9 or at least about 10 times the total number of acidic monomers or moieties in the polymeric catalyst or solid-supported catalyst. In certain embodiments, the ratio of the total number of ionic monomers or moieties to the total number of acidic monomers or moieties is about 1:1, about 2:1, about 3:1, about 4:1, about 5:1, about 6:1, about 7:1, about 8:1, about 9:1 or about 10:1.

Arrangement of Monomers in Polymeric Catalysts

In some embodiments of the polymeric catalysts, the acidic monomers, the ionic monomers, the acidic-ionic monomers and the hydrophobic monomers, where present, can be arranged in alternating sequence or in a random order as blocks of monomers. In some embodiments, each block has not more than twenty, fifteen, ten, six, or three monomers.

Figure 9:
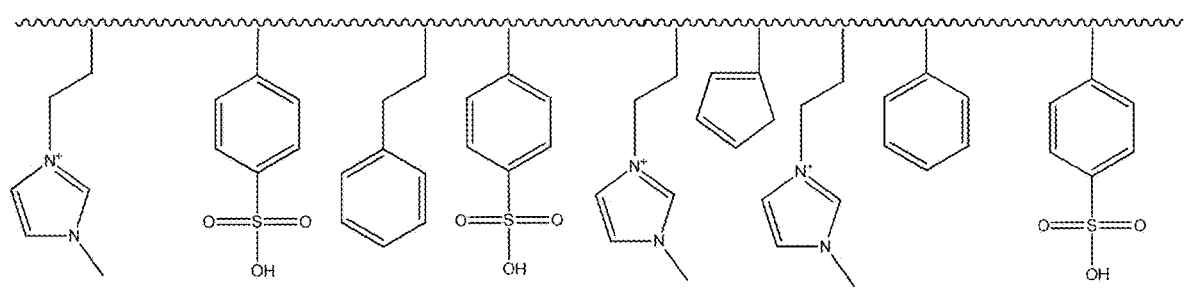
FIG. 9 illustrates a portion of a polymeric catalyst, in which the monomers are randomly arranged in an alternating sequence.

In some embodiments of the polymeric catalysts, the monomers of the polymeric catalyst are randomly arranged in an alternating sequence. With reference to the portion of the polymeric catalyst depicted in FIG. 9, the monomers are randomly arranged in an alternating sequence.

Figure 4:
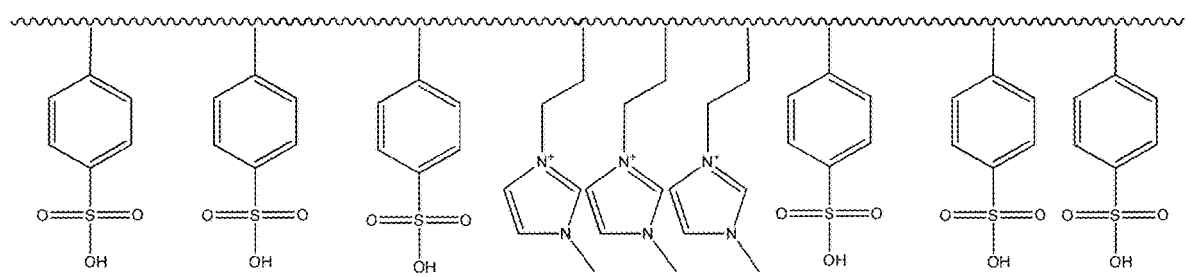
FIG. 4 illustrates a portion of a polymeric catalyst, in which the monomers are arranged in blocks of monomers, and the block of acidic monomers alternates with the block of ionic monomers.

In other embodiments of the polymeric catalysts, the monomers of the polymeric catalyst are randomly arranged as blocks of monomers. With reference to the portion of the polymeric catalyst depicted in FIG. 4, the monomers are arranged in blocks of monomers. In certain embodiments where the acidic monomers and the ionic monomers are arranged in blocks of monomers, each block has no more than 20, 19, 18, 17, 16, 15, 14, 13, 12, 11, 10, 9, 8, 7, 6, 5, 4, or 3 monomers.

The polymeric catalysts described herein can also be cross-linked. Such cross-linked polymeric catalysts can be prepared by introducing cross-linking groups. In some embodiments, cross-linking can occur within a given polymeric chain, with reference to the portion of the polymeric catalysts depicted in FIGS. 5A and 5B. In other embodiments, cross-linking can occur between two or more polymeric chains, with reference to the portion of the polymeric catalysts in FIGS. 6A, 6B, 6C and 6D.

With reference to FIGS. 5A, 5B and 6A, it should be understood that $R^1$, $R^2$ and $R^3$, respectively, are exemplary cross linking groups. Suitable cross-linking groups that can be used to form a cross-linked polymeric catalyst with the polymers described herein include, for example, substituted or unsubstituted divinyl alkanes, substituted or unsubstituted divinyl cycloalkanes, substituted or unsubstituted divinyl aryls, substituted or unsubstituted heteroaryls, dihaloalkanes, dihaloalkenes, and dihaloalkynes, where the substituents are those as defined herein. For example, cross-linking groups can include divinylbenzene, diallylbenzene, dichlorobenzene, divinylmethane, dichloromethane, divinylethane, dichloroethane, divinylpropane, dichloropropane, divinylbutane, dichlorobutane, ethylene glycol, and resorcinol. In one embodiment, the crosslinking group is divinyl benzene.

In some embodiments of the polymeric catalysts, the polymer is cross-linked. In certain embodiments, at least about 1%, at least about 2%, at least about 3%, at least about 4%, at least about 5%, at least about 6%, at least about 7%, at least about 8%, at least about 9%, at least about 10%, at least about 15%, at least about 20%, at least about 30%, at least about 40%, at least about 50%, at least about 60%, at least about 70%, at least about 80%, at least about 90% or at least about 99% of the polymer is cross-linked.

In some embodiments of the polymeric catalysts, the polymers described herein are not substantially cross-linked, such as less than about 0.9% cross-linked, less than about 0.5% cross-linked, less than about 0.1% cross-linked, less than about 0.01% cross-linked, or less than 0.001% cross-linked.

Polymeric Backbones

In some embodiments, the polymeric backbone is formed from one or more substituted or unsubstituted monomers. Polymerization processes using a wide variety of monomers are well known in the art (see, e.g., International Union of Pure and Applied Chemistry, et al., IUPAC Gold Book, *Polymerization*. (2000)). One such process involves monomer(s) with unsaturated substitution, such as vinyl, propenyl, butenyl, or other such substitutent(s). These types of monomers can undergo radical initiation and chain polymerization.

In some embodiments, the polymeric backbone is formed from one or more substituted or unsubstituted monomers selected from ethylene, propylene, hydroxyethylene, acetaldehyde, styrene, divinyl benzene, isocyanates, vinyl chloride, vinyl phenols, tetrafluoroethylene, butylene, terephthalic acid, caprolactam, acrylonitrile, butadiene, ammonias, diammonias, pyrrole, imidazole, pyrazole, oxazole, thiazole, pyridine, pyrimidine, pyrazine, pyridazine, thiazine, morpholine, piperidine, piperizines, pyrollizine, triphenylphosphonate, trimethylphosphonate, triethylphosphonate, tripropylphosphonate, tributylphosphonate, trichlorophosphonate, trifluorophosphonate, and diazole.

The polymeric backbone of the polymeric catalysts described herein can include, for example, polyalkylenes, polyalkenyl alcohols, polycarbonates, polyarylenes, polyaryletherketones, and polyamide-imides. In certain embodiments, the polymeric backbone can be selected from polyethylene, polypropylene, polyvinyl alcohol, polystyrene, polyurethane, polyvinyl chloride, polyphenol-aldehyde, polytetrafluoroethylene, polybutylene terephthalate, polycaprolactam, and poly(acrylonitrile butadiene styrene). In certain embodiments of the polymeric catalyst, the polymeric backbone is polyethyelene or polypropylene. In one embodiment of the polymeric catalyst, the polymeric backbone is polyethylene. In another embodiment of the polymeric catalyst, the polymeric backbone is polyvinyl alcohol. In yet another embodiment of the polymeric catalyst, the polymeric backbone is polystyrene.

Figure 8:
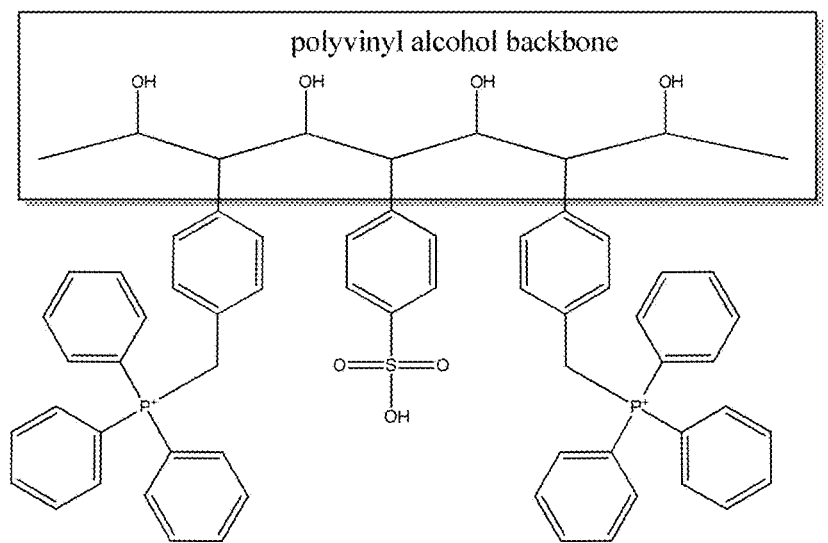
FIG. 8 illustrates a portion of a polymeric catalyst with a polyvinylalcohol backbone.

With reference to FIG. 7, in one embodiment, the polymeric backbone is polyethylene. With reference to FIG. 8, in another embodiment, the polymeric backbone is polyvinyl alcohol.

The polymeric backbone described herein can also include an ionic group integrated as part of the polymeric backbone. Such polymeric backbones can also be called "ionomeric backbones". In certain embodiments, the polymeric backbone can be selected from: polyalkyleneammonium, polyalkylenediammonium, polyalkylenepyrrolium, polyalkyleneimidazolium, polyalkylenepyrazolium, polyalkyleneoxazolium, polyalkylenethiazolium, polyalkylenepyridinium, polyalkylenepyrimidinium, polyalkylenepyrazinium, polyalkylenepyridazinium, polyalkylenethiazinium, polyalkylenemorpholinium, polyalkylenepiperidinium, polyalkylenepiperizinium, polyalkylenepyrollizinium, polyalkylenetriphenylphosphonium, polyalkylenetrimethylphosphonium, polyalkylenetriethylphosphonium, polyalkylenetripropylphosphonium, polyalkylenetributylphosphonium, polyalkylenetrichlorophosphonium, polyalkylenetrifluorophosphonium, and polyalkylenediazolium, polyarylalkyleneammonium, polyarylalkylenediammonium, polyarylalkylenepyrrolium, polyarylalkyleneimidazolium, polyarylalkylenepyrazolium, polyarylalkyleneoxazolium, polyarylalkylenethiazolium, polyarylalkylenepyridinium, polyarylalkylenepyrimidinium, polyarylalkylenepyrazinium, polyarylalkylenepyridazinium, polyarylalkylenethiazinium, polyarylalkylenemorpholinium, polyarylalkylenepiperidinium, polyarylalkylenepiperizinium, polyarylalkylenepyrollizinium, polyarylalkylenetriphenylphosphonium, polyarylalkylenetrimethylphosphonium, polyarylalkylenetriethylphosphonium, polyarylalkylenetripropylphosphonium, polyarylalkylenetributylphosphonium, polyarylalkylenetrichlorophosphonium, polyarylalkylenetrifluorophosphonium, and polyarylalkylenediazolium.

Cationic polymeric backbones can be associated with one or more anions, including for example $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$ where $R^7$ is selected from hydrogen, $C_{1-4}$alkyl, and $C_{1-4}$heteroalkyl. In one embodiment, each anion can be selected from $Cl^-$, $Br^-$, $I^-$, $HSO_4^-$, $HCO_2^-$, $CH_3CO_2^-$, and $NO_3^-$. In other embodiments, each anion is acetate. In other embodiments, each anion is bisulfate. In other embodiments, each anion is chloride. In other embodiments, X is nitrate.

In other embodiments of the polymeric catalysts, the polymeric backbone is alkyleneimidazolium, which refers to an alkylene moiety, in which one or more of the methylene units of the alkylene moiety has been replaced with imidazolium. In one embodiment, the polymeric backbone is selected from polyethyleneimidazolium, polyprolyeneimidazolium, and polybutyleneimidazolium. It should further be understood that, in other embodiments of the polymeric backbone, when a nitrogen-containing cationic group or a phosphorous-containing cationic group follows the term "alkylene", one or more of the methylene units of the alkylene moiety is substituted with that nitrogen-containing cationic group or phosphorous-containing cationic group.

In other embodiments, monomers having heteroatoms can be combined with one or more difunctionalized compounds, such as dihaloalkanes, di(alkylsulfonyloxy)alkanes, and di(arylsulfonyloxy)alkanes to form polymers. The monomers have at least two heteroatoms to link with the difunctionalized alkane to create the polymeric chain. These difunctionalized compounds can be further substituted as described herein. In some embodiments, the difunctionalized compound(s) can be selected from 1,2-dichloroethane, 1,2-dichloropropane, 1,3-dichloropropane, 1,2-dichlorobutane, 1,3-dichlorobutane, 1,4-dichlorobutane, 1,2-dichloropentane, 1,3-dichloropentane, 1,4-dichloropentane, 1,5-dichloropentane, 1,2-dibromoethane, 1,2-dibromopropane, 1,3-dibromopropane, 1,2-dibromobutane, 1,3-dibromobutane, 1,4-dibromobutane, 1,2-dibromopentane, 1,3-dibromopentane, 1,4-dibromopentane, 1,5-dibromopentane, 1,2-diiodoethane, 1,2-diiodopropane, 1,3-diiodopropane, 1,2-diiodobutane, 1,3-diiodobutane, 1,4-diiodobutane, 1,2-diiodopentane, 1,3-diiodopentane, 1,4-diiodopentane, 1,5-diiodopentane, 1,2-dimethanesulfoxyethane, 1,2-dimethanesulfoxypropane, 1,3-dimethanesulfoxypropane, 1,2-dimethanesulfoxybutane, 1,3-dimethanesulfoxybutane, 1,4-dimethanesulfoxybutane, 1,2-dimethanesulfoxypentane, 1,3-dimethanesulfoxypentane, 1,4-dimethanesulfoxypentane, 1,5-dimethanesulfoxypentane, 1,2-diethanesulfoxyethane, 1,2-diethanesulfoxypropane, 1,3-diethanesulfoxypropane, 1,2-diethanesulfoxybutane, 1,3-diethanesulfoxybutane, 1,4-diethanesulfoxybutane, 1,2-diethanesulfoxypentane, 1,3-diethanesulfoxypentane, 1,4-diethanesulfoxypentane, 1,5-diethanesulfoxypentane, 1,2- dibenzenesulfoxyethane, 1,2-dibenzenesulfoxypropane, 1,3-dibenzenesulfoxypropane, 1,2-dibenzenesulfoxybutane, 1,3-dibenzenesulfoxybutane, 1,4-dibenzenesulfoxybutane, 1,2-dibenzenesulfoxypentane, 1,3-dibenzenesulfoxypentane, 1,4-dibenzenesulfoxypentane, 1,5-dibenzenesulfoxypentane, 1,2-di-p-toluenesulfoxyethane, 1,2-di-p-toluenesulfoxypropane, 1,3-di-p-toluenesulfoxypropane, 1,2-di-p-toluenesulfoxybutane, 1,3-di-p-toluenesulfoxybutane, 1,4-di-p-toluenesulfoxybutane, 1,2-di-p-toluenesulfoxypentane, 1,3-di-p-toluene sulfoxypentane, 1,4-di-p-toluene sulfoxypentane, and 1,5-di-p-toluene sulfoxypentane.

Further, the number of atoms between side chains in the polymeric backbone can vary. In some embodiments, there are between zero and twenty atoms, zero and ten atoms, zero and six atoms, or zero and three atoms between side chains attached to the polymeric backbone.

In some embodiments, the polymer can be a homopolymer having at least two monomer units, and where all the units contained within the polymer are derived from the same monomer in the same manner. In other embodiments, the polymer can be a heteropolymer having at least two monomer units, and where at least one monomeric unit contained within the polymer that differs from the other monomeric units in the polymer. The different monomer units in the polymer can be in a random order, in an alternating sequence of any length of a given monomer, or in blocks of monomers.

Other exemplary polymers include, for example, polyalkylene backbones that are substituted with one or more groups selected from hydroxyl, carboxylic acid, unsubstituted and substituted phenyl, halides, unsubstituted and substituted amines, unsubstituted and substituted ammonias, unsubstituted and substituted pyrroles, unsubstituted and substituted imidazoles, unsubstituted and substituted pyrazoles, unsubstituted and substituted oxazoles, unsubstituted and substituted thiazoles, unsubstituted and substituted pyridines, unsubstituted and substituted pyrimidines, unsubstituted and substituted pyrazines, unsubstituted and substituted pyridazines, unsubstituted and substituted thiazines, unsubstituted and substituted morpholines, unsubstituted and substituted piperidines, unsubstituted and substituted piperizines, unsubstituted and substituted pyrollizines, unsubstituted and substituted triphenylphosphonates, unsubstituted and substituted trimethylphosphonates, unsubstituted and substituted triethylphosphonates, unsubstituted and substituted tripropylphosphonates, unsubstituted and substituted tributylphosphonates, unsubstituted and substituted trichlorophosphonates, unsubstituted and substituted trifluorophosphonates, and unsubstituted and substituted diazoles.

For the polymers as described herein, multiple naming conventions are well recognized in the art. For instance, a polyethylene backbone with a direct bond to an unsubstituted phenyl group (—$CH_2$—CH(phenyl)-$CH_2$—CH(phenyl)-) is also known as polystyrene. Should that phenyl group be substituted with an ethenyl group, the polymer can be named a polydivinylbenzene (—$CH_2$—CH(4-vinylphenyl)-$CH_2$—CH(4-vinylphenyl)-). Further examples of heteropolymers may include those that are functionalized after polymerization.

One suitable example would be polystyrene-co-divinylbenzene: (—$CH_2$—CH(phenyl)-$CH_2$—CH(4-ethylenephenyl)-$CH_2$—CH(phenyl)-$CH_2$—CH(4-ethylenephenyl)-).
Here, the ethenyl functionality could be at the 2, 3, or 4 position on the phenyl ring.

Figure 12:
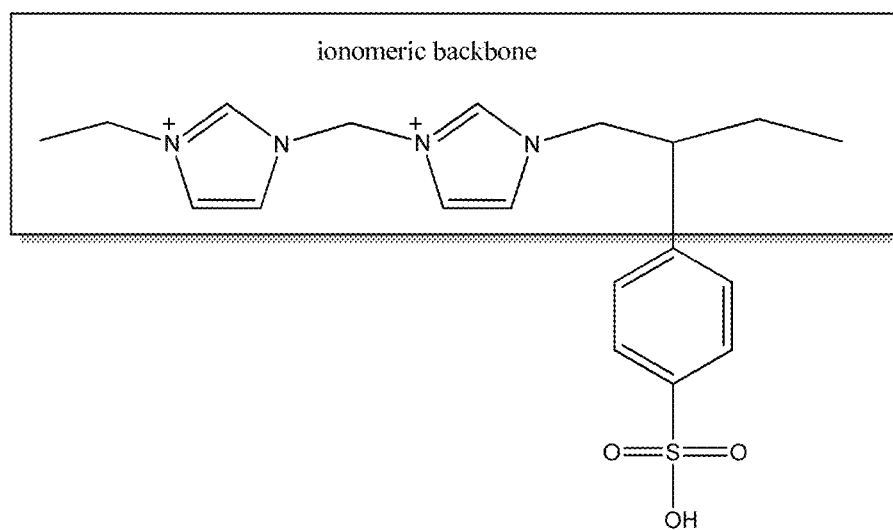
FIG. 12 illustrates a portion of a polymeric catalyst with an ionomeric backbone.

With reference to FIG. 12, in yet another embodiment, the polymeric backbone is a polyalkyleneimidazolium.

Figure 10:
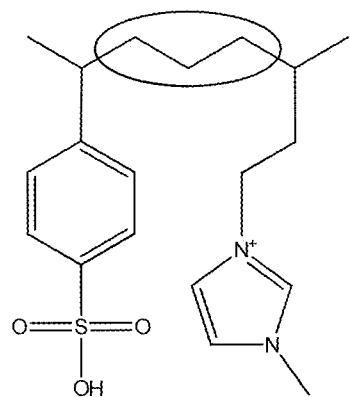
FIG. 10 illustrates two side chains in a polymeric catalyst, in which there are three carbon atoms between the side chain with the Bronsted-Lowry acid and the side chain with the cationic group.
Figure 11:
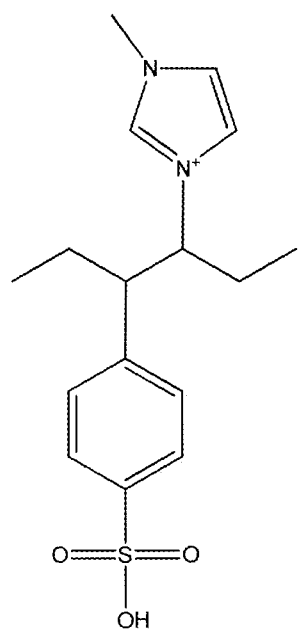
FIG. 11 illustrates two side chains in a polymeric catalyst, in which there are zero carbons between the side chain with the Bronsted-Lowry acid and the side chain with the cationic group.

Further, the number of atoms between side chains in the polymeric backbone can vary. In some embodiments, there are between zero and twenty atoms, zero and ten atoms, or zero and six atoms, or zero and three atoms between side chains attached to the polymeric backbone. With reference to FIG. 10, in one embodiment, there are three carbon atoms between the side chain with the Bronsted-Lowry acid and the side chain with the cationic group. In another example, with reference to FIG. 11, there are zero atoms between the side chain with the acidic moiety and the side chain with the ionic moiety.

Solid Particles for Polymeric Catalysts

The polymeric catalysts described herein can form solid particles. One of skill in the art would recognize the various known techniques and methods to make solid particles from the polymers described herein. For example, a solid particle can be formed through the procedures of emulsion or dispersion polymerization, which are known to one of skill in the art. In other embodiments, the solid particles can be formed by grinding or breaking the polymer into particles, which are also techniques and methods that are known to one of skill in the art. Methods known in the art to prepare solid particles include coating the polymers described herein on the surface of a solid core. Suitable materials for the solid core can include an inert material (e.g., aluminum oxide, corn cob, crushed glass, chipped plastic, pumice, silicon carbide, or walnut shell) or a magnetic material. Polymeric coated core particles can be made by dispersion polymerization to grow a cross-linked polymer shell around the core material, or by spray coating or melting.

Other methods known in the art to prepare solid particles include coating the polymers described herein on the surface of a solid core. The solid core can be a non-catalytic support. Suitable materials for the solid core can include an inert material (e.g., aluminum oxide, corn cob, crushed glass, chipped plastic, pumice, silicon carbide, or walnut shell) or a magnetic material. In one embodiment of the polymeric catalyst, the solid core is made up of iron. Polymeric coated core particles can be made by techniques and methods that are known to one of skill in the art, for example, by dispersion polymerization to grow a cross-linked polymer shell around the core material, or by spray coating or melting.

The solid supported polymer catalyst particle can have a solid core where the polymer is coated on the surface of the solid core. In some embodiments, at least about 5%, at least about 10%, at least about 20%, at least about 30%, at least about 40%, or at least about 50% of the catalytic activity of the solid particle can be present on or near the exterior surface of the solid particle. In some embodiments, the solid core can have an inert material or a magnetic material. In one embodiment, the solid core is made up of iron.

The solid particles coated with the polymer described herein have one or more catalytic properties. In some embodiments, at least about 50%, at least about 60%, at least about 70%, at least about 80% or at least about 90% of the catalytic activity of the solid particle is present on or near the exterior surface of the solid particle.

In some embodiments, the solid particle is substantially free of pores, for example, having no more than about 50%, no more than about 40%, no more than about 30%, no more than about 20%, no more than about 15%, no more than about 10%, no more than about 5%, or no more than about 1% of pores. Porosity can be measured by methods well known in the art, such as determining the Brunauer-Emmett-Teller (BET) surface area using the absorption of nitrogen gas on the internal and external surfaces of a material (Brunauer, S. et al., J. Am. Chem. Soc. 1938, 60:309). Other methods include measuring solvent retention by exposing the material to a suitable solvent (such as water), then removing it thermally to measure the volume of interior pores. Other solvents suitable for porosity measurement of the polymeric catalysts include, for example, polar solvents such as DMF, DMSO, acetone, and alcohols.

In other embodiments, the solid particles include a microporous gel resin. In yet other embodiments, the solid particles include a macroporous gel resin.

Support of the Solid-Supported Catalysts

In certain embodiments of the solid-supported catalyst, the support may be selected from biochar, carbon, amorphous carbon, activated carbon, silica, silica gel, alumina, magnesia, titania, zirconia, clays (e.g., kaolinite), magnesium silicate, silicon carbide, zeolites (e.g., mordenite), ceramics, and any combinations thereof. In one embodiment, the support is carbon. The support for carbon support can be biochar, amorphous carbon, or activated carbon. In one embodiment, the support is activated carbon.

The carbon support can have a surface area from 0.01 to 50 $m^2/g$ of dry material. The carbon support can have a density from 0.5 to 2.5 kg/L. The support can be characterized using any suitable instrumental analysis methods or techniques known in the art, including for example scanning electron microscopy (SEM), powder X-ray diffraction (XRD), Raman spectroscopy, and Fourier Transform infrared spectroscopy (FTIR). The carbon support can be prepared from carbonaceous materials, including for example, shrimp shell, chitin, coconut shell, wood pulp, paper pulp, cotton, cellulose, hard wood, soft wood, wheat straw, sugarcane bagasse, cassava stem, corn stover, oil palm residue, bitumen, asphaltum, tar, coal, pitch, and any combinations thereof. One of skill in the art would recognize suitable methods to prepare the carbon supports used herein. See e.g., M. Inagaki, L. R. Radovic, Carbon, vol. 40, p. 2263 (2002), or A. G. Pandolfo and A. F. Hollenkamp, "Review: Carbon Properties and their role in supercapacitors," *Journal of Power Sources, vol.* 157, pp. 11-27 (2006).

In other embodiments, the support is silica, silica gel, alumina, or silica-alumina. One of skill in the art would recognize suitable methods to prepare these silica- or alumina-based solid supports used herein. See e.g., Catalyst supports and supported catalysts, by A. B. Stiles, Butterworth Publishers, Stoneham Mass., 1987.

In yet other embodiments, the support is a combination of a carbon support, with one or more other supports selected from silica, silica gel, alumina, magnesia, titania, zirconia, clays (e.g., kaolinite), magnesium silicate, silicon carbide, zeolites (e.g., mordenite), and ceramics.

Definitions

"Bronsted-Lowry acid" refers to a molecule, or substituent thereof, in neutral or ionic form that is capable of donating a proton (hydrogen cation, $H^+$).

"Homopolymer" refers to a polymer having at least two monomer units, and where all the units contained within the polymer are derived from the same monomer. One suitable example is polyethylene, where ethylene monomers are linked to form a uniform repeating chain (—$CH_2$—$CH_2$—$CH_2$—). Another suitable example is polyvinyl chloride, having a structure (—$CH_2$—CHCl—$CH_2$—CHCl—) where the —$CH_2$—CHCl— repeating unit is derived from the $H_2C$=CHCl monomer.

"Heteropolymer" refers to a polymer having at least two monomer units, and where at least one monomeric unit differs from the other monomeric units in the polymer. Heteropolymer also refers to polymers having difunctionalized or trifunctionalized monomer units that can be incorporated in the polymer in different ways. The different monomer units in the polymer can be in a random order, in an alternating sequence of any length of a given monomer, or in blocks of monomers. One suitable example is polyethyleneimidazolium, where if in an alternating sequence, would be the polymer depicted in FIG. 12. Another suitable example is polystyrene-co-divinylbenzene, where if in an alternating sequence, could be (—$CH_2$—CH(phenyl)-$CH_2$—CH(4-ethylenephenyl)-$CH_2$—CH(phenyl)-$CH_2$—CH(4-ethylenephenyl)-). Here, the ethenyl functionality could be at the 2, 3, or 4 position on the phenyl ring.

As used herein, ∿∿∿ denotes the attachment point of a moiety to the parent structure.

When a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" includes saturated straight-chained or branched monovalent hydrocarbon radicals, which contain only C and H when unsubstituted. In some embodiments, alkyl as used herein may have 1 to 10 carbon atoms (e.g., $C_{1-10}$ alkyl), 1 to 6 carbon atoms (e.g., $C_{1-6}$ alkyl), or 1 to 3 carbon atoms (e.g., $C_{1-3}$ alkyl). Representative straight-chained alkyls include, for example, methyl, ethyl, n-propyl, n-butyl, n-pentyl, and n-hexyl. Representative branched alkyls include, for example, isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, and 2,3-dimethylbutyl. When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl, and iso-propyl.

"Alkoxy" refers to the group —O-alkyl, which is attached to the parent structure through an oxygen atom. Examples of alkoxy may include methoxy, ethoxy, propoxy, and iso-propoxy. In some embodiments, alkoxy as used herein has 1 to 6 carbon atoms (e.g., O—($C_{1-6}$ alkyl)), or 1 to 4 carbon atoms (e.g., O—($C_{1-4}$ alkyl)).

"Alkenyl" refers to straight-chained or branched monovalent hydrocarbon radicals, which contain only C and H when unsubstituted and at least one double bond. In some embodiments, alkenyl has 2 to 10 carbon atoms (e.g., $C_{2-10}$ alkenyl), or 2 to 5 carbon atoms (e.g., $C_{2-5}$ alkenyl). When an alkenyl residue having a specific number of carbons is named, all geometric isomers having that number of carbons are intended to be encompassed and described; thus, for example, "butenyl" is meant to include n-butenyl, sec-butenyl, and iso-butenyl. Examples of alkenyl may include —CH=$CH_2$, —$CH_2$—CH=$CH_2$ and —$CH_2$—CH=CH—CH=$CH_2$. The one or more carbon-carbon double bonds can be internal (such as in 2-butenyl) or terminal (such as in 1-butenyl). Examples of $C_{2-4}$ alkenyl groups include ethenyl (C2), 1-propenyl (C3), 2-propenyl (C3), 1-butenyl (C4), 2-butenyl (C4), and butadienyl (C4). Examples of $C_{2-6}$ alkenyl groups include the aforementioned $C_{2-4}$ alkenyl groups as well as pentenyl (C5), pentadienyl (C5), and hexenyl (C6). Additional examples of alkenyl include heptenyl (C7), octenyl (C8), and octatrienyl (C8).

"Alkynyl" refers to straight-chained or branched monovalent hydrocarbon radicals, which contain only C and H when unsubstituted and at least one triple bond. In some embodiments, alkynyl has 2 to 10 carbon atoms (e.g., $C_{2-10}$ alkynyl), or 2 to 5 carbon atoms (e.g., $C_{2-5}$ alkynyl). When an alkynyl residue having a specific number of carbons is named, all geometric isomers having that number of carbons are intended to be encompassed and described; thus, for example, "pentynyl" is meant to include n-pentynyl, sec-pentynyl, iso-pentynyl, and tert-pentynyl. Examples of alkynyl may include —C≡CH or —C≡C—CH$_3$.

In some embodiments, alkyl, alkoxy, alkenyl, and alkynyl at each occurrence may independently be unsubstituted or substituted by one or more of substituents. In certain embodiments, substituted alkyl, substituted alkoxy, substituted alkenyl, and substituted alkynyl at each occurrence may independently have 1 to 5 substituents, 1 to 3 substituents, 1 to 2 substituents, or 1 substituent. Examples of alkyl, alkoxy, alkenyl, and alkynyl substituents may include alkoxy, cycloalkyl, aryl, aryloxy, amino, amido, carbamate, carbonyl, oxo (=O), heteroalkyl (e.g., ether), heteroaryl, heterocycloalkyl, cyano, halo, haloalkoxy, haloalkyl, and thio. In certain embodiments, the one or more substituents of substituted alkyl, alkoxy, alkenyl, and alkynyl is independently selected from cycloalkyl, aryl, heteroalkyl (e.g., ether), heteroaryl, heterocycloalkyl, cyano, halo, haloalkoxy, haloalkyl, oxo, —OR$_a$, —N(R$_a$)$_2$, —C(O)N(R$_a$)$_2$, —N(R$_a$)C(O)R$_a$, —C(O)R$_a$, —N(ROS(O)$_t$R$_a$ (where t is 1 or 2), —SR$_a$, and —S(O)$_t$N(R$_a$)$_2$ (where t is 1 or 2). In certain embodiments, each R$_a$ is independently hydrogen, alkyl, alkenyl, alkynyl, haloalkyl, heteroalkyl, cycloalkyl, aryl, heterocycloalkyl, heteroaryl (e.g., bonded through a ring carbon), —C(O)R' and —S(O)$_t$R' (where t is 1 or 2), where each R' is independently hydrogen, alkyl, alkenyl, alkynyl, haloalkyl, heteroalkyl, cycloalkyl, aryl, heterocycloalkyl, or heteroaryl. In one embodiment, R$_a$ is independently hydrogen, alkyl, haloalkyl, cycloalkyl, aryl, aralkyl (e.g., alkyl substituted with aryl, bonded to parent structure through the alkyl group), heterocycloalkyl, or heteroaryl.

"Heteroalkyl", "heteroalkenyl" and "heteroalkynyl" includes alkyl, alkenyl and alkynyl groups, respectively, wherein one or more skeletal chain atoms are selected from an atom other than carbon, e.g., oxygen, nitrogen, sulfur, phosphorus, or any combinations thereof. For example, heteroalkyl may be an ether where at least one of the carbon atoms in the alkyl group is replaced with an oxygen atom. A numerical range can be given, e.g., $C_{1-4}$ heteroalkyl which refers to the chain length in total, which in this example is 4 atoms long. For example, a —CH$_2$OCH$_2$CH$_3$ group is referred to as a "$C_4$" heteroalkyl, which includes the heteroatom center in the atom chain length description. Connection to the rest of the parent structure can be through, in one embodiment, a heteroatom, or, in another embodiment, a carbon atom in the heteroalkyl chain. Heteroalkyl groups may include, for example, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy)methanyl (—CH$_2$OCH$_2$OCH$_3$) and (methoxyethoxy)methanyl (—CH$_2$OCH$_2$CH$_2$OCH$_3$); amines such as —CH$_2$CH$_2$NHCH$_3$, —CH$_2$CH$_2$N(CH$_3$)$_2$, —CH$_2$NHCH$_2$CH$_3$, and —CH$_2$N(CH$_2$CH$_3$)(CH$_3$). In some embodiments, heteroalkyl, heteroalkenyl, or heteroalkynyl may be unsubstituted or substituted by one or more of substituents. In certain embodiments, a substituted heteroalkyl, heteroalkenyl, or heteroalkynyl may have 1 to 5 substituents, 1 to 3 substituents, 1 to 2 substituents, or 1 substituent. Examples for heteroalkyl, heteroalkenyl, or heteroalkynyl substituents may include the substituents described above for alkyl.

"Carbocyclyl" may include cycloalkyl, cycloalkenyl or cycloalkynyl. "Cycloalkyl" refers to a monocyclic or polycyclic alkyl group. "Cycloalkenyl" refers to a monocyclic or polycyclic alkenyl group (e.g., containing at least one double bond). "Cycloalkynyl" refers to a monocyclic or polycyclic alkynyl group (e.g., containing at least one triple bond). The cycloalkyl, cycloalkenyl, or cycloalkynyl can consist of one ring, such as cyclohexyl, or multiple rings, such as adamantyl. A cycloalkyl, cycloalkenyl, or cycloalkynyl with more than one ring can be fused, spiro or bridged, or combinations thereof. In some embodiments, cycloalkyl, cycloalkenyl, and cycloalkynyl has 3 to 10 ring atoms (i.e., $C_3$-$C_{10}$ cycloalkyl, $C_3$-$C_{10}$ cycloalkenyl, and $C_3$-$C_{10}$ cycloalkynyl), 3 to 8 ring atoms (e.g., $C_3$-$C_8$ cycloalkyl, $C_3$-$C_8$ cycloalkenyl, and $C_3$-$C_8$ cycloalkynyl), or 3 to 5 ring atoms (i.e., $C_3$-$C_5$ cycloalkyl, $C_3$-$C_5$ cycloalkenyl, and $C_3$-$C_5$ cycloalkynyl). In certain embodiments, cycloalkyl, cycloalkenyl, or cycloalkynyl includes bridged and spiro-fused cyclic structures containing no heteroatoms. In other embodiments, cycloalkyl, cycloalkenyl, or cycloalkynyl includes monocyclic or fused-ring polycyclic (i.e., rings which share adjacent pairs of ring atoms) groups. $C_{3-6}$ carbocyclyl groups may include, for example, cyclopropyl ($C_3$), cyclobutyl ($C_4$), cyclopentyl ($C_5$), cyclopentenyl (C5), cyclohexyl ($C_6$), cyclohexenyl ($C_6$), and cyclohexadienyl ($C_6$). $C_{3-3}$ carbocyclyl groups may include, for example, the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, and bicyclo[2.2.2]octanyl. $C_{3-10}$ carbocyclyl groups may include, for example, the aforementioned $C_{3-3}$ carbocyclyl groups as well as octahydro-1H-indenyl, decahydronaphthalenyl, and spiro[4.5]decanyl.

"Heterocyclyl" refers to carbocyclyl as described above, with one or more ring heteroatoms independently selected from nitrogen, oxygen, phosphorous, and sulfur. Heterocyclyl may include, for example, heterocycloalkyl, heterocycloalkenyl, and heterocycloalknyl. In some embodiments, heterocyclyl is a 3- to 18-membered non-aromatic monocyclic or polycyclic moiety that has at least one heteroatom selected from nitrogen, oxygen, phosphorous and sulfur. In certain embodiments, the heterocyclyl can be a monocyclic or polycyclic (e.g., bicyclic, tricyclic or tetracyclic), wherein polycyclic ring systems can be a fused, bridged or spiro ring system. Heterocyclyl polycyclic ring systems can include one or more heteroatoms in one or both rings.

An N-containing heterocyclyl moiety refers to an non-aromatic group in which at least one of the skeletal atoms of the ring is a nitrogen atom. The heteroatom(s) in the heterocyclyl group is optionally oxidized. One or more nitrogen atoms, if present, are optionally quaternized. In certain embodiments, heterocyclyl may also include ring systems substituted with one or more oxide (—O—) substituents, such as piperidinyl N-oxides. The heterocyclyl is attached to the parent molecular structure through any atom of the ring(s).

In some embodiments, heterocyclyl also includes ring systems with one or more fused carbocyclyl, aryl or heteroaryl groups, wherein the point of attachment is either on the carbocyclyl or heterocyclyl ring. In some embodiments, heterocyclyl is a 5-10 membered non-aromatic ring system having ring carbon atoms and 1-4 ring heteroatoms, wherein each heteroatom is independently selected from nitrogen, oxygen and sulfur (e.g., 5-10 membered heterocyclyl). In some embodiments, a heterocyclyl group is a 5-8 membered non-aromatic ring system having ring carbon atoms and 1-4 ring heteroatoms, wherein each heteroatom is independently selected from nitrogen, oxygen and sulfur (e.g., 5-8 membered heterocyclyl). In some embodiments, a heterocyclyl group is a 5-6 membered non-aromatic ring system having ring carbon atoms and 1-4 ring heteroatoms, wherein each heteroatom is independently selected from nitrogen, oxygen and sulfur (e.g., 5-6 membered heterocyclyl). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur.

"Aryl" refers to an aromatic group having a single ring (e.g., phenyl), multiple rings (e.g., biphenyl), or multiple fused rings (e.g., naphthyl, fluorenyl, and anthryl). In some embodiments, aryl as used herein has 6 to 10 ring atoms (e.g., $C_6$-$C_{10}$ aromatic or $C_6$-$C_{10}$ aryl) which has at least one ring having a conjugated pi electron system. For example, bivalent radicals formed from substituted benzene derivatives and having the free valences at ring atoms are named as substituted phenylene radicals. In certain embodiments, aryl may have more than one ring where at least one ring is non-aromatic can be connected to the parent structure at either an aromatic ring position or at a non-aromatic ring position. In certain embodiments, aryl includes monocyclic or fused-ring polycyclic (i.e., rings which share adjacent pairs of ring atoms) groups.

"Heteroaryl" refers to an aromatic group having a single ring, multiple rings, or multiple fused rings, with one or more ring heteroatoms independently selected from nitrogen, oxygen, phosphorous, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl is a 5- to 18-membered monocyclic or polycyclic (e.g., bicyclic or tricyclic) aromatic ring system (e.g., having 6, 10 or 14 pi electrons shared in a cyclic array) having ring carbon atoms and 1 to 6 ring heteroatoms provided in the aromatic ring system, wherein each heteroatom is independently selected from nitrogen, oxygen, phosphorous and sulfur (e.g., 5-18 membered heteroaryl). In certain embodiments, heteroaryl may have a single ring (e.g., pyridyl, pyridinyl, imidazolyl) or multiple condensed rings (e.g., indolizinyl, benzothienyl) which condensed rings may or may not be aromatic. In other embodiments, heteroaryl may have more than one ring where at least one ring is non-aromatic can be connected to the parent structure at either an aromatic ring position or at a non-aromatic ring position. In one embodiment, heteroaryl may have more than one ring where at least one ring is non-aromatic is connected to the parent structure at an aromatic ring position. Heteroaryl polycyclic ring systems can include one or more heteroatoms in one or both rings.

For example, in one embodiment, an N-containing "heteroaryl" refers to an aromatic group in which at least one of the skeletal atoms of the ring is a nitrogen atom. One or more heteroatom(s) in the heteroaryl group can be optionally oxidized. One or more nitrogen atoms, if present, are optionally quaternized. In other embodiments, heteroaryl may include ring systems substituted with one or more oxide (—O—) substituents, such as pyridinyl N-oxides. The heteroaryl may be attached to the parent molecular structure through any atom of the ring(s).

In other embodiments, heteroaryl may include ring systems with one or more fused aryl groups, wherein the point of attachment is either on the aryl or on the heteroaryl ring. In yet other embodiments, heteroaryl may include ring systems with one or more carbocyclyl or heterocyclyl groups wherein the point of attachment is on the heteroaryl ring. For polycyclic heteroaryl groups wherein one ring does not contain a heteroatom (e.g., indolyl, quinolinyl, and carbazolyl) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-10 membered heteroaryl). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-8 membered heteroaryl). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-6 membered heteroaryl). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

In some embodiments, carbocyclyl (including, for example, cycloalkyl, cycloalkenyl or cycloalkynyl), aryl, heteroaryl, and heterocyclyl at each occurrence may independently be unsubstituted or substituted by one or more of substituents. In certain embodiments, a substituted carbocyclyl (including, for example, substituted cycloalkyl, substituted cycloalkenyl or substituted cycloalkynyl), substituted aryl, substituted heteroaryl, substituted heterocyclyl at each occurrence may be independently may independently have 1 to 5 substituents, 1 to 3 substituents, 1 to 2 substituents, or 1 substituent. Examples of carbocyclyl (including, for example, cycloalkyl, cycloalkenyl or cycloalkynyl), aryl, heteroaryl, heterocyclyl substituents may include alkyl alkenyl, alkoxy, cycloalkyl, aryl, heteroalkyl (e.g., ether), heteroaryl, heterocycloalkyl, cyano, halo, haloalkoxy, haloalkyl, oxo (=O), —$OR_a$, —$N(R_a)_2$, —$C(O)N(R_a)_2$, —$N(R_a)C(O)R_a$, —$C(O)R_a$, —$N(ROS(O)_tR_a$ (where t is 1 or 2), —$SR_a$, and —$S(O)_tN(R_a)_2$ (where t is 1 or 2), wherein $R_a$ is as described herein.

It should be understood that, as used herein, any moiety referred to as a "linker" refers to the moiety has having bivalency. Thus, for example, "alkyl linker" refers to the same residues as alkyl, but having bivalency. Examples of alkyl linkers include —$CH_2$—, —$CH_2CH_2$—, —$CH_2CH_2CH_2$—, and —$CH_2CH_2CH_2CH_2$—. "Alkenyl linker" refers to the same residues as alkenyl, but having bivalency. Examples of alkenyl linkers include —CH=CH—, —$CH_2$—CH=CH— and —$CH_2$—CH=CH—$CH_2$—. "Alkynyl linker" refers to the same residues as alkynyl, but having bivalency. Examples alkynyl linkers include —C≡C— or —C≡C—$CH_2$—. Similarly, "carbocyclyl linker", "aryl linker", "heteroaryl linker", and "heterocyclyl linker" refer to the same residues as carbocyclyl, aryl, heteroaryl, and heterocyclyl, respectively, but having bivalency.

"Amino" or "amine" refers to —N($R_a$)($R_b$), where each $R_a$ and $R_b$ is independently selected from hydrogen, alkyl, alkenyl, alkynyl, haloalkyl, heteroalkyl (e.g., bonded through a chain carbon), cycloalkyl, aryl, heterocycloalkyl (e.g., bonded through a ring carbon), heteroaryl (e.g., bonded through a ring carbon), —C(O)R' and —S(O)$_t$R' (where t is 1 or 2), where each R' is independently hydrogen, alkyl, alkenyl, alkynyl, haloalkyl, heteroalkyl, cycloalkyl, aryl, heterocycloalkyl, or heteroaryl. It should be understood that, in one embodiment, amino includes amido (e.g., —N$R_a$C(O)$R_b$). It should be further understood that in certain embodiments, the alkyl, alkenyl, alkynyl, haloalkyl, heteroalkyl, cycloalkyl, aryl, heterocycloalkyl, or heteroaryl moiety of $R_a$ and $R_b$ may be further substituted as described herein. $R_a$ and $R_b$ may be the same or different. For example, in one embodiment, amino is —$NH_2$ (where $R_a$ and $R_b$ are each hydrogen). In other embodiments where $R_a$ and $R_b$ are other than hydrogen, $R_a$ and $R_b$ can be combined with the nitrogen atom to which they are attached to form a 3-, 4-, 5-, 6-, or 7-membered ring. Such examples may include 1-pyrrolidinyl and 4-morpholinyl.

"Ammonium" refers to —N($R_a$)($R_b$)($R_c$)$^+$, where each $R_a$, $R_b$ and $R_c$ is independently selected from hydrogen, alkyl, alkenyl, alkynyl, haloalkyl, heteroalkyl (e.g., bonded through a chain carbon), cycloalkyl, aryl, heterocycloalkyl (e.g., bonded through a ring carbon), heteroaryl (e.g., bonded through a ring carbon), —C(O)R' and —S(O)$_t$R' (where t is 1 or 2), where each R' is independently hydrogen, alkyl, alkenyl, alkynyl, haloalkyl, heteroalkyl, cycloalkyl, aryl, heterocycloalkyl, or heteroaryl; or any two of $R_a$, $R_b$ and $R_c$ may be taken together with the atom to which they are attached to form a cycloalkyl, heterocycloalkyl; or any three of $R_a$, $R_b$ and $R_c$ may be taken together with the atom to which they are attached to form aryl or heteroaryl. It should be further understood that in certain embodiments, the alkyl, alkenyl, alkynyl, haloalkyl, heteroalkyl, cycloalkyl, aryl, heterocycloalkyl, or heteroaryl moiety of any one or more of $R_a$, $R_b$ and $R_c$ may be further substituted as described herein. $R_a$, $R_b$ and $R_c$ may be the same or different.

In certain embodiments, "amino" also refers to N-oxides of the groups —$N^+$(H)($R_a$)$O^-$, and —$N^+$($R_a$)($R_b$)O—, where $R_a$ and $R_b$ are as described herein, where the N-oxide is bonded to the parent structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N($R_a$)($R_b$) or —NR$^a$C(O)$R_b$, where $R_a$ and $R_b$ at each occurrence are as described herein. In some embodiments, amido is a $C_{1-4}$ amido, which includes the amide carbonyl in the total number of carbons in the group. When a —C(O)N($R_a$)($R_b$) has $R_a$ and $R_b$ other than hydrogen, they can be combined with the nitrogen atom to form a 3-, 4-, 5-, 6-, or 7-membered ring.

"Carbonyl" refers to —C(O)$R_a$, where $R_a$ is hydrogen, alkyl, alkenyl, alkynyl, haloalkyl, heteroalkyl, cycloalkyl, aryl, heterocycloalkyl, heteroaryl, —N(R')$_2$, —S(O)$_t$R', where each R' is independently hydrogen, alkyl, alkenyl, alkynyl, haloalkyl, heteroalkyl, cycloalkyl, aryl, heterocycloalkyl, or heteroaryl, and t is 1 or 2. In certain embodiments where each R' are other than hydrogen, the two R' moieties can be combined with the nitrogen atom to which they are attached to form a 3-, 4-, 5-, 6-, or 7-membered ring. It should be understood that, in one embodiment, carbonyl includes amido (e.g., —C(O)N($R_a$)($R_b$)).

"Carbamate" refers to any of the following groups: —O—C(=O)—N($R_a$)($R_b$) and —N($R_a$)—C(=O)—O$R_b$, wherein $R_a$ and $R_b$ at each occurrence are as described herein.

"Cyano" refers to a —CN group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy moieties as described above, wherein one or more hydrogen atoms are replaced by halo. For example, where a residue is substituted with more than one halo groups, it may be referred to by using a prefix corresponding to the number of halo groups attached. For example, dihaloaryl, dihaloalkyl, and trihaloaryl refer to aryl and alkyl substituted with two ("di") or three ("tri") halo groups, which may be, but are not necessarily, the same halogen; thus, for example, 3,5-difluorophenyl, 3-chloro-5-fluorophenyl, 4-chloro-3-fluorophenyl, and 3,5-difluoro-4-chlorophenyl is within the scope of dihaloaryl. Other examples of a haloalkyl group include difluoromethyl (—$CHF_2$), trifluoromethyl (—$CF_3$), 2,2,2-trifluoroethyl, and 1-fluoromethyl-2-fluoroethyl. Each of the alkyl, alkenyl, alkynyl and alkoxy groups of haloalkyl, haloalkenyl, haloalkynyl and haloalkoxy, respectively, can be optionally substituted as defined herein. "Perhaloalkyl" refers to an alkyl or alkylene group in which all of the hydrogen atoms have been replaced with a halogen (e.g., fluoro, chloro, bromo, or iodo). In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, and —$CF_2Cl$.

"Thio" refers to —S$R_a$, wherein $R_a$ is as described herein. "Thiol" refers to the group —$R_a$SH, wherein $R_a$ is as described herein.

"Sulfinyl" refers to —S(O)$R_a$. In some embodiments, sulfinyl is —S(O)N($R_a$)($R_b$). "Sulfonyl" refers to the —S($O_2$)$R_a$. In some embodiments, sulfonyl is —S($O_2$)N($R_a$)($R_b$) or —S($O_2$)OH. For each of these moieties, it should be understood that $R_a$ and $R_b$ are as described herein.

"Moiety" refers to a specific segment or functional group of a molecule. Chemical moieties are often recognized chemical entities embedded in or appended to a molecule.

As used herein, the term "unsubstituted" means that for carbon atoms, only hydrogen atoms are present besides those valencies linking the atom to the parent molecular group. One example is propyl (—$CH_2$—$CH_2$—$CH_3$). For nitrogen atoms, valencies not linking the atom to the parent molecular group are either hydrogen or an electron pair. For sulfur atoms, valencies not linking the atom to the parent molecular group are either hydrogen, oxygen or electron pair(s).

As used herein, the term "substituted" or "substitution" means that at least one hydrogen present on a group (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from alkyl alkenyl, alkoxy, cycloalkyl, aryl, heteroalkyl (e.g., ether), heteroaryl, heterocycloalkyl, cyano, halo, haloalkoxy, haloalkyl, oxo (=O), —OR$_a$, —N(R$_a$)$_2$, —C(O)N(R$_a$)$_2$, —N(R$_a$)C(O)R$_a$, —C(O)R$_a$, —N(R$_a$)S(O)$_t$R$_a$ (where t is 1 or 2), —SR$_a$, and —S(O)$_t$N(R$_a$)$_2$ (where t is 1 or 2), wherein R$_a$ is as described herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

Reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of between ±0.1% and ±15% of the stated number. For example, in one variation, "about 1" refers to a range between 0.85 and 1.15.

Reference to "between" two values or parameters herein includes (and describes) embodiments that include those two values or parameters per se. For example, description referring to "between x and y" includes description of "x" and "y" per se.

Representative Examples of Catalysts for Use in Producing Oligosaccharide Compositions It should be understood that the polymeric catalysts and the solid-supported catalysts can include any of the Bronsted-Lowry acids, cationic groups, counterions, linkers, hydrophobic groups, cross-linking groups, and polymeric backbones or solid supports (as the case may be) described herein, as if each and every combination were listed separately. For example, in one embodiment, the catalyst can include benzenesulfonic acid (i.e., a sulfonic acid with a phenyl linker) connected to a polystyrene backbone or attached to the solid support, and an imidazolium chloride connected directly to the polystyrene backbone or attached directly to the solid support. In another embodiment, the polymeric catalyst can include boronyl-benzyl-pyridinium chloride (i.e., a boronic acid and pyridinium chloride in the same monomer unit with a phenyl linker) connected to a polystyrene backbone or attached to the solid support. In yet another embodiment, the catalyst can include benzenesulfonic acid and imidazolium sulfate each individually connected to a polyvinyl alcohol backbone or individually attached to the solid support.

In some embodiments, the polymeric catalyst is selected from:

poly [styrene-co-4-vinylbenzenesulfonic acid-co-3-methyl-1-(4-vinylbenzyl)-3H-imidazol-1-ium chloride-co-divinylbenzene];

poly [styrene-co-4-vinylbenzenesulfonic acid-co-3-methyl-1-(4-vinylbenzyl)-3H-imidazol-1-ium bisulfate-co-divinylbenzene];

poly [styrene-co-4-vinylbenzenesulfonic acid-co-3-methyl-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-imidazol-1-ium nitrate-co-divinylbenzene];

poly [styrene-co-4-vinylbenzenesulfonic acid-co-3-ethyl-1-(4-vinylbenzyl)-3H-imidazol-1-ium chloride-co-divinylbenzene];

poly [styrene-co-4-vinylbenzenesulfonic acid-co-3-ethyl-1-(4-vinylbenzyl)-3H-imidazol-1-ium bisulfate-co-divinylbenzene];

poly [styrene-co-4-vinylbenzenesulfonic acid-co-3-ethyl-1-(4-vinylbenzyl)-3H-imidazol-1-ium acetate-co-divinylbenzene];

poly [styrene-co-4-vinylbenzenesulfonic acid-co-3-ethyl-1-(4-vinylbenzyl)-3H-imidazol-1-ium nitrate-co-divinylbenzene];

poly [styrene-co-4-vinylbenzenesulfonic acid-co-1-(4-vinylbenzyl)-3H-imidazol-1-ium chloride-co-divinylbenzene];

poly [styrene-co-4-vinylbenzenesulfonic acid-co-1-(4-vinylbenzyl)-3H-imidazol-1-ium iodide-co-divinylbenzene];

poly [styrene-co-4-vinylbenzenesulfonic acid-co-1-(4-vinylbenzyl)-3H-imidazol-1-ium bromide-co-divinylbenzene];

poly [styrene-co-4-vinylbenzenesulfonic acid-co-1-(4-vinylbenzyl)-3H-imidazol-1-ium bisulfate-co-divinylbenzene];

poly [styrene-co-4-vinylbenzenesulfonic acid-co-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-benzoimidazol-1-ium chloride-co-divinylbenzene];

poly [styrene-co-4-vinylbenzenesulfonic acid-co-3-methyl-1-(4-vinylbenzyl)-3H-benzoimidazol-1-ium bisulfate-co-divinylbenzene];

poly [styrene-co-4-vinylbenzenesulfonic acid-co-3-methyl-1-(4-vinylbenzyl)-3H-benzoimidazol-1-ium acetate-co-divinylbenzene];

poly [styrene-co-4-vinylbenzenesulfonic acid-co-3-methyl-1-(4-vinylbenzyl)-3H-benzoimidazol-1-ium formate-co-divinylbenzene];

poly [styrene-co-4-vinylbenzenesulfonic acid-co-1-(4-vinylbenzyl)-pyridinium-chloride-co-divinylbenzene];

poly [styrene-co-4-vinylbenzenesulfonic acid-co-1-(4-vinylbenzyl)-pyridinium-bisulfate-co-divinylbenzene];

poly [styrene-co-4-vinylbenzenesulfonic acid-co-1-(4-vinylbenzyl)-pyridinium-acetate-co-divinylbenzene];

poly [styrene-co-4-vinylbenzenesulfonic acid-co-1-(4-vinylbenzyl)-pyridinium-nitrate-co-divinylbenzene];

poly[styrene-co-4-vinylbenzenesulfonic acid-co-1-(4-vinylbenzyl)-pyridinium-chloride-co-3-methyl-1-(4-vinylbenzyl)-3H-imidazol-1-ium bisulfate-co-divinylbenzene];

poly[styrene-co-4-vinylbenzenesulfonic acid-co-1-(4-vinylbenzyl)-pyridinium-bromide-co-3-methyl-1-(4-vinylbenzyl)-3H-imidazol-1-ium bisulfate-co-divinylbenzene];

poly[styrene-co-4-vinylbenzenesulfonic acid-co-1-(4-vinylbenzyl)-pyridinium-iodide-co-3-methyl-1-(4-vinylbenzyl)-3H-imidazol-1-ium bisulfate-co-divinylbenzene];

poly[styrene-co-4-vinylbenzenesulfonic acid-co-1-(4-vinylbenzyl)-pyridinium-bisulfate-co-3-methyl-1-(4-vinylbenzyl)-3H-imidazol-1-ium bisulfate-co-divinylbenzene];

poly[styrene-co-4-vinylbenzenesulfonic acid-co-1-(4-vinylbenzyl)-pyridinium-acetate-co-3-methyl-1-(4-vinylbenzyl)-3H-imidazol-1-ium bisulfate-co-divinylbenzene];

poly[styrene-co-4-vinylbenzenesulfonic acid-co-4-methyl-4-(4-vinylbenzyl)-morpholin-4-ium chloride-co-divinylbenzene];

poly[styrene-co-4-vinylbenzenesulfonic acid-co-4-methyl-4-(4-vinylbenzyl)-morpholin-4-ium bisulfate-co-divinylbenzene];

poly[styrene-co-4-vinylbenzenesulfonic acid-co-4-methyl-4-(4-vinylbenzyl)-morpholin-4-ium acetate-co-divinylbenzene];

poly[styrene-co-4-vinylbenzenesulfonic acid-co-4-methyl-4-(4-vinylbenzyl)-morpholin-4-ium formate-co-divinylbenzene];

poly[styrene-co-4-vinylbenzenesulfonic acid-co-triphenyl-(4-vinylbenzyl)-phosphonium chloride-co-divinylbenzene];

poly[styrene-co-4-vinylbenzenesulfonic acid-co-triphenyl-(4-vinylbenzyl)-phosphonium bisulfate-co-divinylbenzene];

poly[styrene-co-4-vinylbenzenesulfonic acid-co-triphenyl-(4-vinylbenzyl)-phosphonium acetate-co-divinylbenzene];

poly[styrene-co-4-vinylbenzenesulfonic acid-co-1-methyl-1-(4-vinylbenzyl)-piperdin-1-ium chloride-co-divinylbenzene];

poly[styrene-co-4-vinylbenzenesulfonic acid-co-1-methyl-1-(4-vinylbenzyl)-piperdin-1-ium bisulfate-co-divinylbenzene];

poly[styrene-co-4-vinylbenzenesulfonic acid-co-1-methyl-1-(4-vinylbenzyl)-piperdin-1-ium acetate-co-divinylbenzene];

poly[styrene-co-4-vinylbenzenesulfonic acid-co-4-(4-vinylbenzyl)-morpholine-4-oxide-co-divinyl benzene];

poly[styrene-co-4-vinylbenzenesulfonic acid-co-triethyl-(4-vinylbenzyl)-ammonium chloride-co-divinylbenzene];

poly[styrene-co-4-vinylbenzenesulfonic acid-co-triethyl-(4-vinylbenzyl)-ammonium bisulfate-co-divinylbenzene];

poly[styrene-co-4-vinylbenzenesulfonic acid-co-triethyl-(4-vinylbenzyl)-ammonium acetate-co-divinylbenzene];

poly[styrene-co-3-methyl-1-(4-vinylbenzyl)-3H-imidazol-1-ium chloride-co-4-boronyl-1-(4-vinylbenzyl)-pyridinium chloride-co-divinylbenzene];

poly[styrene-co-3-methyl-1-(4-vinylbenzyl)-3H-imidazol-1-ium chloride-co-1-(4-vinylphenyl)methylphosphonic acid-co-divinylbenzene];

poly[styrene-co-3-methyl-1-(4-vinylbenzyl)-3H-imidazol-1-ium bisulfate-co-1-(4-vinylphenyl)methylphosphonic acid-co-divinylbenzene];

poly[styrene-co-3-methyl-1-(4-vinylbenzyl)-3H-imidazol-1-ium acetate-co-1-(4-vinylphenyl)methylphosphonic acid-co-divinylbenzene];

poly[styrene-co-3-methyl-1-(4-vinylbenzyl)-3H-imidazol-1-ium nitrate-co-1-(4-vinylphenyl)methylphosphonic acid-co-divinylbenzene];

poly[styrene-co-4-vinylbenzenesulfonic acid-co-vinylbenzylchloride-co-1-methyl-2-vinyl-pyridinium chloride-co-divinylbenzene];

poly[styrene-co-4-vinylbenzenesulfonic acid-co-vinylbenzylchloride-co-1-methyl-2-vinyl-pyridinium bisulfate-co-divinylbenzene];

poly[styrene-co-4-vinylbenzenesulfonic acid-co-vinylbenzylchloride-co-1-methyl-2-vinyl-pyridinium acetate-co-divinylbenzene];

poly[styrene-co-4-vinylbenzenesulfonic acid-co-4-(4-vinylbenzyl)-morpholine-4-oxide-co-divinyl benzene];

poly [styrene-co-4-vinylphenylphosphonic acid-co-3-methyl-1-(4-vinylbenzyl)-3H-imidazol-1-ium chloride-co-divinylbenzene];

poly [styrene-co-4-vinylphenylphosphonic acid-co-3-methyl-1-(4-vinylbenzyl)-3H-imidazol-1-ium bisulfate-co-divinylbenzene];

poly [styrene-co-4-vinylphenylphosphonic acid-co-3-methyl-1-(4-vinylbenzyl)-3H-imidazol-1-ium acetate-co-divinylbenzene];

poly[styrene-co-3-carboxymethyl-1-(4-vinylbenzyl)-3H-imidazol-1-ium chloride-co-divinylbenzene];

poly[styrene-co-3-carboxymethyl-1-(4-vinylbenzyl)-3H-imidazol-1-ium bisulfate-co-divinylbenzene];

poly[styrene-co-3-carboxymethyl-1-(4-vinylbenzyl)-3H-imidazol-1-ium acetate-co-divinylbenzene];

poly[styrene-co-5-(4-vinylbenzylamino)-isophthalic acid-co-3-methyl-1-(4-vinylbenzyl)-3H-imidazol-1-ium chloride-co-divinylbenzene];

poly[styrene-co-5-(4-vinylbenzylamino)-isophthalic acid-co-3-methyl-1-(4-vinylbenzyl)-3H-imidazol-1-ium bisulfate-co-divinylbenzene];

poly[styrene-co-5-(4-vinylbenzylamino)-isophthalic acid-co-3-methyl-1-(4-vinylbenzyl)-3H-imidazol-1-ium acetate-co-divinylbenzene];

poly[styrene-co-(4-vinylbenzylamino)-acetic acid-co-3-methyl-1-(4-vinylbenzyl)-3H-imidazol-1-ium chloride-co-divinylbenzene];

poly[styrene-co-(4-vinylbenzylamino)-acetic acid-co-3-methyl-1-(4-vinylbenzyl)-3H-imidazol-1-ium bisulfate-co-divinylbenzene];

poly[styrene-co-(4-vinylbenzylamino)-acetic acid-co-3-methyl-1-(4-vinylbenzyl)-3H-imidazol-1-ium acetate-co-divinylbenzene];

poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene);

poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene);

poly(styrene-co-4-vinylbenzenesulfonic acid-co-vinylbenzylmethylimidazolium bisulfate-co-vinylbenzylmethylmorpholinium bisulfate-co-vinylbenzyltriphenyl phosphonium bisulfate-co-divinylbenzene);

poly(styrene-co-4-vinylbenzenephosphonic acid-co-vinylbenzylmethylimidazolium bisulfate-co-vinylbenzylmethylmorpholinium bisulfate-co-vinylbenzyltriphenyl phosphonium bisulfate-co-divinylbenzene);

poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene);

poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene);

poly(styrene-co-4-vinylbenzenesulfonic acid-co-vinylbenzylmethylmorpholinium chloride-co-vinylbenzyltriphenylphosphonium chloride-co-divinylbenzene);

poly(styrene-co-4-vinylbenzenephosphonic acid-co-vinylbenzylmethylmorpholinium chloride-co-vinylbenzyltriphenylphosphonium chloride-co-divinylbenzene);

poly(styrene-co-4-vinylbenzenesulfonic acid-co-vinylbenzylmethylmorpholinium bisulfate-co-vinylbenzyltriphenylphosphonium bisulfate-co-divinylbenzene);

poly(styrene-co-4-vinylbenzenephosphonic acid-co-vinylbenzylmethylmorpholinium bisulfate-co-vinylbenzyltriphenylphosphonium bisulfate-co-divinylbenzene);

poly(styrene-co-4-vinylbenzenesulfonic acid-co-vinylbenzylmethylmorpholinium acetate-co-vinylbenzyltriphenylphosphonium bisulfate-co-divinylbenzene);
poly(styrene-co-4-vinylbenzenephosphonic acid-co-vinylbenzylmethylmorpholinium acetate-co-vinylbenzyltriphenylphosphonium bisulfate-co-divinylbenzene)
poly(styrene-co-4-vinylbenzenesulfonic acid-co-vinylmethylimidazolium chloride-co-divinylbenzene);
poly(styrene-co-4-vinylbenzenesulfonic acid-co-vinylmethylimidazolium bisulfate-co-divinylbenzene);
poly(styrene-co-4-vinylbenzenesulfonic acid-co-vinylmethylimidazolium acetate-co-divinylbenzene);
poly(styrene-co-4-vinylbenzenesulfonic acid-co-vinylmethylimidazolium nitrate-co-divinylbenzene);
poly(styrene-co-4-vinylbenzenephosphonic acid-co-vinylmethylimidazolium chloride-co-divinylbenzene);
poly(styrene-co-4-vinylbenzenephosphonic acid-co-vinylmethylimidazolium bisulfate-co-divinylbenzene);
poly(styrene-co-4-vinylbenzenephosphonic acid-co-vinylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(styrene-co-4-vinylbenzenesulfonic acid-co-vinylbenzylmethylimidazolium chloride-co-divinylbenzene);
poly(styrene-co-4-vinylbenzenesulfonic acid-co-vinylbenzylmethylimidazolium bisulfate-co-divinylbenzene);
poly(styrene-co-4-vinylbenzenesulfonic acid-co-vinylbenzylmethylimidazolium acetate-co-divinylbenzene);
poly(styrene-co-4-vinylbenzenephosphonic acid-co-vinylbenzylmethylimidazolium chloride-co-divinylbenzene);
poly(styrene-co-4-vinylbenzenephosphonic acid-co-vinylbenzylmethylimidazolium bisulfate-co-divinylbenzene);
poly(styrene-co-4-vinylbenzenephosphonic acid-co-vinylbenzylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(butyl-vinylimidazolium chloride-co-butylimidazolium bisulfate-co-4-vinylbenzenesulfonic acid);
poly(butyl-vinylimidazolium bisulfate-co-butylimidazolium bisulfate-co-4-vinylbenzenesulfonic acid);
poly(benzyl alcohol-co-4-vinylbenzylalcohol sulfonic acid-co-vinylbenzyltriphenylphosphonium chloride-co-divinylbenzyl alcohol); and
poly(benzyl alcohol-co-4-vinylbenzylalcohol sulfonic acid-co-vinylbenzyltriphenylphosphonium bisulfate-co-divinylbenzyl alcohol).

In some embodiments, the solid-supported catalyst is selected from:
amorphous carbon-supported pyrrolium chloride sulfonic acid;
amorphous carbon-supported imidazolium chloride sulfonic acid;
amorphous carbon-supported pyrazolium chloride sulfonic acid;
amorphous carbon-supported oxazolium chloride sulfonic acid;
amorphous carbon-supported thiazolium chloride sulfonic acid;
amorphous carbon-supported pyridinium chloride sulfonic acid;
amorphous carbon-supported pyrimidinium chloride sulfonic acid;
amorphous carbon-supported pyrazinium chloride sulfonic acid;
amorphous carbon-supported pyridazinium chloride sulfonic acid;
amorphous carbon-supported thiazinium chloride sulfonic acid;
amorphous carbon-supported morpholinium chloride sulfonic acid;
amorphous carbon-supported piperidinium chloride sulfonic acid;
amorphous carbon-supported piperizinium chloride sulfonic acid;
amorphous carbon-supported pyrollizinium chloride sulfonic acid;
amorphous carbon-supported triphenyl phosphonium chloride sulfonic acid;
amorphous carbon-supported trimethyl phosphonium chloride sulfonic acid;
amorphous carbon-supported triethyl phosphonium chloride sulfonic acid;
amorphous carbon-supported tripropyl phosphonium chloride sulfonic acid;
amorphous carbon-supported tributyl phosphonium chloride sulfonic acid;
amorphous carbon-supported trifluoro phosphonium chloride sulfonic acid;
amorphous carbon-supported pyrrolium bromide sulfonic acid;
amorphous carbon-supported imidazolium bromide sulfonic acid;
amorphous carbon-supported pyrazolium bromide sulfonic acid;
amorphous carbon-supported oxazolium bromide sulfonic acid;
amorphous carbon-supported thiazolium bromide sulfonic acid;
amorphous carbon-supported pyridinium bromide sulfonic acid;
amorphous carbon-supported pyrimidinium bromide sulfonic acid;
amorphous carbon-supported pyrazinium bromide sulfonic acid;
amorphous carbon-supported pyridazinium bromide sulfonic acid;

amorphous carbon-supported thiazinium bromide sulfonic acid;
amorphous carbon-supported morpholinium bromide sulfonic acid;
amorphous carbon-supported piperidinium bromide sulfonic acid;
amorphous carbon-supported piperizinium bromide sulfonic acid;
amorphous carbon-supported pyrollizinium bromide sulfonic acid;
amorphous carbon-supported triphenyl phosphonium bromide sulfonic acid;
amorphous carbon-supported trimethyl phosphonium bromide sulfonic acid;
amorphous carbon-supported triethyl phosphonium bromide sulfonic acid;
amorphous carbon-supported tripropyl phosphonium bromide sulfonic acid;
amorphous carbon-supported tributyl phosphonium bromide sulfonic acid;
amorphous carbon-supported trifluoro phosphonium bromide sulfonic acid;
amorphous carbon-supported pyrrolium bisulfate sulfonic acid;
amorphous carbon-supported imidazolium bisulfate sulfonic acid;
amorphous carbon-supported pyrazolium bisulfate sulfonic acid;
amorphous carbon-supported oxazolium bisulfate sulfonic acid;
amorphous carbon-supported thiazolium bisulfate sulfonic acid;
amorphous carbon-supported pyridinium bisulfate sulfonic acid;
amorphous carbon-supported pyrimidinium bisulfate sulfonic acid;
amorphous carbon-supported pyrazinium bisulfate sulfonic acid;
amorphous carbon-supported pyridazinium bisulfate sulfonic acid;
amorphous carbon-supported thiazinium bisulfate sulfonic acid;
amorphous carbon-supported morpholinium bisulfate sulfonic acid;
amorphous carbon-supported piperidinium bisulfate sulfonic acid;
amorphous carbon-supported piperizinium bisulfate sulfonic acid;
amorphous carbon-supported pyrollizinium bisulfate sulfonic acid;
amorphous carbon-supported triphenyl phosphonium bisulfate sulfonic acid;
amorphous carbon-supported trimethyl phosphonium bisulfate sulfonic acid;
amorphous carbon-supported triethyl phosphonium bisulfate sulfonic acid;
amorphous carbon-supported tripropyl phosphonium bisulfate sulfonic acid;
amorphous carbon-supported tributyl phosphonium bisulfate sulfonic acid;
amorphous carbon-supported trifluoro phosphonium bisulfate sulfonic acid;
amorphous carbon-supported pyrrolium formate sulfonic acid;
amorphous carbon-supported imidazolium formate sulfonic acid;
amorphous carbon-supported pyrazolium formate sulfonic acid;
amorphous carbon-supported oxazolium formate sulfonic acid;
amorphous carbon-supported thiazolium formate sulfonic acid;
amorphous carbon-supported pyridinium formate sulfonic acid;
amorphous carbon-supported pyrimidinium formate sulfonic acid;
amorphous carbon-supported pyrazinium formate sulfonic acid;
amorphous carbon-supported pyridazinium formate sulfonic acid;
amorphous carbon-supported thiazinium formate sulfonic acid;
amorphous carbon supported morpholinium formate sulfonic acid;
amorphous carbon-supported piperidinium formate sulfonic acid;
amorphous carbon-supported piperizinium formate sulfonic acid;
amorphous carbon-supported pyrollizinium formate sulfonic acid;
amorphous carbon-supported triphenyl phosphonium formate sulfonic acid;
amorphous carbon-supported trimethyl phosphonium formate sulfonic acid;
amorphous carbon-supported triethyl phosphonium formate sulfonic acid;
amorphous carbon-supported tripropyl phosphonium formate sulfonic acid;
amorphous carbon-supported tributyl phosphonium formate sulfonic acid;
amorphous carbon-supported trifluoro phosphonium formate sulfonic acid;
amorphous carbon-supported pyrrolium acetate sulfonic acid;
amorphous carbon-supported imidazolium acetate sulfonic acid;
amorphous carbon-supported pyrazolium acetate sulfonic acid;
amorphous carbon-supported oxazolium acetate sulfonic acid;
amorphous carbon-supported thiazolium acetate sulfonic acid;
amorphous carbon-supported pyridinium acetate sulfonic acid;
amorphous carbon-supported pyrimidinium acetate sulfonic acid;
amorphous carbon-supported pyrazinium acetate sulfonic acid;
amorphous carbon-supported pyridazinium acetate sulfonic acid;
amorphous carbon-supported thiazinium acetate sulfonic acid;
amorphous carbon-supported morpholinium acetate sulfonic acid;
amorphous carbon-supported piperidinium acetate sulfonic acid;
amorphous carbon-supported piperizinium acetate sulfonic acid;
amorphous carbon-supported pyrollizinium acetate sulfonic acid;
amorphous carbon-supported triphenyl phosphonium acetate sulfonic acid;

amorphous carbon-supported trimethyl phosphonium acetate sulfonic acid;
amorphous carbon-supported triethyl phosphonium acetate sulfonic acid;
amorphous carbon-supported tripropyl phosphonium acetate sulfonic acid;
amorphous carbon-supported tributyl phosphonium acetate sulfonic acid;
amorphous carbon-supported trifluoro phosphonium acetate sulfonic acid;
amorphous carbon-supported pyrrolium chloride phosphonic acid;
amorphous carbon-supported imidazolium chloride phosphonic acid;
amorphous carbon-supported pyrazolium chloride phosphonic acid;
amorphous carbon-supported oxazolium chloride phosphonic acid;
amorphous carbon-supported thiazolium chloride phosphonic acid;
amorphous carbon-supported pyridinium chloride phosphonic acid;
amorphous carbon-supported pyrimidinium chloride phosphonic acid;
amorphous carbon-supported pyrazinium chloride phosphonic acid;
amorphous carbon-supported pyridazinium chloride phosphonic acid;
amorphous carbon-supported thiazinium chloride phosphonic acid;
amorphous carbon-supported morpholinium chloride phosphonic acid;
amorphous carbon-supported piperidinium chloride phosphonic acid;
amorphous carbon-supported piperizinium chloride phosphonic acid;
amorphous carbon-supported pyrollizinium chloride phosphonic acid;
amorphous carbon-supported triphenyl phosphonium chloride phosphonic acid;
amorphous carbon-supported trimethyl phosphonium chloride phosphonic acid;
amorphous carbon-supported triethyl phosphonium chloride phosphonic acid;
amorphous carbon-supported tripropyl phosphonium chloride phosphonic acid;
amorphous carbon-supported tributyl phosphonium chloride phosphonic acid;
amorphous carbon-supported trifluoro phosphonium chloride phosphonic acid;
amorphous carbon-supported pyrrolium bromide phosphonic acid;
amorphous carbon-supported imidazolium bromide phosphonic acid;
amorphous carbon-supported pyrazolium bromide phosphonic acid;
amorphous carbon-supported oxazolium bromide phosphonic acid;
amorphous carbon-supported thiazolium bromide phosphonic acid;
amorphous carbon-supported pyridinium bromide phosphonic acid;
amorphous carbon-supported pyrimidinium bromide phosphonic acid;
amorphous carbon-supported pyrazinium bromide phosphonic acid;
amorphous carbon-supported pyridazinium bromide phosphonic acid;
amorphous carbon-supported thiazinium bromide phosphonic acid;
amorphous carbon-supported morpholinium bromide phosphonic acid;
amorphous carbon-supported piperidinium bromide phosphonic acid;
amorphous carbon-supported piperizinium bromide phosphonic acid;
amorphous carbon-supported pyrollizinium bromide phosphonic acid;
amorphous carbon-supported triphenyl phosphonium bromide phosphonic acid;
amorphous carbon-supported trimethyl phosphonium bromide phosphonic acid;
amorphous carbon-supported triethyl phosphonium bromide phosphonic acid;
amorphous carbon-supported tripropyl phosphonium bromide phosphonic acid;
amorphous carbon-supported tributyl phosphonium bromide phosphonic acid;
amorphous carbon-supported trifluoro phosphonium bromide phosphonic acid;
amorphous carbon-supported pyrrolium bisulfate phosphonic acid;
amorphous carbon-supported imidazolium bisulfate phosphonic acid;
amorphous carbon-supported pyrazolium bisulfate phosphonic acid;
amorphous carbon-supported oxazolium bisulfate phosphonic acid;
amorphous carbon-supported thiazolium bisulfate phosphonic acid;
amorphous carbon-supported pyridinium bisulfate phosphonic acid;
amorphous carbon-supported pyrimidinium bisulfate phosphonic acid;
amorphous carbon-supported pyrazinium bisulfate phosphonic acid;
amorphous carbon-supported pyridazinium bisulfate phosphonic acid;
amorphous carbon-supported thiazinium bisulfate phosphonic acid;
amorphous carbon-supported morpholinium bisulfate phosphonic acid;
amorphous carbon-supported piperidinium bisulfate phosphonic acid;
amorphous carbon-supported piperizinium bisulfate phosphonic acid;
amorphous carbon-supported pyrollizinium bisulfate phosphonic acid;
amorphous carbon-supported triphenyl phosphonium bisulfate phosphonic acid;
amorphous carbon-supported trimethyl phosphonium bisulfate phosphonic acid;
amorphous carbon-supported triethyl phosphonium bisulfate phosphonic acid;
amorphous carbon-supported tripropyl phosphonium bisulfate phosphonic acid;
amorphous carbon-supported tributyl phosphonium bisulfate phosphonic acid;
amorphous carbon-supported trifluoro phosphonium bisulfate phosphonic acid;
amorphous carbon-supported pyrrolium formate phosphonic acid;

amorphous carbon-supported imidazolium formate phosphonic acid;
amorphous carbon-supported pyrazolium formate phosphonic acid;
amorphous carbon-supported oxazolium formate phosphonic acid;
amorphous carbon-supported thiazolium formate phosphonic acid;
amorphous carbon-supported pyridinium formate phosphonic acid;
amorphous carbon-supported pyrimidinium formate phosphonic acid;
amorphous carbon-supported pyrazinium formate phosphonic acid;
amorphous carbon-supported pyridazinium formate phosphonic acid;
amorphous carbon-supported thiazinium formate phosphonic acid;
amorphous carbon-supported morpholinium formate phosphonic acid;
amorphous carbon-supported piperidinium formate phosphonic acid;
amorphous carbon-supported piperizinium formate phosphonic acid;
amorphous carbon-supported pyrollizinium formate phosphonic acid;
amorphous carbon-supported triphenyl phosphonium formate phosphonic acid;
amorphous carbon-supported trimethyl phosphonium formate phosphonic acid;
amorphous carbon-supported triethyl phosphonium formate phosphonic acid;
amorphous carbon-supported tripropyl phosphonium formate phosphonic acid;
amorphous carbon-supported tributyl phosphonium formate phosphonic acid;
amorphous carbon-supported trifluoro phosphonium formate phosphonic acid;
amorphous carbon-supported pyrrolium acetate phosphonic acid;
amorphous carbon-supported imidazolium acetate phosphonic acid;
amorphous carbon-supported pyrazolium acetate phosphonic acid;
amorphous carbon-supported oxazolium acetate phosphonic acid;
amorphous carbon-supported thiazolium acetate phosphonic acid;
amorphous carbon-supported pyridinium acetate phosphonic acid;
amorphous carbon-supported pyrimidinium acetate phosphonic acid;
amorphous carbon-supported pyrazinium acetate phosphonic acid;
amorphous carbon-supported pyridazinium acetate phosphonic acid;
amorphous carbon-supported thiazinium acetate phosphonic acid;
amorphous carbon-supported morpholinium acetate phosphonic acid;
amorphous carbon-supported piperidinium acetate phosphonic acid;
amorphous carbon-supported piperizinium acetate phosphonic acid;
amorphous carbon-supported pyrollizinium acetate phosphonic acid;
amorphous carbon-supported triphenyl phosphonium acetate phosphonic acid;
amorphous carbon-supported trimethyl phosphonium acetate phosphonic acid;
amorphous carbon-supported triethyl phosphonium acetate phosphonic acid;
amorphous carbon-supported tripropyl phosphonium acetate phosphonic acid;
amorphous carbon-supported tributyl phosphonium acetate phosphonic acid;
amorphous carbon-supported trifluoro phosphonium acetate phosphonic acid;
amorphous carbon-supported ethanoyl-triphosphonium sulfonic acid;
amorphous carbon-supported ethanoyl-methylmorpholinium sulfonic acid; and
amorphous carbon-supported ethanoyl-imidazolium sulfonic acid.

In other embodiments, the solid-supported catalyst is selected from:
activated carbon-supported pyrrolium chloride sulfonic acid;
activated carbon-supported imidazolium chloride sulfonic acid;
activated carbon-supported pyrazolium chloride sulfonic acid;
activated carbon-supported oxazolium chloride sulfonic acid;
activated carbon-supported thiazolium chloride sulfonic acid;
activated carbon-supported pyridinium chloride sulfonic acid;
activated carbon-supported pyrimidinium chloride sulfonic acid;
activated carbon-supported pyrazinium chloride sulfonic acid;
activated carbon-supported pyridazinium chloride sulfonic acid;
activated carbon-supported thiazinium chloride sulfonic acid;
activated carbon-supported morpholinium chloride sulfonic acid;
activated carbon-supported piperidinium chloride sulfonic acid;
activated carbon-supported piperizinium chloride sulfonic acid;
activated carbon-supported pyrollizinium chloride sulfonic acid;
activated carbon-supported triphenyl phosphonium chloride sulfonic acid;
activated carbon-supported trimethyl phosphonium chloride sulfonic acid;
activated carbon-supported triethyl phosphonium chloride sulfonic acid;
activated carbon-supported tripropyl phosphonium chloride sulfonic acid;
activated carbon-supported tributyl phosphonium chloride sulfonic acid;
activated carbon-supported trifluoro phosphonium chloride sulfonic acid;
activated carbon-supported pyrrolium bromide sulfonic acid;
activated carbon-supported imidazolium bromide sulfonic acid;
activated carbon-supported pyrazolium bromide sulfonic acid;

activated carbon-supported oxazolium bromide sulfonic acid;
activated carbon-supported thiazolium bromide sulfonic acid;
activated carbon-supported pyridinium bromide sulfonic acid;
activated carbon-supported pyrimidinium bromide sulfonic acid;
activated carbon-supported pyrazinium bromide sulfonic acid;
activated carbon-supported pyridazinium bromide sulfonic acid;
activated carbon-supported thiazinium bromide sulfonic acid;
activated carbon-supported morpholinium bromide sulfonic acid;
activated carbon-supported piperidinium bromide sulfonic acid;
activated carbon-supported piperizinium bromide sulfonic acid;
activated carbon-supported pyrollizinium bromide sulfonic acid;
activated carbon-supported triphenyl phosphonium bromide sulfonic acid;
activated carbon-supported trimethyl phosphonium bromide sulfonic acid;
activated carbon-supported triethyl phosphonium bromide sulfonic acid;
activated carbon-supported tripropyl phosphonium bromide sulfonic acid;
activated carbon-supported tributyl phosphonium bromide sulfonic acid;
activated carbon-supported trifluoro phosphonium bromide sulfonic acid;
activated carbon-supported pyrrolium bisulfate sulfonic acid;
activated carbon-supported imidazolium bisulfate sulfonic acid;
activated carbon-supported pyrazolium bisulfate sulfonic acid;
activated carbon-supported oxazolium bisulfate sulfonic acid;
activated carbon-supported thiazolium bisulfate sulfonic acid;
activated carbon-supported pyridinium bisulfate sulfonic acid;
activated carbon-supported pyrimidinium bisulfate sulfonic acid;
activated carbon-supported pyrazinium bisulfate sulfonic acid;
activated carbon-supported pyridazinium bisulfate sulfonic acid;
activated carbon-supported thiazinium bisulfate sulfonic acid;
activated carbon-supported morpholinium bisulfate sulfonic acid;
activated carbon-supported piperidinium bisulfate sulfonic acid;
activated carbon-supported piperizinium bisulfate sulfonic acid;
activated carbon-supported pyrollizinium bisulfate sulfonic acid;
activated carbon-supported triphenyl phosphonium bisulfate sulfonic acid;
activated carbon-supported trimethyl phosphonium bisulfate sulfonic acid;
activated carbon-supported triethyl phosphonium bisulfate sulfonic acid;
activated carbon-supported tripropyl phosphonium bisulfate sulfonic acid;
activated carbon-supported tributyl phosphonium bisulfate sulfonic acid;
activated carbon-supported trifluoro phosphonium bisulfate sulfonic acid;
activated carbon-supported pyrrolium formate sulfonic acid;
activated carbon-supported imidazolium formate sulfonic acid;
activated carbon-supported pyrazolium formate sulfonic acid;
activated carbon-supported oxazolium formate sulfonic acid;
activated carbon-supported thiazolium formate sulfonic acid;
activated carbon-supported pyridinium formate sulfonic acid;
activated carbon-supported pyrimidinium formate sulfonic acid;
activated carbon-supported pyrazinium formate sulfonic acid;
activated carbon-supported pyridazinium formate sulfonic acid;
activated carbon-supported thiazinium formate sulfonic acid;
activated carbon supported morpholinium formate sulfonic acid;
activated carbon-supported piperidinium formate sulfonic acid;
activated carbon-supported piperizinium formate sulfonic acid;
activated carbon-supported pyrollizinium formate sulfonic acid;
activated carbon-supported triphenyl phosphonium formate sulfonic acid;
activated carbon-supported trimethyl phosphonium formate sulfonic acid;
activated carbon-supported triethyl phosphonium formate sulfonic acid;
activated carbon-supported tripropyl phosphonium formate sulfonic acid;
activated carbon-supported tributyl phosphonium formate sulfonic acid;
activated carbon-supported trifluoro phosphonium formate sulfonic acid;
activated carbon-supported pyrrolium acetate sulfonic acid;
activated carbon-supported imidazolium acetate sulfonic acid;
activated carbon-supported pyrazolium acetate sulfonic acid;
activated carbon-supported oxazolium acetate sulfonic acid;
activated carbon-supported thiazolium acetate sulfonic acid;
activated carbon-supported pyridinium acetate sulfonic acid;
activated carbon-supported pyrimidinium acetate sulfonic acid;
activated carbon-supported pyrazinium acetate sulfonic acid;
activated carbon-supported pyridazinium acetate sulfonic acid;
activated carbon-supported thiazinium acetate sulfonic acid;
activated carbon-supported morpholinium acetate sulfonic acid;
activated carbon-supported piperidinium acetate sulfonic acid;

activated carbon-supported piperizinium acetate sulfonic acid;
activated carbon-supported pyrollizinium acetate sulfonic acid;
activated carbon-supported triphenyl phosphonium acetate sulfonic acid;
activated carbon-supported trimethyl phosphonium acetate sulfonic acid;
activated carbon-supported triethyl phosphonium acetate sulfonic acid;
activated carbon-supported tripropyl phosphonium acetate sulfonic acid;
activated carbon-supported tributyl phosphonium acetate sulfonic acid;
activated carbon-supported trifluoro phosphonium acetate sulfonic acid;
activated carbon-supported pyrrolium chloride phosphonic acid;
activated carbon-supported imidazolium chloride phosphonic acid;
activated carbon-supported pyrazolium chloride phosphonic acid;
activated carbon-supported oxazolium chloride phosphonic acid;
activated carbon-supported thiazolium chloride phosphonic acid;
activated carbon-supported pyridinium chloride phosphonic acid;
activated carbon-supported pyrimidinium chloride phosphonic acid;
activated carbon-supported pyrazinium chloride phosphonic acid;
activated carbon-supported pyridazinium chloride phosphonic acid;
activated carbon-supported thiazinium chloride phosphonic acid;
activated carbon-supported morpholinium chloride phosphonic acid;
activated carbon-supported piperidinium chloride phosphonic acid;
activated carbon-supported piperizinium chloride phosphonic acid;
activated carbon-supported pyrollizinium chloride phosphonic acid;
activated carbon-supported triphenyl phosphonium chloride phosphonic acid;
activated carbon-supported trimethyl phosphonium chloride phosphonic acid;
activated carbon-supported triethyl phosphonium chloride phosphonic acid;
activated carbon-supported tripropyl phosphonium chloride phosphonic acid;
activated carbon-supported tributyl phosphonium chloride phosphonic acid;
activated carbon-supported trifluoro phosphonium chloride phosphonic acid;
activated carbon-supported pyrrolium bromide phosphonic acid;
activated carbon-supported imidazolium bromide phosphonic acid;
activated carbon-supported pyrazolium bromide phosphonic acid;
activated carbon-supported oxazolium bromide phosphonic acid;
activated carbon-supported thiazolium bromide phosphonic acid;
activated carbon-supported pyridinium bromide phosphonic acid;
activated carbon-supported pyrimidinium bromide phosphonic acid;
activated carbon-supported pyrazinium bromide phosphonic acid;
activated carbon-supported pyridazinium bromide phosphonic acid;
activated carbon-supported thiazinium bromide phosphonic acid;
activated carbon-supported morpholinium bromide phosphonic acid;
activated carbon-supported piperidinium bromide phosphonic acid;
activated carbon-supported piperizinium bromide phosphonic acid;
activated carbon-supported pyrollizinium bromide phosphonic acid;
activated carbon-supported triphenyl phosphonium bromide phosphonic acid;
activated carbon-supported trimethyl phosphonium bromide phosphonic acid;
activated carbon-supported triethyl phosphonium bromide phosphonic acid;
activated carbon-supported tripropyl phosphonium bromide phosphonic acid;
activated carbon-supported tributyl phosphonium bromide phosphonic acid;
activated carbon-supported trifluoro phosphonium bromide phosphonic acid;
activated carbon-supported pyrrolium bisulfate phosphonic acid;
activated carbon-supported imidazolium bisulfate phosphonic acid;
activated carbon-supported pyrazolium bisulfate phosphonic acid;
activated carbon-supported oxazolium bisulfate phosphonic acid;
activated carbon-supported thiazolium bisulfate phosphonic acid;
activated carbon-supported pyridinium bisulfate phosphonic acid;
activated carbon-supported pyrimidinium bisulfate phosphonic acid;
activated carbon-supported pyrazinium bisulfate phosphonic acid;
activated carbon-supported pyridazinium bisulfate phosphonic acid;
activated carbon-supported thiazinium bisulfate phosphonic acid;
activated carbon-supported morpholinium bisulfate phosphonic acid;
activated carbon-supported piperidinium bisulfate phosphonic acid;
activated carbon-supported piperizinium bisulfate phosphonic acid;
activated carbon-supported pyrollizinium bisulfate phosphonic acid;
activated carbon-supported triphenyl phosphonium bisulfate phosphonic acid;
activated carbon-supported trimethyl phosphonium bisulfate phosphonic acid;
activated carbon-supported triethyl phosphonium bisulfate phosphonic acid;
activated carbon-supported tripropyl phosphonium bisulfate phosphonic acid;

activated carbon-supported tributyl phosphonium bisulfate phosphonic acid;
activated carbon-supported trifluoro phosphonium bisulfate phosphonic acid;
activated carbon-supported pyrrolium formate phosphonic acid;
activated carbon-supported imidazolium formate phosphonic acid;
activated carbon-supported pyrazolium formate phosphonic acid;
activated carbon-supported oxazolium formate phosphonic acid;
activated carbon-supported thiazolium formate phosphonic acid;
activated carbon-supported pyridinium formate phosphonic acid;
activated carbon-supported pyrimidinium formate phosphonic acid;
activated carbon-supported pyrazinium formate phosphonic acid;
activated carbon-supported pyridazinium formate phosphonic acid;
activated carbon-supported thiazinium formate phosphonic acid;
activated carbon-supported morpholinium formate phosphonic acid;
activated carbon-supported piperidinium formate phosphonic acid;
activated carbon-supported piperizinium formate phosphonic acid;
activated carbon-supported pyrollizinium formate phosphonic acid;
activated carbon-supported triphenyl phosphonium formate phosphonic acid;
activated carbon-supported trimethyl phosphonium formate phosphonic acid;
activated carbon-supported triethyl phosphonium formate phosphonic acid;
activated carbon-supported tripropyl phosphonium formate phosphonic acid;
activated carbon-supported tributyl phosphonium formate phosphonic acid;
activated carbon-supported trifluoro phosphonium formate phosphonic acid;
activated carbon-supported pyrrolium acetate phosphonic acid;
activated carbon-supported imidazolium acetate phosphonic acid;
activated carbon-supported pyrazolium acetate phosphonic acid;
activated carbon-supported oxazolium acetate phosphonic acid;
activated carbon-supported thiazolium acetate phosphonic acid;
activated carbon-supported pyridinium acetate phosphonic acid;
activated carbon-supported pyrimidinium acetate phosphonic acid;
activated carbon-supported pyrazinium acetate phosphonic acid;
activated carbon-supported pyridazinium acetate phosphonic acid;
activated carbon-supported thiazinium acetate phosphonic acid;
activated carbon-supported morpholinium acetate phosphonic acid;
activated carbon-supported piperidinium acetate phosphonic acid;
activated carbon-supported piperizinium acetate phosphonic acid;
activated carbon-supported pyrollizinium acetate phosphonic acid;
activated carbon-supported triphenyl phosphonium acetate phosphonic acid;
activated carbon-supported trimethyl phosphonium acetate phosphonic acid;
activated carbon-supported triethyl phosphonium acetate phosphonic acid;
activated carbon-supported tripropyl phosphonium acetate phosphonic acid;
activated carbon-supported tributyl phosphonium acetate phosphonic acid;
activated carbon-supported trifluoro phosphonium acetate phosphonic acid;
activated carbon-supported ethanoyl-triphosphonium sulfonic acid;
activated carbon-supported ethanol-methylmorpholinium sulfonic acid; and
activated carbon-supported ethanoyl-imidazolium sulfonic acid.

Methods to prepare the polymeric and solid-supported catalysts described herein can be found in WO 2014/031956, which is hereby incorporated herein specifically with respect to paragraphs [0345]-[0380] and [0382]-[0472].

c) Reaction Conditions for Catalytic Oligosaccharide Formation

In some embodiments, the feed sugar and catalyst (e.g., polymeric catalyst or solid-supported catalyst) are allowed to react for at least 1 hour, at least 2 hours, at least 3 hours, at least 4 hours, at least 6 hours, at least 8 hours, at least 16 hours, at least 24 hours, at least 36 hours, or at least 48 hours; or between 1-24 hours, between 2-12 hours, between 3-6 hours, between 1-96 hours, between 12-72 hours, or between 12-48 hours.

In some embodiments, the degree of polymerization of the one or more oligosaccharides produced according to the methods described herein can be regulated by the reaction time. For example, in some embodiments, the degree of polymerization of the one or more oligosaccharides is increased by increasing the reaction time, while in other embodiments, the degree of polymerization of the one or more oligosaccharides is decreased by decreasing the reaction time.

Reaction Temperature

In some embodiments, the reaction temperature is maintained in the range of about 25° C. to about 150° C. In certain embodiments, the temperature is from about 30° C. to about 125° C., about 60° C. to about 120° C., about 80° C. to about 115° C., about 90° C. to about 110° C., about 95° C. to about 105° C., or about 100° C. to 110° C.

Amount of Feed Sugar

The amount of the feed sugar used in the methods described herein relative to the amount solvent used may affect the rate of reaction and yield. The amount of the feed sugar used may be characterized by the dry solids content. In certain embodiments, dry solids content refers to the total solids of a slurry as a percentage on a dry weight basis. In some embodiments, the dry solids content of the feed sugar is between about 5 wt % to about 95 wt %, between about 10 wt % to about 80 wt %, between about 15 to about 75 wt %, or between about 15 to about 50 wt %.

Amount of Catalyst

The amount of the catalyst used in the methods described herein may depend on several factors including, for example, the selection of the type of feed sugar, the concentration of the feed sugar, and the reaction conditions (e.g., temperature, time, and pH). In some embodiments, the weight ratio of the catalyst to the feed sugar is about 0.01 g/g to about 50 g/g, about 0.01 g/g to about 5 g/g, about 0.05 g/g to about 1.0 g/g, about 0.05 g/g to about 0.5 g/g, about 0.05 g/g to about 0.2 g/g, or about 0.1 g/g to about 0.2 g/g.

Solvent

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) are preferable, as such ionic species may reduce effectiveness of the catalyst. In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters.

Water Content

Moreover, as the dehydration reaction of the methods progresses, water is produced with each coupling of the one or more sugars. In certain embodiments, the methods described herein may further include monitoring the amount of water present in the reaction mixture and/or the ratio of water to sugar or catalyst over a period of time. In some embodiments, the method further includes removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum distillation). It should be understood, however, that the amount of water to sugar may be adjusted based on the reaction conditions and specific catalyst used.

Any method known in the art may be used to remove water in the reaction mixture, including, for example, by vacuum filtration, vacuum distillation, heating, and/or evaporation. In some embodiments, the method comprises including water in the reaction mixture.

In some aspects, provided herein are methods of producing an oligosaccharide composition, by: combining a feed sugar and a catalyst having acidic and ionic moieties to form a reaction mixture, wherein water is produced in the reaction mixture; and removing at least a portion of the water produced in the reaction mixture. In certain variations, at least a portion of water is removed to maintain a water content in the reaction mixture of less than 99%, less than 90%, less than 80%, less than 70%, less than 60%, less than 50%, less than 40%, less than 30%, less than 20%, less than 10%, less than 5%, or less than 1% by weight.

In some embodiments, the degree of polymerization of the one or more oligosaccharides produced according to the methods described herein can be regulated by adjusting or controlling the concentration of water present in the reaction mixture. For example, in some embodiments, the degree of polymerization of the one or more oligosaccharides is increased by decreasing the water concentration, while in other embodiments, the degree of polymerization of the one or more oligosaccharides is decreased by increasing the water concentration. In some embodiments, the water content of the reaction is adjusted during the reaction to regulate the degree of polymerization of the one or more oligosaccharides produced.

Batch Versus Continuous Processing

Generally, the catalyst and the feed sugar are introduced into an interior chamber of a reactor, either concurrently or sequentially. The reaction can be performed in a batch process or a continuous process. For example, in one embodiment, method is performed in a batch process, where the contents of the reactor are continuously mixed or blended, and all or a substantial amount of the products of the reaction are removed. In one variation, the method is performed in a batch process, where the contents of the reactor are initially intermingled or mixed but no further physical mixing is performed. In another variation, the method is performed in a batch process, wherein once further mixing of the contents, or periodic mixing of the contents of the reactor, is performed (e.g., at one or more times per hour), all or a substantial amount of the products of the reaction are removed after a certain period of time.

In some embodiments, the method is repeated in a sequential batch process, wherein at least a portion of the catalyst is separated from at least a portion of the oligosaccharide composition produced (e.g., as described in more detail infra) and is recycled by further contacting additional feed sugar.

For example, in one aspect, provided is a method for producing an oligosaccharide composition, by:

a) combining feed sugar with a catalyst to form a reaction mixture;
  wherein the catalyst comprises acidic monomers and ionic monomers connected to form a polymeric backbone, or
  wherein the catalyst comprises a solid support, acidic moieties attached to the solid support, and ionic moieties attached to the solid support; and b) producing an oligosaccharide composition from at least a portion of the reaction mixture;

c) separating the oligosaccharide composition from the catalyst;

d) combining additional feed sugar with the separated catalyst to form additional reaction mixture; and e) producing additional oligosaccharide composition from at least a portion of the additional reaction mixture.

In some of embodiments wherein the method is performed in a batch process, the catalyst is recycled (e.g., steps (c)-(e) above are repeated) at least 1, at least 2, at least 3, at least 4, at least 5, at least 6, at least 7, at least 8, at least 9 or at least 10 times. In some of these embodiments, the catalyst retains at least 80% activity (e.g., at least 90%, 95%, 96%, 97%, 98%, or 99% activity) after being recycled 1, 2, 3, 4, 5, 6, 7, 8, 9 or 10 times, when compared to the catalytic activity under identical conditions prior to being recycled.

In other embodiments, the method is performed in a continuous process, where the contents flow through the reactor with an average continuous flow rate but with no explicit mixing. After introduction of the catalyst and the feed sugar into the reactor, the contents of the reactor are continuously or periodically mixed or blended, and after a period of time, less than all of the products of the reaction are removed. In one variation, method is performed in a continuous process, where the mixture containing the catalyst and one or more sugars is not actively mixed. Additionally, mixing of catalyst and feed sugar may occur as a result of the redistribution of catalysts settling by gravity, or the non-active mixing that occurs as the material flows through a continuous reactor. In some embodiments of the methods, the steps of combining the feed sugar with a catalyst and isolating the oligosaccharide composition produced are performed concurrently.

Reactors

The reactors used for the methods described herein may be open or closed reactors suitable for use in containing the chemical reactions described herein. Suitable reactors may include, for example, a fed-batch stirred reactor, a batch stirred reactor, a continuous flow stirred reactor with ultrafiltration, a continuous plug-flow column reactor, an attrition reactor, or a reactor with intensive stirring induced by an electromagnetic field. See e.g., Fernanda de Castilhos Corazza, Flavio Faria de Moraes, Gisella Maria Zanin and Ivo Neitzel, Optimal control in fed-batch reactor for the cellobiose hydrolysis, Acta Scientiarum. Technology, 25: 33-38 (2003); Gusakov, A. V., and Sinitsyn, A. P., Kinetics of the enzymatic hydrolysis of cellulose: 1. A mathematical model for a batch reactor process, Enz. Microb. TechnoL, 7: 346-352 (1985); Ryu, S. K., and Lee, J. M., Bioconversion of waste cellulose by using an attrition bioreactor, Biotechnol. Bioeng. 25: 53-65(1983); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, *Appl. Biochem. Biotechnol.*, 56: 141-153(1996). Other suitable reactor types may include, for example, fluidized bed, upflow blanket, immobilized, and extruder type reactors for hydrolysis and/or fermentation.

In certain embodiments where the method is performed as a continuous process, the reactor may include a continuous mixer, such as a screw mixer. The reactors may be generally fabricated from materials that are capable of withstanding the physical and chemical forces exerted during the processes described herein. In some embodiments, such materials used for the reactor are capable of tolerating high concentrations of strong liquid acids; however, in other embodiments, such materials may not be resistant to strong acids.

It should also be understood that additional feed sugar and/or catalyst may be added to the reactor, either at the same time or one after the other.

d) Recyclability of Catalysts

The catalysts containing acidic and ionic groups used in the methods of producing oligosaccharide compositions as described herein may be recycled. Thus, in one aspect, provided herein are methods of producing oligosaccharide compositions using recyclable catalysts.

Any method known in the art may be used to separate the catalyst for reuse, including, for example, centrifugation, filtration (e.g., vacuum filtration), and gravity settling.

The methods described herein may be performed as batch or continuous processes. Recycling in a batch process may involve, for example, recovering the catalyst from the reaction mixture and reusing the recovered catalyst in one or more subsequent reaction cycles. Recycling in a continuous process may involve, for example, introducing additional feed sugar into the reactor, without additional of fresh catalyst.

In some of embodiments wherein at least a portion of the catalyst is recycled, the catalyst is recycled at least 1, at least 2, at least 3, at least 4, at least 5, at least 6, at least 7, at least 8, at least 9 or at least 10 times. In some of these embodiments, the catalyst retains at least 80%, at least 90%, at least 95%, at least 96%, at least 97%, at least 98%, or at least 99% activity after being recycled 1, 2, 3, 4, 5, 6, 7, 8, 9 or 10 times, when compared to the catalytic activity under identical conditions prior to being recycled.

As used herein, the "catalyst activity" refers to the effective first order kinetic rate constant for the molar conversion of reactants, $k=-\ln(1-X(t))/t$. The molar conversion of the reactant A at time t is defined as $X_A(t)=1-\mathrm{mol}(A,t)/\mathrm{mol}(A,0)$, where mol(A,t) refers to the number of moles of species A present in the reaction mixture at time t and mol(A,0) refers to the number of moles of species A present at the start of the reaction, t=0. In practice, the number of moles of the reactant A is often measured at several points in time, $t_1$, $t_2, \ldots t_n$ during a single reaction cycle and used to calculate the conversions $X_A(t_1)$, $X_A(t_2)$, $X_A(t_n)$ at the corresponding times. The first order rate constant k is then calculated by fitting the data for $X_A(t)$.

As used herein, a reaction "cycle" refers to one period of use within a sequence of uses of the catalyst. For example, in a batch process, a reaction cycle corresponds to the discrete steps of charging a reactor system with reactants and catalyst, heating the reaction under suitable conditions to convert the reactants, maintaining the reaction conditions for a specified residence time, separating the reaction products from the catalyst, and recovering the catalyst for re-use. In a continuous process, a cycle refers a single reactor space time during the operation of the continuous process. For example, in a 1,000 liter reactor with a continuous volumetric flow of 200 liters per hour, the continuous reactor space time is two hours, and the first two hour period of continuous operation is the first reaction cycle, the next two hour period of continuous operation is the second reaction cycle, etc.

As used herein, the "loss of activity" or "activity loss" of a catalyst is determined by the average fractional reduction in the catalyst activity between consecutive cycles. For example, if the catalyst activity in reaction cycle 1 is k(1) and the catalyst activity in reaction cycle 2 is k(2), then the loss in catalyst activity between cycle 1 and cycle 2 is calculated as [k(2)−k(1)]/k(1). Over N reaction cycles, the loss of activity is then determined as $$\frac{1}{(N-1)}\sum_{i=2}^{N}\frac{k(i)-k(i-1)}{k(i)},$$

measured in units of fractional loss per cycle.

In some variations, the rate constant for the conversion of additional feed sugar is less than 20% lower than the rate constant for the conversion of the reactant feed sugar in the first reaction. In certain variations, the rate constant for conversion of the additional feed sugar is less than 15%, less than 12%, less than 10%, less than 8%, less than 6%, less than 4%, less than 2%, or less than 1% lower than the rate constant for the conversion of the reactant feed sugar in the first reaction. In some variations, the loss of activity is less than 20% per cycle, less than 15% per cycle, less than 10% per cycle, less than 8% per cycle, less than 4% per cycle, less than 2% per cycle, less than 1% per cycle, less than 0.5% per cycle, or less than 0.2% per cycle.

As used herein "catalyst lifetime" refers to the average number of cycles that a catalyst particle can be re-used before it no longer effectively catalyzes the conversion of additional reactant feed sugar. The catalyst lifetime is calculated as the reciprocal of the loss of activity. For example, if the loss of activity is 1% per cycle, then the catalyst lifetime is 100 cycles. In some variations, the catalyst lifetime is at least 1 cycle, at least 2 cycles, at least 10 cycles, at least 50 cycles, at least 100 cycles, at least 200 cycles, at least 500 cycles.

In certain embodiments, a portion of the total mass of the catalyst in a reaction may be removed and replaced with fresh catalyst between reaction cycles. For example, in some variations, 0.1% of the mass of the catalyst may be replaced between reaction cycles, 1% of the mass of the catalyst may be replaced between reaction cycles, 2% of the mass of the catalyst may be replaced between reaction cycles, 5% of the mass of the catalyst may be replaced between reaction cycles, 10% of the mass of the catalyst may be replaced between reaction cycles, or 20% of the mass of the catalyst may be replaced between reaction cycles.

As used herein, the "catalyst make-up rate" referes to the fraction of the catalyst mass that is replaced with fresh catalyst between reaction cycles.

e) Additional Processing Steps

With reference again to FIG. 1, process 100 may be modified to have additional processing steps. Additional processing steps may include, for example, polishing steps. Polishing steps may include, for example, separation, dilution, concentration, filtration, demineralization, chromatographic separation, or decolorization, or any combination thereof. For example, in one embodiment process 100 is modified to include a dilution step and a decolorization step. In another embodiment process 100 is modified to include a filtration step and a drying step.

Decolorization

In some embodiments, the methods described herein further include a decolorization step. The one or more oligosaccharides produced may undergo a decolorization step using any method known in the art, including, for example, treatment with an absorbent, activated carbon, chromatography (e.g., using ion exchange resin), hydrogenation, and/or filtration (e.g., microfiltration).

In certain embodiments, the one or more oligosaccharides produced are contacted with a color-absorbing material at a particular temperature, at a particular concentration, and/or for a particular duration of time. In some embodiments, the mass of the color absorbing species contacted with the one or more oligosaccharides is less than 50% of the mass of the one or more oligosaccharides, less than 35% of the mass of the one or more oligosaccharides, less than 20% of the mass of the one or more oligosaccharides, less than 10% of the mass of the one or more oligosaccharides, less than 5% of the mass of the one or more oligosaccharides, less than 2% of the mass of the one or more oligosaccharides, or less than 1% of the mass of the one or more oligosaccharides.

In some embodiments, the one or more oligosaccharides are contacted with a color absorbing material. In certain embodiments, the one or more oligosaccharides are contacted with a color absorbing material for less than 10 hours, less than 5 hours, less than 1 hour, or less than 30 minutes. In a particular embodiment, the one or more oligosaccharides are contacted with a color absorbing material for 1 hour.

In certain embodiments, the one or more oligosaccharides are contacted with a color absorbing material at a temperature from 20 to 100 degrees Celsius, 30 to 80 degrees Celsius, 40 to 80 degrees Celsius, or 40 to 65 degrees Celsius. In a particular embodiment, the one or more oligosaccharides are contacted with a color absorbing material at a temperature of 50 degrees Celsius.

In certain embodiments, the color absorbing material is activated carbon. In one embodiment, the color absorbing material is powdered activated carbon. In other embodiments, the color absorbing material is an ion exchange resin. In one embodiment, the color absorbing material is a strong base cationic exchange resin in a chloride form. In another embodiment, the color absorbing material is cross-linked polystyrene. In yet another embodiment, the color absorbing material is cross-linked polyacrylate. In certain embodiments, the color absorbing material is Amberlite FPA91, Amberlite FPA98, Dowex 22, Dowex Marathon MSA, or Dowex Optipore SD-2.

Demineralization

In some embodiments, the one or more oligosaccharides produced are contacted with a material to remove salts, minerals, and/or other ionic species. In certain embodiments, the one or more oligosaccharides are flowed through an anionic/cationic exchange column pair. In one embodiment, the anionic exchange column contains a weak base exchange resin in a hydroxide form and the cationic exchange column contains a strong acid exchange resin in a protonated form.

Separation and Concentration

In some embodiments, the methods described herein further include isolating the one or more oligosaccharides produced. In certain variations, isolating the one or more oligosaccharides comprises separating at least a portion of the one or more oligosaccharides from at least a portion of the catalyst, using any method known in the art, including, for example, centrifugation, filtration (e.g., vacuum filtration, membrane filtration), and gravity settling. In some embodiments, isolating the one or more oligosaccharides comprises separating at least a portion of the one or more oligosaccharides from at least a portion of any unreacted sugar, using any method known in the art, including, for example, filtration (e.g., membrane filtration), chromatography (e.g., chromatographic fractionation), differential solubility, and centrifugation (e.g., differential centrifugation).

In some embodiments, the methods described herein further include a concentration step. For example, in some embodiments, the isolated oligosaccharides undergo evaporation (e.g., vacuum evaporation) to produce a concentrated oligosaccharide composition. In other embodiments, the isolated oligosaccharides undergo a spray drying step to produce an oligosaccharide powder. In certain embodiments, the isolated oligosaccharides undergo both an evaporation step and a spray drying step.

f) Bond Refactoring

Feed sugars comprising non-monomeric sugars used in the methods described herein typically have $\alpha$-1,4 bonds, and when used as reactants in the methods described herein, at least a portion of the $\alpha$-1,4 bonds are converted into $\alpha$-1,2 bonds, $\beta$-1,2 bonds, $\alpha$-1,3 bonds, $\beta$-1,3 bonds, $\beta$-1,4 bonds, $\alpha$-1,6 bonds, and $\beta$-1,6 bonds, as applicable. The feed sugars may comprise non-monomeric hexoses or non-monomeric pentoses, or a combination thereof. It should be clear to one of skill in the art that $\alpha$-1,6 bonds and $\beta$-1,6 bonds may not be applicable to non-monomeric pentoses.

Thus, in certain aspects, provided is a method of producing an oligosaccharide composition, by:

combining feed sugar with a catalyst to form a reaction mixture, wherein the feed sugar has $\alpha$-1,4 bonds, and wherein the catalyst has acidic monomers and ionic monomers connected to form a polymeric backbone, or wherein the catalyst comprises a solid support, acidic moieties attached to the solid support, and ionic moieties attached to the solid support; and converting at least a portion of the $\alpha$-1,4 bonds in the feed sugar to one or more non-$\alpha$-1,4 bonds selected from the group consisting of $\beta$-1,4 bonds, $\alpha$-1,3 bonds, $\beta$-1,3 bonds, $\alpha$-1,6 bonds, and $\beta$-1,6 bonds to produce an oligosaccharide composition from at least a portion of the reaction mixture.

It should generally be understood that $\alpha$-1,4 bonds may also be referred to herein as $\alpha(1\rightarrow4)$ bonds, and similarly, β-1,4 bonds, α-1,3 bonds, β-1,3 bonds, α-1,6 bonds, and β-1,6 bonds may be referred to as β(1→4), α(1→3), β(1→3), α(1→6), and β(1→6) bonds, respectively. It should also generally be understood that α-1,4 bonds may also be referred to herein as α-(1,4) glycyosidic linkages, and similarly, β-1,4 bonds, α-1,3 bonds, β-1,3 bonds, α-1,6 bonds, and β-1,6 bonds may be referred to as β-(1,4), α-(1,3), β-(1,3), α-(1,6), and β-(1,6) glycosidic linkages, respectively.

Enumerated Embodiments

The following enumerated embodiments are representative of some aspects of the invention.
1. An animal feed composition, comprising:
   (i) a base feed, and
   (ii) an oligosaccharide composition,
      wherein the oligosaccharide composition has a glycosidic bond type distribution of:
         at least 10 mol % α-(1,3) glycosidic linkages; and
         at least 10 mol % β-(1,3) glycosidic linkages, and
      wherein at least 10 dry wt % of the oligosaccharide composition has a degree of polymerization of at least 3.
2. The animal feed composition of embodiment 1, wherein the oligosaccharide composition has a glycosidic bond type distribution of less than 9 mol % α-(1,4) glycosidic linkages, and less than 19 mol % α-(1,6) glycosidic linkages.
3. An animal feed composition, comprising:
   (i) a base feed, and
   (ii) an oligosaccharide composition,
      wherein the oligosaccharide composition has a glycosidic bond type distribution of:
         less than 9 mol % α-(1,4) glycosidic linkages; and
         less than 19 mol % α-(1,6) glycosidic linkages, and
      wherein at least 10 dry wt % of the oligosaccharide composition has a degree of polymerization of at least 3.
4. The animal feed composition of any one of embodiments 1 to 3, wherein the oligosaccharide composition has a glycosidic bond type distribution of at least 15 mol % β-(1,2) glycosidic linkages.
5. The animal feed composition of any one of embodiments 1 to 4, wherein the oligosaccharide composition is present in the animal feed composition at below 5,000 ppm weight dry oligosaccharide composition per weight of the animal feed composition.
6. The animal feed composition of any one of embodiments 1 to 5, wherein the oligosaccharide composition is present in the animal feed composition at below 3,000 ppm weight dry oligosaccharide composition per weight of the animal feed composition.
7. The animal feed composition of any one of embodiments 1 to 6, wherein the oligosaccharide composition is present in the animal feed composition at between 10 to 1,000 ppm weight dry oligosaccharide composition per weight of the animal feed composition.
8. The animal feed composition of any one of embodiments 1 to 7, wherein the oligosaccharide composition is present in the animal feed composition at between 10 to 500 ppm weight dry oligosaccharide composition per weight of the animal feed composition.
9. The animal feed composition of any one of embodiments 1 to 8, wherein the base feed comprises:
   between 1200 to 1600 cal/lb apparent metabolizable energy;
   between 16 to 24 wt % crude protein;
   between 1.0 and 1.4 wt % lysine;
   between 0.5 and 0.75 wt % methionine;
   between 0.75 and 1.1 wt % total sulfur amino acids;
   between 0.7 and 1.0 wt % calcium;
   between 0.35 and 0.5 wt % total available phosphorous; and
   between 0.15 and 0.3 wt % sodium.
10. The animal feed composition of any one of embodiments 1 to 9, wherein the oligosaccharide composition comprises an oligosaccharide selected from the group consisting of a gluco-oligosaccharide, a galacto-oligosaccharide, a fructo-oligosaccharide, a manno-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, and a manno-xylo-oligosaccharide, or any combinations thereof.
11. The animal feed composition of any one of embodiments 1 to 10, wherein the oligosaccharide composition comprises an oligosaccharide selected from the group consisting of an arabino-oligosaccharide, a xylo-oligosaccharide, and an arabino-xylo-oligosaccharide, or any combinations thereof.
12. The animal feed composition of any one of embodiments 1 to 11, wherein the oligosaccharide composition has a glycosidic bond type distribution of:
   between 0 to 20 mol % α-(1,2) glycosidic linkages;
   between 0 to 45 mol % β-(1,2) glycosidic linkages;
   between 1 to 30 mol % α-(1,3) glycosidic linkages;
   between 1 to 20 mol % β-(1,3) glycosidic linkages;
   between 0 to 55 mol % β-(1,4) glycosidic linkages; and
   between 10 to 55 mol % β-(1,6) glycosidic linkages.
13. The animal feed composition of any one of embodiments 1 to 12, wherein at least 50 dry wt % of the oligosaccharide composition has a degree of polymerization of at least 3.
14. The animal feed composition of any one of embodiments 1 to 13, wherein between 65 and 80 dry wt % of the oligosaccharide composition has a degree of polymerization of at least 3.
15. The animal feed composition of any one of embodiments 1 to 14, wherein at least 50 dry wt % of the oligosaccharide composition comprises one or more gluco-oligosaccharides.
16. The animal feed composition of any one of embodiments 1 to 14, wherein at least 50 dry wt % of the oligosaccharide composition comprises one or more gluco-galacto-oligosaccharides.
17. The animal feed composition of any one of embodiments 1 to 16, wherein the oligosaccharide composition has a glycosidic bond type distribution of:
   between 0 to 20 mol % α-(1,2) glycosidic linkages;
   between 10 to 45 mol % β-(1,2) glycosidic linkages;
   between 1 to 30 mol % α-(1,3) glycosidic linkages;
   between 1 to 20 mol % β-(1,3) glycosidic linkages;
   between 0 to 55 mol % β-(1,4) glycosidic linkages;
   between 10 to 55 mol % β-(1,6) glycosidic linkages;
   less than 9 mol % α-(1,4) glycosidic linkages; and
   less than 19 mol % α-(1,6) glycosidic linkages.
18. The animal feed composition of any one of embodiments 1 to 16, wherein the oligosaccharide composition has a glycosidic bond type distribution of:
   between 0 to 15 mol % α-(1,2) glycosidic linkages;
   between 0 to 15 mol % β-(1,2) glycosidic linkages;
   between 1 to 20 mol % α-(1,3) glycosidic linkages;
   between 1 to 15 mol % β-(1,3) glycosidic linkages;

between 5 to 55 mol % β-(1,4) glycosidic linkages;
between 15 to 55 mol % β-(1,6) glycosidic linkages;
less than 20 mol % α-(1,4) glycosidic linkages; and
less than 30 mol % α-(1,6) glycosidic linkages.

19. The animal feed composition of any one of embodiments 1 to 18, wherein the animal feed composition is poultry feed.

20. The animal feed composition of embodiment 19, wherein the base feed is starter feed.

21. The animal feed composition of any one of embodiments 1 to 20, comprising less than 50 ppm antibiotic.

22. The animal feed composition of any one of embodiments 1 to 21, comprising less than 50 ppm of an ionophore.

23. The animal feed composition of embodiment 21 or 22, wherein the antibiotic is selected from the group consisting of bacitracin, bacitracin methylene disalicylate, bacitracin-zinc, virginiamycin, bambermycin, avilamycin, and efrotomycin, or any combinations thereof.

24. The animal feed composition of embodiment 22 or 23, wherein the ionophore is selected from the group consisting of monensin, salinomycin, narasin, and lasalocid, or any combinations thereof.

25. The animal feed composition of any one of embodiments 1 to 24, wherein the oligosaccharide composition is a functionalized oligosaccharide composition.

26. An animal feed pre-mix, comprising:
(i) a carrier material; and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages, and
wherein at least 10 dry wt % of the oligosaccharide composition has a degree of polymerization of at least 3.

27. The animal feed pre-mix of embodiment 26, wherein the oligosaccharide composition has a glycosidic bond type distribution of less than 9 mol % α-(1,4) glycosidic linkages, and less than 19 mol % α-(1,6) glycosidic linkages.

28. An animal feed pre-mix, comprising:
(i) a carrier material; and
(ii) an oligosaccharide composition,
wherein the oligosaccharide composition has a glycosidic bond type distribution of:
less than 9 mol % α-(1,4) glycosidic linkages; and
less than 19 mol % α-(1,6) glycosidic linkages, and
wherein at least 10 dry wt % of the oligosaccharide composition has a degree of polymerization of at least 3.

29. The animal feed composition of any one of embodiments 26 to 28, wherein the oligosaccharide composition has a glycosidic bond type distribution of at least 15 mol % β-(1,2) glycosidic linkages.

30. The animal feed pre-mix of any one of embodiments 26 to 29, wherein the animal feed pre-mix comprises at least 10 wt % dry oligosaccharide composition per weight animal feed pre-mix.

31. The animal feed pre-mix of any one of embodiments 26 to 30, wherein the animal feed pre-mix comprises between 10 to 60 wt % dry oligosaccharide composition per weight animal feed pre-mix.

32. The animal feed pre-mix of any one of embodiments 26 to 30, wherein the animal feed pre-mix comprises between 15 to 50 wt % dry oligosaccharide composition per weight animal feed pre-mix.

33. The animal feed pre-mix of any one of embodiments 26 to 30, wherein the animal feed pre-mix comprises between 20 to 50 dry wt % oligosaccharide composition.

34. The animal feed pre-mix of any one of embodiments 26 to 30, wherein the carrier material is selected from the group consisting of rice hulls, feed grade silica gel, feed grade fumed silica, corn gluten feed, corn gluten meal, dried distiller's grains, and milled corn, or any combinations thereof.

35. The animal feed pre-mix of any one of embodiments 26 to 34, wherein the carrier material is milled corn.

36. The animal feed pre-mix of any one of embodiments 26 to 35, wherein the moisture content is less than 20 wt %.

37. The animal feed pre-mix of any one of embodiments 26 to 36, wherein the pre-mix is a solid.

38. The animal feed pre-mix of any one of embodiments 26 to 37, wherein the pre-mix is a flowable powder.

39. The animal feed pre-mix of any one of embodiments 26 to 38, wherein the oligosaccharide composition comprises a gluco-oligosaccharide, a galacto-oligosaccharide, a fructo-oligosaccharide, a manno-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, or a xylo-gluco-galacto-oligosaccharide, or any combinations thereof.

40. The animal feed pre-mix of any one of embodiments 26 to 39, wherein the oligosaccharide composition comprises an oligosaccharide selected from the group consisting of an arabino-oligosaccharide, a xylo-oligosaccharide, and an arabino-xylo-oligosaccharide, or any combinations thereof.

41. The animal feed pre-mix of any one of embodiments 26 to 40, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages; and
between 10 to 55 mol % β-(1,6) glycosidic linkages.

42. The animal feed pre-mix of any one of embodiments 26 to 41, wherein at least 50 dry wt % of the oligosaccharide composition has a degree of polymerization of at least 3.

43. The animal feed pre-mix of any one of embodiments 26 to 42, wherein between 65 and 80 dry wt % of the oligosaccharide composition has a degree of polymerization of at least 3.

44. The animal feed pre-mix of any one of embodiments 26 to 43, wherein at least 50 dry wt % of the oligosaccharide composition comprises one or more gluco-oligosaccharides.

45. The animal feed pre-mix of any one of embodiments 26 to 44, wherein at least 50 dry wt % of the oligosaccharide composition comprises one or more gluco-galacto-oligosaccharides.

46. The animal feed pre-mix of any one of embodiments 26 to 45, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages;
between 10 to 55 mol % β-(1,6) glycosidic linkages;
less than 9 mol % α-(1,4) glycosidic linkages; and
less than 19 mol % α-(1,6) glycosidic linkages.

47. The animal feed pre-mix of any one of embodiments 26 to 45, wherein the oligosaccharide composition has a glycosidic bond type distribution of:
  between 0 to 15 mol % α-(1,2) glycosidic linkages;
  between 0 to 15 mol % β-(1,2) glycosidic linkages;
  between 1 to 20 mol % α-(1,3) glycosidic linkages;
  between 1 to 15 mol % β-(1,3) glycosidic linkages;
  between 5 to 55 mol % β-(1,4) glycosidic linkages;
  between 15 to 55 mol % β-(1,6) glycosidic linkages;
  less than 20 mol % α-(1,4) glycosidic linkages; and
  less than 30 mol % α-(1,6) glycosidic linkages.

48. The animal feed pre-mix of any one of embodiments 26 to 47, wherein the animal feed pre-mix reduces feed conversion ratio (FCR) by between 1 to 10% when fed to an animal as compared to an animal fed a feed composition without the oligosaccharide composition.

49. The animal feed pre-mix of any one of embodiments 26 to 47, wherein the animal feed pre-mix reduces FCR by between 1 to 8% when fed to an animal as compared to an animal fed a feed composition without the oligosaccharide composition.

50. The animal feed pre-mix of any one of embodiments 26 to 47, wherein the animal feed pre-mix reduces FCR by between 1 to 6% when fed to an animal as compared to an animal fed a feed composition without the oligosaccharide composition.

51. The animal feed pre-mix of any one of embodiments 26 to 47, wherein the animal feed pre-mix increases average daily gain by between 1 to 10% when fed to an animal as compared to an animal fed a feed composition without the oligosaccharide composition.

52. The animal feed pre-mix of any one of embodiments 26 to 47, wherein the animal feed pre-mix increases average daily gain by between 1 to 8% when fed to an animal as compared to an animal fed a feed composition without the oligosaccharide composition.

53. The animal feed pre-mix of any one of embodiments 26 to 47, wherein the animal feed pre-mix increases average daily gain by between 1 to 6% when fed to an animal as compared to an animal fed a feed composition without the oligosaccharide composition.

54. The animal feed pre-mix of any one of embodiments 26 to 47, wherein the animal feed pre-mix increases total weight gain by between 1 to 10% when as compared to an animal fed a feed composition without the oligosaccharide composition.

55. The animal feed pre-mix of any one of embodiments 26 to 47, wherein the animal feed pre-mix increases total weight gain by between 1 to 8% when fed to an animal as compared to an animal fed a feed composition without the oligosaccharide composition.

56. The animal feed pre-mix of any one of embodiments 26 to 47, wherein the animal feed pre-mix increases total weight gain by between 1 to 6% when as compared to an animal fed a feed composition without the oligosaccharide composition.

57. The animal feed pre-mix of any one of embodiments 26 to 56, wherein the oligosaccharide composition is a functionalized oligosaccharide composition.

58. An animal feed composition, comprising (i) a base feed and (ii) the animal feed pre-mix of any one of embodiments 26 to 57.

59. A method of enhancing growth of poultry, comprising:
  providing feed to poultry, wherein the feed comprises:
    (i) a base feed; and
    (ii) an oligosaccharide composition,
      wherein the oligosaccharide composition has a glycosidic bond type distribution of:
        at least 10 mol % α-(1,3) glycosidic linkages;
        at least 10 mol % β-(1,3) glycosidic linkages; and
      wherein at least 10 dry wt % of the oligosaccharide composition has a degree of polymerization of at least 3, and
  enhancing growth in the poultry.

60. A method of decreasing feed conversion ratio of feed provided to poultry, comprising:
  providing feed to poultry, wherein the feed comprises:
    (i) a base feed; and
    (ii) an oligosaccharide composition,
      wherein the oligosaccharide composition has a glycosidic bond type distribution of:
        at least 10 mol % α-(1,3) glycosidic linkages; and
        at least 10 mol % β-(1,3) glycosidic linkages,
      wherein at least 10 dry wt % of the oligosaccharide composition has a degree of polymerization of at least 3, and
  decreasing the feed conversion ratio (FCR) of feed provided to the poultry.

61. The method of embodiment 59 or 60, wherein the oligosaccharide composition has a bond distribution of at least 15 mol % β-(1,2) glycosidic linkages.

62. The method of any one of embodiments 59 to 61, wherein the oligosaccharide composition is present in the feed at below 5,000 ppm weight dry oligosaccharide composition per weight of the feed.

63. The method of any one of embodiments 59 to 61, wherein the oligosaccharide composition is present in the feed at below 3,000 ppm weight dry oligosaccharide composition per weight of the feed.

64. The method of any one of embodiments 59 to 61, wherein the oligosaccharide composition is present in the feed at between 10 to 1,000 ppm weight dry oligosaccharide composition per weight of the feed.

65. The method of any one of embodiments 59 to 61, wherein the oligosaccharide composition is present in the feed at between 10 to 500 ppm weight dry oligosaccharide composition per weight of the feed.

66. The method of any one of embodiments 59 to 65, wherein the feed conversion ratio (FCR) is between 0 to 4% higher than the performance target minimum.

67. The method of any one of embodiments 59 to 65, wherein the feed conversion ratio is decreased by between 0 to 4%.

68. The method of any one of embodiments 59 to 67, wherein the feed conversion ratio is decreased between 1 to 10% as compared to poultry provided feed without the oligosaccharide composition.

69. The method of any one of embodiments 59 to 67, wherein the feed conversion ratio is decreased between 1 to 8% as compared to poultry provided feed without the oligosaccharide composition.

70. The method of any one of embodiments 59 to 67, wherein the feed conversion ratio is decreased between 1 to 6% as compared to poultry provided feed without the oligosaccharide composition.

71. The method of any one of embodiments 68 to 70, wherein the feed conversion ratio is decreased over 42 days.

72. The method of any one of embodiments 68 to 70, wherein the feed conversion ratio is decreased over 35 days.

73. The method of any one of embodiments 68 to 70, wherein the feed conversion ratio is decreased over 6 weeks.

74. The method of any one of embodiments 68 to 70, wherein the feed conversion ratio is decreased over 6.5 weeks.
75. The method of any one of embodiments 59 to 70, wherein the poultry are provided feed on a daily basis.
76. The method of any one of embodiments 59 to 70, wherein the poultry are provided feed on a weekly basis.
77. The method of any one of embodiments 59 to 70, wherein the poultry are provided feed every other day.
78. The method of any one of embodiments 59 to 77, wherein the feed is a starter diet.
79. The method of any one of embodiments 59 to 77, wherein the feed is a grower-type diet.
80. The method of any one of embodiments 59 to 77, wherein the feed is a finisher-type diet.
81. The method of any one of embodiments 59 to 78, wherein the feed is provided to the poultry during the starter diet phase.
82. The method of any one of embodiments 59 to 77, 79, and 81, wherein the feed is provided to the poultry during the grower diet phase.
83. The method of any one of embodiments 59 to 77, and 80 to 82, wherein the feed is provided to the poultry during finisher diet phase.
84. The method of any one of embodiments 59 to 83, wherein the poultry is broiler chickens, layer hens, or turkeys.
85. The method of any one of embodiments 59 to 84, wherein short chain fatty acid concentration in the poultry is increased by between 1 to 80% relative to poultry provided feed without the oligosaccharide composition.
86. The method of any one of embodiments 59 to 85, wherein short chain fatty acid concentration in the poultry is increased by between 10 to 50% relative to poultry provided feed without the oligosaccharide composition.
87. The method of any one of embodiments 59 to 86, wherein short chain fatty acid concentration in the poultry is increased by between 30 to 50% relative to poultry provided feed without the oligosaccharide composition.
88. The method of any one of embodiments 85 to 87, wherein the short chain fatty acid concentration is the ileal short chain fatty acid concentration.
89. The method of any one of embodiments 85 to 87, wherein the short chain fatty acid concentration is the cecal short chain fatty acid concentration.
90. The method of any one of embodiments 85 to 89, wherein the short chain fatty acids comprise butyric acid, propionic acid, acetic acid, valeric acid, isobutyric acid, isovaleric acid, 2-methyl-butyric acid, or lactic acid, or any combinations thereof.
91. The method of any one of embodiments 85 to 89, wherein the short chain fatty acids comprise butyric acid or propionic acid, or a combination thereof.
92. The method of any one of embodiments 59 to 91, wherein the poultry is between 0 to 35 days old.
93. The method of any one of embodiments 59 to 91, wherein the poultry is between 0 to 15 days old.
94. The method of any one of embodiments 59 to 91, wherein the poultry is between 16 to 28 days old.
95. The method of any one of embodiments 59 to 91, wherein the poultry is between 29 to 35 days old.
96. The method of any one of embodiments 59 to 91, wherein the poultry is between 0 to 6 weeks old.
97. The method of any one of embodiments 59 to 91, wherein the poultry is between 0 to 6.5 weeks old.
98. The method of any one of embodiments 59 to 97, wherein the poultry has an average daily weight gain, and wherein the average daily weight gain is at least 50 grams.
99. The method of any one of embodiments 59 to 97, wherein the poultry has an average daily weight gain, and wherein the average daily weight gain is at least 2% greater than the average daily weight gain of poultry provided feed without the oligosaccharide composition.
100. The method of any one of embodiments 59 to 99, wherein the poultry has an average weekly weight gain, and wherein the average weekly weight gain is at least 400 grams.
101. The method of any one of embodiments 59 to 100, wherein the poultry has an average weekly weight gain, and wherein the average weekly weight gain is at least 2% greater than poultry provided feed without the oligosaccharide composition.
102. The method of any one of embodiments 59 to 101, wherein the poultry has an average final body weight, and wherein the average final body weight of the poultry is at least 0.05 kg greater than poultry provided feed without the oligosaccharide composition.
103. The method of embodiment 97, wherein the poultry is between 1 to 14 days of age, wherein the average daily weight gain is at least 40 grams.
104. The method of embodiment 97, wherein the poultry is between 14 to 28 days of age, wherein the average daily weight gain is at least 80 grams.
105. The method of embodiment 97, wherein the poultry is between 29 to 35 days of age, wherein the average daily weight gain is at least 60 grams.
106. The method of any one of embodiments 103 to 105, wherein the feed is provided to the poultry on a daily basis.
107. The method of any one of embodiments 59 to 106, further comprising:
    processing the poultry to produce a poultry eviscerated carcass, and
    obtaining leg meat from the poultry eviscerated carcass, wherein the average yield of leg meat is at least 10% of live weight.
108. The method of any one of embodiments 59 to 107, further comprising:
    processing the poultry to produce a poultry eviscerated carcass, and
    obtaining breast meat from the poultry eviscerated carcass,
        wherein the average yield of breast meat from the poultry is at least 15% of live weight.
109. The method of any one of embodiments 59 to 108, further comprising:
    processing the poultry to produce a poultry eviscerated carcass, and
    obtaining drumstick meat from the poultry eviscerated carcass,
        wherein the average yield of drumstick meat is at least 8% of live weight.
110. The method of any one of embodiments 59 to 109, further comprising:
    processing the poultry to produce a poultry eviscerated carcass, and
    obtaining fat from the poultry eviscerated carcass,
        wherein the average yield of fat is at least 0.5% of live weight.
111. The method of any one of embodiments 59 to 110, further comprising:
    processing the poultry to produce a poultry eviscerated carcass, wherein the average yield of poultry eviscerated carcass is at least 70% of live weight.

112. The method of any one of embodiments 59 to 111, wherein the oligosaccharide composition is a functionalized oligosaccharide composition.

113. The method of any one of embodiments 59 to 112, wherein the poultry has a disease or disorder.

114. The method of embodiment 113, wherein the disease or disorder is necrotic enteritis, coccidiosis, nutrient malabsorption syndrome, intestinal barrier breakdown, colisepticemia, yolk sack infection, salmonella infection, or campylobacter infection.

115. The method of embodiment 114, wherein the disease or disorder is necrotic enteritis.

116. A method of enhancing growth of an animal population, comprising:
    feeding to the animal population an animal feed,
        wherein the animal feed comprises an oligosaccharide composition at an inclusion rate of less than 5,000 ppm wt % dry oligosaccharide composition per weight of animal feed;
        wherein the oligosaccharide composition has a glycosidic bond type distribution of:
            at least 1 mol % α-(1,3) glycosidic linkages; and
            at least 1 mol % β-(1,3) glycosidic linkages, and
        wherein at least 10 dry wt % of the oligosaccharide composition has a degree of polymerization of at least 3; and
    enhancing growth of the animal population.

117. The method of embodiment 116, wherein the oligosaccharide composition has a glycosidic bond type distribution of at least 15 mol % β-(1,2) glycosidic linkages.

118. The method of embodiment 116 or 117, wherein the animal population is monogastric.

119. The method of any one of embodiments 116 to 118, wherein the animal population is poultry.

120. The method of any one of embodiments 116 to 119, wherein the animal is selected from the group consisting of broiler chickens, layer hens, and turkeys.

121. The method of any one of embodiments 116 to 120, wherein the feed is provided to the animal population during the starter diet phase.

122. The method of any one of embodiments 116 to 120, wherein the feed is provided to the animal population during the grower diet phase.

123. The method of any one of embodiments 116 to 120, wherein the feed is provided to the animal population during the finisher diet phase.

124. The method of any one of embodiments 116 to 123, wherein the animal feed comprises the oligosaccharide composition at an inclusion rate of less than 3,000 ppm wt % dry oligosaccharide composition per weight of animal feed.

125. The method of any one of embodiments 116 to 123, wherein the animal feed comprises the oligosaccharide composition at an inclusion rate of between 10 to 1,000 ppm wt % dry oligosaccharide composition per weight of animal feed.

126. The method of any one of embodiments 116 to 125, wherein the oligosaccharide composition is a functionalized oligosaccharide composition.

127. The method of any one of embodiments 116 to 112, wherein the animal population has a disease or disorder.

128. The method of embodiment 127, wherein the disease or disorder is necrotic enteritis, coccidiosis, nutrient malabsorption syndrome, intestinal barrier breakdown, colisepticemia, yolk sack infection, salmonella infection, or campylobacter infection.

129. The method of embodiment 128, wherein the disease or disorder is necrotic enteritis.

130. A composition comprising a plurality of oligosaccharides, wherein the composition has a glycosidic bond distribution of:
    at least 1 mol % α-(1,3) glycosidic linkages;
    at least 1 mol % β-(1,3) glycosidic linkages;
    at least 15 mol % β-(1,6) glycosidic linkages;
    less than 20 mol % α-(1,4) glycosidic linkages; and
    less than 30 mol % α-(1,6) glycosidic linkages, and
    wherein at least 10 dry wt % of the oligosaccharide composition has a degree of polymerization of at least 3.

131. The oligosaccharide composition of embodiment 130, comprising at least one oligosaccharide selected from the group consisting of a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, an arabino-xylo-oligosaccharide, and a xylo-gluco-galacto-oligosaccharide, or any combinations thereof.

132. The oligosaccharide composition of embodiment 130 or 131, wherein the glycosidic bond distribution is:
    between 0 to 20 mol % α-(1,2) glycosidic linkages;
    between 10 to 45 mol % β-(1,2) glycosidic linkages;
    between 1 to 30 mol % α-(1,3) glycosidic linkages;
    between 1 to 20 mol % β-(1,3) glycosidic linkages;
    between 0 to 55 mol % β-(1,4) glycosidic linkages;
    between 10 to 55 mol % β-(1,6) glycosidic linkages;
    less than 9 mol % α-(1,4) glycosidic linkages; and
    less than 19 mol % α-(1,6) glycosidic linkages.

133. The oligosaccharide composition of embodiment 130 or 131, wherein the glycosidic bond type distribution is:
    between 0 to 15 mol % α-(1,2) glycosidic linkages;
    between 0 to 15 mol % β-(1,2) glycosidic linkages;
    between 1 to 20 mol % α-(1,3) glycosidic linkages;
    between 1 to 15 mol % β-(1,3) glycosidic linkages;
    between 5 to 55 mol % β-(1,4) glycosidic linkages;
    between 15 to 55 mol % β-(1,6) glycosidic linkages;
    less than 20 mol % α-(1,4) glycosidic linkages; and
    less than 30 mol % α-(1,6) glycosidic linkages.

134. The oligosaccharide composition of any one of embodiments 130 to 133, comprising less than 50 wt % water.

135. The oligosaccharide composition of any one of embodiments 130 to 134, wherein at least 50 dry wt % of the oligosaccharide composition has a degree of polymerization of at least 3.

136. The oligosaccharide composition of any one of embodiments 130 to 135, wherein between 65 and 80 dry wt % of the oligosaccharide composition has a degree of polymerization of at least 3.

137. The oligosaccharide composition of any one of embodiments 130 to 136, wherein the oligosaccharide composition is a functionalized oligosaccharide composition.

138. A method of producing an animal feed composition, comprising:

combining feed sugar with a catalyst to form a reaction mixture,
  wherein the catalyst comprises acidic monomers and ionic monomers connected to form a polymeric backbone, or
  wherein the catalyst comprises a solid support, acidic moieties attached to the solid support, and ionic moieties attached to the solid support; and
producing an oligosaccharide composition from at least a portion of the reaction mixture; and
combining the oligosaccharide composition with a base feed to produce an animal feed composition.

139. The method of embodiment 138, further comprising:
separating at least a portion of the catalyst in the reaction mixture from the oligosaccharide composition produced.

140. The method of embodiment 138, further comprising:
combining additional feed sugar with the separated catalyst to form an additional reaction mixture; and
producing an additional oligosaccharide composition from at least a portion of the additional reaction mixture.

141. The method of any one of embodiments 138 to 140, wherein the feed sugar comprises glucose, galactose, fructose, mannose, arabinose, or xylose, or any combinations thereof.

142. The method of any one of embodiments 138 to 141, wherein the animal feed comprises a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, an arabino-xylo-oligosaccharide, or a xylo-gluco-galacto-oligosaccharide, or any combinations thereof.

143. The method of any one of embodiments 138 to 141, wherein the animal feed comprises a galacto-oligosaccharide, a fructo-oligosaccharide, a manno-oligosaccharide, an arabino-oligosaccharide, a xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, or an arabino-xylo-oligosaccharide, or any combinations thereof.

144. The method of any one of embodiments 138 to 143, wherein the animal feed composition is poultry feed.

145. The method of any one of embodiments 138 to 143, wherein the animal feed composition is swine feed.

146. The method of any one of embodiments 138 to 145, wherein the animal feed composition is in liquid form.

147. The method of any one of embodiments 138 to 145, wherein the animal feed composition is in solid form.

148. The method of any one of embodiments 138 to 147, wherein the feed sugar and the catalyst are further combined with one or more functional groups to form the reaction mixture, and the oligosaccharide composition produced from at least a portion of the reaction mixture is a functionalized oligosaccharide composition.

149. The method of embodiment 148, wherein the one or more functional groups are amine, hydroxyl, carboxylic acid, sulfur trioxide, sulfate, or phosphate.

150. The method of embodiment 148, wherein the one or more functional groups are amines, alcohols, carboxylic acids, sulfates, phosphates, or sulfur oxides.

151. The method of any one of embodiments 138 to 150, wherein the catalyst comprises acidic monomers and ionic monomers connected to form a polymeric backbone.

152. The method of embodiment 151, wherein each acidic monomer independently comprises at least one Bronsted-Lowry acid.

153. The method of embodiment 152, wherein the at least one Bronsted-Lowry acid at each occurrence in the catalyst is independently selected from the group consisting of sulfonic acid, phosphonic acid, acetic acid, isophthalic acid, boronic acid, and perfluorinated acid.

154. The method of embodiment 153, wherein the at least one Bronsted-Lowry acid at each occurrence in the catalyst is independently selected from the group consisting of sulfonic acid and phosphonic acid.

155. The method of embodiment 153, wherein the at least one Bronsted-Lowry acid at each occurrence in the catalyst is sulfonic acid.

156. The method of embodiment 153, wherein the at least one Bronsted-Lowry acid at each occurrence in the catalyst is phosphonic acid.

157. The method of embodiment 153, wherein the at least one Bronsted-Lowry acid at each occurrence in the catalyst is acetic acid.

158. The method of embodiment 153, wherein the at least one Bronsted-Lowry acid at each occurrence in the catalyst is isophthalic acid.

159. The method of embodiment 153, wherein the at least one Bronsted-Lowry acid at each occurrence in the catalyst is boronic acid.

160. The method of embodiment 153, wherein the at least one Bronsted-Lowry acid at each occurrence in the catalyst is perfluorinated acid.

161. The method of any one of embodiments 151 to 160, wherein one or more of the acidic monomers are directly connected to the polymeric backbone.

162. The method of any one of embodiments 151 to 160, wherein one or more of the acidic monomers each further comprise a linker connecting the Bronsted-Lowry acid to the polymeric backbone.

163. The method of embodiment 162, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

164. The method of embodiment 162, wherein the Bronsted-Lowry acid and the linker form a side chain, wherein each side chain is independently selected from the group consisting of:

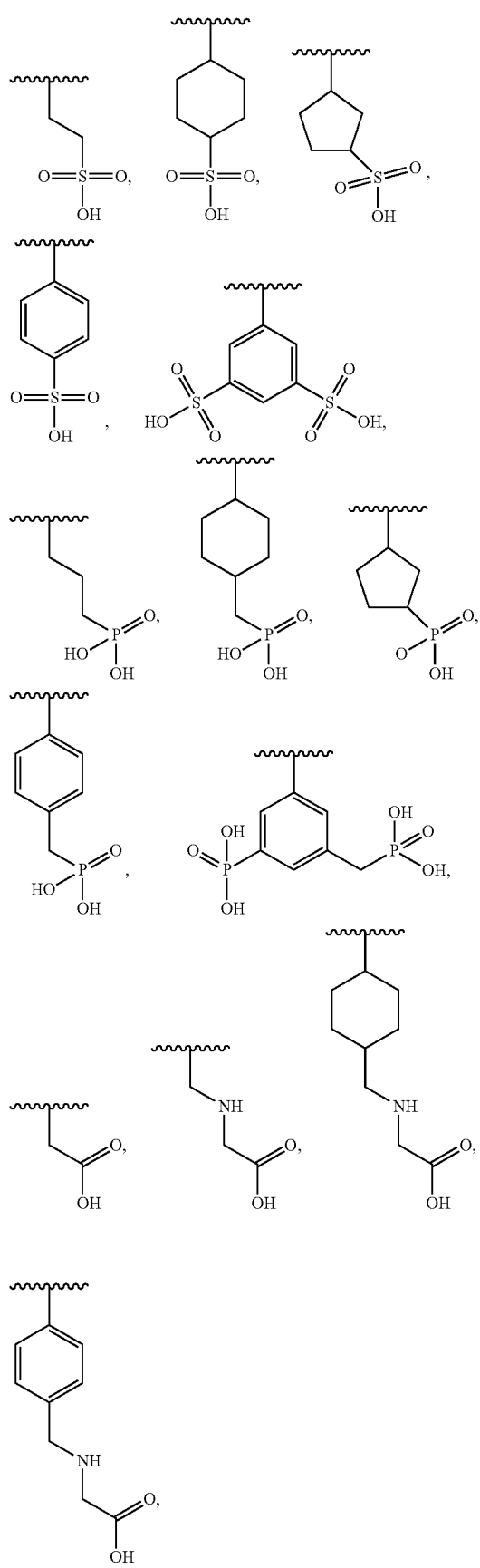

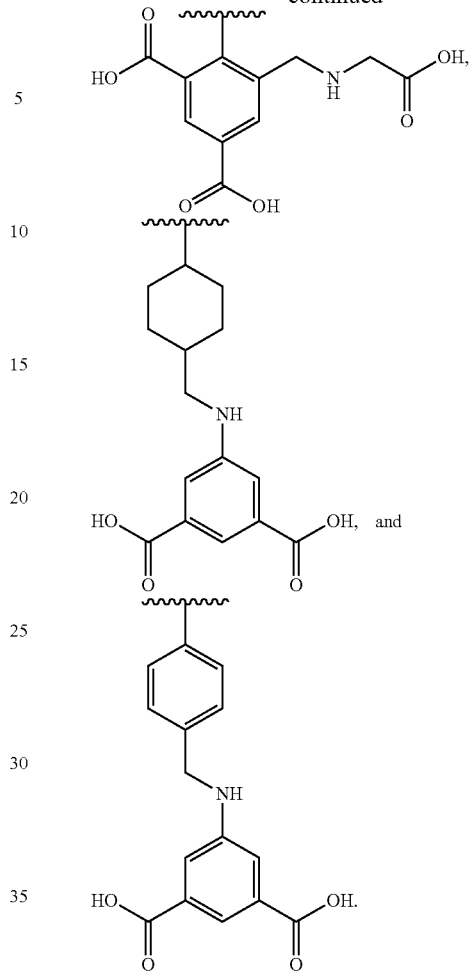

165. The method of any one of embodiments 151 to 164, wherein each ionic monomer independently comprises at least one nitrogen-containing cationic group, at least one phosphorous-containing cationic group, or a combination thereof.

166. The method of embodiment 165, wherein the nitrogen-containing cationic group at each occurrence is independently selected from the group consisting of pyrrolium, imidazolium, pyrazolium, oxazolium, thiazolium, pyridinium, pyrimidinium, pyrazinium, pyridazinium, thiazinium, morpholinium, piperidinium, piperizinium, and pyrollizinium.

167. The method of embodiment 165, wherein the phosphorous-containing cationic group at each occurrence is independently selected from the group consisting of triphenyl phosphonium, trimethyl phosphonium, triethyl phosphonium, tripropyl phosphonium, tributyl phosphonium, trichloro phosphonium, and trifluoro phosphonium.

168. The method of any one of embodiments 151 to 167, wherein one or more of the ionic monomers are directly connected to the polymeric backbone.

169. The method of any one of embodiments 151 to 167, wherein one or more of the ionic monomers each further comprise a linker connecting the nitrogen-containing cationic group or the phosphorous-containing cationic group to the polymeric backbone.

170. The method of embodiment 169, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

171. The method of embodiment 169, wherein the nitrogen-containing cationic group and the linker form a side chain, wherein each side chain is independently selected from the group consisting of:

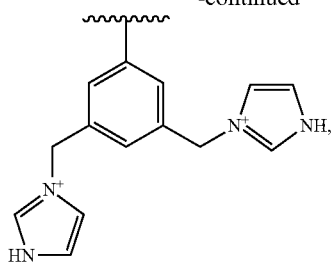

-continued

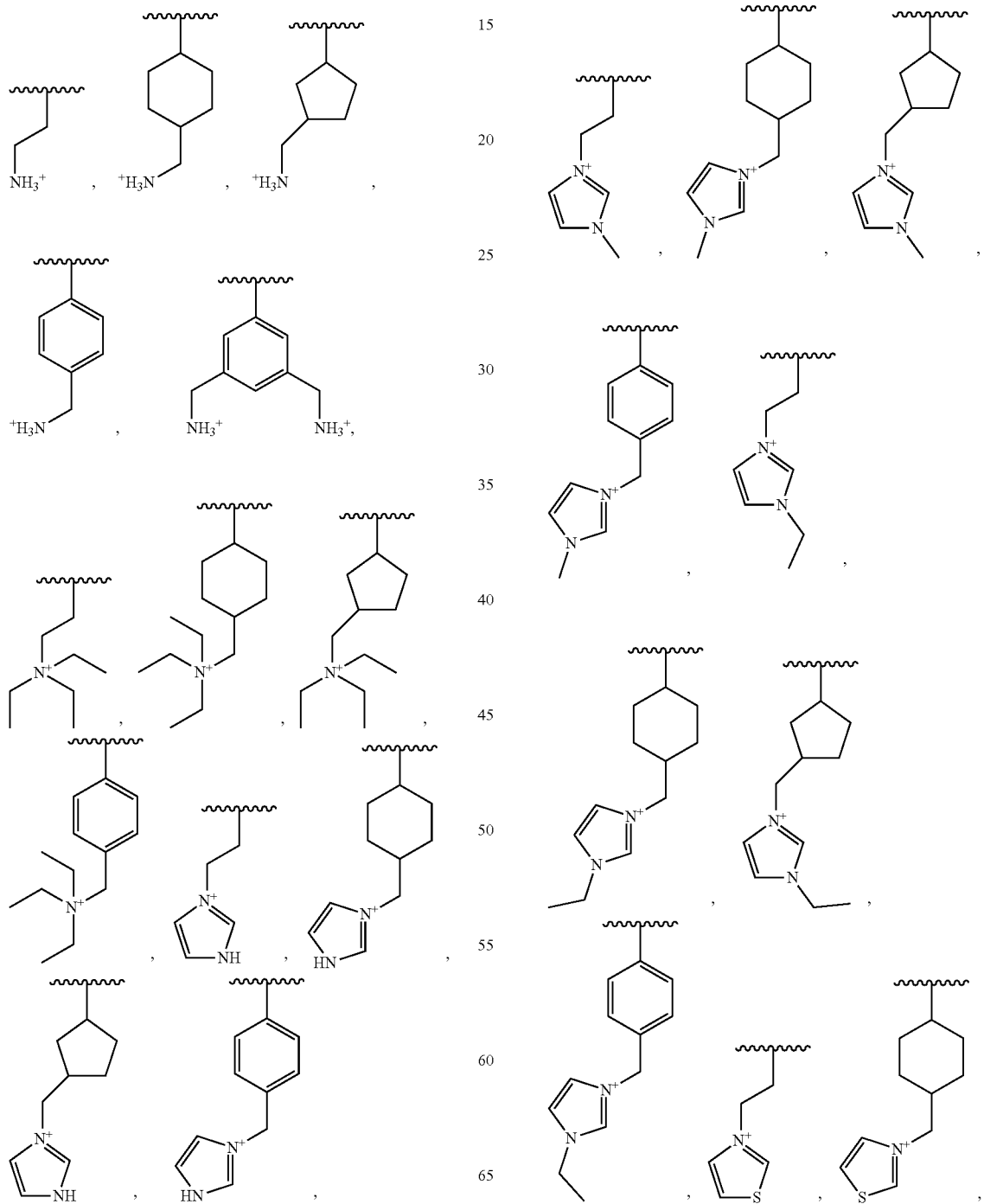

151
-continued
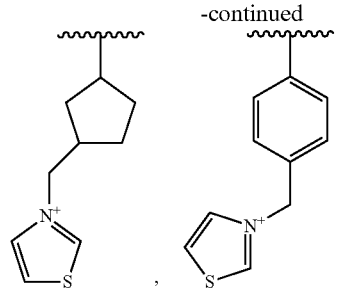
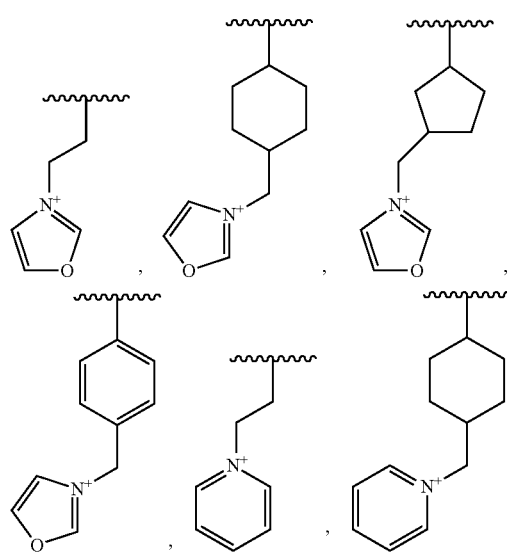
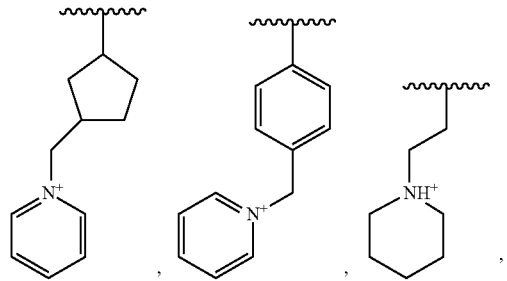
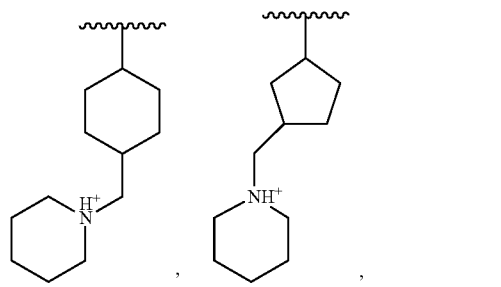
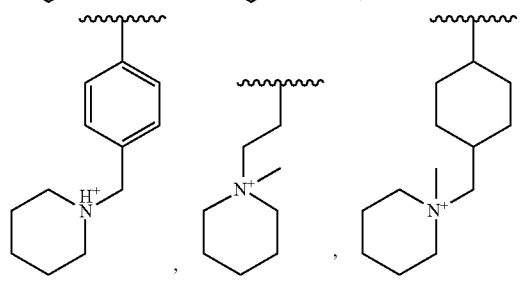
152
-continued
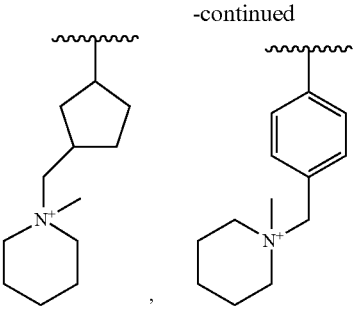
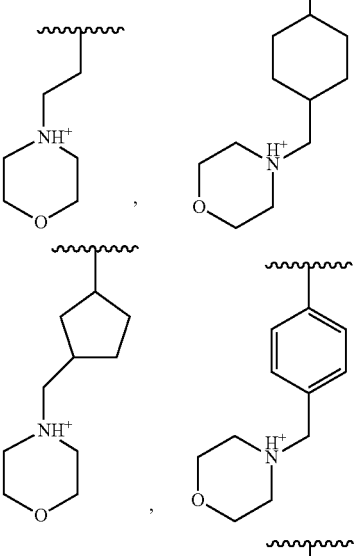
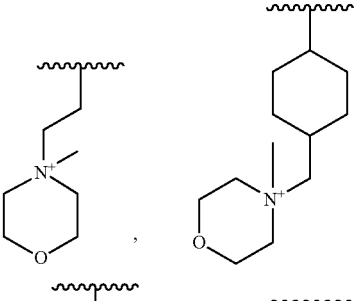
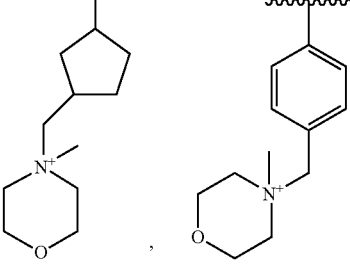
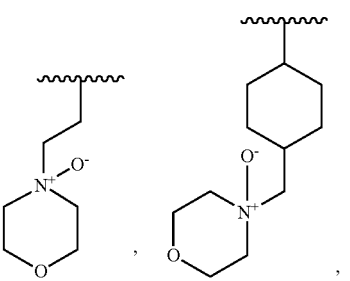

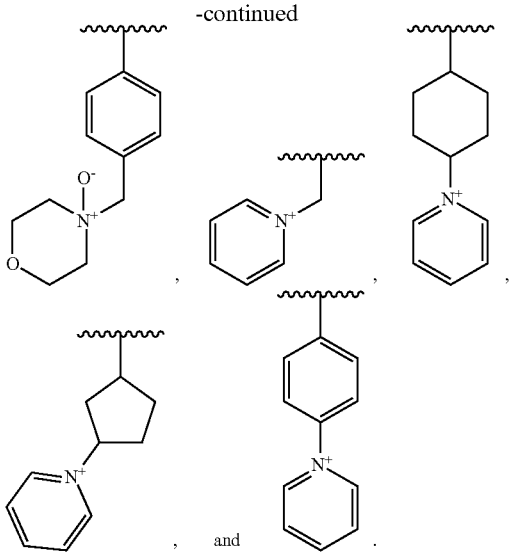

172. The method of embodiment 169, wherein the phosphorous-containing cationic group and the linker form a side chain, wherein each side chain is independently selected from the group consisting of:

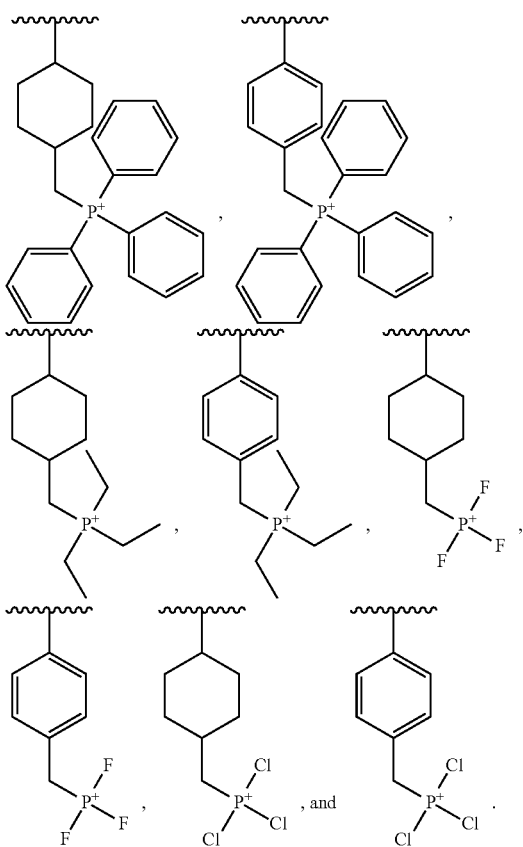

173. The method of any one of embodiments 151 to 172, wherein the polymeric backbone is selected from the group consisting of polyethylene, polypropylene, polyvinyl alcohol, polystyrene, polyurethane, polyvinyl chloride, polyphenol-aldehyde, polytetrafluoroethylene, polybutylene terephthalate, polycaprolactam, poly(acrylonitrile butadiene styrene), polyalkyleneammonium, polyalkylenediammonium, polyalkylenepyrrolium, polyalkyleneimidazolium, polyalkylenepyrazolium, polyalkyleneoxazolium, polyalkylenethiazolium, polyalkylenepyridinium, polyalkylenepyrimidinium, polyalkylenepyrazinium, polyalkylenepyridazinium, polyalkylenethiazinium, polyalkylenemorpholinium, polyalkylenepiperidinium, polyalkylenepiperizinium, polyalkylenepyrollizinium, polyalkylenetriphenylphosphonium, polyalkylenetrimethylphosphonium, polyalkylenetriethylphosphonium, polyalkylenetripropylphosphonium, polyalkylenetributylphosphonium, polyalkylenetrichlorophosphonium, polyalkylenetrifluorophosphonium, and polyalkylenediazolium.

174. The method of any one of embodiments 151 to 173, further comprising hydrophobic monomers connected to the polymeric backbone, wherein each hydrophobic monomer comprises a hydrophobic group.

175. The method of embodiment 174, wherein the hydrophobic group at each occurrence is independently selected from the group consisting of an unsubstituted or substituted alkyl, an unsubstituted or substituted cycloalkyl, an unsubstituted or substituted aryl, or an unsubstituted or substituted heteroaryl.

176. The method of embodiment 174 or 175, wherein the hydrophobic group is directly connected to the polymeric backbone.

177. The method of any one of embodiments 151 to 176, further comprising acidic-ionic monomers connected to the polymeric backbone, wherein each acidic-ionic monomer comprises a Bronsted-Lowry acid and a cationic group.

178. The method of embodiment 177, wherein the cationic group is a nitrogen-containing cationic group or a phosphorous-containing cationic group.

179. The method of embodiment 177 or 178, wherein one or more of the acidic-ionic monomers each further comprise a linker connecting the Bronsted-Lowry acid or the cationic group to the polymeric backbone.

180. The method of embodiment 179, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

181. The method of embodiment 179, wherein the Bronsted-Lowry acid, the cationic group and the linker form a side chain, wherein each side chain is independently selected from the group consisting of:

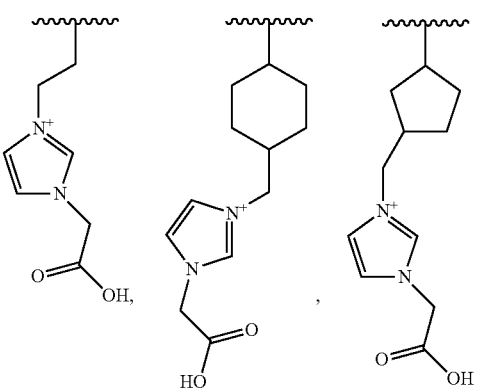

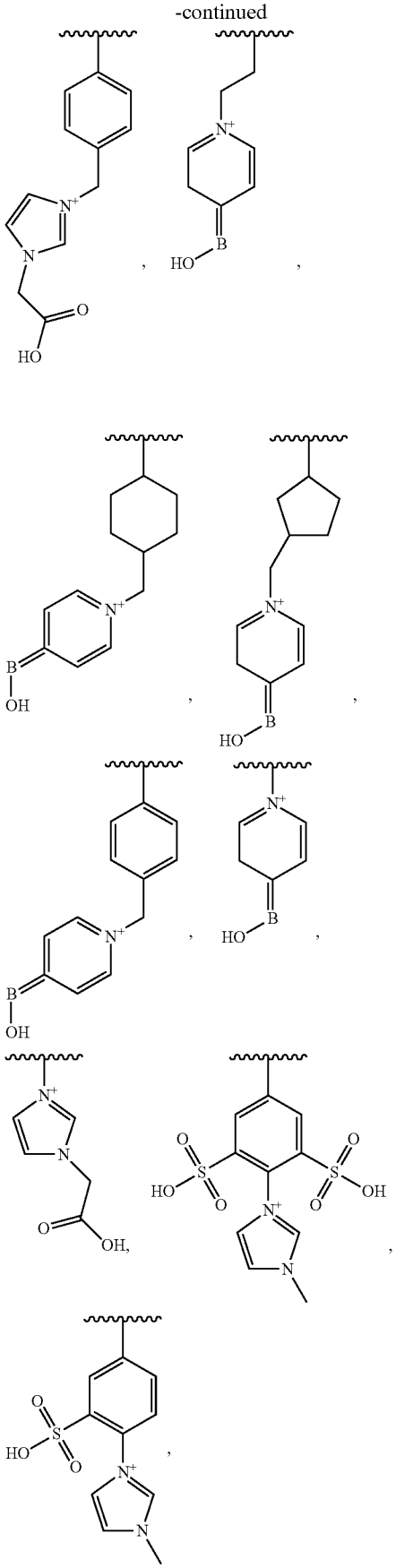

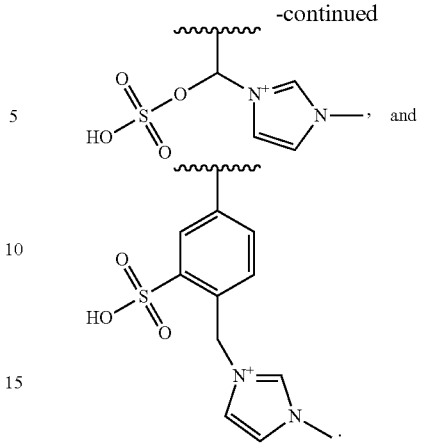

182. The method of any one of embodiments 138 to 150, wherein the catalyst comprises a solid support, acidic moieties attached to the solid support, and ionic moieties attached to the solid support.

183. The method of embodiment 182, wherein the solid support comprises a material, wherein the material is selected from the group consisting of carbon, silica, silica gel, alumina, magnesia, titania, zirconia, clays, magnesium silicate, silicon carbide, zeolites, ceramics, and any combinations thereof.

184. The method of embodiment 183, wherein the material is selected from the group consisting of carbon, magnesia, titania, zirconia, clays, zeolites, ceramics, and any combinations thereof.

185. The method of any one of embodiments 182 to 184, wherein each acidic moiety independently has at least one Bronsted-Lowry acid.

186. The method of embodiment 185, wherein each Bronsted-Lowry acid is independently selected from the group consisting of sulfonic acid, phosphonic acid, acetic acid, isophthalic acid, boronic acid, and perfluorinated acid.

187. The method of embodiment 186, wherein each Bronsted-Lowry acid is independently sulfonic acid or phosphonic acid.

188. The method of embodiment 186, wherein each Bronsted-Lowry acid is sulfonic acid.

189. The method of embodiment 186, wherein each Bronsted-Lowry acid is phosphonic acid.

190. The method of embodiment 186, wherein each Bronsted-Lowry acid is acetic acid.

191. The method of embodiment 186, wherein each Bronsted-Lowry acid is isophthalic acid.

192. The method of embodiment 186, wherein each Bronsted-Lowry acid is boronic acid.

193. The method of embodiment 186, wherein each Bronsted-Lowry acid is perfluorinated acid.

194. The method of any one of embodiments 182 to 193, wherein one or more of the acidic moieties are directly attached to the solid support.

195. The method of any one of embodiments 182 to 193, wherein one or more of the acidic moieties are attached to the solid support by a linker.

196. The method of embodiment 195, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

197. The method of embodiment 195, wherein each acidic moiety independently has at least one Bronsted-Lowry acid, wherein the Bronsted-Lowry acid and the linker form a side chain, wherein each side chain is independently selected from the group consisting of:

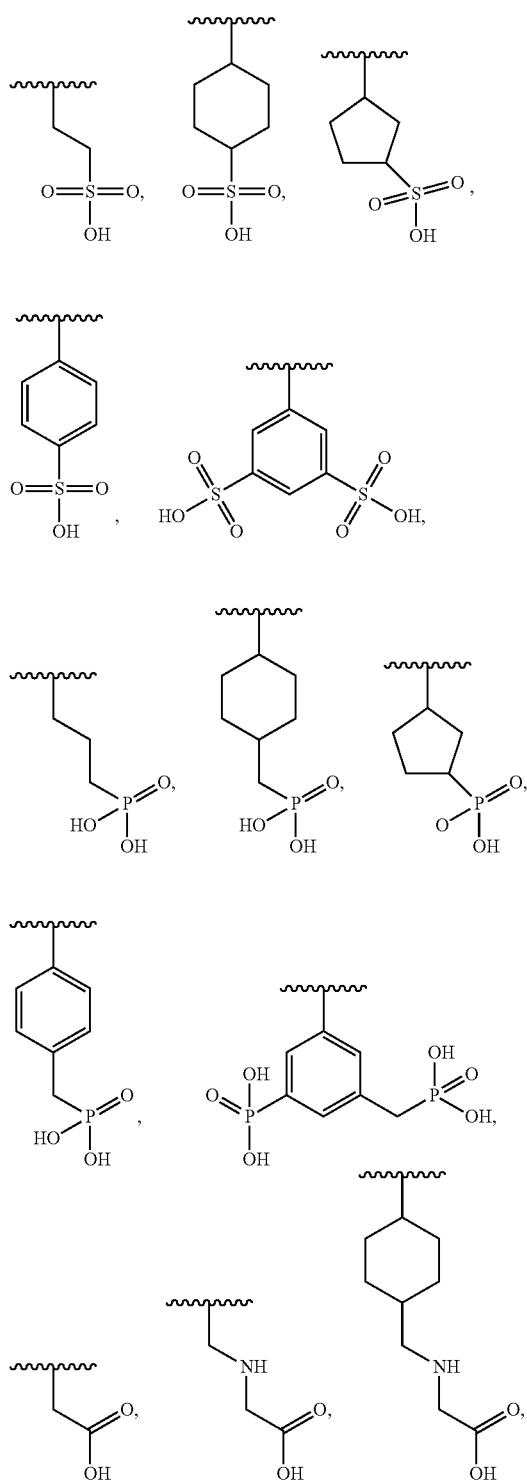

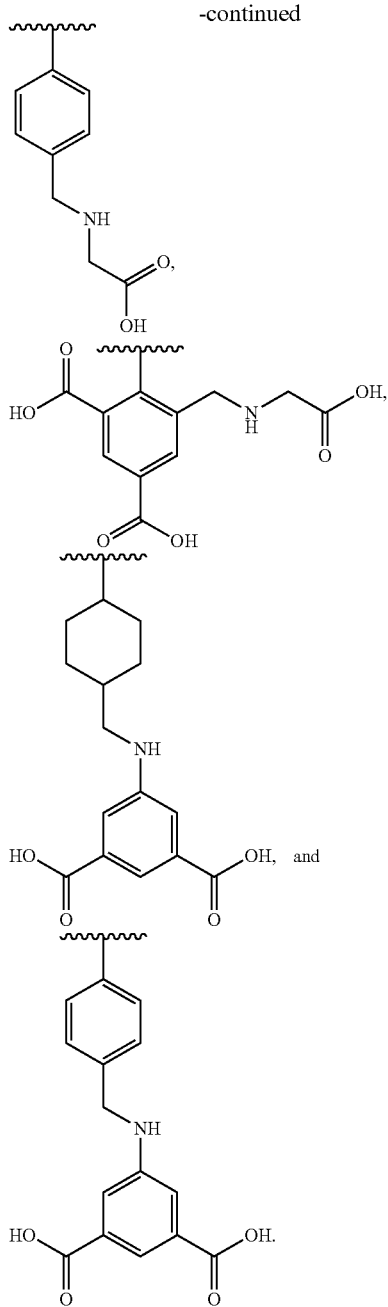

198. The method of any one of embodiments 182 to 197, wherein each ionic moiety independently has at least one nitrogen-containing cationic group or at least one phosphorous-containing cationic group, or a combination thereof.

199. The method of any one of embodiments 182 to 197, wherein each ionic moiety is selected from the group consisting of pyrrolium, imidazolium, pyrazolium, oxazolium, thiazolium, pyridinium, pyrimidinium, pyrazinium, pyridazinium, thiazinium, morpholinium, piperidinium, piperizinium, pyrollizinium, phosphonium, trimethyl phosphonium, triethyl phosphonium, tripropyl phosphonium, tributyl phosphonium, trichloro phosphonium, triphenyl phosphonium and trifluoro phosphonium.

200. The method of any one of embodiments 182 to 197, wherein each ionic moiety independently has at least one nitrogen-containing cationic group, and wherein each nitrogen-containing cationic group is independently selected from the group consisting of pyrrolium, imidazolium, pyrazolium, oxazolium, thiazolium, pyridinium, pyrimidinium, pyrazinium, pyridazinium, thiazinium, morpholinium, piperidinium, piperizinium, and pyrollizinium.

201. The method of any one of embodiments 182 to 197, wherein each ionic moiety independently has at least one phosphorous-containing cationic group, and wherein each phosphorous-containing cationic group is independently selected from the group consisting of triphenyl phosphonium, trimethyl phosphonium, triethyl phosphonium, tripropyl phosphonium, tributyl phosphonium, trichloro phosphonium, and trifluoro phosphonium.

202. The method of any one of embodiments 182 to 201, wherein one or more of the ionic moieties are directed attached to the solid support.

203. The method of any one of embodiments 182 to 201, wherein one or more of the ionic moieties are attached to the solid support by a linker.

204. The method of embodiment 203, wherein each linker is independently selected from the group consisting of unsubstituted or substituted alkyl linker, unsubstituted or substituted cycloalkyl linker, unsubstituted or substituted alkenyl linker, unsubstituted or substituted aryl linker, unsubstituted or substituted heteroaryl linker, unsubstituted or substituted alkyl ether linker, unsubstituted or substituted alkyl ester linker, and unsubstituted or substituted alkyl carbamate linker.

205. The method of embodiment 203, wherein each ionic moiety independently has at least one nitrogen-containing cationic group, wherein the nitrogen-containing cationic group and the linker form a side chain, wherein each side chain is independently selected from the group consisting of:

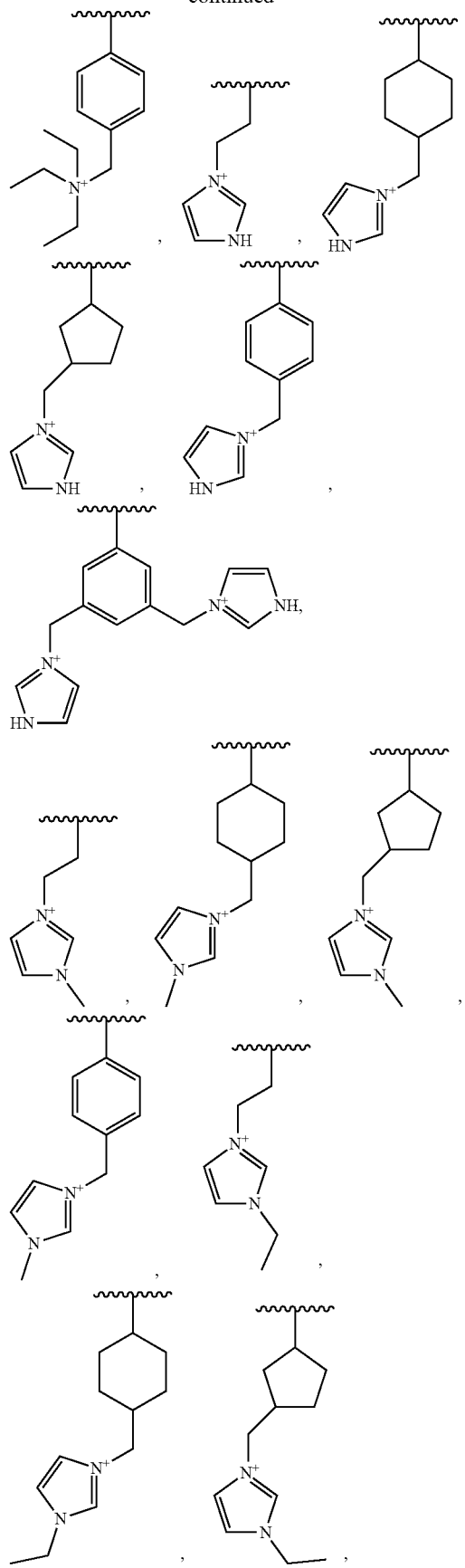

161
-continued
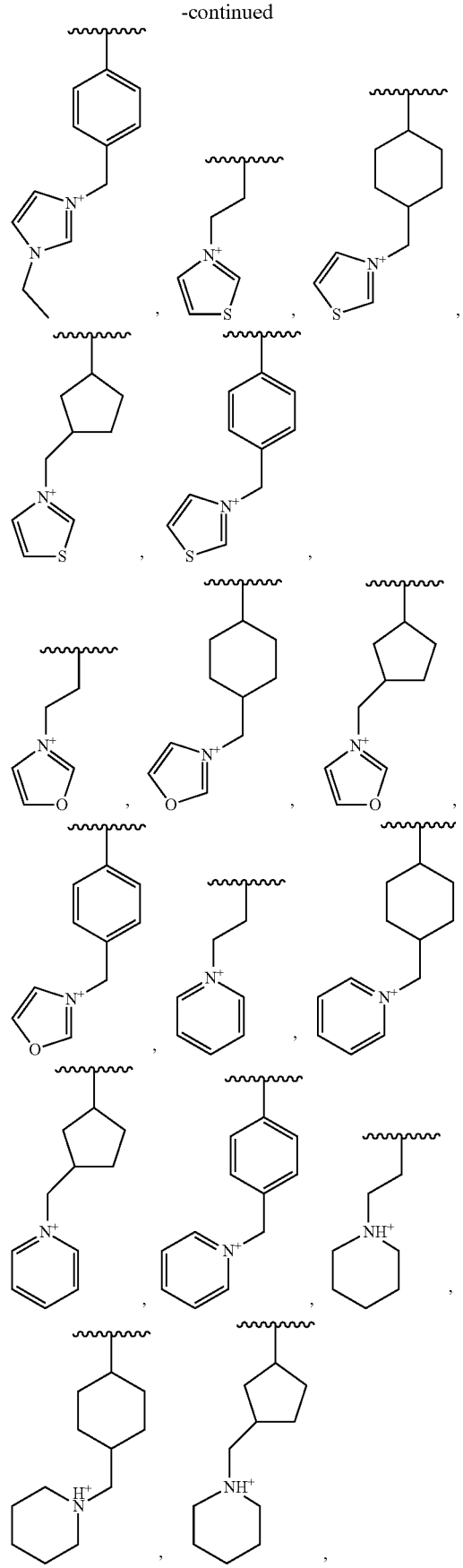
162
-continued
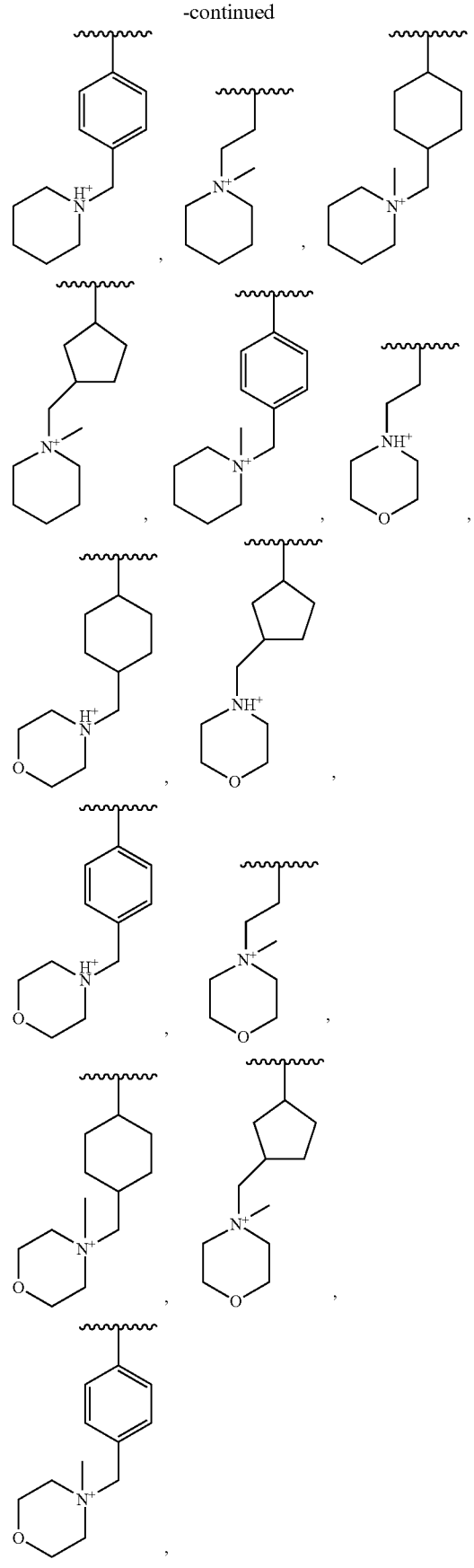

-continued

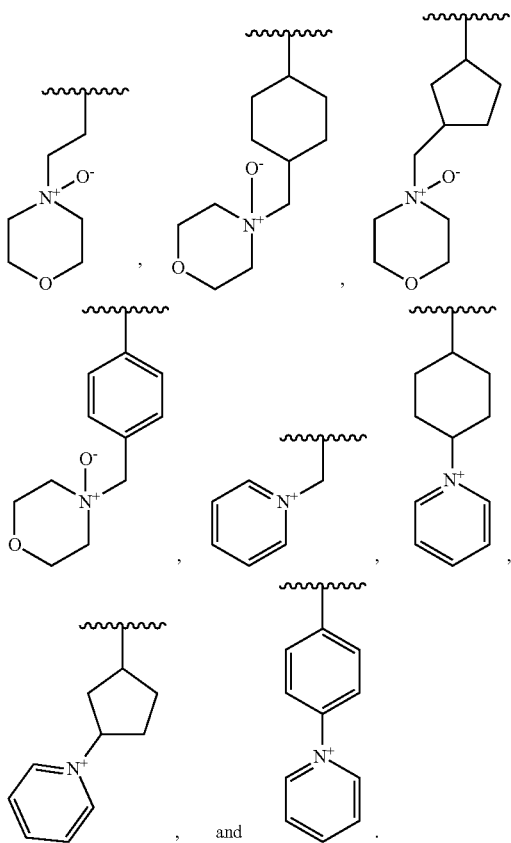

, and

.

206. The method of embodiment 203, wherein each ionic moiety independently has at least one phosphorous-containing cationic group, wherein the phosphorous-containing cationic group and the linker form a side chain, wherein each side chain is independently selected from the group consisting of:

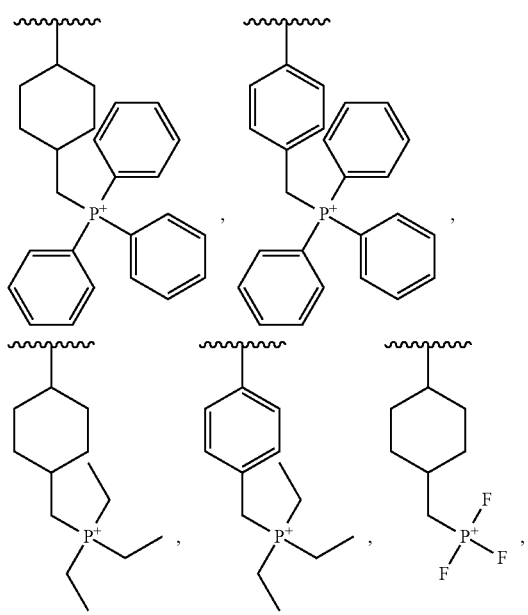

-continued

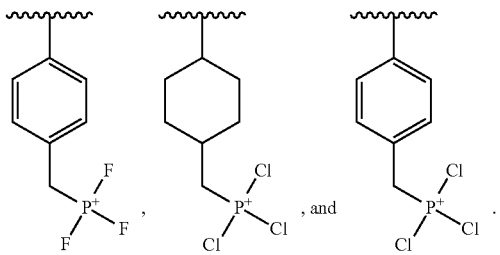

, and

.

207. The method of any one of embodiments, wherein 182 to 206, further comprising hydrophobic moieties attached to the solid support.

208. The method of embodiment 207, wherein each hydrophobic moiety is selected from the group consisting of an unsubstituted or substituted alkyl, an unsubstituted or substituted cycloalkyl, an unsubstituted or substituted aryl, and an unsubstituted or substituted heteroaryl.

209. The method of any one of embodiments 182 to 208, further comprising acidic-ionic moieties attached to the solid support, wherein each acidic-ionic moiety comprises a Bronsted-Lowry acid and a cationic group.

210. The method of embodiment 209, wherein the cationic group is a nitrogen-containing cationic group or a phosphorous-containing cationic group.

211. The method of embodiment 209 or 210, wherein one or more of the acidic-ionic monomers each further comprise a linker connecting the Bronsted-Lowry acid or the cationic group to the polymeric backbone.

212. The method of embodiment 211, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

213. The method of embodiment 211, wherein the Bronsted-Lowry acid, the cationic group and the linker form a side chain, wherein each side chain is independently selected from the group consisting of:

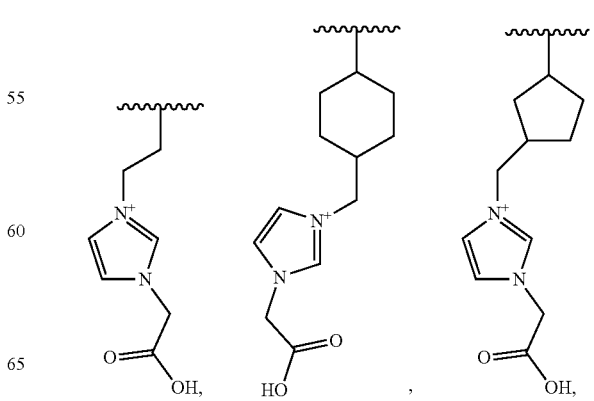

-continued

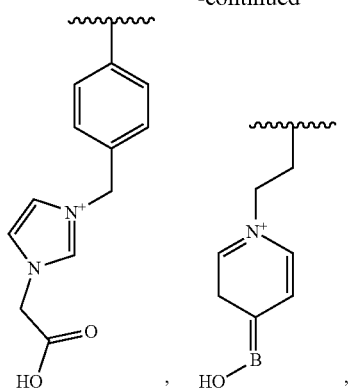

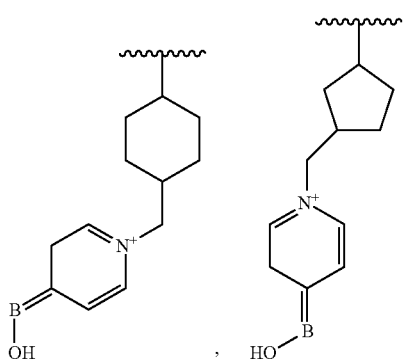

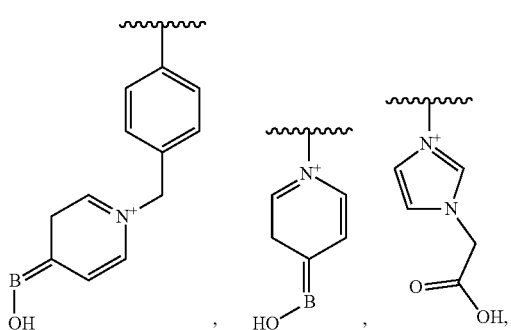

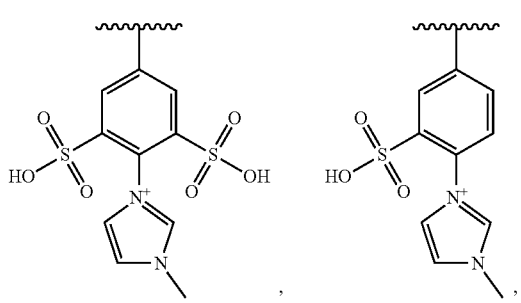

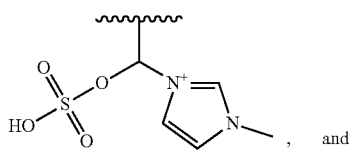

-continued

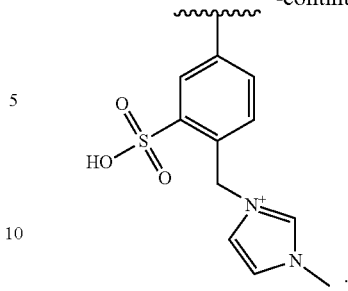

214. The method of any one of embodiments 182 to 213, wherein the material is carbon, and wherein the carbon is selected from the group consisting of biochar, amorphous carbon, and activated carbon.

215. The method of any one of embodiments 138 to 150, wherein the catalyst is selected from the group consisting of:
poly [styrene-co-4-vinylbenzenesulfonic acid-co-3-methyl-1-(4-vinylbenzyl)-3H-imidazol-1-ium chloride-co-divinylbenzene];
poly [styrene-co-4-vinylbenzenesulfonic acid-co-3-methyl-1-(4-vinylbenzyl)-3H-imidazol-1-ium bisulfate-co-divinylbenzene];
poly [styrene-co-4-vinylbenzenesulfonic acid-co-3-methyl-1-(4-vinylbenzyl)-3H-imidazol-1-ium acetate-co-divinylbenzene];
poly [styrene-co-4-vinylbenzenesulfonic acid-co-3-methyl-1-(4-vinylbenzyl)-3H-imidazol-1-ium nitrate-co-divinylbenzene];
poly [styrene-co-4-vinylbenzenesulfonic acid-co-3-ethyl-1-(4-vinylbenzyl)-3H-imidazol-1-ium chloride-co-divinylbenzene];
poly [styrene-co-4-vinylbenzenesulfonic acid-co-3-ethyl-1-(4-vinylbenzyl)-3H-imidazol-1-ium bisulfate-co-divinylbenzene];
poly [styrene-co-4-vinylbenzenesulfonic acid-co-3-ethyl-1-(4-vinylbenzyl)-3H-imidazol-1-ium acetate-co-divinylbenzene];
poly [styrene-co-4-vinylbenzenesulfonic acid-co-3-ethyl-1-(4-vinylbenzyl)-3H-imidazol-1-ium nitrate-co-divinylbenzene];
poly [styrene-co-4-vinylbenzenesulfonic acid-co-1-(4-vinylbenzyl)-3H-imidazol-1-ium chloride-co-divinylbenzene];
poly [styrene-co-4-vinylbenzenesulfonic acid-co-1-(4-vinylbenzyl)-3H-imidazol-1-ium iodide-co-divinylbenzene];
poly [styrene-co-4-vinylbenzenesulfonic acid-co-1-(4-vinylbenzyl)-3H-imidazol-1-ium bromide-co-divinylbenzene];
poly [styrene-co-4-vinylbenzenesulfonic acid-co-1-(4-vinylbenzyl)-3H-imidazol-1-ium bisulfate-co-divinylbenzene];
poly [styrene-co-4-vinylbenzenesulfonic acid-co-1-(4-vinylbenzyl)-3H-imidazol-1-ium acetate-co-divinylbenzene];
poly [styrene-co-4-vinylbenzenesulfonic acid-co-3-methyl-1-(4-vinylbenzyl)-3H-benzoimidazol-1-ium chloride-co-divinylbenzene];
poly [styrene-co-4-vinylbenzenesulfonic acid-co-3-methyl-1-(4-vinylbenzyl)-3H-benzoimidazol-1-ium bisulfate-co-divinylbenzene];
poly [styrene-co-4-vinylbenzenesulfonic acid-co-3-methyl-1-(4-vinylbenzyl)-3H-benzoimidazol-1-ium acetate-co-divinylbenzene];

poly [styrene-co-4-vinylbenzenesulfonic acid-co-3-methyl-1-(4-vinylbenzyl)-3H-benzoimidazol-1-ium formate-co-divinylbenzene];
poly [styrene-co-4-vinylbenzenesulfonic acid-co-1-(4-vinylbenzyl)-pyridinium-chloride-co-divinylbenzene];
poly [styrene-co-4-vinylbenzenesulfonic acid-co-1-(4-vinylbenzyl)-pyridinium-bisulfate-co-divinylbenzene];
poly [styrene-co-4-vinylbenzenesulfonic acid-co-1-(4-vinylbenzyl)-pyridinium-acetate-co-divinylbenzene];
poly [styrene-co-4-vinylbenzenesulfonic acid-co-1-(4-vinylbenzyl)-pyridinium-nitrate-co-divinylbenzene];
poly[styrene-co-4-vinylbenzenesulfonic acid-co-1-(4-vinylbenzyl)-pyridinium-chloride-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bromide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-iodide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bisulfate-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-acetate-co-3-methyl-1-(4-vinylbenzyl)-3H-imidazol-1-ium bisulfate-co-divinylbenzene];
poly[styrene-co-4-vinylbenzenesulfonic acid-co-4-methyl-4-(4-vinylbenzyl)-morpholin-4-ium chloride-co-divinylbenzene];
poly[styrene-co-4-vinylbenzenesulfonic acid-co-4-methyl-4-(4-vinylbenzyl)-morpholin-4-ium bisulfate-co-divinylbenzene];
poly[styrene-co-4-vinylbenzenesulfonic acid-co-4-methyl-4-(4-vinylbenzyl)-morpholin-4-ium acetate-co-divinylbenzene];
poly[styrene-co-4-vinylbenzenesulfonic acid-co-4-methyl-4-(4-vinylbenzyl)-morpholin-4-ium formate-co-divinylbenzene];
poly[styrene-co-4-vinylbenzenesulfonic acid-co-triphenyl-(4-vinylbenzyl)-phosphonium chloride-co-divinylbenzene];
poly[styrene-co-4-vinylbenzenesulfonic acid-co-triphenyl-(4-vinylbenzyl)-phosphonium bisulfate-co-divinylbenzene];
poly[styrene-co-4-vinylbenzenesulfonic acid-co-triphenyl-(4-vinylbenzyl)-phosphonium acetate-co-divinylbenzene];
poly[styrene-co-4-vinylbenzenesulfonic acid-co-1-methyl-1-(4-vinylbenzyl)-piperdin-1-ium chloride-co-divinylbenzene];
poly[styrene-co-4-vinylbenzenesulfonic acid-co-1-methyl-1-(4-vinylbenzyl)-piperdin-1-ium bisulfate-co-divinylbenzene];
poly[styrene-co-4-vinylbenzenesulfonic acid-co-1-methyl-1-(4-vinylbenzyl)-piperdin-1-ium acetate-co-divinylbenzene];
poly[styrene-co-4-vinylbenzenesulfonic acid-co-4-(4-vinylbenzyl)-morpholine-4-oxide-co-divinyl benzene];
poly[styrene-co-4-vinylbenzenesulfonic acid-co-triethyl-(4-vinylbenzyl)-ammonium chloride-co-divinylbenzene];
poly[styrene-co-4-vinylbenzenesulfonic acid-co-triethyl-(4-vinylbenzyl)-ammonium bisulfate-co-divinylbenzene];
poly[styrene-co-4-vinylbenzenesulfonic acid-co-triethyl-(4-vinylbenzyl)-ammonium acetate-co-divinylbenzene];
poly[styrene-co-3-methyl-1-(4-vinylbenzyl)-3H-imidazol-1-ium chloride-co-4-boronyl-1-(4-vinylbenzyl)-pyridinium chloride-co-divinylbenzene];
poly[styrene-co-3-methyl-1-(4-vinylbenzyl)-3H-imidazol-1-ium chloride-co-1-(4-vinylphenyl)methylphosphonic acid-co-divinylbenzene];
poly[styrene-co-3-methyl-1-(4-vinylbenzyl)-3H-imidazol-1-ium bisulfate-co-1-(4-vinylphenyl)methylphosphonic acid-co-divinylbenzene];
poly[styrene-co-3-methyl-1-(4-vinylbenzyl)-3H-imidazol-1-ium acetate-co-1-(4-vinylphenyl)methylphosphonic acid-co-divinylbenzene];
poly[styrene-co-3-methyl-1-(4-vinylbenzyl)-3H-imidazol-1-ium nitrate-co-1-(4-vinylphenyl)methylphosphonic acid-co-divinylbenzene];
poly[styrene-co-4-vinylbenzenesulfonic acid-co-vinylbenzylchloride-co-1-methyl-2-vinyl-pyridinium chloride-co-divinylbenzene];
poly[styrene-co-4-vinylbenzenesulfonic acid-co-vinylbenzylchloride-co-1-methyl-2-vinyl-pyridinium bisulfate-co-divinylbenzene];
poly[styrene-co-4-vinylbenzenesulfonic acid-co-vinylbenzylchloride-co-1-methyl-2-vinyl-pyridinium acetate-co-divinylbenzene];
poly[styrene-co-4-vinylbenzenesulfonic acid-co-4-(4-vinylbenzyl)-morpholine-4-oxide-co-divinyl benzene];
poly [styrene-co-4-vinylphenylphosphonic acid-co-3-methyl-1-(4-vinylbenzyl)-3H-imidazol-1-ium chloride-co-divinylbenzene];
poly [styrene-co-4-vinylphenylphosphonic acid-co-3-methyl-1-(4-vinylbenzyl)-3H-imidazol-1-ium bisulfate-co-divinylbenzene];
poly [styrene-co-4-vinylphenylphosphonic acid-co-3-methyl-1-(4-vinylbenzyl)-3H-imidazol-1-ium acetate-co-divinylbenzene];
poly[styrene-co-3-carboxymethyl-1-(4-vinylbenzyl)-3H-imidazol-1-ium chloride-co-divinylbenzene];
poly[styrene-co-3-carboxymethyl-1-(4-vinylbenzyl)-3H-imidazol-1-ium bisulfate-co-divinylbenzene];
poly[styrene-co-3-carboxymethyl-1-(4-vinylbenzyl)-3H-imidazol-1-ium acetate-co-divinylbenzene];
poly[styrene-co-5-(4-vinylbenzylamino)-isophthalic acid-co-3-methyl-1-(4-vinylbenzyl)-3H-imidazol-1-ium chloride-co-divinylbenzene];
poly[styrene-co-5-(4-vinylbenzylamino)-isophthalic acid-co-3-methyl-1-(4-vinylbenzyl)-3H-imidazol-1-ium bisulfate-co-divinylbenzene];
poly[styrene-co-5-(4-vinylbenzylamino)-isophthalic acid-co-3-methyl-1-(4-vinylbenzyl)-3H-imidazol-1-ium acetate-co-divinylbenzene];
poly[styrene-co-(4-vinylbenzylamino)-acetic acid-co-3-methyl-1-(4-vinylbenzyl)-3H-imidazol-1-ium chloride-co-divinylbenzene];
poly[styrene-co-(4-vinylbenzylamino)-acetic acid-co-3-methyl-1-(4-vinylbenzyl)-3H-imidazol-1-ium bisulfate-co-divinylbenzene];
poly[styrene-co-(4-vinylbenzylamino)-acetic acid-co-3-methyl-1-(4-vinylbenzyl)-3H-imidazol-1-ium acetate-co-divinylbenzene];
poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenesulfonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenephosphonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenesulfonic acid-co-vinylbenzylmethylmorpholinium chloride-co-vinylbenzyltriphenylphosphonium chloride-co-divinylbenzene);
poly(styrene-co-4-vinylbenzenephosphonic acid-co-vinylbenzylmethylmorpholinium chloride-co-vinylbenzyltriphenylphosphonium chloride-co-divinylbenzene);
poly(styrene-co-4-vinylbenzenesulfonic acid-co-vinylbenzylmethylmorpholinium bisulfate-co-vinylbenzyltriphenylphosphonium bisulfate-co-divinylbenzene);
poly(styrene-co-4-vinylbenzenephosphonic acid-co-vinylbenzylmethylmorpholinium bisulfate-co-vinylbenzyltriphenylphosphonium bisulfate-co-divinylbenzene);
poly(styrene-co-4-vinylbenzenesulfonic acid-co-vinylbenzylmethylmorpholinium acetate-co-vinylbenzyltriphenylphosphonium bisulfate-co-divinylbenzene);
poly(styrene-co-4-vinylbenzenephosphonic acid-co-vinylbenzylmethylmorpholinium acetate-co-vinylbenzyltriphenylphosphonium bisulfate-co-divinylbenzene)
poly(styrene-co-4-vinylbenzenesulfonic acid-co-vinylmethylimidazolium chloride-co-divinylbenzene);
poly(styrene-co-4-vinylbenzenesulfonic acid-co-vinylmethylimidazolium bisulfate-co-divinylbenzene);
poly(styrene-co-4-vinylbenzenesulfonic acid-co-vinylmethylimidazolium acetate-co-divinylbenzene);
poly(styrene-co-4-vinylbenzenesulfonic acid-co-vinylmethylimidazolium nitrate-co-divinylbenzene);
poly(styrene-co-4-vinylbenzenephosphonic acid-co-vinylmethylimidazolium chloride-co-divinylbenzene);
poly(styrene-co-4-vinylbenzenephosphonic acid-co-vinylmethylimidazolium bisulfate-co-divinylbenzene);
poly(styrene-co-4-vinylbenzenephosphonic acid-co-vinylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(styrene-co-4-vinylbenzenesulfonic acid-co-vinylbenzylmethylimidazolium chloride-co-divinylbenzene);
poly(styrene-co-4-vinylbenzenesulfonic acid-co-vinylbenzylmethylimidazolium bisulfate-co-divinylbenzene);
poly(styrene-co-4-vinylbenzenesulfonic acid-co-vinylbenzylmethylimidazolium acetate-co-divinylbenzene);
poly(styrene-co-4-vinylbenzenephosphonic acid-co-vinylbenzylmethylimidazolium chloride-co-divinylbenzene);
poly(styrene-co-4-vinylbenzenephosphonic acid-co-vinylbenzylmethylimidazolium bisulfate-co-divinylbenzene);
poly(styrene-co-4-vinylbenzenephosphonic acid-co-vinylbenzylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(butyl-vinylimidazolium chloride-co-butylimidazolium bisulfate-co-4-vinylbenzenesulfonic acid);
poly(butyl-vinylimidazolium bisulfate-co-butylimidazolium bisulfate-co-4-vinylbenzenesulfonic acid);
poly(benzyl alcohol-co-4-vinylbenzylalcohol sulfonic acid-co-vinylbenzyltriphenylphosphonium chloride-co-divinylbenzyl alcohol); and
poly(benzyl alcohol-co-4-vinylbenzylalcohol sulfonic acid-co-vinylbenzyltriphenylphosphonium bisulfate-co-divinylbenzyl alcohol).

216. The method of any one of embodiments 138 to 150, wherein the catalyst is selected from the group consisting of:

carbon-supported pyrrolium chloride sulfonic acid;
carbon-supported imidazolium chloride sulfonic acid;
carbon-supported pyrazolium chloride sulfonic acid;
carbon-supported oxazolium chloride sulfonic acid;
carbon-supported thiazolium chloride sulfonic acid;
carbon-supported pyridinium chloride sulfonic acid;
carbon-supported pyrimidinium chloride sulfonic acid;
carbon-supported pyrazinium chloride sulfonic acid;
carbon-supported pyridazinium chloride sulfonic acid;
carbon-supported thiazinium chloride sulfonic acid;
carbon-supported morpholinium chloride sulfonic acid;
carbon-supported piperidinium chloride sulfonic acid;
carbon-supported piperizinium chloride sulfonic acid;
carbon-supported pyrollizinium chloride sulfonic acid;
carbon-supported triphenyl phosphonium chloride sulfonic acid;
carbon-supported trimethyl phosphonium chloride sulfonic acid;
carbon-supported triethyl phosphonium chloride sulfonic acid;
carbon-supported tripropyl phosphonium chloride sulfonic acid;
carbon-supported tributyl phosphonium chloride sulfonic acid;
carbon-supported trifluoro phosphonium chloride sulfonic acid;
carbon-supported pyrrolium bromide sulfonic acid;
carbon-supported imidazolium bromide sulfonic acid;
carbon-supported pyrazolium bromide sulfonic acid;
carbon-supported oxazolium bromide sulfonic acid;
carbon-supported thiazolium bromide sulfonic acid;
carbon-supported pyridinium bromide sulfonic acid;
carbon-supported pyrimidinium bromide sulfonic acid;

carbon-supported pyrazinium bromide sulfonic acid;
carbon-supported pyridazinium bromide sulfonic acid;
carbon-supported thiazinium bromide sulfonic acid;
carbon-supported morpholinium bromide sulfonic acid;
carbon-supported piperidinium bromide sulfonic acid;
carbon-supported piperizinium bromide sulfonic acid;
carbon-supported pyrollizinium bromide sulfonic acid;
carbon-supported triphenyl phosphonium bromide sulfonic acid;
carbon-supported trimethyl phosphonium bromide sulfonic acid;
carbon-supported triethyl phosphonium bromide sulfonic acid;
carbon-supported tripropyl phosphonium bromide sulfonic acid;
carbon-supported tributyl phosphonium bromide sulfonic acid;
carbon-supported trifluoro phosphonium bromide sulfonic acid;
carbon-supported pyrrolium bisulfate sulfonic acid;
carbon-supported imidazolium bisulfate sulfonic acid;
carbon-supported pyrazolium bisulfate sulfonic acid;
carbon-supported oxazolium bisulfate sulfonic acid;
carbon-supported thiazolium bisulfate sulfonic acid;
carbon-supported pyridinium bisulfate sulfonic acid;
carbon-supported pyrimidinium bisulfate sulfonic acid;
carbon-supported pyrazinium bisulfate sulfonic acid;
carbon-supported pyridazinium bisulfate sulfonic acid;
carbon-supported thiazinium bisulfate sulfonic acid;
carbon-supported morpholinium bisulfate sulfonic acid;
carbon-supported piperidinium bisulfate sulfonic acid;
carbon-supported piperizinium bisulfate sulfonic acid;
carbon-supported pyrollizinium bisulfate sulfonic acid;
carbon-supported triphenyl phosphonium bisulfate sulfonic acid;
carbon-supported trimethyl phosphonium bisulfate sulfonic acid;
carbon-supported triethyl phosphonium bisulfate sulfonic acid;
carbon-supported tripropyl phosphonium bisulfate sulfonic acid;
carbon-supported tributyl phosphonium bisulfate sulfonic acid;
carbon-supported trifluoro phosphonium bisulfate sulfonic acid;
carbon-supported pyrrolium formate sulfonic acid;
carbon-supported imidazolium formate sulfonic acid;
carbon-supported pyrazolium formate sulfonic acid;
carbon-supported oxazolium formate sulfonic acid;
carbon-supported thiazolium formate sulfonic acid;
carbon-supported pyridinium formate sulfonic acid;
carbon-supported pyrimidinium formate sulfonic acid;
carbon-supported pyrazinium formate sulfonic acid;
carbon-supported pyridazinium formate sulfonic acid;
carbon-supported thiazinium formate sulfonic acid;
carbon supported morpholinium formate sulfonic acid;
carbon-supported piperidinium formate sulfonic acid;
carbon-supported piperizinium formate sulfonic acid;
carbon-supported pyrollizinium formate sulfonic acid;
carbon-supported triphenyl phosphonium formate sulfonic acid;
carbon-supported trimethyl phosphonium formate sulfonic acid;
carbon-supported triethyl phosphonium formate sulfonic acid;
carbon-supported tripropyl phosphonium formate sulfonic acid;
carbon-supported tributyl phosphonium formate sulfonic acid;
carbon-supported trifluoro phosphonium formate sulfonic acid;
carbon-supported pyrrolium acetate sulfonic acid;
carbon-supported imidazolium acetate sulfonic acid;
carbon-supported pyrazolium acetate sulfonic acid;
carbon-supported oxazolium acetate sulfonic acid;
carbon-supported thiazolium acetate sulfonic acid;
carbon-supported pyridinium acetate sulfonic acid;
carbon-supported pyrimidinium acetate sulfonic acid;
carbon-supported pyrazinium acetate sulfonic acid;
carbon-supported pyridazinium acetate sulfonic acid;
carbon-supported thiazinium acetate sulfonic acid;
carbon-supported morpholinium acetate sulfonic acid;
carbon-supported piperidinium acetate sulfonic acid;
carbon-supported piperizinium acetate sulfonic acid;
carbon-supported pyrollizinium acetate sulfonic acid;
carbon-supported triphenyl phosphonium acetate sulfonic acid;
carbon-supported trimethyl phosphonium acetate sulfonic acid;
carbon-supported triethyl phosphonium acetate sulfonic acid;
carbon-supported tripropyl phosphonium acetate sulfonic acid;
carbon-supported tributyl phosphonium acetate sulfonic acid;
carbon-supported trifluoro phosphonium acetate sulfonic acid;
carbon-supported pyrrolium chloride phosphonic acid;
carbon-supported imidazolium chloride phosphonic acid;
carbon-supported pyrazolium chloride phosphonic acid;
carbon-supported oxazolium chloride phosphonic acid;
carbon-supported thiazolium chloride phosphonic acid;
carbon-supported pyridinium chloride phosphonic acid;
carbon-supported pyrimidinium chloride phosphonic acid;
carbon-supported pyrazinium chloride phosphonic acid;
carbon-supported pyridazinium chloride phosphonic acid;
carbon-supported thiazinium chloride phosphonic acid;
carbon-supported morpholinium chloride phosphonic acid;
carbon-supported piperidinium chloride phosphonic acid;
carbon-supported piperizinium chloride phosphonic acid;
carbon-supported pyrollizinium chloride phosphonic acid;
carbon-supported triphenyl phosphonium chloride phosphonic acid;
carbon-supported trimethyl phosphonium chloride phosphonic acid;
carbon-supported triethyl phosphonium chloride phosphonic acid;
carbon-supported tripropyl phosphonium chloride phosphonic acid;
carbon-supported tributyl phosphonium chloride phosphonic acid;
carbon-supported trifluoro phosphonium chloride phosphonic acid;
carbon-supported pyrrolium bromide phosphonic acid;
carbon-supported imidazolium bromide phosphonic acid;
carbon-supported pyrazolium bromide phosphonic acid;
carbon-supported oxazolium bromide phosphonic acid;
carbon-supported thiazolium bromide phosphonic acid;
carbon-supported pyridinium bromide phosphonic acid;
carbon-supported pyrimidinium bromide phosphonic acid;
carbon-supported pyrazinium bromide phosphonic acid;
carbon-supported pyridazinium bromide phosphonic acid;
carbon-supported thiazinium bromide phosphonic acid;
carbon-supported morpholinium bromide phosphonic acid;

carbon-supported piperidinium bromide phosphonic acid;
carbon-supported piperizinium bromide phosphonic acid;
carbon-supported pyrollizinium bromide phosphonic acid;
carbon-supported triphenyl phosphonium bromide phosphonic acid;
carbon-supported trimethyl phosphonium bromide phosphonic acid;
carbon-supported triethyl phosphonium bromide phosphonic acid;
carbon-supported tripropyl phosphonium bromide phosphonic acid;
carbon-supported tributyl phosphonium bromide phosphonic acid;
carbon-supported trifluoro phosphonium bromide phosphonic acid;
carbon-supported pyrrolium bisulfate phosphonic acid;
carbon-supported imidazolium bisulfate phosphonic acid;
carbon-supported pyrazolium bisulfate phosphonic acid;
carbon-supported oxazolium bisulfate phosphonic acid;
carbon-supported thiazolium bisulfate phosphonic acid;
carbon-supported pyridinium bisulfate phosphonic acid;
carbon-supported pyrimidinium bisulfate phosphonic acid;
carbon-supported pyrazinium bisulfate phosphonic acid;
carbon-supported pyridazinium bisulfate phosphonic acid;
carbon-supported thiazinium bisulfate phosphonic acid;
carbon-supported morpholinium bisulfate phosphonic acid;
carbon-supported piperidinium bisulfate phosphonic acid;
carbon-supported piperizinium bisulfate phosphonic acid;
carbon-supported pyrollizinium bisulfate phosphonic acid;
carbon-supported triphenyl phosphonium bisulfate phosphonic acid;
carbon-supported trimethyl phosphonium bisulfate phosphonic acid;
carbon-supported triethyl phosphonium bisulfate phosphonic acid;
carbon-supported tripropyl phosphonium bisulfate phosphonic acid;
carbon-supported tributyl phosphonium bisulfate phosphonic acid;
carbon-supported trifluoro phosphonium bisulfate phosphonic acid;
carbon-supported pyrrolium formate phosphonic acid;
carbon-supported imidazolium formate phosphonic acid;
carbon-supported pyrazolium formate phosphonic acid;
carbon-supported oxazolium formate phosphonic acid;
carbon-supported thiazolium formate phosphonic acid;
carbon-supported pyridinium formate phosphonic acid;
carbon-supported pyrimidinium formate phosphonic acid;
carbon-supported pyrazinium formate phosphonic acid;
carbon-supported pyridazinium formate phosphonic acid;
carbon-supported thiazinium formate phosphonic acid;
carbon-supported morpholinium formate phosphonic acid;
carbon-supported piperidinium formate phosphonic acid;
carbon-supported piperizinium formate phosphonic acid;
carbon-supported pyrollizinium formate phosphonic acid;
carbon-supported triphenyl phosphonium formate phosphonic acid;
carbon-supported trimethyl phosphonium formate phosphonic acid;
carbon-supported triethyl phosphonium formate phosphonic acid;
carbon-supported tripropyl phosphonium formate phosphonic acid;
carbon-supported tributyl phosphonium formate phosphonic acid;
carbon-supported trifluoro phosphonium formate phosphonic acid;
carbon-supported pyrrolium acetate phosphonic acid;
carbon-supported imidazolium acetate phosphonic acid;
carbon-supported pyrazolium acetate phosphonic acid;
carbon-supported oxazolium acetate phosphonic acid;
carbon-supported thiazolium acetate phosphonic acid;
carbon-supported pyridinium acetate phosphonic acid;
carbon-supported pyrimidinium acetate phosphonic acid;
carbon-supported pyrazinium acetate phosphonic acid;
carbon-supported pyridazinium acetate phosphonic acid;
carbon-supported thiazinium acetate phosphonic acid;
carbon-supported morpholinium acetate phosphonic acid;
carbon-supported piperidinium acetate phosphonic acid;
carbon-supported piperizinium acetate phosphonic acid;
carbon-supported pyrollizinium acetate phosphonic acid;
carbon-supported triphenyl phosphonium acetate phosphonic acid;
carbon-supported trimethyl phosphonium acetate phosphonic acid;
carbon-supported triethyl phosphonium acetate phosphonic acid;
carbon-supported tripropyl phosphonium acetate phosphonic acid;
carbon-supported tributyl phosphonium acetate phosphonic acid;
carbon-supported trifluoro phosphonium acetate phosphonic acid;
carbon-supported ethanoyl-triphosphonium sulfonic acid;
carbon-supported ethanoyl-methylmorpholinium sulfonic acid; and
carbon-supported ethanoyl-imidazolium sulfonic acid.

217. The method of any one of embodiments 138 to 216, wherein the catalyst has a catalyst activity loss of less than 1% per cycle.

218. The method of any one of embodiments 138 to 217, wherein the animal feed composition is poultry feed.

219. The method of any one of embodiments 138 to 218, wherein the animal feed composition is swine feed.

220. A method of increasing weight gain in an animal, comprising:
feeding to the animal an animal feed composition produced according to the method of any one of embodiments 138 to 219, wherein the animal feed composition is fed to the animal at an inclusion rate of less than 500 mg/kg.

221. A method of improving weight gain and reducing feed conversion ratio of an animal, comprising: feeding to the animal an animal feed composition produced according to the method of any one of embodiments 138 to 219.

222. The method of embodiment 218 or 221, wherein the animal is a chicken.

223. The method of embodiment 218 or 221, wherein the animal has a disease or disorder.

224. The method of embodiment 223, wherein the disease or disorder is necrotic enteritis, coccidiosis, nutrient malabsorption syndrome, intestinal barrier breakdown, colisepticemia, yolk sack infection, salmonella infection, or campylobacter infection.

225. The method of embodiment 223, wherein the disease or disorder is necrotic enteritis.

226. An animal feed composition produced according to the method of any one of embodiments 138 to 219.

227. An animal feed composition, comprising:
an oligosaccharide selected from the group consisting of a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, and an arabino-xylo-oligosaccharide, or any combinations thereof,
wherein the oligosaccharide has a degree of polymerization of at least 3; and
a base feed.

228. The animal feed composition of embodiment 227, wherein the oligosaccharide composition is a functionalized oligosaccharide composition.

229. A swine feed composition, comprising:
(i) a base feed, and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages, and
wherein at least 10 dry wt % of the oligosaccharide composition has a degree of polymerization of at least 3.

230. The swine feed composition of embodiment 229, wherein the oligosaccharide composition has a glycosidic bond type distribution of less than 9 mol % α-(1,4) glycosidic linkages, and less than 19 mol % α-(1,6) glycosidic linkages.

231. A swine feed composition, comprising:
(i) a base feed, and
(ii) an oligosaccharide composition,
wherein the oligosaccharide composition has a glycosidic bond type distribution of:
less than 9 mol % α-(1,4) glycosidic linkages; and
less than 19 mol % α-(1,6) glycosidic linkages, and
wherein at least 10 dry wt % of the oligosaccharide composition has a degree of polymerization of at least 3.

232. The swine feed composition of any one of embodiments 229 to 231, wherein the oligosaccharide composition has a glycosidic bond type distribution of at least 15 mol % β-(1,2) glycosidic linkages.

233. The swine feed composition of any one of embodiments 229 to 232, wherein the oligosaccharide composition is present in the swine feed composition at below 5,000 ppm weight dry oligosaccharide composition per weight of the swine feed composition.

234. The swine feed composition of any one of embodiments 229 to 233, wherein the oligosaccharide composition comprises a gluco-oligosaccharide, a galacto-oligosaccharide, a fructo-oligosaccharide, a manno-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, or a xylo-gluco-galacto-oligosaccharide, or any combinations thereof.

235. The swine feed composition of any one of embodiments 229 to 233, wherein the oligosaccharide composition comprises an arabino-oligosaccharide, a xylo-oligosaccharide, or an arabino-xylo-oligosaccharide, or any combinations thereof.

236. The swine feed composition of any one of embodiments 229 to 235, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages; and
between 10 to 55 mol % β-(1,6) glycosidic linkages.

237. The swine feed composition of any one of embodiments 229 to 236, wherein at least 50 dry wt % of the oligosaccharide composition has a degree of polymerization of at least 3.

238. The swine feed composition of any one of embodiments 229 to 236, wherein between 65 and 80 dry wt % of the oligosaccharide composition has a degree of polymerization of at least 3.

239. The swine feed composition of any one of embodiments 229 to 236, wherein at least 50 dry wt % of the oligosaccharide composition comprises one or more gluco-oligosaccharides.

240. The swine feed composition of any one of embodiments 229 to 236, wherein at least 50 dry wt % of the oligosaccharide composition comprises one or more gluco-galacto-oligosaccharides.

241. The swine feed composition of any one of embodiments 229 to 240, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages;
between 10 to 55 mol % β-(1,6) glycosidic linkages;
less than 9 mol % α-(1,4) glycosidic linkages; and
less than 19 mol % α-(1,6) glycosidic linkages.

242. The swine feed composition of any one of embodiments 229 to 240, wherein the oligosaccharide composition has a glycosidic bond type distribution of:
between 0 to 15 mol % α-(1,2) glycosidic linkages;
between 0 to 15 mol % β-(1,2) glycosidic linkages;
between 1 to 20 mol % α-(1,3) glycosidic linkages;
between 1 to 15 mol % β-(1,3) glycosidic linkages;
between 5 to 55 mol % β-(1,4) glycosidic linkages;
between 15 to 55 mol % β-(1,6) glycosidic linkages;
less than 20 mol % α-(1,4) glycosidic linkages; and
less than 30 mol % α-(1,6) glycosidic linkages.

243. The swine feed composition of any one of embodiments 229 to 242, wherein the oligosaccharide composition is a functionalized oligosaccharide composition.

244. A swine feed pre-mix, comprising:
(i) a carrier material; and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages, and
wherein at least 10 dry wt % of the oligosaccharide composition has a degree of polymerization of at least 3.

245. The swine feed pre-mix of embodiment 244, wherein the oligosaccharide composition has a glycosidic bond type distribution of less than 9 mol % α-(1,4) glycosidic linkages, and less than 19 mol % α-(1,6) glycosidic linkages.

246. A swine feed pre-mix, comprising:
(i) a carrier material; and
(ii) an oligosaccharide composition,
wherein the oligosaccharide composition has a glycosidic bond type distribution of:
less than 9 mol % α-(1,4) glycosidic linkages; and
less than 19 mol % α-(1,6) glycosidic linkages, and
wherein at least 10 dry wt % of the oligosaccharide composition has a degree of polymerization of at least 3.

247. The swine feed pre-mix of any one of embodiments 244 to 246, wherein the oligosaccharide composition has a glycosidic bond type distribution of at least 15 mol % β-(1,2) glycosidic linkages.

248. The swine feed pre-mix of any one of embodiments 244 to 247, wherein the swine feed pre-mix comprises at least 10 wt % dry oligosaccharide composition per weight swine feed pre-mix.

249. The swine feed pre-mix of any one of embodiments 244 to 248, wherein the swine feed pre-mix comprises between 10 to 60 wt % dry oligosaccharide composition per weight swine feed pre-mix.

250. The swine feed pre-mix of any one of embodiments 244 to 248, wherein the swine feed pre-mix comprises between 15 to 50 wt % dry oligosaccharide composition per weight swine feed pre-mix.

251. The swine feed pre-mix of any one of embodiments 244 to 248, wherein the swine feed pre-mix comprises between 20 to 50 dry wt % oligosaccharide composition.

252. The swine feed pre-mix of any one of embodiments 244 to 251, wherein the carrier material is selected from the group consisting of rice hulls, feed grade silica gel, feed grade fumed silica, corn gluten feed, corn gluten meal, dried distiller's grains, and milled corn, or any combinations thereof.

253. The swine feed pre-mix of any one of embodiments 244 to 251, wherein the carrier material is milled corn.

254. The swine feed pre-mix of any one of embodiments 244 to 253, wherein the moisture content is less than 20 wt %.

255. The swine feed pre-mix of any one of embodiments 244 to 255, wherein the pre-mix is a solid.

256. The swine feed pre-mix of any one of embodiments 244 to 255, wherein the pre-mix is a flowable powder.

257. The swine feed pre-mix of any one of embodiments 244 to 256, wherein the oligosaccharide composition comprises a gluco-oligosaccharide, a galacto-oligosaccharide, a fructo-oligosaccharide, a manno-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, or a xylo-gluco-galacto-oligosaccharide, or any combinations thereof.

258. The swine feed pre-mix of any one of embodiments 244 to 256, wherein the oligosaccharide composition comprises an arabino-oligosaccharide, a xylo-oligosaccharide, or an arabino-xylo-oligosaccharide, or any combinations thereof.

259. The swine feed pre-mix of any one of embodiments 244 to 258, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages; and
between 10 to 55 mol % β-(1,6) glycosidic linkages.

260. The swine feed pre-mix of any one of embodiments 244 to 259, wherein at least 50 dry wt % of the oligosaccharide composition has a degree of polymerization of at least 3.

261. The swine feed pre-mix of any one of embodiments 244 to 259, wherein between 65 and 80 dry wt % of the oligosaccharide composition has a degree of polymerization of at least 3.

262. The swine feed pre-mix of any one of embodiments 244 to 259, wherein at least 50 dry wt % of the oligosaccharide composition comprises one or more gluco-oligosaccharides.

263. The swine feed pre-mix of any one of embodiments 244 to 259, wherein at least 50 dry wt % of the oligosaccharide composition comprises one or more gluco-galacto-oligosaccharides.

264. The swine feed pre-mix of any one of embodiments 244 to 263, wherein the oligosaccharide composition has a glycosidic bond type distribution of:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages;
between 10 to 55 mol % β-(1,6) glycosidic linkages;
less than 9 mol % α-(1,4) glycosidic linkages; and
less than 19 mol % α-(1,6) glycosidic linkages.

265. The swine feed pre-mix of any one of embodiments 244 to 263, wherein the oligosaccharide composition has a glycosidic bond type distribution of:
between 0 to 15 mol % α-(1,2) glycosidic linkages;
between 0 to 15 mol % β-(1,2) glycosidic linkages;
between 1 to 20 mol % α-(1,3) glycosidic linkages;
between 1 to 15 mol % β-(1,3) glycosidic linkages;
between 5 to 55 mol % β-(1,4) glycosidic linkages;
between 15 to 55 mol % β-(1,6) glycosidic linkages;
less than 20 mol % α-(1,4) glycosidic linkages; and
less than 30 mol % α-(1,6) glycosidic linkages.

266. The swine feed pre-mix of any one of embodiments 244 to 265, wherein the swine feed pre-mix reduces feed conversion ratio (FCR) by between 1 to 10% when fed to swine as compared to a swine fed a feed composition without the oligosaccharide composition.

267. The swine feed pre-mix of any one of embodiments 244 to 266, wherein the swine feed pre-mix increases average daily gain by between 1 to 10% when fed to an animal as compared to an animal fed a feed composition without the oligosaccharide composition.

268. The swine feed pre-mix of any one of embodiments 244 to 267, wherein the swine feed pre-mix increases total weight gain by between 1 to 10% when as compared to an animal fed a feed composition without the oligosaccharide composition.

269. The swine feed pre-mix of any one of embodiments 244 to 268, wherein the oligosaccharide composition is a functionalized oligosaccharide composition 270. An swine feed composition, comprising (i) a base feed and (ii) the swine feed pre-mix of any one of embodiments 244 to 269.

271. A method of enhancing growth of swine, comprising:
providing feed to swine, wherein the feed comprises:
(i) a base feed; and
(ii) an oligosaccharide composition,
wherein the oligosaccharide composition has a glycosidic bond type distribution of:
at least 10 mol % α-(1,3) glycosidic linkages;
at least 10 mol % β-(1,3) glycosidic linkages; and wherein at least 10 dry wt % of the oligosaccharide composition has a degree of polymerization of at least 3, and
enhancing growth in the swine.

272. A method of decreasing feed conversion ratio of feed provided to swine, comprising:
providing feed to swine, wherein the feed comprises:
(i) a base feed; and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages,
wherein at least 10 dry wt % of the oligosaccharide composition has a degree of polymerization of at least 3, and
decreasing the feed conversion ratio (FCR) of feed provided to the swine.

273. The method of embodiment 272, wherein the feed conversion ratio is between 0 to 4% higher than the performance target minimum 274. The method of embodiment 272 or 273, wherein the feed conversion ratio is decreased by between 0 to 4%.

275. The method of any one of embodiments 272 to 274, wherein the feed conversion ratio is decreased between 1 to 10% as compared to swine provided feed without the oligosaccharide composition.

276. The method of any one of embodiments 272 to 274, wherein the feed conversion ratio is decreased by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to swine fed a feed composition without the oligosaccharide composition.

277. The method of embodiment 272, wherein the swine suffers from a disease or a disorder, or is raised in a challenged environment.

278. The method of embodiment 277, wherein the feed conversion ratio is decreased by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, between 1% and 5%, as compared to swine fed a feed composition without the oligosaccharide composition.

279. A method of increasing average daily gain in swine, comprising:
providing feed to swine, wherein the feed comprises:
(i) a base feed; and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages,
wherein at least 10 dry wt % of the oligosaccharide composition has a degree of polymerization of at least 3, and
increasing average daily gain in swine.

280. The method of embodiment 279, wherein the average daily gain is increased by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to swine fed a feed composition without the oligosaccharide composition.

281. The method of embodiment 280, wherein the swine suffers from a disease or a disorder, or is raised in a challenged environment.

282. The method of embodiment 281, wherein the average daily gain is increased by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to swine fed a feed composition without the oligosaccharide composition.

283. A method of increasing average daily feed intake in swine, comprising:
providing feed to swine, wherein the feed comprises:
(i) a base feed; and
(ii) an oligosaccharide composition,
wherein the oligosaccharide composition has a glycosidic bond type distribution of:
at least 10 mol % α-(1,3) glycosidic linkages; and
at least 10 mol % β-(1,3) glycosidic linkages,
wherein at least 10 dry wt % of the oligosaccharide composition has a degree of polymerization of at least 3, and
increasing average daily feed intake in swine.

284. The method of embodiment 283, wherein the average daily feed intake is increased by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to swine fed a feed composition without the oligosaccharide composition.

285. The method of embodiment 283, wherein the swine suffers from a disease or a disorder, or is raised in a challenged environment.

286. The method of embodiment 285, wherein the average daily feed intake is increased by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to swine fed a feed composition without the oligosaccharide composition.

287. The method of any one of embodiments 271 to 286, wherein the oligosaccharide composition has a bond distribution of at least 15 mol % β-(1,2) glycosidic linkages.

288. The method of any one of embodiments 271 to 287, wherein the oligosaccharide composition is present in the feed at below 5,000 ppm weight dry oligosaccharide composition per weight of the feed.

289. The method of any one of embodiments 271 to 288, wherein the feed is a nursery diet.

290. The method of any one of embodiments 271 to 288, wherein the feed is a grower-type diet.

291. The method of any one of embodiments 271 to 288, wherein the feed is a finisher-type diet.

292. The method of any one of embodiments 271 to 288, wherein the feed is provided to the swine during the nursery diet phase.

293. The method of any one of embodiments 271 to 292, wherein the oligosaccharide composition is a functionalized oligosaccharide composition.

294. The method of any one of embodiments 271 to 293, wherein the swine has a disease or disorder.

295. The method of any one of embodiments 271 to 294, wherein the base feed comprises an antibiotic, or wherein the method further comprising providing an antibiotic to the swine.

296. The method of any one of embodiments 271 to 294, wherein less than 1,000 ppm, or less than 500 ppm, or less than 100 ppm, or less than 50 ppm; or between 10 ppm and 200 ppm, or between 50 ppm and 200 ppm, or between 500 ppm and 100 ppm of an antibiotic is provided to the swine.

297. A method of enhancing growth of poultry, comprising:
   providing feed to poultry, wherein the feed comprises:
      (i) a base feed; and
      (ii) an oligosaccharide composition,
         wherein the oligosaccharide composition has a glycosidic bond type distribution of:
            at least 10 mol % α-(1,3) glycosidic linkages;
            at least 10 mol % β-(1,3) glycosidic linkages; and
         wherein at least 10 dry wt % of the oligosaccharide composition has a degree of polymerization of at least 3, and
   enhancing growth in the poultry.

298. A method of decreasing feed conversion ratio of feed provided to poultry, comprising:
   providing feed to poultry, wherein the feed comprises:
      (i) a base feed; and
      (ii) an oligosaccharide composition,
         wherein the oligosaccharide composition has a glycosidic bond type distribution of:
            at least 10 mol % α-(1,3) glycosidic linkages; and
            at least 10 mol % β-(1,3) glycosidic linkages,
         wherein at least 10 dry wt % of the oligosaccharide composition has a degree of polymerization of at least 3, and
   decreasing the feed conversion ratio (FCR) of feed provided to the poultry.

299. The method of embodiment 298, wherein the feed conversion ratio is decreased by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

300. The method of embodiment 298, wherein the poultry suffers from a disease or a disorder, or is raised in a challenged environment.

301. The method of embodiment 300, wherein the feed conversion ratio is decreased by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

302. A method of increasing average daily gain in poultry, comprising:
   providing feed to poultry, wherein the feed comprises:
      (i) a base feed; and
      (ii) an oligosaccharide composition,
         wherein the oligosaccharide composition has a glycosidic bond type distribution of:
            at least 10 mol % α-(1,3) glycosidic linkages; and
            at least 10 mol % β-(1,3) glycosidic linkages,
         wherein at least 10 dry wt % of the oligosaccharide composition has a degree of polymerization of at least 3, and
   increasing average daily gain in poultry.

303. The method of embodiment 302, wherein the average daily gain is increased by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

304. The method of embodiment 302, wherein the poultry suffers from a disease or a disorder, or is raised in a challenged environment.

305. The method of embodiment 304, wherein the average daily gain is increased by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

306. A method of increasing average daily feed intake in poultry, comprising:
   providing feed to poultry, wherein the feed comprises:
      (i) a base feed; and
      (ii) an oligosaccharide composition,
         wherein the oligosaccharide composition has a glycosidic bond type distribution of:
            at least 10 mol % α-(1,3) glycosidic linkages; and
            at least 10 mol % β-(1,3) glycosidic linkages, wherein at least 10 dry wt % of the oligosaccharide composition has a degree of polymerization of at least 3, and
increasing average daily feed intake in poultry.

307. The method of embodiment 306, wherein the average daily feed intake is increased by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

308. The method of embodiment 283, wherein the poultry suffers from a disease or a disorder, or is raised in a challenged environment.

309. The method of embodiment 285, wherein the average daily feed intake is increased by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, as compared to poultry fed a feed composition without the oligosaccharide composition.

310. The method of any one of embodiments 297 to 309, wherein the oligosaccharide composition has a bond distribution of at least 15 mol % β-(1,2) glycosidic linkages.

311. The method of any one of embodiments 297 to 310, wherein the oligosaccharide composition is present in the feed at below 5,000 ppm weight dry oligosaccharide composition per weight of the feed.

312. The method of any one of embodiments 297 to 311, wherein the oligosaccharide composition is a functionalized oligosaccharide composition.

313. The method of any one of embodiments 297 to 312, wherein the poultry has a disease or disorder.

314. The method of any one of embodiments 297 to 313, wherein the base feed comprises an antibiotic, or wherein the method further comprising providing an antibiotic to the poultry.

315. The method of any one of embodiments 297 to 314, wherein less than 1,000 ppm, or less than 500 ppm, or less than 100 ppm, or less than 50 ppm; or between 10 ppm and 200 ppm, or between 50 ppm and 200 ppm, or between 500 ppm and 100 ppm of an antibiotic is provided to the poultry.

316. A composition comprising a plurality of oligosaccharides, wherein the composition has a glycosidic bond distribution of:
at least 1 mol % α-(1,3) glycosidic linkages;
at least 1 mol % β-(1,3) glycosidic linkages;
at least 15 mol % β-(1,6) glycosidic linkages;
less than 20 mol % α-(1,4) glycosidic linkages; and
less than 30 mol % α-(1,6) glycosidic linkages, and
wherein at least 10 dry wt % of the oligosaccharide composition has a degree of polymerization of at least 3.

317. The oligosaccharide composition of embodiment 316, comprising at least one oligosaccharide selected from the group consisting of a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, an arabino-xylo-oligosaccharide, and a xylo-gluco-galacto-oligosaccharide, or any combinations thereof.

318. The oligosaccharide composition of embodiment 316 or 317, wherein the glycosidic bond distribution is:
between 0 to 20 mol % α-(1,2) glycosidic linkages;
between 10 to 45 mol % β-(1,2) glycosidic linkages;
between 1 to 30 mol % α-(1,3) glycosidic linkages;
between 1 to 20 mol % β-(1,3) glycosidic linkages;
between 0 to 55 mol % β-(1,4) glycosidic linkages;
between 10 to 55 mol % β-(1,6) glycosidic linkages;
less than 9 mol % α-(1,4) glycosidic linkages; and
less than 19 mol % α-(1,6) glycosidic linkages.

319. The oligosaccharide composition of embodiment 316 or 317, wherein the glycosidic bond type distribution is:
between 0 to 15 mol % α-(1,2) glycosidic linkages;
between 0 to 15 mol % β-(1,2) glycosidic linkages;
between 1 to 20 mol % α-(1,3) glycosidic linkages;
between 1 to 15 mol % β-(1,3) glycosidic linkages;
between 5 to 55 mol % β-(1,4) glycosidic linkages;
between 15 to 55 mol % β-(1,6) glycosidic linkages;
less than 20 mol % α-(1,4) glycosidic linkages; and
less than 30 mol % α-(1,6) glycosidic linkages.

320. The oligosaccharide composition of any one of embodiments 316 to 319, comprising less than 50 wt % water.

321. The oligosaccharide composition of any one of embodiments 316 to 320, wherein at least 50 dry wt % of the oligosaccharide composition has a degree of polymerization of at least 3.

322. The oligosaccharide composition of any one of embodiments 316 to 320, wherein between 65 and 80 dry wt % of the oligosaccharide composition has a degree of polymerization of at least 3.

323. The oligosaccharide composition of any one of embodiments 316 to 322, wherein the oligosaccharide composition is a functionalized oligosaccharide composition 324. A method of increasing weight gain in swine, comprising:
feeding to the swine a swine feed composition produced according to the method of any one of embodiments 316 to 323, wherein the swine feed composition is fed to the swine at an inclusion rate of less than 5000 mg/kg.

325. A method of improving weight gain and reducing feed conversion ratio of swine, comprising: feeding to the swine a swine feed composition produced according to the method of any one of embodiments 316 to 323.

326. An swine feed composition, comprising:
an oligosaccharide selected from the group consisting of a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, an arabino-xylo-oligosaccharide, and a xylo-gluco-galacto-oligosaccharide, or any combinations thereof, wherein the oligosaccharide has a degree of polymerization of at least 3; and
a base feed.
327. The swine feed composition of embodiment 294, wherein the oligosaccharide composition is a functionalized oligosaccharide composition.
328. An poultry feed composition, comprising:
an oligosaccharide selected from the group consisting of a gluco-oligosaccharide, a galacto-oligosaccharide, a fructo-oligosaccharide, a manno-oligosaccharide, an arabino-oligosaccharide, a xylo-oligosaccharide, a gluco-galacto-oligosaccharide, a gluco-fructo-oligosaccharide, a gluco-manno-oligosaccharide, a gluco-arabino-oligosaccharide, a gluco-xylo-oligosaccharide, a galacto-fructo-oligosaccharide, a galacto-manno-oligosaccharide, a galacto-arabino-oligosaccharide, a galacto-xylo-oligosaccharide, a fructo-manno-oligosaccharide, a fructo-arabino-oligosaccharide, a fructo-xylo-oligosaccharide, a manno-arabino-oligosaccharide, a manno-xylo-oligosaccharide, an arabino-xylo-oligosaccharide, and a xylo-gluco-galacto-oligosaccharide, or any combinations thereof,
wherein the oligosaccharide has a degree of polymerization of at least 3; and
a base feed.
329. The poultry feed composition of embodiment 328, wherein the oligosaccharide composition is a functionalized oligosaccharide composition.

EXAMPLES

Except where otherwise indicated, commercial reagents were purified prior to use following the guidelines of Perrin and Armarego (Perrin, D. D. & Armarego, W. L. F., *Purification of Laboratory Chemicals*, 3rd ed.; Pergamon Press, Oxford (1988)). Nitrogen gas for use in chemical reactions was of ultra-pure grade and was dried over phosphorous pentoxide or calcium chloride as required. Unless indicated otherwise, at bench-scale, all non-aqueous reagents were transferred under an inert atmosphere via syringe or Schlenk flask. Where necessary, chromatographic purification of reactants or products was performed using forced-flow chromatography on 60 mesh silica gel according to the method described in Still et al., *J. Org. Chem.*, 43: 2923 (1978). Thin-layer chromatography (TLC) was performed using silica-coated glass plates. Visualization of the developed chromatographic plate was performed using either Cerium Molybdate (i.e., Hanessian) stain or $KMnO_4$ stain, with gentle heating as required. Fourier-Transform Infrared (FTIR) spectroscopic analysis of solid samples was performed on a Perkin-Elmer 1600 instrument using a horizontal attenuated total reflectance (ATR) configuration with a zinc selenide crystal.

The moisture content of reagents was determined using a Mettler-Toledo MJ-33 moisture-analyzing balance with a sample size of 0.5-1.0 g. All moisture contents were determined as the average percent weight (% wt) loss on drying obtained from triplicate measurements.

The soluble sugar and oligosaccharide content of reaction products was determined by a combination of high performance liquid chromatography (HPLC) and spectrophotometric methods. HPLC determination of soluble sugars and oligosaccharides was performed on a Hewlett-Packard 1100 Series instrument equipped with a refractive index (RI) detector using a 30 cm×7.8 mm BioRad Aminex HPX-87P column with water as the mobile phase. The sugar column was protected by both a lead-exchanged sulfonated-polystyrene guard column and a tri-alkylammoniumhydroxide anionic-exchange guard column. All HPLC samples were microfiltered using a 0.2 µm syringe filter prior to injection. Sample concentrations were determined by reference to calibrations generated from a standard solution containing glucose, xylose, arabinose, galactose, and gluco-oligosaccharides in known concentrations.

The production of soluble sugar degradation products was determined by high performance liquid chromatography (HPLC) on a Hewlett-Packard 1100 Series instrument equipped with a refractive index (RI) detector using a 30 cm×7.8 mm BioRad Aminex HPX-87H column with 50 mM sulfuric acid as the mobile phase. The sugar column was protected by both a sulfonated-polystyrene guard column and all HPLC samples were microfiltered using a 0.2 µm syringe filter prior to injection. Sample concentrations were determined by reference to calibrations generated from a standard solution containing formic acid, acetic acid, levulinic acid, 5-hydroxymethylfurfural, and 2-furaldehyde.

The average degree of polymerization (DP) for oligosaccharides was determined as the number average of species containing one, two, three, four, five, six, seven, eight, nine, ten to fifteen, and greater than fifteen, anhydrosugar monomer units. The relative concentrations of oligosaccharides corresponding to these different DPs was determined by high performance liquid chromatography (HPLC) on a Hewlett-Packard 1100 Series instrument equipped with a refractive index (RI) detector using a 30 cm×7.8 mm BioRad Aminex HPX-87A column with water as the mobile phase. The analytical column was protected by a silver-coordinated, sulfonated-polystyrene guard column and all HPLC samples were microfiltered using a 0.2 pin syringe filter prior to injection.

The conversion X(t) of monomeric (DP 1) sugars at time t was determined according to $$X(t) = 1 - \frac{\mathrm{mol}(DP1, t)}{\mathrm{mol}(DP1, 0)},$$

where mol(DP1,t) denotes the total moles of monomeric sugars present in the reaction at time t and mol(DP1,0) denotes the total moles of monomeric sugars initially charged to the reaction. Similarly, the yield to oligosaccharides of a given DP was determined according to $$Y_n(t) = \frac{\mathrm{mol}(DPn, t)}{\mathrm{mol}(DP1, 0)},$$

where mol(DPn,t) denotes the total molar equivalents of species with a DP of n, measured in units of monomeric sugar equivalents. Total yield to oligosaccharides with DP>1 was determined according to $$Y_{n>1}(t) = \sum_{n>1} \frac{\mathrm{mol}(DPn, t)}{\mathrm{mol}(DP1, 0)}$$

and the total yield to oligosaccharides with DP>2 was determined according to $$Y_{n>2}(t) = \sum_{n>2} \frac{\mathrm{mol}(DPn, t)}{\mathrm{mol}(DP1, 0)}.$$

The molar yield to sugar degradation products was determine analogously to that for oligosaccharides, where are molar quantities were measured as monomeric sugar equivalents. Finally, the molar selectivity to a given product species was determined as the ratio of the species yield to the sugar conversion, namely $S(t)=Y(t)/X(t)$ The distribution over glycosidic linkages was determined by two-dimensional J-resolved nuclear magnetic resonance (2D-JRES NMR) spectroscopy. Spectra were obtained at room temperature at 400 MHz using deuterium oxide as the solvent with trimethylsilyl propanoic acid (TMSP-d4) as the internal reference. Prior to analysis, oligosaccharides were pre-exchanged by drying the oligosaccharide to constant mass under vacuum at 40 degrees Celsius and redisolving the resulting solid in deuterium oxide. At least two drying/re-disolving cycles were performed for each sample. For gluco-oligosaccharides and gluco-galacto-oligosaccharides, the abundance of a particular glycosidic bond was determined as the ratio of integrated protons for that particular glycosidic bond to the total number of protons integrated over all glycosidic linkages. Proton integral(s) for glycosidic linkages were determined from the following peak assignments: for α-(1,2) linkages $^1$H δ=5.423 and 3.540 ppm; for β-(1,2) linkages $^1$H δ=4.649 and 3.460 ppm; for α-(1,3) linkages $^1$H δ=5.212, 3.850 and 3.760 ppm; for β-(1,3) linkages $^1$H δ=4.750, 4.550, 4.520, 4.503, and 3.502 ppm; for α-(1,4) linkages $^1$H δ=5.046 and 3.960 ppm; for β-(1,4) linkages $^1$H δ=4.680, 4.370, 3.890, and 3.410 ppm; for α-(1,6) linkages $^1$H δ=5.220, 4.960, 4.140, and 3.800 ppm; for β-(1,6) linkages $^1$H δ=4.227, 3.610, and 3.290 ppm.

The production of undesirable non-carbohydrate bi-products, such as polyfuranics, solid humins, and other condensation products, was determined by inference from the reaction molar balance. Specifically, the molar yield to undesirable bi-products was determined as the arithmetic difference of the monomeric sugar conversion minus the sum of the yields to all quantifiable species. Equivalently, the total molar yield to carbohydrates was determined by hydrolyzing a given oligosaccharide mixture back to its constituent monomeric sugars under dilute acid conditions at elevated temperature (e.g., incubating at 121 degrees Celsius for 1 hour in 2%-4% sulfuric acid) and measuring the resulting moles of monomeric sugars, corrected by a standard monomeric control solution that was treated under identical hydrolysis conditions.

The viscosity of oligosaccharide mixtures was determined using a Brookfield viscometer mounted above a temperature-controlled water bath used to set the temperature of the solution being measured from room temperature up to approximately 95 degrees Celsius. The acid content of catalyst samples and aqueous solutions was determined using a Hana Instruments 902-C autotitrator with sodium hydroxide as the titrant, calibrated against a standard solution of potassium hydrogen phthalate (KHP).

Concentration of liquid samples was performed using a Buchi r124 series rotary evaporator unit. For oligosaccharide solutions in water, a bath temperature of approximately 60 degrees Celsius was used. Vacuum pressure of 50-150 mTorr was provided by an oil-immersion pump, which was protected by an acetone-dry ice trap to prevent volatilized solvents from being drawn into the pump system.

Freeze drying of oligosaccharide samples for analytical analysis was performed by coating the walls of a 100 mL round bottom flask (RBF) with approximately 2 grams of the oligosaccharide solution with a starting concentration of 60-70 wt % dissolved solids. The loaded flask was placed in a −20 degree Celsius freezer for two hours, after which the flask was quickly removed to a room temperature environment and subjected to a vacuum. A resting pressure of 50-150 mTorr was provided by an oil-immersion pump, which was protected by an acetone-dry ice trap to prevent volatilized solvents from being drawn into the pump system. Typically three sequential freeze-pump cycles were performed.

Example 1

Preparation of Catalyst

This Example demonstrates the preparation and characterization of poly-(styrene sulfonic acid-co-vinylbenzylimidazolium sulfate-co-clivinylbenzene).

To a 30 L jacketed glass reactor, housed within a walk-in fume hood and equipped with a 2 inch bottom drain port and a multi-element mixer attached to an overhead air-driven stirrer, was charged 14 L of N,N-dimethylformamide (DMF, ACS Reagent Grade, Sigma-Aldrich, St. Louis, Mo., USA) and 2.1 kg of 1H-imidazole (ACS Reagent Grade, Sigma-Aldrich, St. Louis, Mo., USA) at room temperature. The DMF was stirred with continuous mixing at a stirrer speed of approximately 300 RPM to dissolve the imidazole. 7.0 kg of cross-linked poly-(styrene-co-divinylbenzene-co-vinylbenzyl chloride) was then added to the reactor to form a stirred suspension. The reaction mixture was heated to 90 degrees Celsius by pumping heated bath fluid through the reactor jacket, and the resulting heated suspension was maintained for 24 hours, after which it was gradually cooled.

The DMF and residual unreacted 1H-imidazole was drained from the resin through the bottom port of the reactor, after which the retained resin was washed repeatedly with acetone to remove any residual heavy solvent or unreacted reagents that had become entrained in the resin bed. The reaction yielded cross-linked poly-(styrene-co-clivinylbenzene-co-1H-imidazolium chloride) as off-white spherical resin beads. The resin beads were removed from the reactor through the bottom port and heated at 70 degrees Celsius in air to dry.

After being thoroughly cleaned, the 30 L reactor system was charged with 2.5 L of 95% sulfuric acid (ACS Reagent Grade) and then approximately 13 L of oleum (20% free $SO_3$ content by weight, Puritan Products, Inc., Philadelphia, Pa., USA). To the stirred acid solution was gradually added 5.1 kg of the cross-linked poly-(styrene-co-clivinylbenzene-co-1H-imidazolium chloride). After the addition, the reactor was flushed with dry nitrogen gas, the stirred suspension was heated to 90 degrees Celsius by pumping heated bath fluid through the reactor jacket, and the suspension was maintained at 90 degrees Celsius for approximately four hours. After completion of the reaction, the mixture was allowed to cool to approximately 60 degrees Celsius and the residual sulfuric acid mixture was drained from the reactor through the bottom port. After thorough draining, the resin was washed gradually with 80 wt % sulfuric acid solution and then 60 wt % sulfuric acid solution. Finally the resin was washed repeatedly with distilled water until the pH of the wash water was above 5.0, as determined by pH paper. The resin was removed from the reactor through the bottom port to yield the solid catalyst. The acid functional density of catalyst was determined to be at least 2.0 mmol H+/g dry resin by ion-exchange acid-base titration.

Example 2

Preparation of Short Gluco-Oligosaccharides ("GLOS Short")

This Example demonstrates the preparation of gluco-oligosaccharides from dextrose using a catalyst with both acidic and ionic groups. The catalyst was prepared according to the procedure set forth in Example 1 above.

A 22 L jacketed 316L stainless steel reactor (M/DVT-22 mixer/reactor unit, Littleford-Day, Inc., Florence, Ky., USA) was equipped with a mixing element comprising four ploughs with an effective diameter of approximately 95% that of the reactor clear diameter, a bottom-mounted 2 inch diameter outlet port fitted with an 80 mesh stainless steel screen accessed through a manual ball valve assembly, and a top-mounted 3 inch diameter inlet port, also accessed through a manual ball valve assembly. Additional fittings provided the ability to inject compressed gases, steam, and to vent the reactor to relieve pressure. The temperature of the reactor contents was controlled by flowing heated/chilled oil through the reactor jacket and measured via a thermocouple installed along the internal wall of the reactor cylinder.

The reactor was charged with 1.8 wet kg of catalyst prepared according to the procedure described in Example 1 above (moisture content of 44% kg/kg), 5.0 dry kg of food grade dextrose, and 0.2 kg of de-ionized water. The reactants were gradually heated to 105° C. with mixing maintained at 51 rotations of the mixing element per minute. After achieving a uniform temperature, hot air at a temperature of 70-90° C. was injected through the bottom port of the reactor and vented through the top port. The temperature was increased to 115° C. and mixing was maintained for a total of 4 hours.

At the completion of the reaction, approximately 16 kilograms of deionized water were added to the reactor and the contents mixed at 60 degrees Celsius for 15 minutes to dilute the product mixture. The mixing was stopped, and the bottom outlet port was opened to collect the liquid product, leaving the solid catalyst in the reactor vessel. The reactor was pressurized to 5 psig using compressed air to aid in the solid/liquid separation and product recovery. The resulting liquor was vacuum-filtered through a 0.45 micron polyethersulfone membrane to remove any residual solids, such as fine catalyst particulates, and then concentrated to approximately 70 Brix by vacuum rotary evaporation at 50 mTorr. The resulting oligosaccharide concentrate was analyzed by HPLC to determine the product distribution over DP, the extent of formation of sugar degradation products, and the reaction mass balance closure. The product was determined to contain 67.8% kg/kg DP3+, 12.4% kg/kg DP2, 18.4% kg/kg and 1.0% kg/kg sugar caramelization products (levulinic acid, acetic acid, and levoglucosan).

Example 3

Preparation of Long Gluco-Oligosaccharides ("GLOS Long")

This Example demonstrates the preparation of gluco-oligosaccharides from dextran using a catalyst with both acidic and ionic groups. The catalyst was prepared according to the procedure set forth in Example 1 above.

The gluco-oligosaccharides were prepared from dextrose following the procedure of Example 2 as described above, except that the total reaction time was extended to 6 hours. The resulting oligosaccharide concentrate was analyzed by HPLC to determine the product distribution over DP, the extent of formation of sugar degradation products, and the reaction mass balance closure. The product was determined to contain 82.5% kg/kg DP3+ oligosaccharides, 6.9% kg/kg DP2 oligosaccharides, 9.5% kg/kg DP1 sugars, and 0.8% kg/kg total levoglucosan, levulinic acid, acetic acid, and 5-hydroxymethylfurfural.

Example 4

Preparation of Short Gluco-Galacto-Oligosaccharides ("GOS Short")

This Example demonstrates the preparation of gluco-galacto-oligosaccharides from lactose using a catalyst with both acidic and ionic groups. The catalyst was prepared according to the procedure set forth in Example 1 above.

The gluco-galacto-oligosaccharides were prepared following the procedure of Example 2 as described above, except that food-grade lactose was used as the starting material instead of dextrose. The resulting oligosaccharide concentrate was analyzed by HPLC to determine the product distribution over DP, the extent of formation of sugar degradation products, and the reaction mass balance closure. The product was determined to contain 71.8% kg/kg DP3+ oligosaccharides, 11.3% kg/kg DP2 oligosaccharides, 15.2% kg/kg DP1 sugars, and 0.8% kg/kg total levoglucosan, levulinic acid, acetic acid, and 5-hydroxymethylfurfural.

Example 5

Preparation of Long Gluco-Galacto-Oligosaccharides ("GOS Long")

This Example demonstrates the preparation of long gluco-galacto-oligosaccharides from lactose using a catalyst with both acidic and ionic groups. The catalyst was prepared according to the procedure set forth in Example 1 above.

The gluco-galacto-oligosaccharides were prepared following the procedure of Example 2 as described above, except that food-grade lactose was used as the starting material instead of dextrose and the total reaction time was extended to 6 hours. The resulting oligosaccharide concentrate was analyzed by HPLC to determine the product distribution over DP, the extent of formation of sugar degradation products, and the reaction mass balance closure. The product was determined to contain 83.2% kg/kg DP3+ oligosaccharides, 5.8% kg/kg DP2 oligosaccharides, 9.0% kg/kg DP1 sugars, and 0.5% kg/kg total levoglucosan, levulinic acid, acetic acid, and 5-hydroxymethylfurfural.

Example 6

Preparation of Short Manno-Oligosaccharides ("MOS Short")

This Example demonstrates the preparation of short manno-oligosaccharides from mannose using a catalyst with both acidic and ionic groups. The catalyst was prepared according to the procedure set forth in Example 1 above.

A 5 L jacketed 316L stainless steel reactor (Parr Instrument Company, Moline, Ill. USA) was equipped with an anchor mixing element with an effective diameter of approximately 95% that of the reactor clear diameter and a vacuum condenser. The temperature of the reactor contents was controlled by flowing pressurized hot water through the reactor jacket and measured via a thermocouple installed along the internal wall of the reactor cylinder.

The reactor was charged with 0.35 wet kg of catalyst prepared according to the procedure described in Example 1 above (moisture content of 44% kg/kg), 1.0 dry kg of reagent grade mannose, and 0.15 kg of de-ionized water. The contents were mixed at a speed of 60 rotations of the mixing element per minute, the pressure was reduced to 50-100

Torr, and the temperature was gradually increased to 105° C. After reaching a steady temperature, the reactants were maintained at 105° C. and 100 Torr with mixing for a total of 4 hours.

At the completion of the reaction, approximately 5 kilograms of deionized water were added to the reactor and the contents mixed at 60 degrees Celsius for 15 minutes to dilute the product mixture. The reactor was drained and the resulting slurry was vacuum-filtered through a 0.45 micron polyethersulfone membrane to remove the product oligosaccharide solution from the solid catalyst. Two additional reaction batches were performed and the resulting filtrates were combined into a single product liquor that was concentrated to approximately 70 Brix by vacuum rotary evaporation at 50 mTorr. The resulting oligosaccharide concentrate was analyzed by HPLC to determine the product distribution over DP, the extent of formation of sugar degradation products, and the reaction mass balance closure. The product was determined to contain 42.0% kg/kg DP3+, 17.4% kg/kg DP2, 36.9% kg/kg and <0.1% kg/kg sugar caramelization products (levulinic acid, acetic acid, and levoglucosan).

Example 7

Preparation of Long Manno-Oligosaccharides ("MOS Long")

This Example demonstrates the preparation of long manno-oligosaccharides from mannose using a catalyst with both acidic and ionic groups. The catalyst was prepared according to the procedure set forth in Example 1 above.

The manno-oligosaccharides were prepared following the procedure of Example 6 as described above, except that the total reaction time was extended to 6 hours. The resulting oligosaccharide concentrate was analyzed by HPLC to determine the product distribution over DP, the extent of formation of sugar degradation products, and the reaction mass balance closure. The product was determined to contain 65.2% kg/kg DP3+ oligosaccharides, 11.7% kg/kg DP2 oligosaccharides, 20.4% kg/kg DP1 sugars, and 0.5% kg/kg total levoglucosan, levulinic acid, acetic acid, and 5-hydroxymethylfurfural.

Example 8

Preparation of Xylo-Oligosaccharides ("XOS")

This Example demonstrates the preparation of xylo-oligosaccharides from xylose using a catalyst with both acidic and ionic groups. The catalyst was prepared according to the procedure set forth in Example 1 above.

The xylo-oligosaccharides were prepared following the procedure of Example 6 as described above, except that xylose was used as the starting sugar instead of mannose. The resulting oligosaccharide concentrate was analyzed by HPLC to determine the product distribution over DP, the extent of formation of sugar degradation products, and the reaction mass balance closure. The product was determined to contain 45.0% kg/kg DP3+ oligosaccharides, 23.2% kg/kg DP2 oligosaccharides, 31.7% kg/kg DP1 sugars, and <0.1% kg/kg total levoglucosan, levulinic acid, acetic acid, 5-hydroxymethylfurfural, and furfural.

Example 9

Preparation of Arabino-Xylo-Oligosaccharides ("AXOS")

This Example demonstrates the preparation of arabino-xylo-oligosaccharides from arabinose and xylose using a catalyst with both acidic and ionic groups. The catalyst was prepared according to the procedure set forth in Example 1 above.

The xylo-oligosaccharides were prepared following the procedure of Example 6 as described above, except that a 50/50 mixture of xylose and arabinose was used as the starting material instead of mannose. The resulting oligosaccharide concentrate was analyzed by HPLC to determine the product distribution over DP, the extent of formation of sugar degradation products, and the reaction mass balance closure. The product was determined to contain 50.6% kg/kg DP3+ oligosaccharides, 18.0% kg/kg DP2 oligosaccharides, 31.4% kg/kg DP1 sugars, and <0.1% kg/kg total levoglucosan, levulinic acid, acetic acid, 5-hydroxymethylfurfural, and furfural.

Example 10

Feed Trials and Determination of Weight Gain and Feed Conversion in Poultry

This Example demonstrates the effect that feeding oligosaccharides prepared using a catalyst with both acidic and ionic groups has on the weight gain and feed conversion in poultry.

The catalyst was prepared according to the procedure set forth in Example 1 above. The oligosaccharides were prepared according to the procedures set forth in Examples 2 through 9 above.

Nineteen groups of broiler hens were fed a diet for 35 days, prepared by blending a standard poultry feed with either one oligosaccharide prepared according to according to Example 2 through Example 9 above; a commercially-available fructo-oligosaccharide obtained from inulin; a commercially-available enzymatic feed additive (Econase® XT, AB Vista Feed Ingredients, UK); or no additive. The standard poultry feed included the components listed in Table 2 below. The additive identity and concentration used (inclusion rate) for each group is listed in Table 3 below.

The mass gain, ileal volatile fatty acid (VFA) content, ileal short chain fatty acid (SCFA) content, caecal CFA content, and caecal SCFA content for each group of poultry was measured on days 14 and 35.

TABLE 2

Components of standard base feeds used in blending

| Component | Starter (1) | Grower (2) |
| --- | --- | --- |
| Wheat | 57.37% | 67.88% |
| Soybean Meal | 34.7% | 27.09% |
| Sunflower Oil | 4% | 1.47% |
| Monocalcium phosphate | 1.5% | 1.5% |
| Limestone | 1.3% | 1.3% |
| NaCl | 0.4% | 0.4% |
| Mineral premix (3) | 0.2% | 0.2% |
| Vitamin premix (4) | 0.2% | 0.2% |
| Methionine | 0.24% | 0.24% |

TABLE 2-continued

Components of standard base feeds used in blending

| Component | Starter (1) | Grower (2) |
|---|---|---|
| Lysine | 0.09% | 0.09% |
| Threonine | 0.0% | 0.0% |

(1) Starter formulation used for the first two weeks
(2) Grower formulation used for the following three weeks
(3) Calcium 296.8 g/kg, iron 12.5 g/kg, copper 4 g/kg, manganese 25 g/kg, zinc 32.5 g/kg, iodine 0.225 g/kg, selenium 0.1 g/kg
(4) Calcium 331.3 g/kg, vitamin A 6,000,000 ID, vitamin D3 225000 IU, vitamin E 3000, tocoferol 27270 mg/mk, vitamin K3 1505 mg/kg, vitamin B1 1257.3 mg/kg, vitamin B2 3000 mg/kg, vitamin B6 2009.7 mg/kg, vitamin B12 12.5 mg/kg, biotin 75 mg/kg, folic acid 504 mg/kg, niacin 20072 mg/kg, panthotenic acid 7506.8 mg/kg

TABLE 3

Feeds additives included in diet

| Trial # | Oligosaccharide | Feed Label | # Replicate Pens | Inclusion Rate in Diet (wt %) |
|---|---|---|---|---|
| 1 | None | Control | 6 | — |
| 2 | GLOS Short | GLOS Short 100 | 4 | 0.01% |
| 3 | GLOS Short | GLOS Short 1000 | 5 | 0.1% |
| 4 | GLOS Long | GLOS Long 100 | 4 | 0.01% |
| 5 | GLOS Long | GLOS Long 1000 | 5 | 0.1% |
| 6 | GOS Short | GOS Short 100 | 4 | 0.01% |
| 7 | GOS Short | GOS Short 1000 | 5 | 0.1% |
| 8 | GOS Long | GOS Long 100 | 4 | 0.01% |
| 9 | GOS Long | GOS Long 1000 | 5 | 0.1% |
| 10 | MOS Short | MOS Short 100 | 4 | 0.01% |
| 11 | MOS Short | MOS Short 1000 | 5 | 0.1% |
| 12 | MOS Long | MOS Long 100 | 4 | 0.01% |
| 13 | MOS Long | MOS Long 1000 | 5 | 0.1% |
| 14 | XOS | XOS 100 | 4 | 0.01% |
| 15 | XOS | XOS 1000 | 5 | 0.1% |
| 16 | AXOS | AXOS 100 | 4 | 0.01% |
| 17 | AXOS | AXOS 1000 | 5 | 0.1% |
| 18 | Comparative Example FOS | FOS 500 | 5 | 0.5% |
| 19 | Comparative Example Econase | Econase 100 | 5 | 0.1% |

The temperature of the enclosure used for the poultry was raised to 32° C. two days before the chicks arrived. Luminosity was adjusted to 20 lux. Brooder lamps were adjusted to provide extra heating to the chicks during the first week. The temperature was gradually decreased to 22° C. over the rearing period. Temperature, ventilation and humidity were monitored and recorded throughout the experiment on a daily basis. The dark hours were gradually increased within a week, so that light-dark cycle was 18 hours light and 6 hours dark daily.

Newly-hatched male Ross 508 broiler chicks were randomly allocated to treatment. Each chick was marked with permanent color on the feathers that identified the treatment but not the individual animal. Birds were housed in 88 open pens (1.125 square meters each) with wood shavings litter. The numbers of replicate pens for the treatments are shown in Table 3.

At the start of the trial, there were 15 birds in each pen and the total number of birds was 1320. A veterinarian checked the health of the chicks at the beginning of the trial and 4 birds from one pen of the control treatment had to be euthanized. The birds were observed twice a day. Chicks with compromised health were excluded from the trial. Feed and water were available ad libitum at all times.

The chicks were weighed on days 0, 14, 21 and 35. Correspondingly, feed intake per pen and the feed conversion ratio (FCR) were measured for the following periods: days 0-14, starter diet period; days 14-21, early grower diet period; days 21-35, later grower diet period. Dead birds and birds euthanized because of health problems were weighed. Daily mortality was recorded. FCR was calculated both corrected and uncorrected for mortality.

On day 14 two birds per pen were euthanized by cervical dislocation, the abdominal cavity opened, and the entire ileum and the paired caeca removed for various analyses. On day 35 three birds per pen were euthanized and sampled in the same way as on day 14. Ileal and caecal digesta samples were packed in individual plastic bags, and frozen immediately for analyses. On day 35 blood samples (1.5 ml+heparin) were taken from 2 birds per pen and frozen immediately for analysis. Cumulatively, 440 ileal, 440 caecal digesta and 176 blood samples were collected in the trial.

Immediately after recovering the ileal digesta from a bird, the digesta was thoroughly mixed with a plastic rod, 1 gram introduced in a microfuge tube, centrifuged at 5 000×g for 10 minutes and the supernatant immediately measured for viscosity. At 14- and 35-day time points ileal digesta viscosity was measured in 2 birds from 56 pens (pens being fed with diets 1, 3, 5, 7, 9, 11, 13, 15, 17, 18 and 19), with 224 measurements taken in total (2 time points×56 pens×2 birds).

The lactic acid and volatile fatty acid ("VFA") content were analysed by gas chromatography using a packed column for the analysis of free acids. The short-chain fatty acids (SCFAs) quantified were acetic, propionic, butyric, iso-butyric, 2-methyl-butyric, valeric, iso-valeric and lactic acid. SCFAs were analysed in ileal and caecal digesta of two birds per pen at both sampling points. Thus SCFAs were analysed in 352 ileal and 352 caecal digesta samples, with 704 samples analysed in total (2 time points×88 pens×2 birds).

Performance data was analysed by Dunnett's (2-sided) test using JMP statistical software package (version 12 EA). Results of the SCFA analysis were analysed by independent samples T-test. In all tests, the treatment group 1 (unamended diet) was used as a control against which the test treatments were compared.

Figure 13:
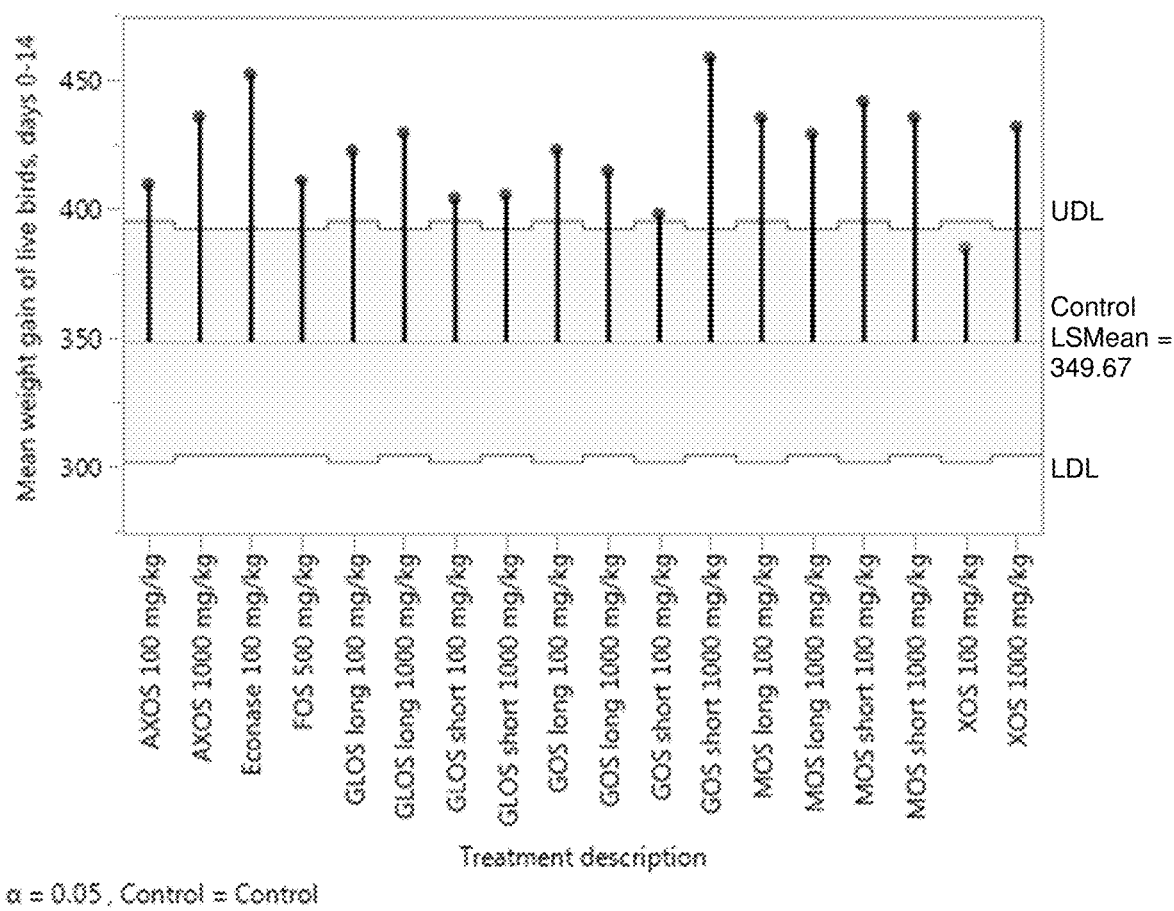
FIG. 13 is a graph depicting the mean weight gain of poultry after the first 14 days of a diet supplemented with an oligosaccharide additive prepared with a catalyst including acidic moieties and ionic moieties, additives prepared by other methods, or no additive.

The mean weight gain in grams of each group after the first 14 days is shown in FIG. 13. The upper decision limit (UDP) and lower decision limit (LDP) using a threshold of 0.05 are depicted.

Figure 14:
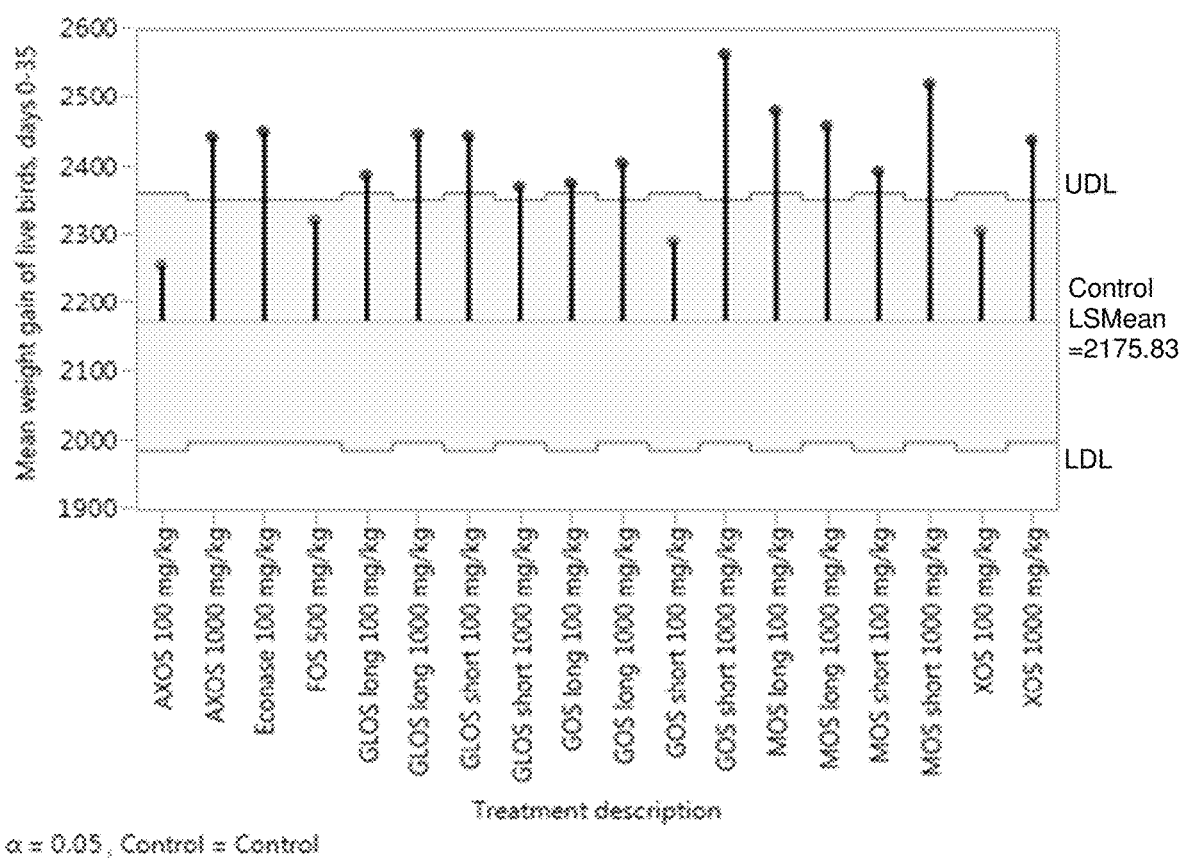
FIG. 14 is a graph depicting the mean weight gain of poultry following 35 days of a diet supplemented with an oligosaccharide additive prepared with a catalyst including acidic moieties and ionic moieties, additives prepared by other methods, or no additive.

The mean weight gain in grams of each group at the end of the 35 day period is shown in FIG. 14. The upper decision limit (UDP) and lower decision limit (LDP) using a threshold of 0.05 are depicted.

Figure 15:
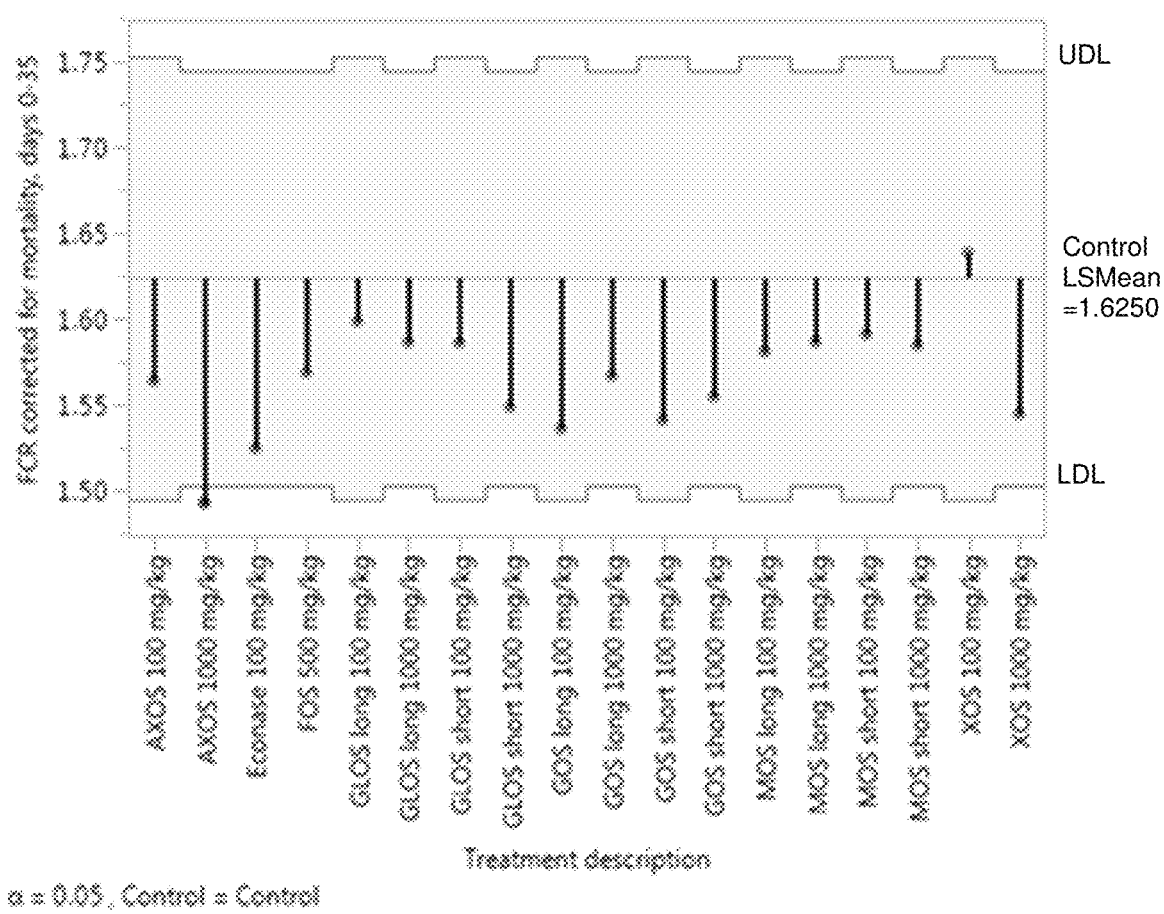
FIG. 15 is a graph depicting the feed conversion ratio (FCR) of poultry following 35 days of a diet supplemented with an oligosaccharide additive prepared with a catalyst including acidic moieties and ionic moieties, additives prepared by other methods, or no additive.

The feed conversion ratio (FCR) for each group at the end of the 35 day period, corrected for mortality, is shown in FIG. 15.

Figure 16:
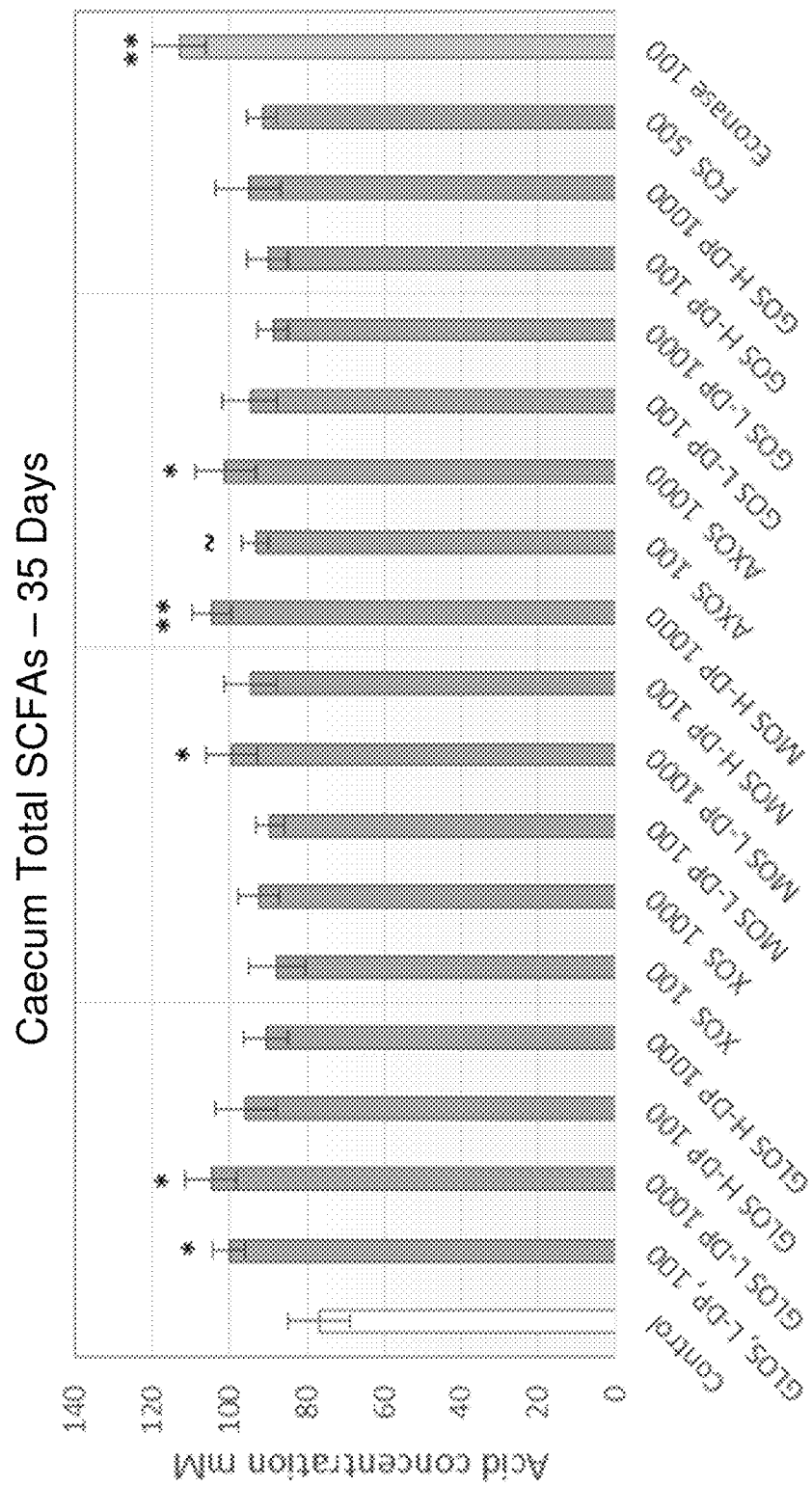
FIG. 16 is a graph depicting the short chain fatty acid (SCFA) concentration in the caecum from a sample of birds in each group of poultry following 35 days of a diet supplemented with an oligosaccharide additive prepared with a catalyst including acidic moieties and ionic moieties, additives prepared by other methods, or no additive.

The total SCFA concentration in the caecum from a sample of birds in each group at the end of 35 days is shown in FIG. 16.

Figure 17:
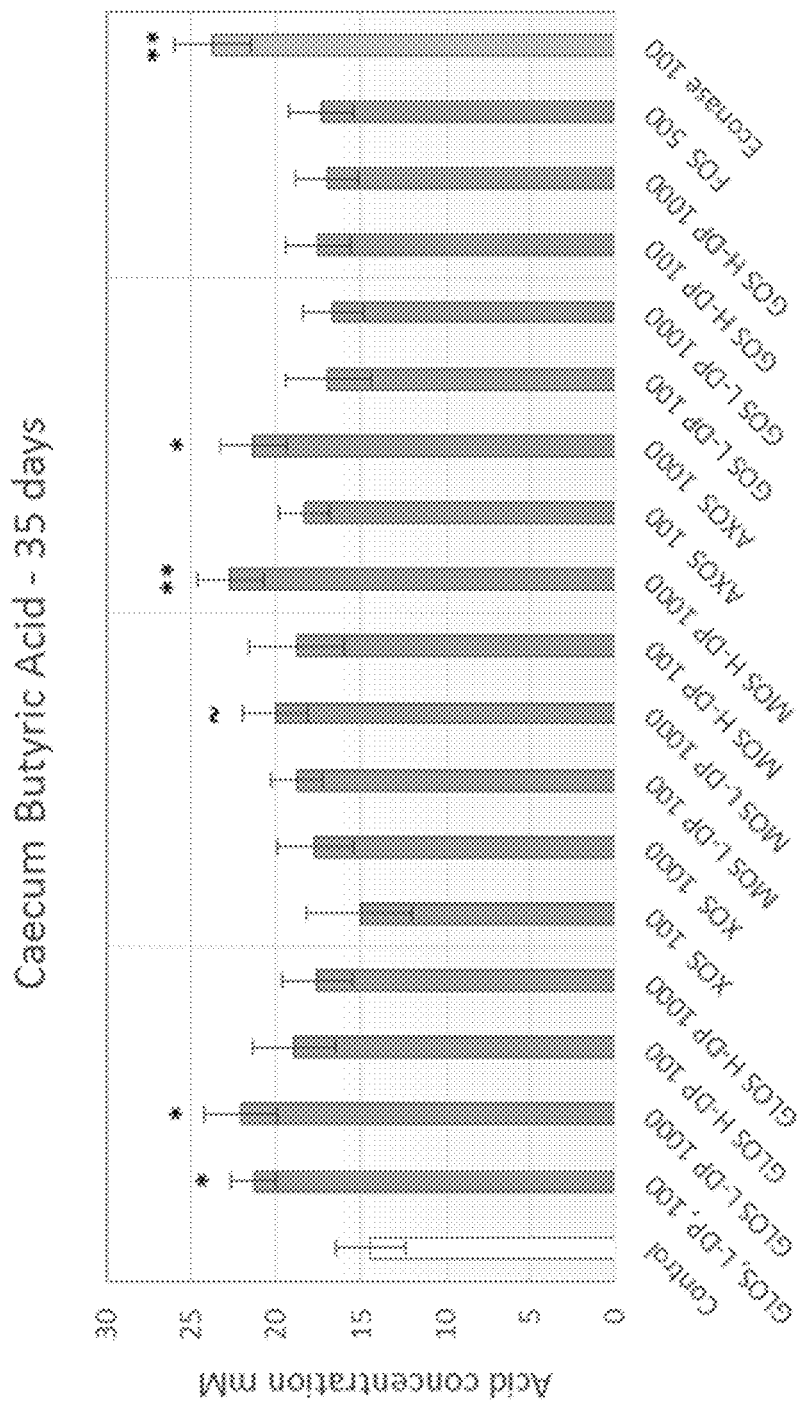
FIG. 17 is a graph depicting the butyric acid concentration in the caecum from a sample of birds in each group of poultry following 35 days of a diet supplemented with an oligosaccharide additive prepared with a catalyst including acidic moieties and ionic moieties, additives prepared by other methods, or no additive.

The butyric acid concentration in the caecum from a sample of birds in each group at the end of 35 days is shown in FIG. 17.

The mean weight gain of each group at the end of the 35 day period is shown in FIG. 14. All treatments resulted in heavier birds relative to the control (control gain=2175.83 g). It was unexpectedly observed that several of the oligosaccharide additives, in particular "GLOS Long" (prepared as in Example 3), "GOS Short" (prepared as in Example 4), "GOS Long" (prepared as in Example 5), "MOS Short" (prepared as in Example 6), and "MOS Long" (prepared as in Example 7), provided a statistically significant (p<0.05, Dunnetts) increase in poultry weight at the low inclusion rate of 0.01%, as compared to the control (no additive).

The oligosaccharide additives "AXOS" (prepared as in Example 9), "GOS Short" (prepared as in Example 2), and "XOS" (prepared as in Example 8) did not result in a statistically significant increase in poultry weight at the inclusion rate of 0.01%, as compared to the control. In contrast, the commercial prebiotic FOS failed to provide a statistically significant increase in weight even at the inclusion rate of 0.05%, which is up to five times the inclusion rate of the oligosaccharide additives.

The feed conversion ratio (FCR) was decreased for most groups fed additives, compared to the control (control mean FCR=1.625). The group fed "AXOS" (prepared as in Example 9) exhibited a statistically significant reduction in FCR at the inclusion rate of 0.1%.

The presence of the various oligosaccharide additives did not result in any significant change to the ileal digesta viscosity of the birds at 35 days relative to the control, as shown in Table 4.

TABLE 4

Ileal digesta viscosity of at the end of 35 day period

| Trial # | Treatment | Viscosity |
|---|---|---|
| 1 | Control | 6.0 |
| 3 | GLOS L-DP 1000 | 5.8 |
| 5 | GLOS H-DP 1000 | 7.4 |
| 7 | XOS 1000 | 6.4 |
| 9 | MOS L-DP 1000 | 5.8 |
| 11 | MOS H-DP 1000 | 6.3 |
| 13 | AXOS 1000 | 6.3 |
| 15 | GOS L-DP 1000 | 6.8 |
| 17 | GOS H-DP 1000 | 7.3 |
| 18 | FOS 500 | 7.5 |
| 19 | Econase 100 | 4.8 |

Compared to the control, the concentrations of caecal SCFA increased for groups fed a diet including an oligosaccharide additive. In particular, the group fed "GLOS Long" (prepared as in Example 3) showed a caecal butyric acid concentration of 21.5 mM at an inclusion rate of 0.01%, as shown in FIG. 17.

These results indicate that including oligosaccharide additives prepared using a catalyst with both acidic and ionic moieties in poultry feed effectively increases the weight gain of poultry.

Example 11

Preparation and Purification of Gluco-oligosaccharides

This Example demonstrates the preparation and purification of gluco-oligosaccharides from food grade dextrose using a catalyst with both acidic and ionic groups. The catalyst was prepared according to the procedure set forth in Example 1 above.

The gluco-oligosaccharides were prepared from dextrose following the procedure of Example 2 as described above, except as follows. The DP3+ content of the product mixture was monitored by HPLC, and the reaction was stopped when the DP3+ content reached 73%±2% dry kg DP3+ oligosaccharides per dry kilogram of solids. Following recovery from the reactor, the syrup was filtered through a 0.2 micron ceramic membrane filter (Pall Corporation, Westborough, Mass. USA) using a backpressure of 30-60 psi. The permeate was then run sequentially through a 3 liter packed bed of Dowex Monosphere 88 strong acid cationic exchange resin, a 3 liter bed of Dowex Monosphere 66 weak base anionic exchange resin, and a 3 liter bed of Dowex Optipore-SD-2 absorbant resin, resulting in a pale-yellow syrup with neutral pH and minimal odor. The syrup was then concentrated to a final solids content of 65% kg dry solids per kg of syrup using a horizontal wiped-film vacuum evaporator.

The resulting concentrated gluco-oligosaccharide syrup was determined by HPLC and conductivity to contain less than 1 ppm total formic acid, levulinic acid, and 5-hydroxymethylfurfural. Bacterial analysis confirmed a total aerobic plate count <10 cfu/g, *Escherichia coli* <10 cfu/g, *Staphylococcus aureus* <10 cfu/g, total coliform <10 cfu/g, and that the syrup was negative for *Salmonella* spp, under the methods of the US FDA Bacterial Analytical Manual (BAM), Edition 8, Rev. A, 1998. The resulting concentrated gluco-oligosaccharide syrup was determined by ICP-MS to contain less than 10 ppb arsenic, less than 10 ppb cadmium, less than 10 ppb lead, less than 10 ppb mercury, less than 0.2 ppm nickel, and 1.2 ppm zinc.

The distribution over glycosidic bond types in the gluco-oligosaccharide mixture was determined by 2D-JRES NMR to be: 11±1 mol % α-(1,2) glycosidic linkages, 35±4 mol % β-(1,2) glycosidic linkages, 6±1 mol % α-(1,3) glycosidic linkages, 3±1 mol % β-(1,3) glycosidic linkages, 1±0.5 mol % α-(1,4) glycosidic linkages, 21±2 mol % β-(1,4) glycosidic linkages, 15±2 mol % α-(1,6) glycosidic linkages, and 8±1 mol % β-(1,6) glycosidic linkages.

Example 12

Preparation and Purification of Gluco-galacto-oligosaccharides

This Example demonstrates the preparation and purification of gluco-galacto-oligosaccharides from food grade lactose using a catalyst with both acidic and ionic groups. The catalyst was prepared according to the procedure set forth in Example 1 above.

The gluco-galacto-oligosaccharides were prepared from lactose following the procedure of Example 4 as described above, except as follows. The total reaction time was adjusted to yield a reaction product with a DP3+ content of 73%±2% dry kg DP3+ oligosaccharides per dry kilogram of solids, as determined by HPLC. Following recovery from the reactor, the syrup was filtered through a 0.2 micron ceramic membrane filter (Pall Corporation, Westborough, Mass. USA) using a backpressure of 30-60 psi. The permeate was then run sequentially through a 3 liter packed bed of Dowex Monosphere 88 strong acid cationic exchange resin, a 3 liter bed of Dowex Monosphere 66 weak base anionic exchange resin, and a 3 liter bed of Dowex Optipore-SD-2 absorbant resin, resulting in a pale-yellow syrup with neutral pH and minimal odor. The syrup was then concentrated to a final solids content of 65% kg dry solids per kg of syrup using a horizontal wiped-film vacuum evaporator.

The resulting concentrated gluco-galacto-oligosaccharide syrup was determined by HPLC and conductivity to contain less than 1 ppm total formic acid, levulinic acid, and 5-hydroxymethylfurfural. Bacterial analysis confirmed a total aerobic plate count <10 cfu/g, *Escherichia coli* <10 cfu/g, *Staphylococcus aureus* <10 cfu/g, total coliform <10 cfu/g, and that the syrup was negative for *Salmonella* spp, under the methods of the US FDA Bacterial Analytical Manual (BAM), Edition 8, Rev. A, 1998. The resulting concentrated gluco-oligosaccharide syrup was determined by ICP-MS to contain less than 10 ppb arsenic, less than 10 ppb cadmium, less than 10 ppb lead, less than 10 ppb mercury, less than 0.2 ppm nickel, and 0.520 ppm zinc.

The distribution over glycosidic bond types in the gluco-oligosaccharide mixture was determined by proton and JRES NMR to be: between 0-10 mol % α-(1,2) glycosidic linkages, between 0-10 mol % β-(1,2) glycosidic linkages, between 5-15 mol % α-(1,3) glycosidic linkages, between 2-10 mol % β-(1,3) glycosidic linkages, between 2-15 mol % α-(1,4) glycosidic linkages, between 10-50 mol % β-(1,4) glycosidic linkages, between 5-25 mol % α-(1,6) glycosidic linkages, and between 20-50 mol % β-(1,6) glycosidic linkages.

Example 13

Preparation of a Gluco-Oligosaccharide Pre-Mix

The gluco-oligosaccharide from Example 11 was combined with milled corn meal as a carrier material in a ratio of approximately 1 kg gluco-oligosaccharide syrup to 4 kg of corn meal. The resulting mixture was blended to achieve a uniform distribution of gluco-oligosaccharides, producing a dry, flowable power with a moisture content below 12% kg/kg Example 14

Preparation of Gluco-Oligosaccharide Pre-Mixes

The procedure of Example 13 was repeated for each of following carriers, used in place of milled corn: ground rice hulls, feed grade silica gel, feed grade fumed silica, corn gluten feed, corn gluten meal, and dried distiller's grains. Where necessary, the blended material was dried to a maximum final moisture content of 10 wt %.

Example 15

Preparation of a Gluco-Galacto-Oligosaccharide Pre-Mix

The gluco-galacto-oligosaccharide from Example 12 was combined with milled corn meal as a carrier material in a ratio of approximately 1 kg gluco-galacto-oligosaccharide syrup to 4 kg of corn meal. The resulting mixture was blended to achieve a uniform distribution of gluco-oligosaccharides, producing a dry, flowable power with a moisture content below 12% kg/kg.

Example 16

Preparation of Gluco-Galacto-Oligosaccharide Pre-Mixes

The procedure of Example 15 was repeated for each of the following carriers, used in place of milled corn: ground rice hulls, feed grade silica gel, feed grade fumed silica, corn gluten feed, corn gluten meal, and dried distiller's grains. Where necessary, the blended material was dried to a maximum final moisture content of 10 wt %

Example 17

Preparation and Purification of Gluco-Oligosaccharides

This Example demonstrates the rapid preparation and purification of gluco-oligosaccharides from food grade dextrose using a catalyst with both acidic and ionic groups. The catalyst was prepared according to the procedure set forth in Example 1 above.

The gluco-oligosaccharides were prepared from dextrose following the procedure of Example 2 as described above, except as follows. The reaction temperature was increased to 140-160 degrees C. and the reaction time was reduced to 60-90 minutes. Following recovery from the reactor and removal of the catalyst, the product syrup was neutralized to a pH between 5.0 and 6.5 with aqueous sodium hydroxide solution and then filtered through a series of 20, 10, 5, 1 and 0.2 micron inline cartridge filters. The filtered syrup was then concentrated to a final solids content of 65% kg dry solids per kg of syrup using a horizontal wiped-film vacuum evaporator.

The resulting concentrated gluco-oligosaccharide syrup was determined by HPLC to have a DP3+ content of 73%±2% dry kg DP3+ oligosaccharides per dry kilogram of solids. The distribution over glycosidic bond types in the gluco-oligosaccharide mixture was determined by 2D-JRES NMR to be: 15±1 mol % α-(1,2) glycosidic linkages, 27±4 mol % β-(1,2) glycosidic linkages, 8±1 mol % α-(1,3) glycosidic linkages, 5±1 mol % β-(1,3) glycosidic linkages, 1±0.5 mol % α-(1,4) glycosidic linkages, 20±2 mol % β-(1,4) glycosidic linkages, 11±2 mol % α-(1,6) glycosidic linkages, and 15±1 mol % β-(1,6) glycosidic linkages.

Example 18

Scaled-Up Production of a Gluco-Oligosaccharide Pre-Mix 50.9 kg of the gluco-oligosaccharide from Example 17 was blended in batches with 95.2 kg of milled corn meal using a bowl-mixer with an overhead orbital mixer equipped with a dough-blending element. The resulting 146.1 kg of wet pre-mix were dried in 13 kg batches using a rotating drum drier with a rotation rate of approximately 60 rpm and an air flow rate of approximately 1,000 cubic feet per minute. 127.0 kg of dried pre-mix were recovered. The moisture content was determined to be below 15 wt %.

Example 19

Preparation of Basal Corn-Soy Poultry Feeds

Complete corn-soy starter, grower, and finisher poultry feeds, typical of those used in the U.S. broiler industry, were produced by blending ingredients in the following proportions:

| Ingredient (lbs, as received) | Starter | Grower | Finisher |
| --- | --- | --- | --- |
| Corn | 638.61 | 689.22 | 747.31 |
| Soybean meal | 275.21 | 221.09 | 167.42 |
| Animal by-product blend | 50.28 | 50.27 | 50.28 |
| Dicalcium phosphate | 10.56 | 11.06 | 8.65 |
| Limestone | 5.13 | 5.33 | 4.73 |
| Poultry Fat | 5.03 | 8.85 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Bacitracin | 0.00 | 0.00 | 0.00 |

-continued

| Ingredient (lbs, as received) | Starter | Grower | Finisher |
|---|---|---|---|
| Saccox | 0.50 | 0.50 | 0.50 |
| Enzyme blend | 0.20 | 0.20 | 0.20 |
| Total | 1000.00 | 1000.00 | 1000.00 |

The nutritional properties of the feeds were calculated to be:

| Nutritional Property | Starter | Grower | Finisher |
|---|---|---|---|
| Apparent metabolizable energy (cal/lb) | 1381 | 1413 | 1437 |
| Crude protein, wt % | 22.11 | 19.96 | 17.92 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

The feeds contained an ionophore anti-coccidial and an enzyme blend comprising a phytase and non-starch polysaccharide carbohydratases (NSPases). Raw ingredients were formed into peletized poultry feed as follows. The raw ingredients were combined in a ribbon blender, after which they were conveyed to a 160-180 degree F. steam-injected conditioner. The conditioned feed was pressed through a rotating-dye peletizer to produce hot pellets, which were then cooled in a fluidized air cooler. The resulting feed pellets were metered into 50 pound lined, multi-wall paper bags, which were sealed until use. The starter feed pellets were crumbled prior to bagging.

Example 20

Preparation of Basal Corn-Soy Poultry Feeds

Complete corn-soy starter, grower, and finisher poultry feeds, typical those used in the U.S. broiler industry, were produced by blending ingredients as follows:

| Ingredient (lbs, as received) | Starter | Grower | Finisher |
|---|---|---|---|
| Corn | 1187.36 | 1281.44 | 1400.68 |
| Soybean meal | 714.71 | 619.51 | 516.94 |
| Bone meal | 40.00 | 40.00 | 20.00 |
| Limestone | 23.24 | 22.73 | 22.97 |
| Phosphate (defluorinated) | 7.83 | 3.89 | 6.60 |
| Salt | 7.63 | 8.13 | 8.29 |
| DL-Methionine | 7.14 | 6.11 | 5.47 |
| Threonine | 2.28 | 1.75 | 1.82 |
| L-Lysine | 2.25 | 1.75 | 2.45 |
| Vitamin and Mineral Premix | 4.00 | 4.00 | 4.00 |
| Soy oil | 1.42 | 8.55 | 9.48 |
| Salinomycin | 0.84 | 0.84 | 0.00 |
| Choline | 0.80 | 0.80 | 0.80 |
| Enzyme blend | 0.50 | 0.50 | 0.50 |
| Total | 2000.00 | 2000.00 | 2000.00 |

The nutritional content of the feed based on the ingredient inclusions was calculated to be:

| Nutritional Property | Starter | Grower | Finisher |
|---|---|---|---|
| Apparent metabolizable energy (cal/lb) | 1379 | 1412 | 1436 |
| Crude protein, wt % | 22.10 | 20.84 | 18.33 |
| Total Lys, wt % | 1.35 | 1.20 | 1.06 |
| Total Methionine, wt % | 0.69 | 0.61 | 0.55 |
| Total TSAA, wt % | 1.02 | 0.92 | 0.83 |
| Total Threonine, wt % | 0.918 | 0.82 | 0.733 |
| Calcium, wt % | 0.965 | 0.88 | 0.82 |
| Available P, wt % | 0.47 | 0.43 | 0.40 |
| Sodium, wt % | 0.21 | 0.21 | 0.21 |

The starter and grower feeds contained an ionophore anti-coccidial and an enzyme blend comprising a phytase and a mixture of non-starch polysaccharide carbohydratases (NSPases), while the finisher feed contained the enzyme blend but not the ionophore. Raw ingredients were formed into peletized poultry feed as follows. The raw ingredients were combined in a ribbon blender, after which they were conveyed to a steam-injected conditioner. The conditioned feed was pressed through a rotating-dye peletizer to produce hot pellets, which were then cooled in a fluidized air cooler. The starter feed pellets were crumbled, and the resulting feeds were metered into bulk storage bins until use.

Example 21 (Comparative Example 1)

Preparation of Feeds Containing Antibiotic Growth Promoters

Complete starter, grower, and finisher feeds were produced according to the procedure of Example 19, except that bacitracin (BMD®-50, Zoetis) was added on top of the basal diet, resulting in diets with the following compositions:

| Ingredient (lbs, dry solids basis) | Starter | Grower | Finisher |
|---|---|---|---|
| Corn | 638.29 | 688.88 | 746.93 |
| Soybean meal | 275.08 | 220.98 | 167.34 |
| Animal by-product blend | 50.25 | 50.25 | 50.25 |
| Dicalcium phosphate | 10.55 | 11.05 | 8.64 |
| Limestone | 5.13 | 5.33 | 4.72 |
| Poultry Fat | 5.03 | 8.84 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Bacitracin | 0.50 | 0.50 | 0.50 |
| Saccox | 0.50 | 0.50 | 0.50 |
| Enzyme blend | 0.20 | 0.20 | 0.20 |
| Total | 1000.00 | 1000.00 | 1000.00 |

| Nutritional Property | Starter | Grower | Finisher |
|---|---|---|---|
| Apparent metabolizable energy (cal/lb) | 1380 | 1412 | 1436 |
| Crude protein, wt % | 22.10 | 19.95 | 17.91 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

Example 22 (Comparative Example 2)

Preparation of Feeds Containing Soluble Corn Fiber

Complete starter, grower, and finisher feeds were produced according to the procedure of Example 20, except that soluble corn fiber (Fibersol®-LQ, Acher Daniels Midland Company, USA) was added on top of the basal diet. The distribution over glycosidic bond types in the soluble corn fiber was determined by 2D-JRES NMR to be: <10 mol % α-(1,2) glycosidic linkages, ≤9 mol % β-(1,2) glycosidic linkages, ≤9 mol % α-(1,3) glycosidic linkages, ≥16 mol % β-(1,3) glycosidic linkages, ≥9 mol % α-(1,4) glycosidic linkages, ≤15% mol % β-(1,4) glycosidic linkages, ≥19 mol % α-(1,6) glycosidic linkages, and ≤12 mol % β-(1,6) glycosidic linkages. Diets were prepared by adding the soluble corn fiber at an inclusion rate of 625 ppm (dry solids basis per total final feed), resulting in the following compositions:

| Ingredient (lbs, dry solids basis) | Starter | Grower | Finisher |
|---|---|---|---|
| Corn | 1186.61 | 1280.64 | 1399.81 |
| Soybean meal | 714.27 | 619.12 | 516.62 |
| Animal by-product blend | 39.98 | 39.98 | 19.99 |
| Dicalcium phosphate | 23.23 | 22.72 | 22.96 |
| Limestone | 7.83 | 3.89 | 6.60 |
| Poultry Fat | 7.63 | 8.12 | 8.28 |
| L-Lysine | 7.14 | 6.11 | 5.47 |
| Salt | 2.28 | 1.75 | 1.82 |
| DL-Methionine | 2.25 | 1.75 | 2.45 |
| Vitamin and Mineral Premix | 4.00 | 4.00 | 4.00 |
| L-Threonine | 1.42 | 8.54 | 9.47 |
| Soluble Corn Fiber | 0.84 | 0.84 | 0.00 |
| Saccox | 0.80 | 0.80 | 0.80 |
| Enzyme blend | 1.25 | 1.25 | 1.25 |
| Total | 0.50 | 0.50 | 0.50 |
| | 2000.00 | 2000.00 | 2000.00 |

Example 23 (Comparative Example 3)

Preparation of Feeds Containing Soluble Wheat Fiber

Complete starter, grower, and finisher feeds were produced according to the procedure of Example 20, except that soluble wheat fiber (PremiDex™, modified wheat starch, Acher Daniels Midland Company, USA) was added on top of the basal diet at an inclusion rate of 714 ppm (dry solids basis per total final feed), resulting in diets with the following compositions:

| Ingredient (lbs, dry solids basis) | Starter | Grower | Finisher |
|---|---|---|---|
| Corn | 1186.51 | 1280.53 | 1399.68 |
| Soybean meal | 714.20 | 619.07 | 516.57 |
| Animal by-product blend | 39.97 | 39.97 | 19.99 |
| Dicalcium phosphate | 23.22 | 22.71 | 22.95 |
| Limestone | 7.82 | 3.89 | 6.60 |
| Poultry Fat | 7.62 | 8.12 | 8.28 |
| L-Lysine | 7.13 | 6.11 | 5.47 |
| Salt | 2.28 | 1.75 | 1.82 |
| DL-Methionine | 2.25 | 1.75 | 2.45 |
| Vitamin and Mineral Premix | 4.00 | 4.00 | 4.00 |
| L-Threonine | 1.42 | 8.54 | 9.47 |
| Modified Wheat Starch | 0.84 | 0.84 | 0.00 |
| Saccox | 0.80 | 0.80 | 0.80 |
| Enzyme blend | 1.43 | 1.43 | 1.43 |
| Total | 0.50 | 0.50 | 0.50 |
| | 2000.00 | 2000.00 | 2000.00 |

Example 24 (Comparative Example 4)

Preparation of Feeds Containing Yeast Mannans

Complete starter, grower, and finisher feeds were produced according to the procedure of Example 20, except that yeast cell-wall mannan (CitriStim®, Archer Daniels Midland Company, USA) was added on top of the basal diet at an inclusion rate of 2,273 ppm (dry solids basis per total final feed), resulting in diets with the following compositions:

| Ingredient (lbs, dry solids basis) | Starter | Grower | Finisher |
|---|---|---|---|
| Corn | 1184.66 | 1278.53 | 1397.50 |
| Soybean meal | 713.09 | 618.11 | 515.77 |
| Animal by-product blend | 39.91 | 39.91 | 19.95 |
| Dicalcium phosphate | 23.19 | 22.68 | 22.92 |
| Limestone | 7.81 | 3.88 | 6.59 |
| Poultry Fat | 7.61 | 8.11 | 8.27 |
| L-Lysine | 7.12 | 6.10 | 5.46 |
| Salt | 2.27 | 1.75 | 1.82 |
| DL-Methionine | 2.24 | 1.75 | 2.44 |
| Vitamin and Mineral Premix | 3.99 | 3.99 | 3.99 |
| L-Threonine | 1.42 | 8.53 | 9.46 |
| Yeast Mannan | 0.84 | 0.84 | 0.00 |
| Saccox | 0.80 | 0.80 | 0.80 |
| Enzyme blend | 4.54 | 4.54 | 4.54 |
| Total | 0.50 | 0.50 | 0.50 |
| | 2000.00 | 2000.00 | 2000.00 |

Example 25 (Comparative Example 5)

Preparation of Feeds Containing Xylo-Oligosaccharides

Complete starter, grower, and finisher feeds were produced according to the procedure of Example 20, except that xylo-oligosaccharides (X35P™, LongLive, China) was added on top of the basal diet at an inclusion rate of 1,429 ppm (dry solids basis per total final feed), resulting in diets with the following compositions:

| Ingredient (lbs, dry solids basis) | Starter | Grower | Finisher |
|---|---|---|---|
| Corn | 1185.66 | 1279.61 | 1398.68 |
| Soybean meal | 713.69 | 618.63 | 516.20 |
| Animal by-product blend | 39.94 | 39.94 | 19.97 |
| Dicalcium phosphate | 23.21 | 22.70 | 22.94 |
| Limestone | 7.82 | 3.88 | 6.59 |
| Poultry Fat | 7.62 | 8.12 | 8.28 |
| L-Lysine | 7.13 | 6.10 | 5.46 |
| Salt | 2.28 | 1.75 | 1.82 |
| DL-Methionine | 2.25 | 1.75 | 2.45 |
| Vitamin and Mineral Premix | 3.99 | 3.99 | 3.99 |
| L-Threonine | 1.42 | 8.54 | 9.47 |
| xylo-oligosaccharide | 0.84 | 0.84 | 0.00 |
| Saccox | 0.80 | 0.80 | 0.80 |

-continued

| Ingredient (lbs, dry solids basis) | Starter | Grower | Finisher |
|---|---|---|---|
| Enzyme blend | 2.85 | 2.85 | 2.85 |
| Total | 0.50 | 0.50 | 0.50 |
|  | 2000.00 | 2000.00 | 2000.00 |

Example 26

Preparation of Finished Poultry Feeds Containing Gluco-Oligosaccharides

Complete starter, grower, and finisher corn-soy poultry feeds were prepared following the procedure of Example 19, except that the gluco-oligosaccharide from Example 11 (provided in the form of the premix of Example 13) was added on top of the diets to prepare final feeds with 50±5, 100±5, 250±5, and 500±5 ppm inclusion rates.

Example 26.1

The 50 ppm gluco-oligosaccharide diet was prepared as follows:

| Ingredient (lbs, dry solids basis) | Starter | Grower | Finisher |
|---|---|---|---|
| Corn | 638.58 | 689.19 | 747.27 |
| Soybean meal | 275.20 | 221.08 | 167.41 |
| Animal by-product blend | 50.27 | 50.27 | 50.27 |
| Dicalcium phosphate | 10.56 | 11.06 | 8.65 |
| Limestone | 5.13 | 5.33 | 4.73 |
| Poultry Fat | 5.03 | 8.85 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Gluco-oligosaccharide | 0.05 | 0.05 | 0.05 |
| Saccox | 0.50 | 0.50 | 0.50 |
| Enzyme blend | 0.20 | 0.20 | 0.20 |
| Total | 1000.00 | 1000.00 | 1000.00 |

| Nutritional Property | Starter | Grower | Finisher |
|---|---|---|---|
| Apparent metabolizable energy (cal/lb) | 1381 | 1413 | 1437 |
| Crude protein, wt % | 22.11 | 19.96 | 17.92 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

Example 26.2

The 100 ppm gluco-oligosaccharide diet was prepared as follows:

| Ingredient (lbs, dry solids basis) | Starter | Grower | Finisher |
|---|---|---|---|
| Corn | 638.58 | 689.19 | 747.27 |
| Soybean meal | 275.20 | 221.08 | 167.41 |
| Animal by-product blend | 50.27 | 50.27 | 50.27 |
| Dicalcium phosphate | 10.56 | 11.06 | 8.65 |
| Limestone | 5.13 | 5.33 | 4.73 |
| Poultry Fat | 5.03 | 8.85 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Gluco-oligosaccharide | 0.10 | 0.10 | 0.10 |
| Saccox | 0.50 | 0.50 | 0.50 |
| Enzyme blend | 0.20 | 0.20 | 0.20 |
| Total | 1000.00 | 1000.00 | 1000.00 |

| Nutritional Property | Starter | Grower | Finisher |
|---|---|---|---|
| Apparent metabolizable energy (cal/lb) | 1380 | 1412 | 1436 |
| Crude protein, wt % | 22.10 | 19.95 | 17.91 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

Example 26.3

The 250 ppm gluco-oligosaccharide diet was prepared as follows:

| Ingredient (lbs, dry solids basis) | Starter | Grower | Finisher |
|---|---|---|---|
| Corn | 638.58 | 689.19 | 747.27 |
| Soybean meal | 275.20 | 221.08 | 167.41 |
| Animal by-product blend | 50.27 | 50.27 | 50.27 |
| Dicalcium phosphate | 10.56 | 11.06 | 8.65 |
| Limestone | 5.13 | 5.33 | 4.73 |
| Poultry Fat | 5.03 | 8.85 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Gluco-oligosaccharide | 0.25 | 0.25 | 0.25 |
| Saccox | 0.50 | 0.50 | 0.50 |
| Enzyme blend | 0.20 | 0.20 | 0.20 |
| Total | 1000.00 | 1000.00 | 1000.00 |

| Nutritional Property | Starter | Grower | Finisher |
|---|---|---|---|
| Apparent metabolizable energy (cal/lb) | 1380 | 1412 | 1436 |
| Crude protein, wt % | 22.10 | 19.95 | 17.91 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

Example 26.4

The 500 ppm gluco-oligosaccharide diet was prepared as follows:

| Ingredient (lbs, dry solids basis) | Starter | Grower | Finisher |
|---|---|---|---|
| Corn | 638.58 | 689.19 | 747.27 |
| Soybean meal | 275.20 | 221.08 | 167.41 |
| Animal by-product blend | 50.27 | 50.27 | 50.27 |
| Dicalcium phosphate | 10.56 | 11.06 | 8.65 |
| Limestone | 5.13 | 5.33 | 4.73 |
| Poultry Fat | 5.03 | 8.85 | 7.44 |
| L-Lysine | 4.32 | 3.92 | 3.82 |
| Salt | 3.52 | 3.52 | 4.02 |
| DL-Methionine | 3.22 | 2.71 | 2.31 |
| Vitamin and Mineral Premix | 2.51 | 2.51 | 2.51 |
| L-Threonine | 0.90 | 0.80 | 0.80 |
| Gluco-oligosaccharide | 0.50 | 0.50 | 0.50 |
| Saccox | 0.50 | 0.50 | 0.50 |
| Enzyme blend | 0.20 | 0.20 | 0.20 |
| Total | 1000.00 | 1000.00 | 1000.00 |

| Nutritional Property | Starter | Grower | Finisher |
|---|---|---|---|
| Apparent metabolizable energy (cal/lb) | 1379 | 1411 | 1435 |
| Crude protein, wt % | 22.09 | 19.94 | 17.90 |
| Total Lys, wt % | 1.35 | 1.20 | 1.06 |
| Total Methionine, wt % | 0.70 | 0.63 | 0.56 |
| Total TSAA, wt % | 1.02 | 0.92 | 0.83 |
| Total Threonine, wt % | 0.92 | 0.82 | 0.73 |
| Calcium, wt % | 0.90 | 0.90 | 0.80 |
| Available P, wt % | 0.45 | 0.45 | 0.40 |
| Sodium, wt % | 0.20 | 0.20 | 0.22 |

Example 27

Preparation of Finished Poultry Feeds Containing Gluco-Galacto-Oligosaccharides

Complete starter, grower, and finisher corn-soy poultry feeds were prepared following the procedure of Example 26, except that the gluco-galacto-oligosaccharide from Example 12 (provided as the premix of Example 15) was used in place of gluco-oligosaccharide. The resulting feeds contained 50±5 (Example 27.1), 100±5 (Example 27.2), 250±5 Example 27.3), and 500±5 (Example 27.3) ppm of gluco-galacto-oligosaccharide, respectively.

Example 28

Demonstration of Live Performance Benefits at Low Inclusion Rate

Newly hatched straight-run Cobb 500 broiler chickens, vaccinated for Marek's and Newcastle Disease, were placed on built-up litter in floor pens with a packing density typical of the U.S. broiler industry. Water was provided ad libitum throughout the study via nipple drinkers. Feed was provided ad libitum throughout the study via one hanging overhead feeder per pen. Feed added and removed from pens from day 0 to study end was weighed and recorded. Lighting was provided by incandescent lights following a standard commercial program. The test facility, pens and birds were observed at least twice daily for general flock condition, lighting, water, feed, ventilation and unanticipated events.

Starter diets were fed from Day 1 until Day 14. Grower diets were fed from Day 14 until Day 28. Finisher diets were fed from Day 28 until Day 35. At the end of each phase, all birds and feed were weighed to determine body weight (BW), body weight gain (BWG), feed consumption (FC), and feed conversion ratio (FCR). Mortality was recorded and weighed daily and feed conversion was corrected to a common final weight and adjusted for mortality (cFCR). The mean 0-35d BWG and 0-35d cFCR for each treatment was determined by averaging the BWG and cFCR over pens corresponding to the same treatment. The standard deviation for each treatment across pens was determined accordingly.

Each dietary treatment was fed to 6 replicate pens randomized throughout the building as follows:

| Treatment | Treatment Description | Inclusion Rate (dry solids basis) |
|---|---|---|
| 1 | Basal Diet (Example 19) | n/a |
| 2 | Antibiotic Positive Control (Comparative Example 1) | as labeled |
| 3 | gluco-oligosaccharide (Example 26.1) | 50 ppm |
| 4 | gluco-oligosaccharide (Example 26.2) | 100 ppm |
| 5 | gluco-oligosaccharide (Example 26.3) | 250 ppm |
| 6 | gluco-oligosaccharide (Example 26.4) | 500 ppm |

The BWG Benefit for a given treatment with respect to (w.r.t.) the basal diet (negative control) was calculated as the mean 0-35d BWG for the treated diet divided by the mean 0-35d BWG for the basal diet, minus one. The cFCR Benefit for a given treatment w.r.t. the basal diet was calculated as one minus the mean 0-35d cFCR for the treated diet divided by the mean 0-35d cFCR for the basal diet.

Mean 0-35 day body weight gains (BWG) were determined to be:

| Diet Description | Inclusion Rate (ppm) | 0-35 day BWG (g) | Benefit w.r.t Basal Diet |
|---|---|---|---|
| Basal Diet (Example 19) | n/a | 1,983 ± 11 | 0.0% |
| Antibiotic Positive Control (Comparative Example 1) | As labeled | 1,999 ± 21 | 0.8% |
| gluco-oligosaccharide (Example 26.1) | 50 | 2,002 ± 33 | 1.0% |
| gluco-oligosaccharide (Example 26.2) | 100 | 1,968 ± 35 | −0.7% |
| gluco-oligosaccharide (Example 26.3) | 250 | 2,016 ± 24 | 1.7% |
| gluco-oligosaccharide (Example 26.4) | 500 | 2,054 ± 29 | 3.6% |

Mean 0-35 day corrected feed conversion ratios (cFCR) were determined to be:

| Diet Description | Inclusion Rate (ppm) | 0-35 d cFCR (kg/kg) | Benefit w.r.t Basal Diet |
|---|---|---|---|
| Basal Diet (Example 19) | n/a | 1.612 ± 0.047 | 0.0% |
| Antibiotic Positive Control (Comparative Example 1) | as labeled | 1.582 ± 0.025 | 1.9% |
| gluco-oligosaccharide (Example 26.1) | 50 | 1.598 ± 0.039 | 0.8% |
| gluco-oligosaccharide (Example 26.2) | 100 | 1.596 ± 0.023 | 1.0% |
| gluco-oligosaccharide (Example 26.3) | 250 | 1.582 ± 0.033 | 1.8% |
| gluco-oligosaccharide (Example 26.4) | 500 | 1.532 ± 0.032 | 4.9% |

Figure 18:
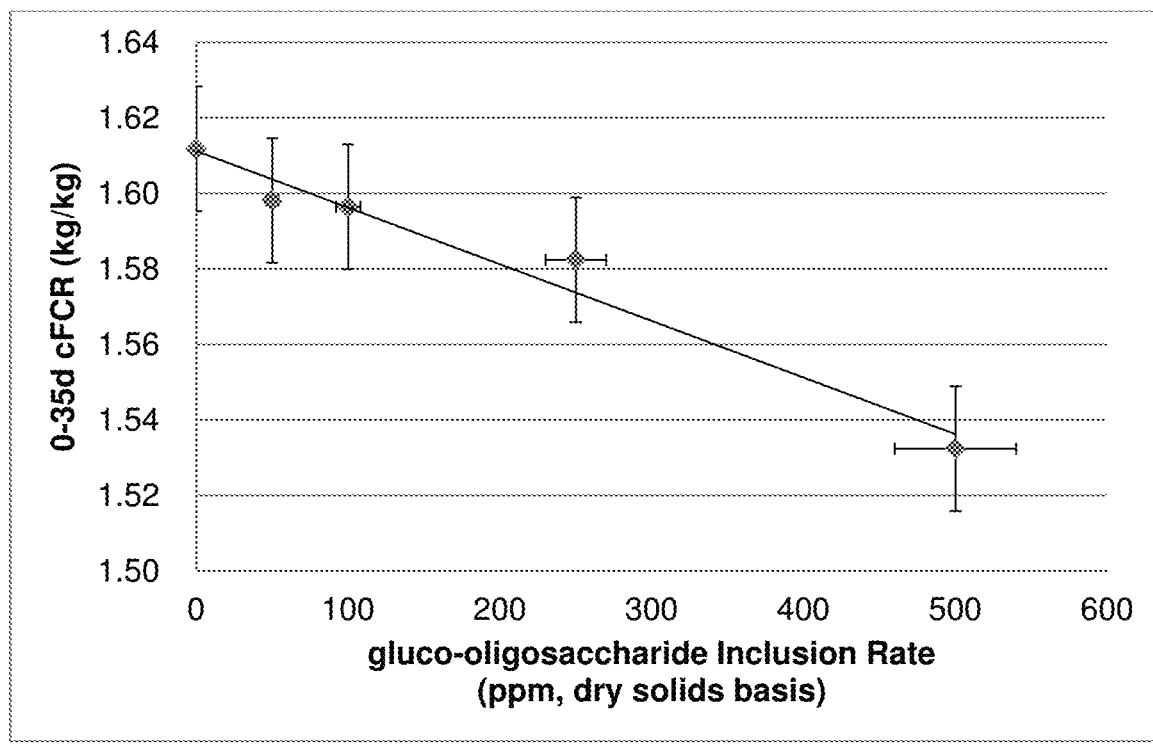
FIG. 18 is a graph depicting the mean 0-35 day corrected feed conversion ratios (cFCR) for populations of poultry as a function of gluco-oligosaccharide inclusion rate.

The mean cFCR as a function of gluco-oligosaccharide inclusion rate is depicted in FIG. 18. For 500 ppm gluco-oligosaccahride, the observed cFCR of 1.532 reflects a statistically significant ($p<0.02$, as determined by two-factor ANOVA, accounting for the pen blocking structure) benefit of 4.9% with respect to the negative control 0-35 day cFCR of 1.612, whereas the antibiotic provided only a 1.9% benefit. Similarly, the observed a 0-35 day BWG of 2.054 kg reflects a statistically significant (p<0.05, as determined by two-factor ANOVA, accounting for the pen blocking structure) benefit of 3.6% with respect to the negative control BWG of 1.983 kg, whereas the antibiotic provided only a 0.8% benefit.

The 0-35 day mortality rate for birds fed the basal diet of Example 19 was determined to be 1.7%, on a per head basis. The average 0-35 day mortality rate for birds fed diets containing the gluco-oligosaccharide of Example 11 was 0.8%, on a per head basis. Diet compositions containing the gluco-oligosaccharide of Example 11 therefore provide a 51% reduction in the 0-35 day mortality rate with respect to the basal feed.

Example 29

Processing of Birds

After an overnight fast, 4 birds from each of the pens in Example 28 were tagged, weighed and processed as follows: birds were electrically stunned, and mechanically eviscerated. Hot carcass weight and abdominal fat pad were determined. Carcasses were then split into front and back halves and the front halves were chilled in an ice bath for 4 hours. Front halves were then deboned to determine pectoralis major (fillet) and pectoralis minor (tender) weights.

Example 30

Limited Benefit of Other Carbohydrate Feed Ingredients (Comparative Examples)

Male Cobb 500 broiler chickens were obtained from a hatchery and placed in 3×5 ft concrete floor pens containing used wood shavings. Birds were vaccinated for Mareks at the hatchery and vaccinated for Newcastle and Infectious Bronchitis by spray application on on study Day 0. Water was provided ad libitum throughout the study via nipple drinkers, which were checked twice daily and cleansed as needed to ensure a constant and clean water supply to the birds. Feed was provided ad libitum throughout the study via one hanging, ~17-inch diameter tube feeder per pen. A chick feeder tray was placed in each pen for approximately the first 4 days. Feed added and removed from pens from day 0 to study end was weighed and recorded. Lighting was provided by incandescent lights following a standard commercial program. The test facility, pens and birds were observed at least twice daily for general flock condition, lighting, water, feed, ventilation and unanticipated events.

Any mortalities or birds sacrificed for culling and/or sampling were weighed and necropsied. Starter diets were fed from Day 1 until Day 14. Grower diets were fed from Day 14 until Day 28. Finisher diets were fed from Day 28 until Day 35. At the end of each phase, all birds and feed were weighed to determine body weight (BW), body weight gain (BWG), feed consumption (FC), and feed conversion ratio (FCR). Mortality was recorded and weighed daily and feed conversion was corrected to a common final weight and adjusted for mortality (cFCR). The mean 0-35d BWG and 0-35d cFCR for each treatment was determined by averaging the BWG and cFCR over pens corresponding to the same treatment. The standard deviation for each treatment across pens was determined accordingly.

The BWG Benefit for a given treatment with respect to (w.r.t.) the basal diet (negative control) was calculated as the mean 0-35d BWG for the treated diet divided by the mean 0-35d BWG for the basal diet, minus one. The FCR Benefit for a given treatment w.r.t. the basal diet was calculated as one minus the mean 0-35d FCR for the treated diet divided by the mean 0-35d FCR for the basal diet.

The BWG Benefits and FCR Benefits were determined to be:

| Diet Description | Inclusion Rate (ppm) | BWG Benefit w.r.t Basal Diet | FCR Benefit w.r.t Basal Diet |
|---|---|---|---|
| Soluble Corn Fiber (Comparative Example 2) | 625 | −0.1% | 0.2% |
| Modified Wheat Starch (Comparative Example 3) | 714 | −2.3% | −0.3% |
| Yeast Mannan (Comparative Example 4) | 2273 | 1.2% | 0.4% |
| Xylo-oligosaccharides (Comparative Example 5) | 1429 | 0.2% | 0.3% |

The largest benefit observed for the Comparative Examples was a 1.2% BWG benefit for Yeast Mannan (Comparative Example 4) at the high dose of 2,273 ppm. In particular, Modified Wheat Starch had a negative effect on BWG and FCR.

Example 31

Reduction of Variability of Final Body Weight

The procedure of Example 10 was repeated, except that the treated starter, grower, and finisher diets contained 50 ppm of the gluco-oligosaccharide of Example 11. The mean 35 day body weight (BW) across pens fed the basal diet was 2,310 grams with a standard deviation of 90 grams. The relative variability in final BW (standard deviation divided by the mean) was therefore 3.9%. Fort the diets containing 50 ppm of the gluco-oligosaccharide from Example 11, the mean 0-35 day BWG was determined to be 2,428 grams, with a standard deviation of 59 grams. The relative variability in final BW for the diet comprising the gluco-oligosaccharide from Example 11 was therefore, 2.4%. This represents a 38% reduction in the relative variability of final bird weight.

Example 32

Growth Performance Study in Necrotic Enteritis Challenge Model in Broiler Chickens This study evaluates the impact of gluco-oligosaccharides prepared according to the protocols described in the Examples above (e.g., Example 11), in a necrotic enteritis challenge model in broiler chickens. The effects of dietary supplementation of gluco-oligosaccharides with and without an alternative feeding program in a necrotic enteritis challenge model is evaluated.

The schedule of events for this study is performed as set forth in Table 5 below.

TABLE 5

Schedule of events

| Activity | Study Day |
|---|---|
| Assign newly hatched male broiler chicks to specific treatment pens (15 chicks/pen) | 0 |
| Weigh birds (pen basis) and weigh back feed. Raise the feeder in each pen in the AM (no access to feed). Feed with challenge material after approximately 8 hours. | 15 |
| Weigh back challenge material. Feed with Starter diet. | 16 |
| Select 2 birds/pen for NE lesion scoring, Cp counts and ceca collection. | 18 |
| Weigh birds (pen basis) and weigh back feed. Switch to Grower diet. | 22 |
| Weigh birds (pen basis) and weigh back feed. Switch to Finisher diet. | 28 |
| Weigh birds (pen basis) and weigh back feed. End of study. | 35 |
| Weigh, record and necropsy all mortalities throughout the study. Observe birds twice daily. | 0-35 |

Treatments

The treatments described in Table 6 below are used in this study, with 12 pens for each treatment (60 pens in total). Birds are fed starter (days 0-21), grower (days 21-28) and finisher (days 28-35) diets based on average US nutrient levels.

TABLE 6

Description of dietary treatments

| Treatment | Description |
|---|---|
| 1 | Challenged control: no additives |
| 2 | Challenged control: BMD |
| 3 | Challenge: Gluco-oligosaccharide |

BMD® 110G (bacitracin premix; Alpharma Canada Corporation) used in treatment 2 is a feed medication premix approved for use in broiler chickens in Canada. It contains 110 g of bacitracin methylene disalicylate per kg of premix. 0.5 kg of premix per tonne of feed provides 55 mg of bacitracin methylene disalicylate per kg of feed.

The gluco-oligosaccharide of treatment 3 is prepared according to the protocols described in the Examples above (e.g., Example 11). The gluco-oligosaccharide is in liquid form with a concentration of 0.65 kg dry oligosaccharide per kg of syrup and a density of 1.28 g/mL. Inclusion rate will be 500 g of dry oligosaccharide (equivalently 600 mL of syrup or 770 grams of syrup) per tonne of feed as described in this study.

Study Design

The study is conducted as a completely randomized block design. There are 12 blocks of pens in each block, each containing 15 male broiler chicks per pen (900 chicks in total). Treatments are randomly assigned to each pen within each block as per facility procedures.

Bird Selection/Identification

A commercial strain of male broiler chicks are obtained from a local commercial hatchery. Fifteen male broiler chicks re placed in each pen providing an approximate stocking density of 0.6 square feet per bird at the time of placement. Birds re weighed when they are removed from each pen. All birds are evaluated and only chicks that are in good physical conditions are placed in pens. Birds that die or are culled are not replaced.

Bird Management

Birds are fed commercial broiler starter, grower and finisher diets. All diets are supplemented with Saccox (0.5 kg/MT) as anticoccidial medication, and no in-feed antibiotics are used except for treatment 2 which will receive BMD. Birds will not be treated for any diseases that may occur during the study.

Necrotic Enteritis Challenge Model

A moderately virulent strain of *Clostridium perfringens* (Cp; NCP-1) is used in the study. An inoculum containing approximately $10^8$ colony forming units (CFUs) of Cp per ml is produced. Feed is removed from all pens on day 15 in the morning by raising the feeders for about 8 hours. Birds are weighed (pen basis) and counted and feed in each pen is weighed back. About 8 hours later after the start of the feed withdrawal, challenge materials (a mixture of bacterial broth and non-medicated starter feed at the ratio of 1 kg broth: 0.666 kg feed in a tray) is put in pens for approximately 16 hr. Water (instead of bacterial broth) is used to make the mixture for birds in the non-challenged control group. Five trays containing the mixture are used in each pen.

On morning of day 16, the challenge materials are removed from the pens. Birds are fed with respective starter diets as indicated in Table 6 above. The remainder of challenge materials from each pen are weighed and disposed.

A 2 ml sample of inoculum is collected from each jug at the time that jugs are removed from the incubator using aseptic technique. The samples are analyzed for Cp count (CFU of Cp per ml of inoculum). After the sampling and prior to issuing of challenge materials, all jugs are poured into a container and then it is issued to respective pens.

On day 18 of the study, two (2) birds are randomly selected from each pen, tagged, weighed, euthanized, sacrificed and ileal contents are collected for Cp counts and cecal contents collected for microbiota sequencing. The content from the Meckel's diverticulum to the ileocecal junction are collected into a container from each bird and labelled with bird and treatment number for Cp counts. The containers are placed in a cooler containing ice pack and sent to the lab as soon as possible (i.e., on the same day). For microbiota sampling cecal contents are collected into individual containers for each bird, labelled with bird and treatment and frozen at −70° C. until shipment to a laboratory for testing. The entire intestinal tract is examined and scored for NE lesions by a veterinarian according to the following assessment criteria (Prescott et al., 1978):

0=no gross lesions
1=thin-walled or friable small intestine
2=focal necrosis or ulceration
3=larger patches of necrosis
4=severe, extensive necrosis All mortalities occurring throughout the study are necropsied. Birds that die before day 15 are not included in NE-related mortality, however, they are included in total mortality calculations. Any mortality that occurs after day 15 and has a NE lesion score of 1 or higher are considered as NE mortality.

Assessment of Effectiveness

The following variables are measured:
Pen body weight on days 0, 15, 22, 28 and 35.
Average daily gain, average daily feed intake, and feed conversion ratio for days 0 to 15, 15 to 22, 22 to 28, 28 to 35, and 0 to 35.
Mortality rate for 0 to 15, 15 to 22, 22 to 28, 28 to 35, and 0 to 35.
Intestinal lesion scores.
NE related mortality 15-35.

The following variables are calculated as follows:

Body weight gain (g/d): [(Weight of all birds remaining at end of period+weight of all birds removed during the period)−Pen weight at start of period]/number of bird days in the period Feed intake (g/d): [(Feed remaining in pen at start of period+total feed addition weight)−feed weigh back weight at end of period]/number of bird days in the period Number of bird days=sum of bird count for each day (taken at the beginning of the day) for all days in the period Statistical Analysis The study is a completely randomized block design. Pen is the experimental unit. Block and treatment are random and fixed effects, respectively. Statistical analysis is done using the Mixed procedure of SAS (SAS Institute Inc., Cary, N.C., USA). Where treatment effect is significant (P<0.05), a multiple comparison test is used to compare treatments means.

Example 33

Growth Performance Study in Necrotic Enteritis Challenge Model in Broiler Chickens This study evaluated the impact of gluco-oligosaccharides prepared according to the protocols described in the Examples above (e.g., Example 11), in a necrotic enteritis challenge model in broiler chickens. The effects of dietary supplementation of gluco-oligosaccharides with and without an alternative feeding program in a necrotic enteritis challenge model were evaluated.

The schedule of events for this study was performed as set forth in Table 7 below.

TABLE 7

Schedule of events

| Activity | Study Day |
|---|---|
| Assign newly hatched male broiler chicks to specific treatment pens (15 chicks/pen) | 0 |
| Weigh birds (pen basis) and weigh back feed. Raise the feeder in each pen in the AM (no access to feed). Feed with challenge material after approximately 8 hours. | 15 |
| Weigh back challenge material. Feed with Starter diet. | 16 |
| Select 2 birds/pen for NE lesion scoring, Cp counts and ceca collection. | 18 |
| Weigh birds (pen basis) and weigh back feed. Switch to Grower diet. | 22 |
| Weigh birds (pen basis) and weigh back feed. Switch to Finisher diet. | 28 |
| Weigh birds (pen basis) and weigh back feed. End of study. | 35 |
| Weigh, record and necropsy all mortalities throughout the study. Observe birds twice daily. | 0-35 |

Treatments

The treatments described in Table 8 below were used in this study, with 12 pens for each treatment (60 pens in total). Birds were fed starter (days 0-21), grower (days 21-28) and finisher (days 28-35) diets based on average US nutrient levels.

TABLE 8

Description of dietary treatments

| Treatment | Description |
|---|---|
| 1 | Challenged negative control: no additives |
| 2 | Challenged positive control: BMD |
| 3 | Challenged: Gluco-oligosaccharide |

BMD® 110G (bacitracin premix; Alpharma Canada Corporation) used in treatment 2 is a feed medication premix approved for use in broiler chickens in Canada. It contains 110 g of bacitracin methylene disalicylate per kg of premix. 0.5 kg of premix per tonne of feed provided 55 mg of bacitracin methylene disalicylate per kg of feed.

The gluco-oligosaccharide of treatment 3 was prepared according to the protocols described in the Examples above (e.g., Example 11). The gluco-oligosaccharide was provided in liquid form with a concentration of 0.65 kg dry oligosaccharide per kg of syrup and a density of 1.28 g/mL. The inclusion rate was 500 g of dry oligosaccharide (equivalently 600 mL of syrup or 770 grams of syrup) per tonne of feed as described in this study.

Study Design

The study was conducted as a completely randomized block design. There were 12 blocks of pens in each block, each containing 15 male broiler chicks per pen (900 chicks in total). Treatments were randomly assigned to each pen within each block as per facility procedures.

Bird Selection/Identification

A commercial strain of male broiler chicks were obtained from a local commercial hatchery. Fifteen male broiler chicks were placed in each pen providing an approximate stocking density of 0.6 square feet per bird at the time of placement. Birds were weighed when they were removed from each pen. All birds were evaluated and only chicks that were in good physical conditions were placed in pens. Birds that died or were culled were not replaced.

Bird Management

Birds were fed commercial broiler starter, grower and finisher diets. All diets were supplemented with Saccox (0.5 kg/MT) as anticoccidial medication, and no in-feed antibiotics were used except for treatment 2 which received BMD. Birds were not treated for any diseases that might have occurred during the study.

Necrotic Enteritis Challenge Model

A moderately virulent strain of Clostridium perfringens (Cp; NCP-1) was used in the study. An inoculum containing approximately $10^8$ colony forming units (CFUs) of Cp per ml was produced. Feed was removed from all pens on day 15 in the morning by raising the feeders for about 8 hours. Birds were weighed (pen basis) and counted and the feed in each pen was weighed back. About 8 hours after the start of the feed withdrawal, challenge materials (a mixture of bacterial broth and non-medicated starter feed at the ratio of 1 kg broth: 0.666 kg feed in a tray) were put in pens for approximately 16 hr. Water (instead of bacterial broth) was used to make the mixture for birds in the non-challenged control group. Five trays containing the mixture were used in each pen.

On the morning of day 16, the challenge materials were removed from the pens. Birds were fed with respective starter diets as indicated in Table 6 above. The remainder of challenge materials from each pen were weighed and disposed.

A 2 ml sample of inoculum was collected from each jug at the time that the jugs were removed from the incubator using aseptic technique. The samples were analyzed for Cp count (CFU of Cp per ml of inoculum). After the sampling and prior to issuing of challenge materials, all jugs were poured into a container and then it was issued to respective pens.

On day 18 of the study, two (2) birds were randomly selected from each pen, tagged, weighed, euthanized, sacrificed and ileal contents were collected for Cp counts and cecal contents were collected for microbiota sequencing. The content from the Meckel's diverticulum to the ileocecal junction were collected into a container from each bird and were labelled with bird and treatment number for Cp counts. The containers were placed in a cooler containing ice and sent to the lab as soon as possible (i.e., on the same day). For microbiota sampling cecal contents were collected into individual containers for each bird, labelled with bird and treatment and frozen at −70° C. until shipment to a laboratory for testing. The entire intestinal tract was examined and scored for NE lesions by a veterinarian according to the following assessment criteria (Prescott et al., 1978):
0=no gross lesions
1=thin-walled or friable small intestine
2=focal necrosis or ulceration
3=larger patches of necrosis
4=severe, extensive necrosis All mortalities occurring throughout the study were necropsied. Birds that died before day 15 were not included in NE-related mortality, however, they were included in total mortality calculations. Any mortality that occurred after day 15 and had a NE lesion score of 1 or higher were considered as NE mortality.

Assessment of Effectiveness
The following variables were measured:
Pen body weight on days 0, 15, 22, 28 and 35.
Average daily gain, average daily feed intake, and feed conversion ratio for days 0 to 15, 15 to 22, 22 to 28, 28 to 35, and 0 to 35.
Mortality rate for 0 to 15, 15 to 22, 22 to 28, 28 to 35, and 0 to 35.
Intestinal lesion scores.
NE related mortality 15-35.
The following variables were calculated as follows:
Body weight gain (g/d): [(Weight of all birds remaining at end of period+weight of all birds removed during the period)−Pen weight at start of period]/number of bird days in the period
Feed intake (g/d): [(Feed remaining in pen at start of period+total feed addition weight)−feed weigh back weight at end of period]/number of bird days in the period
Number of bird days=sum of bird count for each day (taken at the beginning of the day) for all days in the period Statistical Analysis
The study was a completely randomized block design. Pen was the experimental unit. Block and treatment were random and fixed effects, respectively. Statistical analysis was done using the Mixed procedure of SAS (SAS Institute Inc., Cary, N.C., USA). Where treatment effect was significant ($P \leq 0.05$), a multiple comparison test was used to compare treatments means.

Results
Day 35 body weights were determined to be 2.380 kg for BMD treated diets and 2.375 kg for the gluco-oligosaccharide diets, which were statistically indistinguishable to $p<0.04$. Therefore, the gluco-oligosaccharide was as effective as the antibiotic treatment in maintaining body weight in the presence of the disease challenge. Similarly, the average daily feed intake (ADFI) of birds fed the gluco-oligosaccharide was 96.5 g/day, which was statistically indistinguishable from the 96.8 g/day consumed by birds fed the antibiotic.

Bacterial enumeration indicated that birds fed the gluco-oligosaccharide exhibited a lower number of Cp organisms than the negative control, with 4.31 cfu/g for birds fed the gluco-oligosaccharide versus 5.40 cgu/g for the negative control.

Example 34

Determining the Effects of Oligosaccharide on Growth Performance of Nursery Pigs This Example will be conducted to determine the effects of oligosaccharide level in diets with or without growth promoting levels of trace minerals and antibiotics on growth performance of nursery pigs.

Procedures
Pigs: Approximately 3,240 pigs will be placed in three rooms at a nursery farm with 27 pigs per pen and 15 pens per treatment in a randomized complete block design (a total of 8 treatments across 40 pens in each of 3 rooms). All pens will be balanced with 14 gilts and 13 barrows. At weaning, weight, age and sow farm source will be recorded. At weaning, pigs will be placed with the same number of pigs from each sow farm per pen.

Allotment: Prior to allotment and each weighing event, standard weights will be put on each corner of the scale will ensure that the scale is measuring weights correctly. At placement, the average weight of the pigs in each pen will be determined and data provided as soon as possible for treatment allotment. At weaning, pens will be ranked by average weight and weight blocks and pens assigned to the ranked weights. Treatments will then be randomly assigned within weight blocks. When the treatment assignments are done, pen assignments will be provided also as soon as possible so dietary treatments information can be entered into the feeding system and pigs can fed. Pigs will have free access to feed and water at all moments of the trial.

Schedule: At arrival, pigs will be allotted to pens. A common pelleted diet will be fed to all pigs for 7 days. This diet will contain 55 ppm of Mecadox (50 g/ton). Dietary treatments will be fed from day 7 to the end of the nursery phase (approximately 55 lb). Pens will be allotted to dietary treatments on day 7. Diets will be fed in two phases with the first phase from day 7 to 21 after weaning and the second phase from day 21 to the end of the nursery phase (day 21 to 42 after weaning).

Treatments: Dietary treatments will be randomly assigned to 40 pens in each of 3 rooms for 5 replications per room and 15 replications total. The 8 treatments are structured as a 2×4 factorial with two diet types (with and without antibiotic; 55 ppm of Mecadox) and four levels of gluco-oligosaccharide (0, 200, 400 or 600 ppm). The gluco-oligosaccharides are prepared according to the procedures set forth in Examples above. The gluco-oligosaccharides will be provided on a dry carrier such that the 600 ppm will be in a 0.25% final diet inclusion rate (5 lb/ton). All diets will contain the same growth promoting levels of Cu and Zn at 200 ppm Cu and 2,000 ppm Zn, in the phase 2 diets and 200 ppm Cu in the phase 3 diet. The diets containing 0 and 0.25% of the premix containing the gluco-oligosaccharides will be blended to form the intermediate treatments.

Diet Preparation: Diets will be fed in meal form. The four diets required will be the control diets for each diet type and the diets containing 0.25% gluco-oligosaccharide premix. The actual oligosaccharide levels in the test will be 0, 200, 400, and 600 ppm with a carrier used such that the premix at 0.25% (5 lb/ton) will provide 0.45% oligosaccharide. Treatments will be equally spaced with the control and 0.25% diets blended as set forth in Table 9 below.

TABLE 9

| | Ratio of control: 0.25% diet to form each treatment | | | |
|---|---|---|---|---|
| Premix: | Control | 0.083% | 0.167% | 0.25% |
| Oligosaccharide, ppm: | 0 | 200 | 400 | 600 |
| Control: 0.25% | 100:0 | 66.7:33.3 | 33.3:66.7 | 0:100 |

A gallon sample bag full of each diet will be collected from the feed system as diet is being dispensed 3 days after beginning feeding of each treatment and 3 days before the end of each phase and kept refrigerated until the end of the experiment when all samples will be forwarded to the swine lab for analysis and storage. Samples will be labeled with date, diet, and trial number. Complete diet samples will be sent for proximate analysis and analysis of gluco-oligosaccharide level.

Live Animal Data Collection: Pigs will be weighed, counted and feed disappearance determined every 7 days during the experiment. Prior to each weighing event standard weights will be put on each corner of the scale will ensure that the scale is measuring weights correctly. Pig inventory, weight, removal and feed intake data will be recorded and maintained throughout the trial. Data will be collected on the standard data collection spreadsheet.

Removals: For pigs that die or must be treated or removed from the study for any reason, the date and weight will be recorded as soon as they occur. This will be accompanied with notes on the suspected cause of death or reason for removal. If any pig is treated with medication, the date, reason for treatment and medication used will be recorded.

Statistical analysis: Pens will be randomly allotted to treatments using body weight as a blocking factor. Weight block will be added to the model as a random effect. Main effects and interaction between diet type and gluco-oligosaccharide level will be determined Data will also be analyzed for linear and quadratic effect of gluco-oligosaccharide levels. The experimental data will be analyzed using a statistical analysis tools.

Example 35

Determining the Effects of Oligosaccharide on Growth Performance of Nursery Pigs This Example was conducted to determine the effects of oligosaccharide level in diets with or without growth promoting levels of trace minerals and antibiotics on growth performance of nursery pigs.
Procedures Pigs: Approximately 3,240 pigs were placed in three rooms at a nursery farm with 27 pigs per pen and 15 pens per treatment using a randomized complete block design (a total of 8 treatments across 40 pens in each of 3 rooms). All pens were balanced with 14 gilts and 13 barrows. At weaning, weight, age and sow farm source were recorded. At weaning, pigs were placed with the same number of pigs from each sow farm per pen.

Allotment: Prior to allotment and each weighing event, standard weights were placed on each corner of the scale to ensure that the scale was correctly calibrated. At placement, the average weight of the pigs in each pen were determined and the data was provided as soon as possible for treatment allotment. At weaning, pens were ranked by average weight and weight blocks and pens were assigned to the ranked weights. Treatments were then randomly assigned within weight blocks. When the treatment assignments were done, pen assignments were provided also as soon as possible, and dietary treatments information was entered into the feeding system. Pigs were granted free access to feed and water throughout the trial.

Schedule: At arrival, the pigs were allotted to pens. A common pelleted diet was fed to all pigs for 7 days. This diet contained 55 ppm of Mecadox (50 g/ton). Dietary treatments were fed from day 7 to the end of the nursery phase (approximately 55 lb). Pens were allotted to dietary treatments on day 7. Diets were fed in two phases with the first phase from day 7 to 21 after weaning and the second phase from day 21 to the end of the nursery phase (day 21 to 42 after weaning).

Treatments: Dietary treatments were randomly assigned to 40 pens in each of 3 rooms for 5 replications per room and 15 replications total. The 8 treatments were structured as a 2×4 factorial with two diet types (with and without antibiotic; 55 ppm of Mecadox) and four levels of gluco-oligosaccharide (0, 200, 400 or 600 ppm). The gluco-oligosaccharides were prepared according to the procedures set forth in Examples above. The gluco-oligosaccharides were provided on a corn meal carrier, as described in Example 18, such that the 600 ppm dose was obtained with a 0.25% final diet inclusion rate (5 lb premix per ton final feed). All diets contained the same growth promoting levels of Cu and Zn at 200 ppm Cu and 2,000 ppm Zn, in the phase 2 diets and 200 ppm Cu in the phase 3 diet. The diets containing 0 and 0.25% of the premix containing the gluco-oligosaccharides were blended to form the intermediate treatments.

Diet Preparation: Diets were fed in meal form. The four diets required were the control diets for each diet type and the diets containing 0.25% gluco-oligosaccharide premix. The actual oligosaccharide levels in the test were 0, 200, 400, and 600 ppm with a carrier used such that the premix at 0.25% (5 lb/ton) will provide 600 ppm oligosaccharide. Treatments were equally spaced with the control and 0.25% diets blended as set forth in Table 10 below.

TABLE 10

| | Ratio of control: 0.25% diet to form each treatment | | | |
|---|---|---|---|---|
| Premix: | Control | 0.083% | 0.167% | 0.25% |
| Oligosaccharide, ppm: | 0 | 200 | 400 | 600 |
| Control: 0.25% | 100:0 | 66.7:33.3 | 33.3:66.7 | 0:100 |

A gallon sample bag full of each diet was collected from the feed system as the diet was dispensed 3 days after beginning feeding of each treatment and 3 days before the end of each phase and kept refrigerated until the end of the experiment when all samples were forwarded to the swine lab for analysis and storage. Samples were labeled with date, diet, and trial number. Complete diet samples were sent for proximate analysis and analysis of gluco-oligosaccharide level.

Live Animal Data Collection: Pigs were weighed, counted and feed disappearance determined every 7 days during the experiment. Prior to each weighing event standard weights were placed on each corner of the scale to ensure proper calibration of the scale. Pig inventory, weight, removal and feed intake data were recorded and maintained throughout the trial. Data were collected on the standard data collection spreadsheet.

Removals: For pigs that died, required treatment, or were removed from the study for any reason, the date and weight of the corresponding pig were recorded as soon as they occur. This record was accompanied with notes on the suspected cause of death or reason for removal. If any pig was treated with medication, the date, reason for treatment and medication used was recorded.

Statistical analysis: Pens were randomly allotted to treatments using body weight as a blocking factor. Weight block was added to the model as a random effect. Main effects and interaction between diet type and gluco-oligosaccharide level were determined Data was analyzed for linear and quadratic effect of gluco-oligosaccharide levels.

Results

Average values of the 0-42d Body Weight Gain (BWG), 0-42d Average Daily Gain (ADG), 0-42d Average Daily Feed Intake (ADFI), and 0-42d Feed Conversion Ratio (FCR) for nursery pigs fed control and treated diets were determined to be as summarized in Table 11 below.

TABLE 11

|  | Antibiotic Negative Control | Negative Control + Oligo Dose 1 | Negative Control + Oligo Dose 2 | Negative Contorl + Oligo Dose 3 | Antibiotic Positive Control | Positive Control + Oligo Dose 1 | Postitive Control + Oligo Dose 2 | Positive Control + Oligo Dose 3 |
|---|---|---|---|---|---|---|---|---|
| Mecadox, ppm | 0 | 0 | 0 | 0 | 55 | 55 | 55 | 55 |
| Oligo, ppm | 0 | 200 | 400 | 600 | 0 | 200 | 400 | 600 |
| BWG, lbs | 39.98 | 39.72 | 40.52 | 40.68 | 40.69 | 42.31 | 42.15 | 43.22 |
| ADG, lbs/day | 0.91 | 0.92 | 0.93 | 0.93 | 0.93 | 0.98 | 0.96 | 1.00 |
| ADFI, lbs/day | 1.35 | 1.34 | 1.37 | 1.36 | 1.37 | 1.42 | 1.41 | 1.43 |
| FCR, lbs/lbs | 1.47 | 1.46 | 1.47 | 1.46 | 1.47 | 1.46 | 1.46 | 1.43 |

Statistical variation and the effect of increasing dose of the gluco-oligosaccharide was determined by linear regression analysis, as illustrated by FIGS. 1, 2, 3 and 4. Error bars in the figures denote the standard error in the mean (SEM), and the dotted lines indicate the resulting linear regression analyses. See FIGS. 20-23.

The BWG benefit, ADG benefit, ADFI benefit, and FCR benefit were calculated for 0-42 days by taking the ratio of the respective values with respect to their corresponding controls and performing linear regression to determine the dose-effect of the gluco-oligosaccharide, resulting in the following regression equations set forth in Table 12 below.

TABLE 12

|  | Antibiotic Negative Control plus Gluco-Oligosaccharide | | | Antibiotic Positive Control plus Gluco-Oligosaccharide | | |
|---|---|---|---|---|---|---|
|  | Intercept, % | Slope, %/ppm | p-value | Intercept, % | Slope, %/ppm | p-value |
| BWG Benefit | 0.0% | 2.61E−05 | p < 0.10 | 2.5% | 9.29E−05 | p < 0.10 |
| ADG Benefit | 0.0% | 4.32E−05 | p < 0.01 | 3.2% | 1.04E−04 | p < 0.20 |
| ADFI Benefit | 0.0% | 1.59E−05 | p < 0.20 | 2.4% | 6.30E−05 | p < 0.20 |
| FCR Benefit | 0.0% | 4.86E−06 | p < 0.15 | −0.2% | 4.08E−05 | p < 0.10 |

The regression equations were used to determine the BWG, ADG, ADFI, and FCR benefit provided by 600 ppm gluco-oligosaccharide, both in the presence and absence of the antibiotic growth promoter as set forth in Table 13 below.

TABLE 13

|  | ABX Positive Control | ABX Negative Control + 600 ppm gluco-oligosaccharide | ABX Positive Control + 600 ppm gluco-oligosaccharide |
|---|---|---|---|
| BWG Benefit | 2.5% | 1.6% | 8.1% |
| ADG Benefit | 3.2% | 2.6% | 9.5% |
| ADFI Benefit | 2.4% | 1.0% | 6.1% |
| FCR Benefit | −0.2% | 0.3% | 2.2% |

As expected, addition of the antibiotic growth promoter Mecadox (ABX Positive Control) resulted in an improved 0-42d BWG of 2.5%, and improved 0-42d ADG of 3.2%, and an improved 0-42d ADGI of 2.4%. Also as expected, the addition of the antibiotic growth promoter did not improve the 0-42d FCR.

As apparent from the positive slope of the linear regressions, addition of the gluco-oligosaccharide provided a positive benefit in the 0-42d BWG, 0-42d ADG, 0-42d ADGI, and 0-42d FCR. At a particular dose of 600 ppm, addition of the gluco-oligosaccharide resulted in an improved 0-42d BWG of 1.6%, statistically comparable to that of the antibiotic, an improved 0-42d ADG of 2.6%, statistically comparable to the antibiotic, and an improved 0-42d ADGI of 1.0%, statistically comparable to the antibiotic. Furthermore, the addition of the gluco-oligosaccharide resulted in an improved FCR, in contrast to the antibiotic.

Surprisingly, the combination of the antibiotic and the gluco-oligosaccharide provided a significant improvement in the live growth performance, greater than that obtained with either the gluco-oligosaccharide or antibiotic alone, or the sum of their individual contributions.

What is claimed is:

1. An animal feed composition, comprising:
(i) a base feed, and
(ii) a gluco-oligosaccharide composition,
wherein the gluco-oligosaccharide composition has a glycosidic bond type distribution consisting of:
0 to 20 mol % α-(1,2) glycosidic linkages;
0 to 45 mol % β-(1,2) glycosidic linkages;
1 to 30 mol % α-(1,3) glycosidic linkages;
1 to 20 mol % β-(1,3) glycosidic linkages;
less than 9 mol % α-(1,4) glycosidic linkages;
0 to 55 mol % β-(1,4) glycosidic linkages;
0 to 30 mol % α-(1,6) glycosidic linkages; and
5 to 55 mol % β-(1,6) glycosidic linkages, and
wherein at least 10 dry wt % of the gluco-oligosaccharide composition has a degree of polymerization of at least 3; and wherein the animal feed composition has less than 50 ppm by weight of an antibiotic.

2. The animal feed composition of claim 1, wherein the gluco-oligosaccharide composition is present in the animal feed composition at below 5,000 ppm by weight.

3. The animal feed composition of claim 1, wherein the base feed comprises:
1200 to 1600 cal/lb apparent metabolizable energy;
16 to 24 wt % crude protein;
1.0 to 1.4 wt % lysine;
0.5 to 0.75 wt % methionine;
0.75 to 1.1 wt % total sulfur amino acids;
0.7 to 1.0 wt % calcium;
0.35 to 0.5 wt % total available phosphorous; and
0.15 to 0.3 wt % sodium.

4. The animal feed composition of claim 1, wherein at least 50 dry wt % of the gluco-oligosaccharide composition has a degree of polymerization of at least 3.

5. The animal feed composition of claim 1, wherein the animal feed composition is poultry feed.

6. The animal feed composition of claim 5, wherein the poultry feed:
(i) reduces feed conversion ratio (FCR) by 1% to 10%; or
(ii) increases average daily weight gain by 1% to 10%; or
(iii) increases average daily feed intake by 1% to 10%; or
any combination of (i), (ii), and (iii),
when fed to poultry as compared to poultry fed a feed composition without the gluco-oligosaccharide composition.

7. The animal feed composition of claim 1, wherein the animal feed composition is swine feed.

8. The animal feed composition of claim 7, wherein the swine feed:
(i) reduces feed conversion ratio (FCR) by 1% to 15%; or
(ii) increases average daily weight gain by 1% to 15%; or
(iii) increases average daily feed intake by 1% to 15%; or
any combination of (i), (ii), and (iii),
when fed to swine as compared to swine fed a feed composition without the gluco-oligosaccharide composition.

9. The animal feed composition of claim 1, wherein the antibiotic is selected from the group consisting of bacitracin, bacitracin methylene disalicylate, bacitracin-zinc, virginiamycin, bambermycin, avilamycin, efrotomycin, and any combination thereof.

10. The animal feed composition of claim 1, wherein the gluco-oligosaccharide composition is a functionalized gluco-oligosaccharide composition comprising a pendant functional group selected from the group consisting of glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate and phosphate.

11. An animal feed pre-mix, comprising:
(i) a carrier material; and
(ii) a gluco-oligosaccharide composition,
wherein the gluco-oligosaccharide composition has a glycosidic bond type distribution consisting of:
0 to 20 mol % α-(1,2) glycosidic linkages;
0 to 45 mol % β-(1,2) glycosidic linkages;
1 to 30 mol % α-(1,3) glycosidic linkages;
1 to 20 mol % β-(1,3) glycosidic linkages;
less than 9 mol % α-(1,4) glycosidic linkages;
0 to 55 mol % β-(1,4) glycosidic linkages;
0 to 30 mol % α-(1,6) glycosidic linkages; and
5 to 55 mol % β-(1,6) glycosidic linkages, and wherein at least 10 dry wt % of the gluco-oligosaccharide composition has a degree of polymerization of at least 3; and
wherein the carrier material has less than 50 ppm by weight of an antibiotic.

12. The animal feed pre-mix of claim 11, wherein the animal feed pre-mix comprises at least 10 wt % dry gluco-oligosaccharide composition.

13. The animal feed pre-mix of claim 11, wherein the carrier material is selected from the group consisting of rice hulls, feed grade silica gel, feed grade fumed silica, corn gluten feed, corn gluten meal, dried distiller's grains, milled corn, and any combination thereof.

14. The animal feed pre-mix of claim 11, wherein at least 50 dry wt % of the gluco-oligosaccharide composition has a degree of polymerization of at least 3.

15. The animal feed pre-mix of claim 11, wherein the animal feed pre-mix is poultry feed.

16. The animal feed pre-mix of claim 15, wherein the poultry feed:
(i) reduces feed conversion ratio (FCR) by 1% to 10%; or
(ii) increases average daily weight gain by 1% to 10%; or
(iii) increases average daily feed intake by 1% to 10%; or
any combination of (i), (ii), and (iii),
when fed to poultry as compared to poultry fed a feed composition without the gluco-oligosaccharide composition.

17. The animal feed pre-mix of claim 11, wherein the animal feed pre-mix is swine feed.

18. The animal feed pre-mix of claim 17, wherein the swine feed:
(i) reduces feed conversion ratio (FCR) by 1% to 15%; or
(ii) increases average daily weight gain by 1% to 15%; or
(iii) increases average daily feed intake by 1% to 15%; or
any combination of (i), (ii), and (iii),
when fed to swine as compared to swine fed a feed composition without the gluco-oligosaccharide composition.

19. The animal feed pre-mix of claim 11, wherein the antibiotic is selected from the group consisting of bacitracin, bacitracin methylene disalicylate, bacitracin-zinc, virginiamycin, bambermycin, avilamycin, efrotomycin, and any combination thereof.

20. The animal feed pre-mix of claim 11, wherein the gluco-oligosaccharide composition is a functionalized gluco-oligosaccharide composition comprising a pendant functional group selected from the group consisting of glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate and phosphate.

21. An animal feed composition, comprising (i) a base feed and (ii) the animal feed pre-mix of claim 11.

22. The animal feed composition of claim 1, wherein the animal feed composition comprises between 100 ppm and 750 ppm of the gluco-oligosaccharide composition by weight.

23. The animal feed composition of claim 1, wherein the animal feed composition comprises between 200 ppm and 750 ppm of the gluco-oligosaccharide composition by weight.

24. The animal feed composition of claim 1, wherein the animal feed composition comprises between 200 ppm and 600 ppm of the gluco-oligosaccharide composition by weight.

25. The animal feed composition of claim 1, wherein at least 60 dry wt % of the gluco-oligosaccharide composition has a degree of polymerization of at least 3.

26. The animal feed pre-mix of claim 11, wherein at least 60 dry wt % of the gluco-oligosaccharide composition has a degree of polymerization of at least 3.

* * * * *